US010273307B2

(12) United States Patent
Simons et al.

(10) Patent No.: US 10,273,307 B2
(45) Date of Patent: Apr. 30, 2019

(54) HUMANIZED ANTI-CD134 (OX40) ANTIBODIES AND USES THEREOF

(71) Applicants: BiocerOX Products B.V., GJ Almere (NL); Janssen Pharmaceuticals, Inc., Titusville, NJ (US)

(72) Inventors: Petrus Johannes Simons, Almere (NL); Louis Boon, Almere (NL); Jinquan Luo, Spring House, PA (US); Randall Brezski, Spring House, PA (US); Monica Goldberg, Spring House, PA (US)

(73) Assignees: Biocerox Products B.V., Almere (NL); Janssen Pharmaceuticals, Inc., Titusville, NJ (US)

( * ) Notice: Subject to any disclaimer, the term of this patent is extended or adjusted under 35 U.S.C. 154(b) by 0 days.

(21) Appl. No.: 15/700,986

(22) Filed: Sep. 11, 2017

(65) Prior Publication Data
US 2017/0369586 A1    Dec. 28, 2017

Related U.S. Application Data

(60) Division of application No. 14/221,212, filed on Mar. 20, 2014, now Pat. No. 9,790,281, which is a continuation of application No. PCT/NL2014/050162, filed on Mar. 18, 2014.

(30) Foreign Application Priority Data

Mar. 18, 2013    (EP) .................................... 13159794

(51) Int. Cl.
| A61K 39/395 | (2006.01) |
| C07K 16/30 | (2006.01) |
| C07K 16/28 | (2006.01) |

(52) U.S. Cl.
CPC .......... *C07K 16/30* (2013.01); *C07K 16/2878* (2013.01); *C07K 2317/24* (2013.01); *C07K 2317/34* (2013.01); *C07K 2317/56* (2013.01); *C07K 2317/565* (2013.01); *C07K 2317/74* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| 4,946,778 A | 8/1990 | Ladner et al. |
| 5,225,539 A | 7/1993 | Winter |
| 5,463,564 A | 10/1995 | Agrafiotis et al. |
| 5,534,254 A | 7/1996 | Huston et al. |
| 5,565,332 A | 10/1996 | Hoogenboom et al. |
| 5,723,322 A | 3/1998 | Guettler et al. |
| 5,901,069 A | 5/1999 | Agrafiotis et al. |
| 5,932,448 A | 8/1999 | Tso et al. |
| 6,291,158 B1 | 9/2001 | Winter et al. |
| 6,582,915 B1 | 6/2003 | Griffiths et al. |
| 6,593,081 B1 | 7/2003 | Griffiths et al. |
| 6,737,056 B1 | 5/2004 | Presta |
| 6,765,087 B1 | 7/2004 | Casterman et al. |
| 6,818,749 B1 | 11/2004 | Kashmiri et al. |
| 6,833,441 B2 | 12/2004 | Wang et al. |
| 6,838,254 B1 | 1/2005 | Hamers et al. |
| 7,550,140 B2 | 6/2009 | Bakker et al. |
| 7,666,412 B2 | 2/2010 | Bander |
| 7,695,936 B2 | 4/2010 | Carter et al. |
| 7,709,226 B2 | 5/2010 | Foote |
| 8,133,983 B2 | 3/2012 | Bakker et al. |
| 8,137,933 B2 | 3/2012 | Saha |
| 9,475,880 B2 | 10/2016 | Simons et al. |
| 9,738,723 B2 | 8/2017 | Hammond et al. |
| 9,789,183 B1 | 10/2017 | Wang et al. |
| 9,790,281 B2 | 10/2017 | Simons et al. |
| 2001/0044522 A1 | 11/2001 | Godfrey et al. |
| 2002/0004041 A1 | 1/2002 | Albert et al. |
| 2006/0153808 A1 | 7/2006 | Cristofanilli et al. |
| 2007/0117809 A1 | 5/2007 | Fridman |
| 2007/0287170 A1 | 12/2007 | Davis et al. |
| 2008/0287309 A1 | 11/2008 | Bowdish |

(Continued)

FOREIGN PATENT DOCUMENTS

| JP | 2008-512995 A | 5/2008 |
| JP | 2009-518005 | 5/2009 |

(Continued)

OTHER PUBLICATIONS

Antibody Engineering, Methods and Protocols, vol. 248, Edited by Benny Lo, 2004, Humana Press Inc., Totawa NJ, Chapter 7, pp. 135-159.*
Ablexis, "Developing a Next Generation Platform for Antibody Drug Discovery", www.ablexis.com , accessed May 29, 2015, 1 page.
Al-Shamkhani, et al., "OX40 is Differentially Expressed on Activated Rat and Mouse T Cells and is the Sole Receptor for the OX40 Ligand", Eur J Chem., vol. 26 Aug. 1996, 1695-1699.

(Continued)

*Primary Examiner* — Laura B Goddard
(74) *Attorney, Agent, or Firm* — BakerHostetler

(57) ABSTRACT

The invention provides antibodies that specifically bind to human CD134. Anti-human CD134 antibodies specifically bind to the extracellular domain of human CD134, including non-OX40 ligand (OX40L) binding domains on human CD134, which is expressed on e.g. activated human conventional effector CD4 and/or CD8 T lymphocytes (Teffs) and on activated human suppressive regulatory CD4 T lymphocytes (Tregs). Humanized anti-human CD134 antibodies are useful (e.g. to empower Teffs anti-cancer effector function and/or to inhibit Tregs suppressive function) for cancer treatment.

17 Claims, 62 Drawing Sheets
Specification includes a Sequence Listing.

(56) References Cited

U.S. PATENT DOCUMENTS

| | | | |
|---|---|---|---|
| 2009/0118127 A1 | 5/2009 | Raghunathan | |
| 2009/0214560 A1 | 8/2009 | Min et al. | |
| 2010/0015133 A1 | 1/2010 | Igawa et al. | |
| 2010/0261620 A1 | 10/2010 | Almagro et al. | |
| 2010/0285036 A1 | 11/2010 | Smith et al. | |
| 2010/0286374 A1 | 11/2010 | Kannan et al. | |
| 2011/0028688 A1 | 2/2011 | Hymowitz et al. | |
| 2011/0104053 A1 | 5/2011 | Rodriguez et al. | |
| 2011/0123532 A1 | 5/2011 | Gurney et al. | |
| 2011/0123552 A1 | 5/2011 | Bakker et al. | |
| 2012/0022811 A1 | 1/2012 | Dickinson et al. | |
| 2012/0149876 A1 | 6/2012 | Von Kreudenstein et al. | |
| 2014/0377284 A1 | 12/2014 | Simons et al. | |
| 2015/0132288 A1* | 5/2015 | Simons | C07K 16/2878 424/133.1 |
| 2015/0190506 A1 | 7/2015 | Cheung et al. | |
| 2015/0307617 A1 | 10/2015 | Du et al. | |
| 2016/0152720 A1 | 6/2016 | Kim et al. | |
| 2016/0160290 A1 | 6/2016 | Huseni et al. | |
| 2016/0161485 A1 | 6/2016 | Chu et al. | |
| 2016/0166685 A1 | 6/2016 | Cheung et al. | |
| 2016/0347847 A1 | 12/2016 | Van Dijk et al. | |
| 2017/0015755 A1 | 1/2017 | Walsh et al. | |
| 2017/0290913 A1 | 10/2017 | Cheung et al. | |
| 2017/0319690 A1 | 11/2017 | Wang et al. | |
| 2017/0369586 A1 | 12/2017 | Simons et al. | |
| 2018/0002423 A1 | 1/2018 | Wang et al. | |
| 2018/0022813 A1 | 1/2018 | Lazar et al. | |
| 2018/0044427 A1 | 2/2018 | Armstrong et al. | |

FOREIGN PATENT DOCUMENTS

| | | |
|---|---|---|
| JP | 2011-505836 A | 3/2011 |
| JP | 2012-521191 A | 9/2012 |
| WO | WO 1990/007861 A1 | 7/1990 |
| WO | WO 1992/001047 A1 | 1/1992 |
| WO | WO 1992/022653 A1 | 12/1992 |
| WO | WO 1995/030004 A1 | 11/1995 |
| WO | WO 1999/042585 A1 | 8/1999 |
| WO | WO 2003/002609 A2 | 1/2003 |
| WO | WO 2003/040170 A2 | 5/2003 |
| WO | WO 2003/106498 A2 | 12/2003 |
| WO | WO 2004/003019 A2 | 1/2004 |
| WO | WO 2004/111233 A1 | 12/2004 |
| WO | WO 2006/029879 A2 | 3/2006 |
| WO | WO 2006/079372 A1 | 8/2006 |
| WO | WO 2006/088639 A1 | 8/2006 |
| WO | WO 2006/119107 A2 | 11/2006 |
| WO | WO 2006/129163 A1 | 12/2006 |
| WO | WO 2007/059782 A1 | 5/2007 |
| WO | WO 2007/062235 A2 | 5/2007 |
| WO | WO 2007/062245 A2 | 5/2007 |
| WO | WO 2008/079849 A2 | 7/2008 |
| WO | WO 2008/106116 A2 | 9/2008 |
| WO | WO 2008/119353 A1 | 10/2008 |
| WO | WO 2008/128455 A1 | 10/2008 |
| WO | WO 2008/133851 A1 | 11/2008 |
| WO | WO 2009/079335 A1 | 6/2009 |
| WO | WO 2009/085462 A1 | 7/2009 |
| WO | WO 2009/134776 A2 | 11/2009 |
| WO | WO 2010/019702 A2 | 2/2010 |
| WO | WO 2010/096418 A2 | 8/2010 |
| WO | WO 2011/066501 A1 | 6/2011 |
| WO | WO 2011/131746 A2 | 10/2011 |
| WO | WO 2011/143545 A1 | 11/2011 |
| WO | WO 2012-027328 A2 | 3/2012 |
| WO | WO 2013-002831 A1 | 1/2013 |
| WO | WO 2013-008171 A1 | 1/2013 |
| WO | WO 2013/008171 A1 | 1/2013 |
| WO | WO 2013/028231 A1 | 2/2013 |
| WO | WO 2013/038191 A2 | 3/2013 |
| WO | WO 2013/068563 A2 | 5/2013 |
| WO | WO 2015/153513 A1 | 10/2015 |
| WO | WO 2016/057667 A1 | 4/2016 |

OTHER PUBLICATIONS

Angal, et al., "A Single Amino Acid Substitution Abolishes the Heterogeneity of Chimeric Mouse/Human (IgG4) Antibody",Mol. Immunol., 1993, vol. 30(1), 105-108.

Anti-Mouse CD134 (OX40) PE, Clone : OX-86, e-Biosciences, 2000-2012, 2 pages, http://www.ebioscience.com/mousecd134 antibody pe ox 66 hlm.

Attucci et al., "EPI-Hne4, A Proteolysis-Resistant Inhibitor of Human Neutrophil Elastase and Potential Anti-Inflammatory Drug for Treating Cystic Fibrosis", J. Pharmacal. Exp. Ther., vol. 318, Aug. 2006, 803-809.

Bashyam, H. and Sedwick, C., "How Alum Works", The Journal of Experimental Medicine, Mar. 24, 2008, 205(4), 742-743.

Bianchi et al. "High Level Expression and Rational Mutagenesis of a Designed Protein, The Minibody. From an Insoluble to a Soluble Molecule", J. Mol. Biol., vol. 236(2), Feb. 18, 1994, 649-59.

Binz et al., "High-Affinity Binders Selected from Designed Ankyrin Repeat Protein Libraries", Nat. Biotechnol., vol. 22, Apr. 18, 2004, 575-582.

Bird et al., "Single-Chain Antigen-Binding Proteins", Science, Oct. 1988, vol. 242(4877), 423-426.

Bodmer et al., "The Molecualr Architecture of the TNF Superfamily", Trends Biochem Sci., Jan. 2002, vol. 27(1), 19-26.

Borghouts et al., "Peptide Aptamers: Recent Developments for Cancer Therapy", Expert. Opin. Biol. Ther., Jun. 2005, vol. 5(6), 783-797.

Brorson et al, "Mutational Analysis of Avidity and Fine Specificity of Anti-Levan Antibodies", The Journal of Immunology, Dec. 15, 1999, 163(12), 6694-6701.

Brummell et al, "Probing the Combining Site of an Anti-Carbohydrate Antibody by Saturation-Mutagenesis: Role of the Heavy-Chain CDR3 Residues", Biochemistry, Feb. 1993, 32(4), 1180-1187.

Burks et al, "In Vitro Scanning Saturation Mutagenesis of an Antibody Binding Pocket", Proceedings of the National Academy of Sciences of the United States of America, Jan. 21, 1997, 94(2), 412-417.

Casset et al, "A Peptide Mimetic of an Anti-CD4 Monoclonal Antibody by Rational Design", Biochemical and Biophysical Research Communications, 2003, 307, 98-105.

Chen et al, "Selection and Analysis of an Optimized Anti-VEGF Antibody: Crystal Structure of an Affinity-Matured Fab in Complex with Antigen", Journal of Molecular Biology, Nov. 5, 1999, 293(4), 865-881.

Chile Application No. 631-2014: Office Action dated May 9, 2016, 1 page.

Chothia et al. Conformations of immunoglobulin hypervariable regions, Nature, 1989, 342(6252), 877-83.

Coleman, P.M., "Effects of Amino Acid Sequence Changes on Antibody-Antigen Interactions", Research in Immunology, Jan. 1994, 145(1), 33-36.

Columbian Application No. 15-240.954: Office Action dated Oct. 20, 2016.

Compaan et al., "The Crystal Structure of the Costimulatory OX40-OX40L Complex", Structure, Aug. 2006, vol. 14(8), 1321-1330.

Dall' Acqua et al, "Properties of Human IgGls Engineered for Enhanced Binding to the Neonatal Fc Receptor (FcRn)", J. Biol. Chem., May 4, 2006, vol. 281(235), 14-24.

Doppalapudi, et al., "Chemically Programmed Antibodies: Endothelin Receptor Targeting Cov X-Bodies", Jan. 15, 2007, Bioorg. Med. Chem. Lett., vol. 17(2), 501-6.

Dubrot et al, "Delivery of Immunostimulatory Monoclonal Antibodies by Encapsulated Hybridoma Cells", Cancer Immunology Immunotherapy, Nov. 1, 2010, 59,1621-1631, (Abstract, 1 page).

Evans, et al. "Rapid Expression of an Anti-Human C5 Chimeric Fab Utilizing a Vector that Replicates in COS and 293 Cells", J. Immunol., Meth, Jul. 1995, 184(1), 123-138.

Gabrielli et al, "Antibody Complementarity-Determining Regions (CDRs): A Baridge Between Adaptive and Innate Immunity", PloS One, Dec. 4, 2009, 4(12), e8187, 1-12.

(56) References Cited

OTHER PUBLICATIONS

Gao et al. "Molecular Cloning of a Proteolytic Antibody Light Chain", J. Biol. Chem. Dec. 23, 1994, vol. 269(51), 32389-93.
Gray et al, "Therapeutic Potential of Immunostimulatory Monoclonal Antibodies", Clinical Science, Jul. 2006, 111, 93-106.
Gri et al. "CD4+CD25+Regulatory T Cells Suppress Mast Cell Degranulation and Allergic Responses Through OX40-OX40L Interaction", Immunity, Nov. 14, 2008, vol. 29(5), 771-81.
"Harbour Antibodies", www.harbourantibodies.com, accessed May 29, 2015, 1 page.
Heap et al., "Analysis of a 17-Amino Acid Residue, Virus-Neutralizing Microantibody", J. Gen. Virol., Jun. 2005, vol. 86(Pt 6), 1791-1800.
Hey et al., "Artifical, Non-Antibody Binding Protiens for Pharmaceutical and Industrial Applications", Trends. Biotechnol., Oct. 2005, vol. 23(10), 514-522.
Hirschhorn-Cymerman, et al., "OX40 Engagement and Chemotherapy Combination Provides Potent Antitumore Immunity with Concomitant Regulatory T Cells Apoptosis", J. Exp. Med, May 4, 2009, vol. 206(5), 1103-1116.
Holliger, et al., "Diabodies: Small Bivalent and Bispecific Antibody Fragments", Jul. 15, 1993, vol. 90(14), Proc. Natl. Acad. Sci. USA, 6444-6448.
Holm et al, "Functional Mapping and Single Chain Construction of the Anti-Cytokeratin 8 Monoclonal Antibody TS1", Molecular Immunology, Feb. 2007, 44(6), 1075-1084.
Huston et al., "Protein Engeneering of Antibody Binding Sites: Recovery of Specific Activity in an Anti-Digoxin Single-Chain Fv Analogue Produced in *Escherichia coli*", Aug. 1988, Proc. Natl. Acad. Sci. USA 85(16), 5879-5883.
Imura, et al., "The Human OX40/gp34 System Directly Mediates Adhesion of Activated T Cells to Vascular Endothelial Cells", J. Exp. Med., May 1, 1996, vol. 183(5), 2185-95.
International Appln. No. PCT/GB2012/052268: International Search Report dated Apr. 31, 2013, 6 pages.
International Application No. PCT/NL2014/050162: International Search Report dated Jan. 9, 2014, 2 pages.
Israel Application No. 231540: Office Action dated Dec. 6, 2016.
Jang et al, "The Structural Basis for DNA Binding by an Anti-DNA Autoantibody", Molecular Immunology, Dec. 15, 1998, 35(18), 1207-1217.
Kashiwakura, et al., T Cell Proliferation by Direct Cross-Talk Between OX40 Ligand on Human Mast Cells and OX40 on Human T Cells: Comparison of Gene Expression Profiles Between Human Tonsillar and Lung-Cultures Mast Cells, J. Immunol., Oct. 1, 2004, vol. 173, 5247-5257.
Kim, et al., "CD4(+)CD3(−) Accessory Cells Costimulate Primed CD4 T Cells Through OX40 and CD30 at Sites Where T Cells Collaborate with B Cells", May 18, 2003, vol. 18(5), 643-54.
Kipriyanov, et al."Single-Chaim Antibody Streptavidin Fusions: Tetrameric Bifunctional scFv-Complexes with Biotin Binding Acivity and Enhanced Affinity and Antigen", Hum Antibodies Hybridomas, 1995, vol. 6(3), 93-101.
Klein, et al, "Epitope Interactions of Monoclonal Antibodies Targeting CD20 and Their Relationship to Functional Properties", MAbs, Jan. 1, 2013 vol. 5(1), 22-33.
Kobayashi et al, "Tryptophan H33 Plays an Important Role in Pyrimidine (6-4) Pyrimidone Photoproduct Binding by a High-Affinity Antibody", Protein Engineering, 1999, 12(10), 879-844.
Kohler, et al., "Continuous Cultures of Fused Cells Secreting Antibody of Predefined Specificity", Nature, Aug. 7, 1975, vol. 256(5517),495-497.
Koide et al., "Monobodies: Antibody Mimics Based on the Scaffold of the Fibronectin Type III Domain", Meth. Mol. Biol., 2007, 352, 95-109.
Krause et al., Grafting of Thrombopoietin-Mimetic Peptides into Cystine Knot Miniproteins Yields High-Affinity Thrombopoietin Antagonists and Agonists, FEBS J, Jan. 2007, vol. 274(1), 86-95.

Kumar et al, "Molecular Cloning and Expression of the Fabs of Human Autoantibodies in *Escherichia coli*", The Journal of Biological Chemistry, Nov. 10, 2000, 275, 35129-35136.
KyMab, "Advanced Therapeutic Antibody Discovery & Development", www.kymab.com, May 29, 2015.
Ladner et al., "Antibodies Cut Down to Size", Nature Biotechnology, Aug. 2007, 25(8), 875-7.
Latza et al., "The Humans OX40 Homolog: cDNA Structure, Expression and Chromosomal Assignment of the ACT35 Antigen", Eur. J. Immunol. Mar. 1994; 24(3), 677-683.
Laune, et al., "Systematic Exploration of the Antigen Binding Activity of Synthetic Peptides Isolated from the Variable Regions of Immunoglobulins", J. Biol. Chem., 1997, 272(49), 30937-44.
Linton, et al., "Costimulation Via OX40L Expressed by B Cells is Sufficient to Determine the Extent of Primary CD4 Cell Expansion and Th2 Cytokine Secretion in Vivi", J. Exp. Med. Apr. 7, 2003, vol. 197(7) 875-83.
MacLennan, et al., "Structure-Function Relationships in the Ca(2+)-Binding and Translocation Domain of Serca1: Physiological Correlates in Brody Disease", Act Physiol. Scand. Suppl., Aug. 1998, vol. 643, 55-67.
Mayes et al., "Synthetic Strategies for the Generation of Molecularly Imprinted Organic Polymers", Adv. Drug Deliv. Rev., 2005, vol. 57(17), 42-78.
Monnet, et al., "Synthetic Peptides Derived from the Variable Regions of an Anti-CD4 and Inhibit HIV-1 Promoter Activation in Virus Infected Cells", J. Biol. Chem., 1999, 274, 378-996.
Morris, et al., "Development and Characterization of Recombinant Human Fc: OX40L Fusion Protein Linked Via a Coiled-Coil Trimerization Domain", Mol. Immunol., May 2007, 44(12), 3112-3121.
Nakae, et al., "Mast Cells Enhance T Cell Activation: Importance of Mast Cell Costimulatory Molecules and Secreted TNF", J. Immunol., 2006, vol. 176, 2238-2248.
Nicaise, et al., "Affinity Transfer by CDR Grafting om A Nonimmunoglobulin Scaffold", Protein Science, Jul. 2004, vol. 13(7), 1882-91.
Nygren, et al., "Alternative Binding Proteins: Affibody Binding Proteins Developed from a Small Three-Helix Bundle Scaffold", Jun. 2008, FEBS J, vol. 275(11), 2668-2676.
Open Monoclonal Technology, "Naturally Optimized Human Antibodies", www.omtinc.net, accessed May 29, 2015, 2 pages.
Osborn et al., "From Rodent Reagents to Human Therapeutics Using Antibody Guided Selection", Methods, May 2005, vol. 36(1), 61-68.
Padlan, "A Possible Procedure for Reducing the Immunogenicity of Antibody Variable Domains While Preserving Their Ligand-Binding Properties", Mol. Immunol., 1991, vol. 28(4/5), 489-499.
Pandiyan, et al., "CD4+CD25+Foxp3+Regulatory T Cells Induce Cytokine Deprivation-Mediated Apoptosis of Effector CD4+ T Cells", Nat. Immunol., Dec. 2007, 8(12), 1353-62.
Peggs et al, "Cancer Immunotherapy: Co-Stimulatory Agonists and Co-Inhibitory Antagonists", Clinical & Experimental Immunology, Jul. 2009, 157(1), 9-19.
Pessi, et al., "A Designed Metal-Binding Protein with a Novel Fold", Nature, Mar. 25, 1993, vol. 362(6418), 367-9.
Piconese, et al., "Mast Cells Couteract Regulatory T-Cell Suppression Through Interleukin-6 and OX40/OX40L Axis Toward Th17-Cell Differentiation", Blood, Sep. 24, 2009, vol. 114(13), 2639-48.
Piconese, et al., "OX40 Triggering Blocks Suppression by Regulatory T Cells and Facilitates Tumor Rejection", J. Exp. Med., Apr. 14, 2008, vol. 205(4), 825-839.
Poljak, et al., "Production and Structure of Diabodies", Structure, 1994, vol. 2, 1121-1123.
Qiu, et al., "Small Antibody Mimetics Comprising Two Complementarity-Determining Regions and a Framework Region for Tumor Targeting", Nature Biotechnology, Aug. 5, 2007, vol. 25(8), 921-9.
Quezda, et al., "Shifting the Equilibrium in Cancer Immunoediting: From Tumor Tolerance to Eradication", Immunol. Rev., 2011, vol. 241, 104-118.
Quiocho, "Protein Engineering. Making of the Minibody", Nature, Mar. 25, 1993, vol. 362(6418), 293-4.

(56) References Cited

OTHER PUBLICATIONS

Ramstad, et al., "Immunohistochemical Analysis of Primary Breast Tumors and Tumor-Draining Lymph Nodes by Means of the T-Cell Costimulatory Molecule OX-40", Am. J. Surg., May 2000, 179(5), 400-406.
Root-Bernstein, et al., "Small Molecule Complementarity as a Source of Novel Pharmaceutical Agents and Combination Therapies", Cur. Pharm. Des., 2008, vol. 14, 55-62.
Ruby, C.E. and Weinberg, A.D., "The Effect of Aging on OX40 Agonist-Mediated Cancer Immunotherapy", Cancer Immunology Immunotherapy, Dec. 2009, 58(12), 1941-1947.
Santa Cruz Biotechnology Inc., "anti-OX40-receptor Antibody (H-10)" Jan. 2001, http://datasheets.scbt.com/sc-376014.pdf, retreived on Dec. 5, 2012.
Santa Cruz Biotechnology Inc., "anti-OX40-receptor Antibody (H-133)", Jan. 2011, http://datasheets.scbt.com/sc-11403.pdf, retreived on Dec. 5, 2012.
Sasaki, et al., "Structure-Mutation Analysis of the ATPase Site of Dictyostelium Discoideum Myosin II", Jan. 20, 1998. Adv. Biopsy's., vol. 35, 1-24.
Scheffold, et al., "Competition for Cytokines: T reg Cells Take All", Nat Immunol, 2007, vol. 8, 1285-1287.
Schlehuber et al., "Lipocalins in Drug Discovery: From Natural Ligans-Binding Protiens to Anticalins", Drug Discovery Today, 2005, vol. 10(1), 23-33.
"Science to Medicine", www.regeneron.com, accessed May 29, 2015, 2 pages.
Shi, et al, "De Novo Selection of High-Affinity Antibodies from Synthetic Fab Libraties Displayed on Phage as Pix Fusion Proteins", Mar. 26, 2010, J. Mol. Biol., vol. 397(2), 385-96.
Silverman, et al., "Multivalent Avimer Proteins Evolved by Exon Shuffling of a Family of Human Receptor Domains". Nat. Biotechnol., Nov. 20, 2005, 23, 1556-1561.
Singapore Application No. 112014007065: Search Report dated May 23, 2016, 1-21 pages.
Skerra, et al., "Alternative Non-Antibody Scaffolds for Molecular Recognition", Aug. 18, 2007, Curr. Opin. Biotech., vol. 18(4), 295-304.
Smith-Gill et al, "Contributions of Immunoglobulin Heavy and Light Chains to Antibody Specificity for Lysozyme and Two Haptens", The Journal of Immunology, Dec. 15, 1987, 139(12), 4135-4144.
Song et al, "Light Chain of Natural Antibody Plays a Dominant Role in Protein Antigen Binding", Biochemical and Biophysical Research Communication, Feb. 16, 2000, 268, 390-394.
Soroosh, et al., "OX40-OX40 Ligand Interaction Through T Cell—T Cell Contact Contributes to CD4 T Cell Longevity", J. Immunol., May 15, 2006, vol. 176(10), 5975-87.
Sugamura, et al., "A Therapeutic targeting of the effector T-cell co-stimulatory molecule OX40", Nature Rev. Imm., 2004, vol. 4, 420-431.
Swiss-Prot, "Tumor Necrosis Factor Receptor Superfamily Member 4", www.uniprot.org/uniprot/ P43489, accessed Jun. 4, 2015, 9 pages.
Taylor, et al., "Identification of a Soluble OX40 Isoform: Development of a Specific and Quantitative Immunoassay", J. Immunol. Methods, Sep. 1, 2001, vol. 255, 67-72.
Thogersen et al., "A Tetranectin-Based Platform for Protein Engineering", Innovations Pharmac. Technol, 2006, 27-30.
Trianni, "New Technologies to Generate an Advanced Human Monoclonal Antibody Resource", http://www.trianni.com, accessed May 29, 2015, 1 pg.
Vajdos et al, "Comprehensive Functional Maps of the Antigen-Binding Site of an Anti-ErbB2 Antibody Obtained with Shotgun Scanning Mutagenesis", Journal of Molecular Biology, Jul. 5, 2002, 320(2), 415-428.
Vaughan, et al., "Of Minibody, Camel and Bacteriophage", Combinatorial Chemistry & High Throughput Screening, Aug. 2001, vol. 4(5), 417-430.
Vercoulen, et al., "Human Regulatory T Cell Suppressive Function Is Independent of Apoptosis Induction in Activated Effector T Cells", Plos One, Sep. 25, 2009, 4(9) e7183.
Vetto, et al., "Presence of the T-Cell Activation Marker OX-40 on Tumor Infiltrating Lymphocytes and Draining Lymph Node Cells From Patients with Melanoma and Head and Neck Cancers", Am J Surg., Sep. 1997, vol. 174(3), 258-265.
Ward et al, "Binding Activities of a Repertoire of Single Immunoglobulin Variable Domains Secreted From *Escherichia coli*", Nature, Oct. 12, 1989, 341, 544-546.
Weinberg, et al., "Anti-OX40 (CD123) Administration to Nonhuman Primates: Immunostimulatory Effects and Toxicokinetic Study", J. Immunother, 2006, 29(6), 575-585.
Worn et al., "Stability Engineering of Antibody Single-Chain Fv Fragments", J. Mol. Biol., Feb. 2, 2001, vol. 305(5), 989-1010.
Wu et al, "Humanization of a Murine Monoclonal Antibody by Simultaneous Optimization of Framework and CDR Residues", Journal of Molecular Biology, Nov. 19, 1999, 294(1), 151-162.
Xie et al., "Costimulatory molecule OX40/OX40L Expression in Ductal Carcinoma in Situ and Invasive Ductal Carcinoma of Breast: An Innunohistochemistry-Based Pilot Study", Pathology—Research and Practice., Nov. 15, 2010, 206(11), 735-739.
Casadevall et al., "Immunoglobulin isotype influences affinity and specificity", PNAS, 2012, 109(31), 12272-12273.
Panagioti et al., "Enforced OX40 Stimulation Empowers Booster Vaccines to Induce Effective CD4+ and CD8+ T Cell Responses Against Mouse Cytomegalovirus Infection", Frontiers in Immunology, 2017, vol. 8, 14 pages.

\* cited by examiner

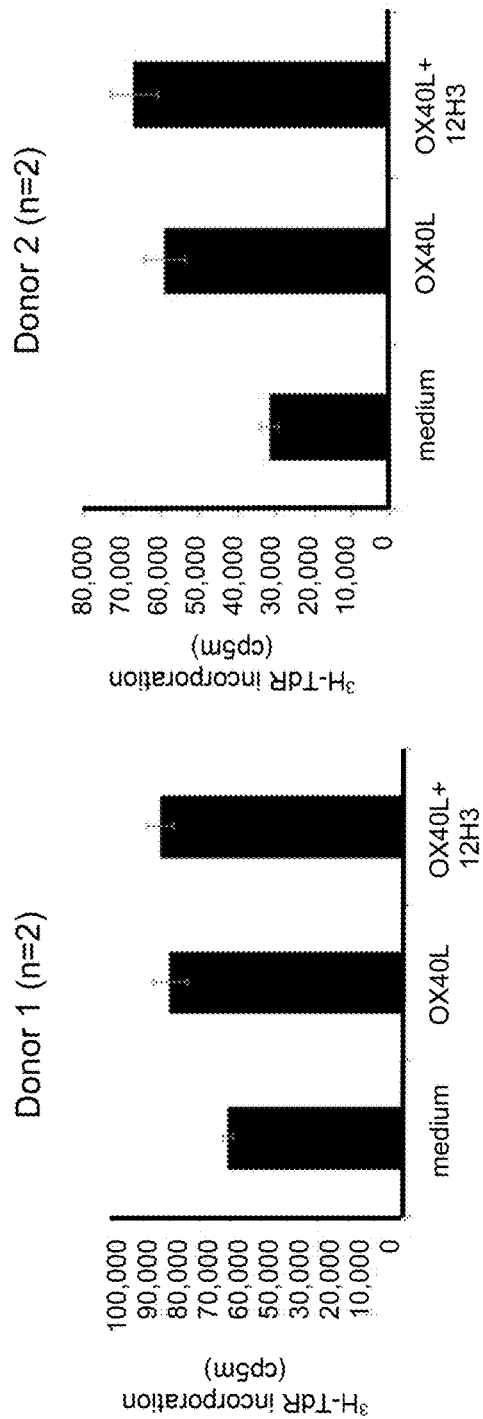
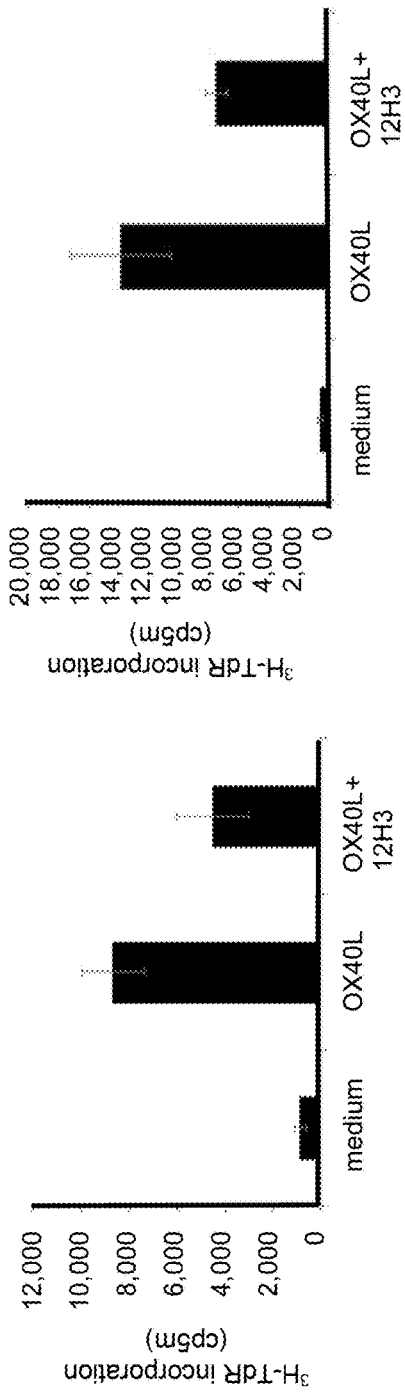
Figure 12A
Figure 12B

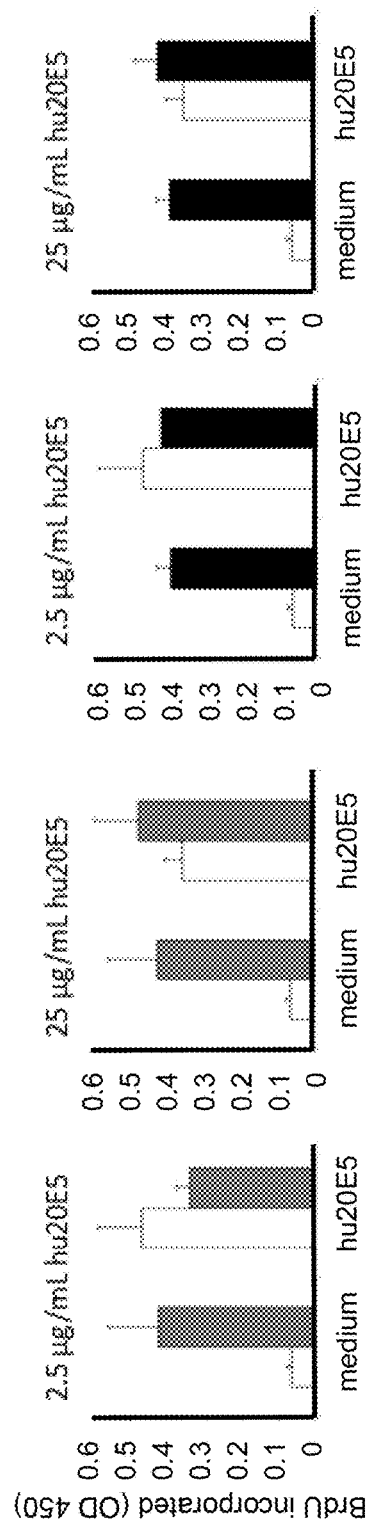
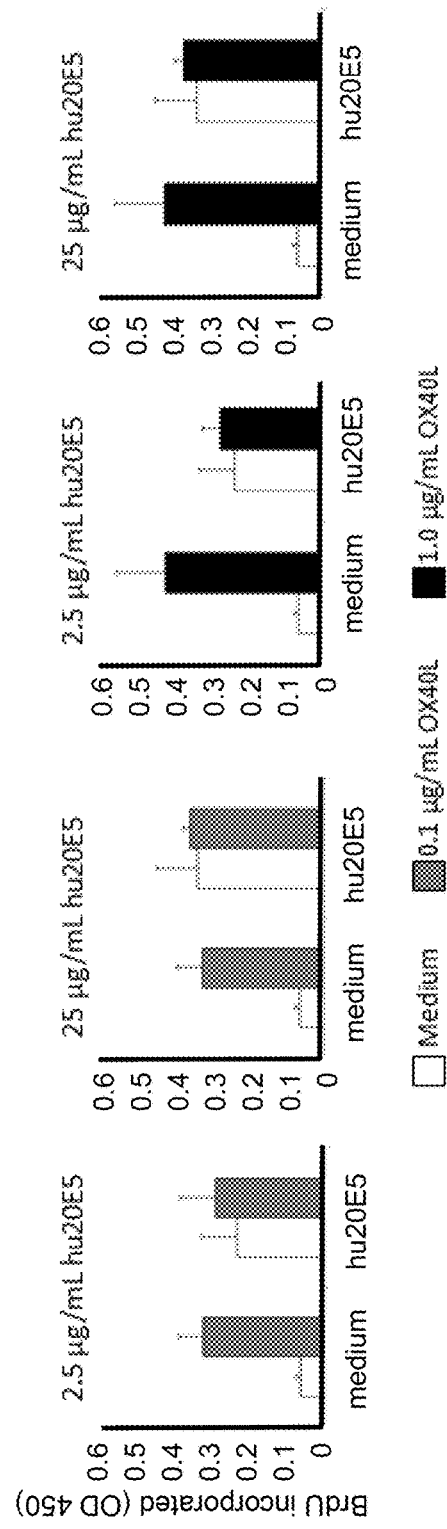
Figure 17

| | |
|---|---|
| mu12H3VH | evqlqqsgpelvkpgasvkisckt sgytfkdytmhwvkqshgkslewigriypnggstynqpfkdkatltvdkssta ymefrsltsedsavyycarmgyhgphldfdvwgaqttvtvsp |
| hu12H3_h1 | qvqlvqsgaevkkpgasvkvsckasgytfkdytmhwvrqapgqglewmggiypnggstynqpfkdrvtitadksts taymelssirsedtavyycarmgyhgphldfdvwgqgttvtvss |
| hu12H3_h2 | qvqlvqsgaevkkpgssvkvsckasgytfkdytmhwvrqapgqglewigglypnggstynqpfkdrvtitadkst staymelssirsedtavyycarmgyhgphldfdvwgqgttvtvss |
| hu12H3_h3 | qvqlvqsgaevkkpgssvkvsckasgytfkdytmhwvrqapgqglewigglypnggstynqpfkdratltvdkst staymelssirsedtavyycarmgyhgphldfdvwgqgttvtvss |

| | |
|---|---|
| mu12H3VH | evqlqqsgpelvkpgasvkisctkscy....... |
| hu12H3_h1 | ................................. |
| hu12H3_h2 | ................................. |
| hu12H3_h3 | ................................. |

| | |
|---|---|
| mu12H3VL | divmtqshkfmstslgdrvsitckasqdvgsaavawyqqkpgqspkllyw asttrhtgvpdrftgggsgtdftltisnvqsedltdyfcqqyinyplt fggqtkleikr |
| hu12H3_l1 | diqmtqspsslsasvgdrvtitckasqdvgsaavawyqqkpgkapkllyw astrhtgvpsrfsgsgsgtdftltisslqpedfatyycqqyinyplt fgqgtkveikr |
| hu12H3_l2 | diqmtqspsslsasvgdrvtitckasqdvgaavawyqqkpgkapkllyw astrhtgvpdrfsgsgsgtdftltisslqpedfatyycqqyinyplt fgqgtkveikr |

| | |
|---|---|
| mu12H3VL | divmtqshkfmstslgdrvsitck................ |
| hu12H3_l1 | ........................................ |
| hu12H3_l2 | ........................................ |

Hu 12H3_l1 = SEQ 67
Hu 12H3_l2 = SEQ 68
Hu 12H3_h1 = SEQ 69
Hu 12H3_h2 = SEQ 70
Hu 12H3_h3 = SEQ 71

Figure 26

Humanized 20E5 antibody variable heavy chain (SEQ ID NO: 97)

QVQLV QSGAE VKKPG ASVKV SCKAS GYTFT SYVMH WVRQA PGQRL EWX$_1$GY INPYN DGTKY NEKFK GRX$_2$TX$_3$ TSDX$_4$S ASTAY MELSS LRSED TAVYY CANYY GSSLS MDYWG QGTLV TVSS;

wherein X$_1$ = I or M,
X$_2$ = A or V,
X$_3$ = L OR I, and
X$_4$ = K or T.

Humanized 20E5 antibody variable light chain (SEQ ID NO: 98)

DIQMT QSPSS LSASV GDRVT ITCRA SQDIS NYLNW YQQKP GKAX$_5$K LLIYY TSRLH SGVPS RFSGS GSGTD YTLTI SSLQP EDFAT YX$_6$CQQ GNTLP WTFGQ GTKVE IKR wherein X$_5$ = V or P, and
X$_6$ = F or Y.

Figure 27

Humanized 12H3 antibody variable heavy chain (SEQ ID NO: 99)

QVQLV QSGAE VKKPG SSVKV SCKAS GYTFK DYTMH WVRQA PGQGL EWX$_7$GG IYPNN GGSTY NQNFK DRX$_8$TX$_9$ TX$_{10}$DKS TSTAY MELSS LRSED TAVYY CARMG YHGPH LDFDV WGQGT TVTVS S;

wherein X$_7$ = I or M,
X$_8$ = A or V,
X$_9$ = L OR I, and
X$_{10}$ = V or A.

Humanized 12H3 antibody variable light chain (SEQ ID NO: 100)

DIQMT QSPSS LSASV GDRVT ITCKA SQDVG AAVAW YQQKP GKAPK LLIYW ASTRH TGVPX$_{11}$ RFSGX$_{12}$ GSGTD FTLTI SSLQP EDFAT YYCQQ YINYP LTFGG GTKVE IKR wherein X$_{11}$ = D or S, and
X$_{12}$ = G or S.

Figure 43

| | | |
|---|---|---|
| 20E5_VH1_64 | QVQLVQSGAEVKKPGASVKVSCKASGYTFTSYVMHWVRQAPGQRLEWMGYINPYNDGTKY |
| 20E5_VH2_65 | QVQLVQSGAEVKKPGASVKVSCKASGYTFTSYVMHWVRQAPGQRLEWIGYINPYNDGTKY |
| 20E5_VH3_66 | QVQLVQSGAEVKKPGASVKVSCKASGYTFTSYVMHWVRQAPGQRLEWIGYINPYNDGTKY |
| 20E5_VH1_D56G_101 | QVQLVQSGAEVKKPGASVKVSCKASGYTFTSYVMHWVRQAPGQRLEWMGYINPYNGGTKY |
| 20E5_VH2_D56G_102 | QVQLVQSGAEVKKPGASVKVSCKASGYTFTSYVMHWVRQAPGQRLEWIGYINPYNGGTKY |
| 20E5_VH3_D56G_103 | QVQLVQSGAEVKKPGASVKVSCKASGYTFTSYVMHWVRQAPGQRLEWIGYINPYNGGTKY |
| 20E5_VH1_D56A_104 | QVQLVQSGAEVKKPGASVKVSCKASGYTFTSYVMHWVRQAPGQRLEWMGYINPYNAGTKY |
| 20E5_VH2_D56A_105 | QVQLVQSGAEVKKPGASVKVSCKASGYTFTSYVMHWVRQAPGQRLEWIGYINPYNAGTKY |
| 20E5_VH3_D56A_106 | QVQLVQSGAEVKKPGASVKVSCKASGYTFTSYVMHWVRQAPGQRLEWIGYINPYNAGTKY |
| 20E5_VH1_D56S_107 | QVQLVQSGAEVKKPGASVKVSCKASGYTFTSYVMHWVRQAPGQRLEWMGYINPYNSGTKY |
| 20E5_VH2_D56S_108 | QVQLVQSGAEVKKPGASVKVSCKASGYTFTSYVMHWVRQAPGQRLEWIGYINPYNSGTKY |
| 20E5_VH3_D56S_109 | QVQLVQSGAEVKKPGASVKVSCKASGYTFTSYVMHWVRQAPGQRLEWIGYINPYNSGTKY |
| 20E5_VH1_D56E_110 | QVQLVQSGAEVKKPGASVKVSCKASGYTFTSYVMHWVRQAPGQRLEWMGYINPYNEGTKY |
| 20E5_VH2_D56E_111 | QVQLVQSGAEVKKPGASVKVSCKASGYTFTSYVMHWVRQAPGQRLEWIGYINPYNEGTKY |
| 20E5_VH3_D56E_112 | QVQLVQSGAEVKKPGASVKVSCKASGYTFTSYVMHWVRQAPGQRLEWIGYINPYNEGTKY |
| 20E5_VH1_M106I_113 | QVQLVQSGAEVKKPGASVKVSCKASGYTFTSYVMHWVRQAPGQRLEWIGYINPYNDGTKY |
| 20E5_VH2_M106I_114 | QVQLVQSGAEVKKPGASVKVSCKASGYTFTSYVMHWVRQAPGQRLEWIGYINPYNDGTKY |
| 20E5_VH3_M106I_115 | QVQLVQSGAEVKKPGASVKVSCKASGYTFTSYVMHWVRQAPGQRLEWIGYINPYNDGTKY |
| 20E5_VH1_M106L_116 | QVQLVQSGAEVKKPGASVKVSCKASGYTFTSYVMHWVRQAPGQRLEWIGYINPYNDGTKY |
| 20E5_VH2_M106L_117 | QVQLVQSGAEVKKPGASVKVSCKASGYTFTSYVMHWVRQAPGQRLEWIGYINPYNDGTKY |
| 20E5_VH3_M106L_118 | QVQLVQSGAEVKKPGASVKVSCKASGYTFTSYVMHWVRQAPGQRLEWIGYINPYNDGTKY |
| 20E5_VH1_V11L_149 | QVQLVQSGAELKKPGASVKVSCKASGYTFTSYVMHWVRQAPGQRLEWMGYINPYNDGTKY |
| 20E5_VH2_V11L_150 | QVQLVQSGAELKKPGASVKVSCKASGYTFTSYVMHWVRQAPGQRLEWIGYINPYNDGTKY |
| 20E5_VH3_V11L_151 | QVQLVQSGAELKKPGASVKVSCKASGYTFTSYVMHWVRQAPGQRLEWIGYINPYNDGTKY |
| | ********:*********************************:.*******  |

Figure 43 (cont.)

| Name | Sequence |
|---|---|
| 20E5_VH1_64 | NEKFKGRVTITSDTSASTAYMELSSLRSEDTAVYYCANYYGSSLSMDYWGQGTLVTVSS |
| 20E5_VH2_65 | NEKFKGRATITSDTSASTAYMELSSLRSEDTAVYYCANYYGSSLSMDYWGQGTLVTVSS |
| 20E5_VH3_66 | NEKFKGRATLTSDKSASTAYMELSSLRSEDTAVYYCANYYGSSLSMDYWGQGTLVTVSS |
| 20E5_VH1_D56G_101 | NEKFKGRVTITSDTSASTAYMELSSLRSEDTAVYYCANYYGSSLSMDYWGQGTLVTVSS |
| 20E5_VH2_D56G_102 | NEKFKGRATITSDTSASTAYMELSSLRSEDTAVYYCANYYGSSLSMDYWGQGTLVTVSS |
| 20E5_VH3_D56G_103 | NEKFKGRATLTSDKSASTAYMELSSLRSEDTAVYYCANYYGSSLSMDYWGQGTLVTVSS |
| 20E5_VH1_D56A_104 | NEKFKGRVTITSDTSASTAYMELSSLRSEDTAVYYCANYYGSSLSMDYWGQGTLVTVSS |
| 20E5_VH2_D56A_105 | NEKFKGRATITSDTSASTAYMELSSLRSEDTAVYYCANYYGSSLSMDYWGQGTLVTVSS |
| 20E5_VH3_D56A_106 | NEKFKGRATLTSDKSASTAYMELSSLRSEDTAVYYCANYYGSSLSMDYWGQGTLVTVSS |
| 20E5_VH1_D56S_107 | NEKFKGRVTITSDTSASTAYMELSSLRSEDTAVYYCANYYGSSLSMDYWGQGTLVTVSS |
| 20E5_VH2_D56S_108 | NEKFKGRATITSDTSASTAYMELSSLRSEDTAVYYCANYYGSSLSMDYWGQGTLVTVSS |
| 20E5_VH3_D56S_109 | NEKFKGRATLTSDKSASTAYMELSSLRSEDTAVYYCANYYGSSLSMDYWGQGTLVTVSS |
| 20E5_VH1_D56E_110 | NEKFKGRVTITSDTSASTAYMELSSLRSEDTAVYYCANYYGSSLSMDYWGQGTLVTVSS |
| 20E5_VH2_D56E_111 | NEKFKGRATITSDTSASTAYMELSSLRSEDTAVYYCANYYGSSLSMDYWGQGTLVTVSS |
| 20E5_VH3_D56E_112 | NEKFKGRATLTSDKSASTAYMELSSLRSEDTAVYYCANYYGSSLSMDYWGQGTLVTVSS |
| 20E5_VH1_M106L_113 | NEKFKGRVTITSDTSASTAYMELSSLRSEDTAVYYCANYYGSSLSLDYWGQGTLVTVSS |
| 20E5_VH2_M106L_114 | NEKFKGRATITSDTSASTAYMELSSLRSEDTAVYYCANYYGSSLSLDYWGQGTLVTVSS |
| 20E5_VH3_M106L_115 | NEKFKGRATLTSDKSASTAYMELSSLRSEDTAVYYCANYYGSSLSLDYWGQGTLVTVSS |
| 20E5_VH1_M106I_116 | NEKFKGRVTITSDTSASTAYMELSSLRSEDTAVYYCANYYGSSLSIDYWGQGTLVTVSS |
| 20E5_VH2_M106I_117 | NEKFKGRATITSDTSASTAYMELSSLRSEDTAVYYCANYYGSSLSIDYWGQGTLVTVSS |
| 20E5_VH3_M106I_118 | NEKFKGRATLTSDKSASTAYMELSSLRSEDTAVYYCANYYGSSLSIDYWGQGTLVTVSS |
| 20E5_VH1_V11L_149 | NEKFKGRVTITSDTSASTAYMELSSLRSEDTAVYYCANYYGSSLSMDYWGQGTLVTVSS |
| 20E5_VH2_V11L_150 | NEKFKGRATITSDTSASTAYMELSSLRSEDTAVYYCANYYGSSLSMDYWGQGTLVTVSS |
| 20E5_VH3_V11L_151 | NEKFKGRATLTSDKSASTAYMELSSLRSEDTAVYYCANYYGSSLSMDYWGQGTLVTVSS |
| | ******.:**.:*:.*********************************** |

Figure 44.

| | |
|---|---|
| 12H3_VH1_69 | QVQLVQSGAEVKKPGSSVKVSCKASGYTFKDYTMHWVRQAPGQGLEWMGGIYPNNGGSTY |
| 12H3_VH2_70 | QVQLVQSGAEVKKPGSSVKVSCKASGYTFKDYTMHWVRQAPGQGLEWIGGIYPNNGGSTY |
| 12H3_VH3_71 | QVQLVQSGAEVKKPGSSVKVSCKASGYTFKDYTMHWVRQAPGQGLEWIGGIYPNNGGSTY |
| 12H3_VH1_N55Q_119 | QVQLVQSGAEVKKPGSSVKVSCKASGYTFKDYTMHWVRQAPGQGLEWMGGIYPNQGGSTY |
| 12H3_VH2_N55Q_120 | QVQLVQSGAEVKKPGSSVKVSCKASGYTFKDYTMHWVRQAPGQGLEWIGGIYPNQGGSTY |
| 12H3_VH3_N55Q_121 | QVQLVQSGAEVKKPGSSVKVSCKASGYTFKDYTMHWVRQAPGQGLEWIGGIYPNQGGSTY |
| 12H3_VH1_N55A_122 | QVQLVQSGAEVKKPGSSVKVSCKASGYTFKDYTMHWVRQAPGQGLEWMGGIYPNAGGSTY |
| 12H3_VH2_N55A_123 | QVQLVQSGAEVKKPGSSVKVSCKASGYTFKDYTMHWVRQAPGQGLEWIGGIYPNAGGSTY |
| 12H3_VH3_N55A_124 | QVQLVQSGAEVKKPGSSVKVSCKASGYTFKDYTMHWVRQAPGQGLEWIGGIYPNAGGSTY |
| 12H3_VH1_N55E_125 | QVQLVQSGAEVKKPGSSVKVSCKASGYTFKDYTMHWVRQAPGQGLEWMGGIYPNEGGSTY |
| 12H3_VH2_N55E_126 | QVQLVQSGAEVKKPGSSVKVSCKASGYTFKDYTMHWVRQAPGQGLEWIGGIYPNEGGSTY |
| 12H3_VH3_N55E_127 | QVQLVQSGAEVKKPGSSVKVSCKASGYTFKDYTMHWVRQAPGQGLEWIGGIYPNEGGSTY |
| 12H3_VH1_M99L_128 | QVQLVQSGAEVKKPGSSVKVSCKASGYTFKDYTMHWVRQAPGQGLEWMGGIYPNNGGSTY |
| 12H3_VH2_M99L_129 | QVQLVQSGAEVKKPGSSVKVSCKASGYTFKDYTMHWVRQAPGQGLEWIGGIYPNNGGSTY |
| 12H3_VH3_M99L_130 | QVQLVQSGAEVKKPGSSVKVSCKASGYTFKDYTMHWVRQAPGQGLEWIGGIYPNNGGSTY |
| 12H3_VH1_M99I_131 | QVQLVQSGAEVKKPGSSVKVSCKASGYTFKDYTMHWVRQAPGQGLEWMGGIYPNNGGSTY |
| 12H3_VH2_M99I_132 | QVQLVQSGAEVKKPGSSVKVSCKASGYTFKDYTMHWVRQAPGQGLEWIGGIYPNNGGSTY |
| 12H3_VH3_M99I_133 | QVQLVQSGAEVKKPGSSVKVSCKASGYTFKDYTMHWVRQAPGQGLEWIGGIYPNNGGSTY |
| 12H3_VH1_V11L_146 | QVQLVQSGAELKKPGSSVKVSCKASGYTFKDYTMHWVRQAPGQGLEWMGGIYPNNGGSTY |
| 12H3_VH2_V11L_147 | QVQLVQSGAELKKPGSSVKVSCKASGYTFKDYTMHWVRQAPGQGLEWIGGIYPNNGGSTY |
| 12H3_VH3_V11L_148 | QVQLVQSGAELKKPGSSVKVSCKASGYTFKDYTMHWVRQAPGQGLEWIGGIYPNNGGSTY |
| | *********::****************************..********* |

Figure 44 (Cont.)

| | |
|---|---|
| 12H3_VH1_69 | NQNFKDRVTITADKSTSTAYMELSSLRSEDTAVYYCARMGYHGPHLDFDVWGQGTTVTVSS |
| 12H3_VH2_70 | NQNFKDRVTLTADKSTSTAYMELSSLRSEDTAVYYCARMGYHGPHLDFDVWGQGTTVTVSS |
| 12H3_VH3_71 | NQNFKDRATLTVDKSTSTAYMELSSLRSEDTAVYYCARMGYHGPHLDFDVWGQGTTVTVSS |
| 12H3_VH1_N55Q_119 | NQNFKDRVTITADKSTSTAYMELSSLRSEDTAVYYCARMGYHGPHLDFDVWGQGTTVTVSS |
| 12H3_VH2_N55Q_120 | NQNFKDRVTLTADKSTSTAYMELSSLRSEDTAVYYCARMGYHGPHLDFDVWGQGTTVTVSS |
| 12H3_VH3_N55Q_121 | NQNFKDRATLTVDKSTSTAYMELSSLRSEDTAVYYCARMGYHGPHLDFDVWGQGTTVTVSS |
| 12H3_VH1_N55A_122 | NQNFKDRVTITADKSTSTAYMELSSLRSEDTAVYYCARMGYHGPHLDFDVWGQGTTVTVSS |
| 12H3_VH2_N55A_123 | NQNFKDRVTLTADKSTSTAYMELSSLRSEDTAVYYCARMGYHGPHLDFDVWGQGTTVTVSS |
| 12H3_VH3_N55A_124 | NQNFKDRATLTVDKSTSTAYMELSSLRSEDTAVYYCARMGYHGPHLDFDVWGQGTTVTVSS |
| 12H3_VH1_N55E_125 | NQNFKDRVTITADKSTSTAYMELSSLRSEDTAVYYCARMGYHGPHLDFDVWGQGTTVTVSS |
| 12H3_VH2_N55E_126 | NQNFKDRVTLTADKSTSTAYMELSSLRSEDTAVYYCARMGYHGPHLDFDVWGQGTTVTVSS |
| 12H3_VH3_N55E_127 | NQNFKDRATLTVDKSTSTAYMELSSLRSEDTAVYYCARMGYHGPHLDFDVWGQGTTVTVSS |
| 12H3_VH1_M99L_128 | NQNFKDRVTITADKSTSTAYMELSSLRSEDTAVYYCARLGYHGPHLDFDVWGQGTTVTVSS |
| 12H3_VH2_M99L_129 | NQNFKDRVTLTADKSTSTAYMELSSLRSEDTAVYYCARLGYHGPHLDFDVWGQGTTVTVSS |
| 12H3_VH3_M99L_130 | NQNFKDRATLTVDKSTSTAYMELSSLRSEDTAVYYCARLGYHGPHLDFDVWGQGTTVTVSS |
| 12H3_VH1_M99I_131 | NQNFKDRVTITADKSTSTAYMELSSLRSEDTAVYYCARIGYHGPHLDFDVWGQGTTVTVSS |
| 12H3_VH2_M99I_132 | NQNFKDRVTLTADKSTSTAYMELSSLRSEDTAVYYCARIGYHGPHLDFDVWGQGTTVTVSS |
| 12H3_VH3_M99I_133 | NQNFKDRATLTVDKSTSTAYMELSSLRSEDTAVYYCARIGYHGPHLDFDVWGQGTTVTVSS |
| 12H3_VH1_V11L_146 | NQNFKDRVTITADKSTSTAYMELSSLRSEDTAVYYCARMGYHGPHLDFDVWGQGTTVTVSS |
| 12H3_VH2_V11L_147 | NQNFKDRVTLTADKSTSTAYMELSSLRSEDTAVYYCARMGYHGPHLDFDVWGQGTTVTVSS |
| 12H3_VH3_V11L_148 | NQNFKDRATLTVDKSTSTAYMELSSLRSEDTAVYYCARMGYHGPHLDFDVWGQGTTVTVSS |
| | *****:*:**:**********************:*:****************** |

SEQUENCE LISTING

<160> NUMBER OF SEQ ID NOS: 152

<210> SEQ ID NO 1
<211> LENGTH: 277
<212> TYPE: PRT
<213> ORGANISM: homo sapiens
<220> FEATURE:
<221> NAME/KEY: SIGNAL
<222> LOCATION: (1)..(28)
<220> FEATURE:
<221> NAME/KEY: TRANSMEM
<222> LOCATION: (215)..(235)

<400> SEQUENCE: 1

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275
```

<210> SEQ ID NO 2
<211> LENGTH: 834
<212> TYPE: DNA
<213> ORGANISM: Artificial
<220> FEATURE:
<223> OTHER INFORMATION: Sf9 insect cell-optimized cDNA sequence for human CD134

<400> SEQUENCE: 2

```
atgtgcgtgg gcgctcgtcg tctgggtcgt ggtccctgcg ctgctctgct gctgctgggt      60
ctgggcctgt ccactgtcac tggactccac tgcgtgggcg acacctaccc ctccaacgac     120
cgttgctgcc acgaatgcag gcctggcaac ggcatggtgt cccgttgctc ccgttcccag     180
aacaccgtgt gccgtccctg cggtcccggt ttctacaacg acgtggtgtc ctccaagccc     240
tgcaagcctt gcacttggtg taacctccgc tccggttccg agcgcaagca gctgtgcacc     300
gctacccagg acactgtctg taggtgcagg gctggcaccc agcccctgga ctcctacaag     360
cccggtgtcg actgcgctcc ctgccccct ggtcacttct ctcccggcga caaccaggct     420
tgcaaaccat ggaccaactg caccctggct ggcaagcaca ccctgcagcc cgcttccaac     480
tcctccgacg ctatctgcga ggaccgtgac ccccctgcta tcaacctca ggagactcag      540
ggtcccccccg ctcgtcccat caccgtgcag cccaccgagg cttggccccg tacctcccaa     600
ggacctagca ctaggcctgt ggaggtgccc ggtggtcgtg ctgtggctgc tatcctgggc     660
ctgggtctgg tgctgggcct gctgggtccc ctggctatcc tgctggctct gtacctcctg     720
cgtcgtgacc agcgtctgcc ccccgacgct cacaagcccc ctggtggtgg ttccttccgt     780
accccccatcc aggaggagca ggctgacgct cactccaccc tggccaagat ctaa           834
```

<210> SEQ ID NO 3
<211> LENGTH: 11
<212> TYPE: PRT
<213> ORGANISM: Artificial
<220> FEATURE:
<223> OTHER INFORMATION: N-terminus amino acid sequence of clone 20E5 heavy chain

<400> SEQUENCE: 3

```
Glu Val Gln Leu Gln Gln Ser Gly Pro Glu Leu
1               5                   10
```

<210> SEQ ID NO 4
<211> LENGTH: 119
<212> TYPE: PRT
<213> ORGANISM: Artificial
<220> FEATURE:
<223> OTHER INFORMATION: Amino acid sequence of clone 20E5 heavy chain variable region

<400> SEQUENCE: 4

```
Glu Val Gln Leu Gln Gln Ser Gly Pro Glu Leu Val Lys Pro Gly Ala
1               5                   10                  15
Ser Val Lys Met Ser Cys Lys Ala Ser Gly Tyr Thr Phe Thr Ser Tyr
            20                  25                  30
Val Met His Trp Val Lys Gln Lys Pro Gly Gln Gly Leu Glu Trp Ile
        35                  40                  45
Gly Tyr Ile Asn Pro Tyr Asn Asp Gly Thr Lys Tyr Asn Glu Lys Phe
    50                  55                  60
Lys Gly Lys Ala Thr Leu Thr Ser Asp Lys Ser Ser Ser Thr Ala Tyr
65                  70                  75                  80
Met Glu Leu Ser Ser Leu Thr Ser Glu Asp Ser Ala Val Tyr Tyr Cys
                85                  90                  95
Ala Asn Tyr Tyr Gly Ser Ser Leu Ser Met Asp Tyr Trp Gly Gln Gly
            100                 105                 110
Thr Ser Val Thr Val Ser Ser
        115
```

<210> SEQ ID NO 5
<211> LENGTH: 108
<212> TYPE: PRT
<213> ORGANISM: Artificial
<220> FEATURE:
<223> OTHER INFORMATION: Amino acid sequence of clone 20E5 light chain
      variable region

<400> SEQUENCE: 5

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

<210> SEQ ID NO 6
<211> LENGTH: 10
<212> TYPE: PRT
<213> ORGANISM: Artificial
<220> FEATURE:
<223> OTHER INFORMATION: Amino acid sequence of clone 20E5 heavy chain
      CDR1

<400> SEQUENCE: 6

Gly Tyr Thr Phe Thr Ser Tyr Val Met His
1               5                   10

<210> SEQ ID NO 7
<211> LENGTH: 17
<212> TYPE: PRT
<213> ORGANISM: Artificial
<220> FEATURE:
<223> OTHER INFORMATION: Amino acid sequence of clone 20E5 heavy chain
      CDR2

<400> SEQUENCE: 7

Tyr Ile Asn Pro Tyr Asn Asp Gly Thr Lys Tyr Asn Glu Lys Phe Lys
1               5                   10                  15

Gly

<210> SEQ ID NO 8
<211> LENGTH: 10
<212> TYPE: PRT
<213> ORGANISM: Artificial
<220> FEATURE:
<223> OTHER INFORMATION: Amino acid sequence of clone 20E5 heavy chain
      CDR3

<400> SEQUENCE: 8

Tyr Tyr Gly Ser Ser Leu Ser Met Asp Tyr
1               5                   10

<210> SEQ ID NO 9
<211> LENGTH: 11

```
<212> TYPE: PRT
<213> ORGANISM: Artificial
<220> FEATURE:
<223> OTHER INFORMATION: Amino acid sequence of clone 20E5 light chain
      CDR1

<400> SEQUENCE: 9

Arg Ala Ser Gln Asp Ile Ser Asn Tyr Leu Asn
1               5                   10

<210> SEQ ID NO 10
<211> LENGTH: 7
<212> TYPE: PRT
<213> ORGANISM: Artificial
<220> FEATURE:
<223> OTHER INFORMATION: Amino acid sequence of clone 20E5 light chain
      CDR2

<400> SEQUENCE: 10

Tyr Thr Ser Arg Leu His Ser
1               5

<210> SEQ ID NO 11
<211> LENGTH: 9
<212> TYPE: PRT
<213> ORGANISM: Artificial
<220> FEATURE:
<223> OTHER INFORMATION: Amino acid sequence of clone 20E5 light chain
      CDR3

<400> SEQUENCE: 11

Gln Gln Gly Asn Thr Leu Pro Trp Thr
1               5

<210> SEQ ID NO 12
<211> LENGTH: 121
<212> TYPE: PRT
<213> ORGANISM: Artificial
<220> FEATURE:
<223> OTHER INFORMATION: Amino acid sequence of clone 12H3 heavy chain
      variable region

<400> SEQUENCE: 12

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Lys Asp Tyr
            20                  25                  30

Thr Met His Trp Val Lys Gln Ser His Gly Lys Ser Leu Glu Trp Ile
        35                  40                  45

Gly Gly Ile Tyr Pro Asn Asn Gly Gly Ser Thr Tyr Asn Gln Asn Phe
    50                  55                  60

Lys Asp Lys Ala Thr Leu Thr Val Asp Lys Ser Ser Thr Ala Tyr
65                  70                  75                  80

Met Glu Phe Arg Ser Leu Thr Ser Glu Asp Ser Ala Val Tyr Tyr Cys
                85                  90                  95

Ala Arg Met Gly Tyr His Gly Pro His Leu Asp Phe Asp Val Trp Gly
            100                 105                 110

Ala Gly Thr Thr Val Thr Val Ser Pro
        115                 120

<210> SEQ ID NO 13
<211> LENGTH: 108
<212> TYPE: PRT
<213> ORGANISM: Artificial
```

```
<220> FEATURE:
<223> OTHER INFORMATION: Amino acid sequence of clone 12H3 light chain
      variable region

<400> SEQUENCE: 13

Asp Ile Val Met Thr Gln Ser His Lys Phe Met Ser Thr Ser Leu Gly
1               5                   10                  15

Asp Arg Val Ser Ile Thr Cys Lys Ala Ser Gln Asp Val Gly Ala Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys Arg
            100                 105

<210> SEQ ID NO 14
<211> LENGTH: 10
<212> TYPE: PRT
<213> ORGANISM: Artificial
<220> FEATURE:
<223> OTHER INFORMATION: Amino acid sequence of clone 12H3 heavy chain
      CDR1

<400> SEQUENCE: 14

Gly Tyr Thr Phe Lys Asp Tyr Thr Met His
1               5                   10

<210> SEQ ID NO 15
<211> LENGTH: 17
<212> TYPE: PRT
<213> ORGANISM: Artificial
<220> FEATURE:
<223> OTHER INFORMATION: Amino acid sequence of clone 12H3 heavy chain
      CDR2

<400> SEQUENCE: 15

Gly Ile Tyr Pro Asn Asn Gly Gly Ser Thr Tyr Asn Gln Asn Phe Lys
1               5                   10                  15

Asp

<210> SEQ ID NO 16
<211> LENGTH: 12
<212> TYPE: PRT
<213> ORGANISM: Artificial
<220> FEATURE:
<223> OTHER INFORMATION: Amino acid sequence of clone 12H3 heavy chain
      CDR3

<400> SEQUENCE: 16

Met Gly Tyr His Gly Pro His Leu Asp Phe Asp Val
1               5                   10

<210> SEQ ID NO 17
<211> LENGTH: 11
<212> TYPE: PRT
<213> ORGANISM: Artificial
<220> FEATURE:
<223> OTHER INFORMATION: Amino acid sequence of clone 12H3 light chain
      CDR1
```

```
<400> SEQUENCE: 17

Lys Ala Ser Gln Asp Val Gly Ala Ala Val Ala
1               5                   10

<210> SEQ ID NO 18
<211> LENGTH: 7
<212> TYPE: PRT
<213> ORGANISM: Artificial
<220> FEATURE:
<223> OTHER INFORMATION: Amino acid sequence of clone 12H3 light chain
      CDR2

<400> SEQUENCE: 18

Trp Ala Ser Thr Arg His Thr
1               5

<210> SEQ ID NO 19
<211> LENGTH: 9
<212> TYPE: PRT
<213> ORGANISM: Artificial
<220> FEATURE:
<223> OTHER INFORMATION: Amino acid sequence of clone 12H3 light chain
      CDR3

<400> SEQUENCE: 19

Gln Gln Tyr Ile Asn Tyr Pro Leu Thr
1               5

<210> SEQ ID NO 20
<211> LENGTH: 1398
<212> TYPE: DNA
<213> ORGANISM: Artificial
<220> FEATURE:
<223> OTHER INFORMATION: CHO-optimized cDNA sequence coding for chimeric
      clone 20E5 human IgG4 chain

<400> SEQUENCE: 20
atggagtgga gcggagtgtt tatgttcctg ctgagcgtga ccgctggcgt gcactcagag        60
gtgcagctgc agcagtcagg ccccgagctg gtcaagcctg cgctagcgt gaagatgagc       120 tgtaaagcta gcggctacac cttcactagc tacgtgatgc actgggtcaa gcagaagccc      180
ggccagggcc tggagtggat cggctatatt aaccctata acgacggcac taagtataac       240
gagaagttta agggcaaggc tacctgact agcgataagt ctagctctac cgcctatatg       300
gaactgtcta gtctgactag tgaagatagc gccgtctact actgcgctaa ctactacggc      360
tctagcctgt ctatggacta ctggggccag ggcactagcg tgaccgtgtc tagcgctagc      420
actaagggcc ctagcgtgtt ccccctggcc cctgctctca gatctactag cgagtctacc      480
gccgctctgg gctgcctggt caaggactac ttccccgagc ccgtgaccgt cagctggaat      540
agcggcgctc tgactagcgg cgtgcacacc ttccctgccg tgctgcagtc tagcggcctg      600
tatagtctgt ctagcgtggt caccgtgcct agttctagcc tgggcactaa gacctacacc      660
tgtaacgtgg accacaagcc ctctaacact aaggtggaca agcgggtgga atctaagtac      720
ggccctccct gcccccctg ccctgcccct gaatttctgg gcggacctag tgtgttcctg       780
ttcccaccta gcctaagga caccctgatg atctctagaa cccccgaagt gacctgcgtg       840
gtggtggacg tgtcacagga agatcccgag gtccagttta attggtacgt ggacggcgtg      900
gaagtgcaca acgctaagac taagcctaga gaggaacagt ttaactctac ctataggtc       960 gtcagcgtgc tgaccgtgct gcaccaggac tggctgaacg gcaaagagta taagtgtaaa    1020
```

```
gtgtctaaca agggcctgcc tagctctatc gaaaagacta tctctaaggc taagggccag    1080
cctagagaac ctcaggtcta caccctgccc cctagtcagg aagagatgac taagaatcag    1140
gtgtcactga cctgtctggt caagggcttc taccctagcg atatcgccgt cgagtgggag    1200
tctaacggcc agcccgagaa caactataag actacccccc ctgtgctgga tagcgacggt    1260
agcttcttcc tgtactcacg gctgaccgtg ataagtctag gtggcagga aggcaacgtc     1320 tttagctgta gcgtgatgca cgaggccctg cacaatcact acactcagaa gtcactgagc    1380
ctgagcctgg gcaagtga                                                   1398

<210> SEQ ID NO 21
<211> LENGTH: 702
<212> TYPE: DNA
<213> ORGANISM: Artificial
<220> FEATURE:
<223> OTHER INFORMATION: CHO-optimized cDNA sequence coding for chimeric
      clone 20E5 human kappa chain

<400> SEQUENCE: 21
atggagtgga gcggagtgtt tatgttcctg ctgagcgtga ccgctggcgt gcactcagat    60
attcagatga ctcagactac ctctagcctg agcgctagcc tgggcgatag agtgactatt    120
agctgtagag ctagtcagga tatctctaac tacctgaact ggtatcagca gaaacccgac    180
ggcaccgtga agctgctgat ctactacacc tctagactgc actcaggcgt gccctctagg    240
tttagcggta gcggtagtgg caccgactat agcctgacta tctctaacct ggaacaggaa    300
gatatcgcta cctacttctg tcagcagggc aacaccctgc cctggacctt cggcggaggc    360
actaagctgg aaatcaagcg gaccgtggcc gctccctcag tgtttatctt cccacctagc    420
gacgagcagc tgaagtccgg caccgctagc gtcgtgtgcc tgctgaacaa cttctaccct    480
agagaagcta aggtgcagtg gaaagtggat aacgccctgc agtcaggcaa ctctcaggaa    540
tcagtcaccg agcaggactc taaggatagc acctatagcc tgtctagcac cctgaccctg    600
tctaaggccg actacgagaa gcacaaggtc tacgcctgcg aagtgactca ccagggactg    660
tctagccccg tgactaagtc ctttaataga ggcgagtgct ga                       702

<210> SEQ ID NO 22
<211> LENGTH: 1407
<212> TYPE: DNA
<213> ORGANISM: Artificial
<220> FEATURE:
<223> OTHER INFORMATION: CHO-optimized cDNA sequence coding for chimeric
      clone 20E5 human IgG1 chain

<400> SEQUENCE: 22
atggagtggt caggcgtgtt catgttcctg ctgagcgtga ccgctggcgt gcactcagag    60
gtgcagctgc agcagtcagg ccccgagctg gtcaagcctg gcgctagcgt gaagatgagc    120
tgtaaagcta gcggctacac cttcactagc tacgtgatgc actgggtcaa gcagaagccc    180
ggtcagggcc tggagtggat cggctatatt aaccccctata cgacggcac taagtataac    240 gagaagttta aggtaaagc taccctgact agcgataagt ctagctctac cgcctatatg    300
gaactgtcta gtctgactag tgaagatagc gccgtctact actgcgctaa ctactacggc    360
tctagcctgt ctatggacta ctggggtcag ggcactagcg tgaccgtgtc tagcgctagc    420
actaagggcc ctagcgtgtt ccccctggcc cctagctcta gtctactag cggcggcacc    480 gccgctctgg gctgcctggt caaggactac ttccccgagc ccgtgaccgt cagctggaat    540
agcggcgctc tgactagcgg agtgcacacc ttccccgccg tgctgcagtc tagcggcctg    600
```

-continued

```
tatagtctgt ctagcgtggt caccgtgcct agttctagcc tgggcactca gacctatatc      660
tgtaacgtga accacaagcc ctctaacact aaggtggaca agaaggtgga acctaagtcc      720
tgcgataaga ctcacacctg tcccccctgc cctgccctg agctgctggg aggacctagt       780
gtgttcctgt tcccacctaa gcctaaggac accctgatga tctctagaac ccccgaagtg     840
acctgcgtgg tggtggacgt cagtcacgag gaccctgaag tgaagtttaa ttggtacgtg     900
gacggcgtgg aagtgcacaa cgctaagact aagcctagag aggaacagta taactctacc    960
tatagggtcg tcagcgtgct gaccgtgctg caccaggact ggctgaacgg taaagagtat   1020
aagtgtaaag tgtctaacaa ggccctgcca gcccctatcg aaaagactat ctctaaggct   1080
aagggtcagc ctagggaacc tcaggtctac accctgcccc ctagtaggga cgagctgact   1140
aagaatcagg tcagcctgac ttgtctggtc aagggcttct accctagcga tatcgccgtc   1200
gagtgggagt ctaacggtca gcccgagaac aactataaga ctaccccccc tgtgctggat   1260
agcgacggta gcttcttcct gtactctaaa ctgaccgtgg ataagtctag gtggcagcag   1320
ggtaacgtgt tcagctgtag cgtgatgcac gaggccctgc acaatcacta cactcagaag   1380
tcactgagcc tgagccccgg taagtga                                        1407
```

<210> SEQ ID NO 23
<211> LENGTH: 1404
<212> TYPE: DNA
<213> ORGANISM: Artificial
<220> FEATURE:
<223> OTHER INFORMATION: CHO-optimized cDNA sequence coding for chimeric
      clone 12H3 human IgG4 chain

<400> SEQUENCE: 23

```
atggagtggt ctggtgtctt tatgttcctg ctgtccgtga ccgcgggtgt ccacagcgag      60
gtgcagctgc agcagtccgg ccctgagctg gtgaaacctg gcgcctccgt gaagatctcc    120
tgcaagaccc ccggctacac cttcaaggac tacacaatgc actgggtgaa acagtcccac    180
ggcaagtcct tggagtggat cggcggaatc taccccaaca cggcggctc cacctacaac     240
cagaacttca aggacaaggc caccctgacc gtggacaagt cctcctccac cgcctatatg    300
gaatttcggt ccctgacctc cgaggactcc gccgtgtact actgcgcccg gatgggctac    360
cacggccccc acctggattt cgacgtgtgg ggcgctggca ccaccgtgac cgtgtctcca    420
gctagcacca agggcccctc cgtgttccct ctggcccctt gctccggtc cacctccgag    480
tctaccgccg ctctgggctg cctggtgaaa gactacttcc ccgagcccgt gacagtgtcc    540
tggaactctg gcgccctgac cagcggcgtg cacaccttcc ctgccgtgct gcagtcctcc    600
ggcctgtact ccctgtcctc cgtggtgaca gtgccctcct ccagcctggg caccaagacc    660
tacacctgta acgtggacca caagccctcc aacaccaagg tggacaagcg gtggaatct   720
aagtacggcc ctccctgccc accttgccct gcccctgaat ttctgggcgg accttccgtg   780
ttcctgttcc ccccaaagcc caaggacacc ctgatgatct cccggacccc cgaagtgacc   840
tgcgtggtgg tggacgtgtc caagaagat cccgaggtcc agttcaattg gtacgtggac   900
ggcgtggaag tgcacaacgc caagaccaag cccagagagg aacagttcaa ctccacctac   960
cgggtggtgt ccgtgctgac cgtgctgcac caggactggc tgaacggcaa agagtacaag  1020
tgcaaggtct ccaacaaggg cctgcccagc tctatcgaaa agacaatctc caaggccaag  1080
ggccagcccc gcgagcccca ggtgtacacc ctgcctccca gccaagaaga gatgaccaag  1140
aaccaggtgt ccctgacttg tctggtgaaa ggcttctacc cctccgatat cgccgtcgag  1200
```

```
tgggagtcca acggccagcc cgagaacaac tacaagacca ccccccctgt gctggactcc    1260
gacggctcct tcttcctgta ctctcggctg acagtggata agtcccggtg caagaaggc     1320 aacgtcttct cctgctccgt gatgcacgag ccctgcaca accactacac ccagaagtcc     1380
ctgtccctga gcctgggcaa gtag                                            1404
```

<210> SEQ ID NO 24
<211> LENGTH: 702
<212> TYPE: DNA
<213> ORGANISM: Artificial
<220> FEATURE:
<223> OTHER INFORMATION: CHO-optimized cDNA sequence coding for chimeric
      clone 12H3 human kappa chain

<400> SEQUENCE: 24

```
atggagtggt ccggtgtctt tatgttcctg ctgtccgtga ccgctggcgt gcactccgat      60
atcgtgatga cccagtccca caagtttatg tccacctccc tgggcgacag agtctctatt    120
acctgcaagg cctcccagga cgtgggcgct gccgtggcct ggtatcagca gaagcccggc    180
cagtccccca agctgctgat ctactgggcc tccaccagac acaccggcgt gcccgacaga    240
ttcaccggcg gaggctctgg caccgacttc accctgacaa tctccaacgt gcagtccgag    300
gacctgaccg actacttctg ccagcagtat atcaactacc ccctgacctt cggcggaggc    360
accaagctgg aaatcaagcg gaccgtggcc gctcccctccg tgtttatctt cccacccctcc   420 gacgagcagc tgaagtccgg caccgcctcc gtggtctgcc tgctgaacaa cttctacccc    480
cgcgaggcca aggtgcagtg gaaggtggac aacgccctgc agtccggcaa ctcccaagaa    540
tccgtgaccg agcaggactc caaggacagc acctactccc tgtcctccac cctgaccctg    600
tccaaggccg actacgagaa gcacaaggtg tacgcctgcg aagtgaccca ccagggcctg    660
tccagccccg tgaccaagtc cttcaaccgg ggcgagtgct aa                        702
```

<210> SEQ ID NO 25
<211> LENGTH: 465
<212> TYPE: PRT
<213> ORGANISM: Artificial
<220> FEATURE:
<223> OTHER INFORMATION: Amino acid sequence of chimeric clone 20E5
      human IgG4 chain

<400> SEQUENCE: 25

```
Met Glu Trp Ser Gly Val Phe Met Phe Leu Leu Ser Val Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser
            85                  90                  95

Thr Ala Tyr Met Glu Leu Ser Ser Leu Thr Ser Glu Asp Ser Ala Val
            100                 105                 110

Tyr Tyr Cys Ala Asn Tyr Tyr Gly Ser Ser Leu Ser Met Asp Tyr Trp
        115                 120                 125
```

Gly Gln Gly Thr Ser Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Ser Leu Gly Thr Lys Thr Tyr Thr Cys Asn Val Asp
210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser Gln Glu Asp
            275                 280                 285

Pro Glu Val Gln Phe Asn Trp Tyr Val Asp Gly Val Glu Val His Asn
        290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
                340                 345                 350

Thr Ile Ser Lys Ala Lys Gly Gln Pro Arg Glu Pro Gln Val Tyr Thr
            355                 360                 365

Leu Pro Pro Ser Gln Glu Glu Met Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
                420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
        450                 455                 460

Lys
465

<210> SEQ ID NO 26
<211> LENGTH: 233
<212> TYPE: PRT
<213> ORGANISM: Artificial
<220> FEATURE:
<223> OTHER INFORMATION: Amino acid sequence of chimeric clone 20E5
      human kappa chain

<400> SEQUENCE: 26

Met Glu Trp Ser Gly Val Phe Met Phe Leu Leu Ser Val Thr Ala Gly
1               5                   10                  15

```
Val His Ser Asp Ile Gln Met Thr Gln Thr Thr Ser Ser Leu Ser Ala
         20                  25                  30

Ser Leu Gly Asp Arg Val Thr Ile Ser Cys Arg Ala Ser Gln Asp Ile
         35                  40                  45

Ser Asn Tyr Leu Asn Trp Tyr Gln Gln Lys Pro Asp Gly Thr Val Lys
 50                  55                  60

Leu Leu Ile Tyr Tyr Thr Ser Arg Leu His Ser Gly Val Pro Ser Arg
 65                  70                  75                  80

Phe Ser Gly Ser Gly Ser Gly Thr Asp Tyr Ser Leu Thr Ile Ser Asn
             85                  90                  95

Leu Glu Gln Glu Asp Ile Ala Thr Tyr Phe Cys Gln Gln Gly Asn Thr
            100                 105                 110

Leu Pro Trp Thr Phe Gly Gly Gly Thr Lys Leu Glu Ile Lys Arg Thr
            115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
        210                 215                 220

Thr Lys Ser Phe Asn Arg Gly Glu Cys
225                 230

<210> SEQ ID NO 27
<211> LENGTH: 468
<212> TYPE: PRT
<213> ORGANISM: Artificial
<220> FEATURE:
<223> OTHER INFORMATION: Amino acid sequence of chimeric clone 20E5
      human IgG1 chain

<400> SEQUENCE: 27

Met Glu Trp Ser Gly Val Phe Met Phe Leu Leu Ser Val Thr Ala Gly
 1               5                  10                  15

Val His Ser Glu Val Gln Leu Gln Gln Ser Gly Pro Glu Leu Val Lys
         20                  25                  30

Pro Gly Ala Ser Val Lys Met Ser Cys Lys Ala Ser Gly Tyr Thr Phe
             35                  40                  45

Thr Ser Tyr Val Met His Trp Val Lys Gln Lys Pro Gly Gln Gly Leu
 50                  55                  60

Glu Trp Ile Gly Tyr Ile Asn Pro Tyr Asn Asp Gly Thr Lys Tyr Asn
 65                  70                  75                  80

Glu Lys Phe Lys Gly Lys Ala Thr Leu Thr Ser Asp Lys Ser Ser Ser
             85                  90                  95

Thr Ala Tyr Met Glu Leu Ser Ser Leu Thr Ser Glu Asp Ser Ala Val
            100                 105                 110

Tyr Tyr Cys Ala Asn Tyr Tyr Gly Ser Ser Leu Ser Met Asp Tyr Trp
        115                 120                 125

Gly Gln Gly Thr Ser Val Thr Val Ser Ser Ala Ser Thr Lys Gly Pro
```

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Val Val Thr
                195                 200                 205

Val Pro Ser Ser Ser Leu Gly Thr Gln Thr Tyr Ile Cys Asn Val Asn
        210                 215                 220

His Lys Pro Ser Asn Thr Lys Val Asp Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 28
<211> LENGTH: 467
<212> TYPE: PRT
<213> ORGANISM: Artificial
<220> FEATURE:
<223> OTHER INFORMATION: Amino acid sequence of chimeric clone 12H3
      human IgG4 chain

<400> SEQUENCE: 28

Met Glu Trp Ser Gly Val Phe Met Phe Leu Leu Ser Val Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Thr Ser Gly Tyr Thr Phe
            35                  40                  45

Lys Asp Tyr Thr Met His Trp Val Lys Gln Ser His Gly Lys Ser Leu
50                      55                  60

Glu Trp Ile Gly Gly Ile Tyr Pro Asn Asn Gly Ser Thr Tyr Asn
65                  70                  75                  80

Gln Asn Phe Lys Asp Lys Ala Thr Leu Thr Val Asp Lys Ser Ser Ser
                85                  90                  95

Thr Ala Tyr Met Glu Phe Arg Ser Leu Thr Ser Glu Asp Ser Ala Val
                100                 105                 110

Tyr Tyr Cys Ala Arg Met Gly Tyr His Gly Pro His Leu Asp Phe Asp
            115                 120                 125

Val Trp Gly Ala Gly Thr Thr Val Thr Val Ser Pro Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Lys Thr Tyr Thr Cys Asn
210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
            275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Gln Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met

```
                    435                 440                 445

His Glu Ala Leu His Asn His Tyr Thr Gln Lys Ser Leu Ser Leu Ser
        450                 455                 460

Leu Gly Lys
465

<210> SEQ ID NO 29
<211> LENGTH: 233
<212> TYPE: PRT
<213> ORGANISM: Artificial
<220> FEATURE:
<223> OTHER INFORMATION: Amino acid sequence of chimeric clone 12H3
      human kappa chain

<400> SEQUENCE: 29

Met Glu Trp Ser Gly Val Phe Met Phe Leu Leu Ser Val Thr Ala Gly
1               5                   10                  15

Val His Ser Asp Ile Val Met Thr Gln Ser His Lys Phe Met Ser Thr
                20                  25                  30

Ser Leu Gly Asp Arg Val Ser Ile Thr Cys Lys Ala Ser Gln Asp Val
            35                  40                  45

Gly Ala Ala Val Ala Trp Tyr Gln Gln Lys Pro Gly Gln Ser Pro Lys
        50                  55                  60

Leu Leu Ile Tyr Trp Ala Ser Thr Arg His Thr Gly Val Pro Asp Arg
65                  70                  75                  80

Phe Thr Gly Gly Gly Ser Gly Thr Asp Phe Thr Leu Thr Ile Ser Asn
                85                  90                  95

Val Gln Ser Glu Asp Leu Thr Asp Tyr Phe Cys Gln Gln Tyr Ile Asn
            100                 105                 110

Tyr Pro Leu Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 30
<211> LENGTH: 240
<212> TYPE: PRT
<213> ORGANISM: Artificial
<220> FEATURE:
<223> OTHER INFORMATION: Amino acid sequence of human CD134_CRD2
<220> FEATURE:
<221> NAME/KEY: SIGNAL
<222> LOCATION: (1)..(28)
<220> FEATURE:
<221> NAME/KEY: TRANSMEM
<222> LOCATION: (178)..(198)

<400> SEQUENCE: 30
```

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Pro Cys Gly Pro
            20                  25                  30

Gly Phe Tyr Asn Asp Val Val Ser Ser Lys Pro Cys Lys Pro Cys Thr
        35                  40                  45

Trp Cys Asn Leu Arg Ser Gly Ser Glu Arg Lys Gln Leu Cys Thr Ala
    50                  55                  60

Thr Gln Asp Thr Val Cys Arg Cys Arg Ala Gly Thr Gln Pro Leu Asp
65              70                  75                  80

Ser Tyr Lys Pro Gly Val Asp Cys Ala Pro Cys Pro Pro Gly His Phe
            85                  90                  95

Ser Pro Gly Asp Asn Gln Ala Cys Lys Pro Trp Thr Asn Cys Thr Leu
            100                 105                 110

Ala Gly Lys His Thr Leu Gln Pro Ala Ser Asn Ser Ser Asp Ala Ile
        115                 120                 125

Cys Glu Asp Arg Asp Pro Pro Ala Thr Gln Pro Gln Glu Thr Gln Gly
    130                 135                 140

Pro Pro Ala Arg Pro Ile Thr Val Gln Pro Thr Glu Ala Trp Pro Arg
145                 150                 155                 160

Thr Ser Gln Gly Pro Ser Thr Arg Pro Val Glu Val Pro Gly Gly Arg
                165                 170                 175

Ala Val Ala Ala Ile Leu Gly Leu Gly Leu Val Leu Gly Leu Leu Gly
                180                 185                 190

Pro Leu Ala Ile Leu Leu Ala Leu Tyr Leu Leu Arg Arg Asp Gln Arg
            195                 200                 205

Leu Pro Pro Asp Ala His Lys Pro Pro Gly Gly Gly Ser Phe Arg Thr
            210                 215                 220

Pro Ile Gln Glu Glu Gln Ala Asp Ala His Ser Thr Leu Ala Lys Ile
225                 230                 235                 240
```

<210> SEQ ID NO 31
<211> LENGTH: 198
<212> TYPE: PRT
<213> ORGANISM: Artificial
<220> FEATURE:
<223> OTHER INFORMATION: Amino acid sequence of human CD134_CRD3
<220> FEATURE:
<221> NAME/KEY: SIGNAL
<222> LOCATION: (1)..(28)
<220> FEATURE:
<221> NAME/KEY: TRANSMEM
<222> LOCATION: (136)..(156)

<400> SEQUENCE: 31

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Arg Cys Arg Ala
            20                  25                  30

Gly Thr Gln Pro Leu Asp Ser Tyr Lys Pro Gly Val Asp Cys Ala Pro
        35                  40                  45

Cys Pro Pro Gly His Phe Ser Pro Gly Asp Asn Gln Ala Cys Lys Pro
    50                  55                  60

Trp Thr Asn Cys Thr Leu Ala Gly Lys His Thr Leu Gln Pro Ala Ser
65              70                  75                  80

Asn Ser Ser Asp Ala Ile Cys Glu Asp Arg Asp Pro Pro Ala Thr Gln
            85                  90                  95
```

```
Pro Gln Glu Thr Gln Gly Pro Pro Ala Arg Pro Ile Thr Val Gln Pro
            100                 105                 110

Thr Glu Ala Trp Pro Arg Thr Ser Gln Gly Pro Ser Thr Arg Pro Val
        115                 120                 125

Glu Val Pro Gly Gly Arg Ala Val Ala Ala Ile Leu Gly Leu Gly Leu
130                 135                 140

Val Leu Gly Leu Leu Gly Pro Leu Ala Ile Leu Leu Ala Leu Tyr Leu
145                 150                 155                 160

Leu Arg Arg Asp Gln Arg Leu Pro Pro Asp Ala His Lys Pro Pro Gly
                165                 170                 175

Gly Gly Ser Phe Arg Thr Pro Ile Gln Glu Glu Gln Ala Asp Ala His
            180                 185                 190

Ser Thr Leu Ala Lys Ile
            195

<210> SEQ ID NO 32
<211> LENGTH: 179
<212> TYPE: PRT
<213> ORGANISM: Artificial
<220> FEATURE:
<223> OTHER INFORMATION: Amino acid sequence of human CD134_CRD4
<220> FEATURE:
<221> NAME/KEY: SIGNAL
<222> LOCATION: (1)..(28)
<220> FEATURE:
<221> NAME/KEY: TRANSMEM
<222> LOCATION: (117)..(137)

<400> SEQUENCE: 32

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Pro Cys Pro Pro
            20                  25                  30

Gly His Phe Ser Pro Gly Asp Asn Gln Ala Cys Lys Pro Trp Thr Asn
            35                  40                  45

Cys Thr Leu Ala Gly Lys His Thr Leu Gln Pro Ala Ser Asn Ser Ser
    50                  55                  60

Asp Ala Ile Cys Glu Asp Arg Asp Pro Pro Ala Thr Gln Pro Gln Glu
65                  70                  75                  80

Thr Gln Gly Pro Pro Ala Arg Pro Ile Thr Val Gln Pro Thr Glu Ala
                85                  90                  95

Trp Pro Arg Thr Ser Gln Gly Pro Ser Thr Arg Pro Val Glu Val Pro
            100                 105                 110

Gly Gly Arg Ala Val Ala Ala Ile Leu Gly Leu Gly Leu Val Leu Gly
            115                 120                 125

Leu Leu Gly Pro Leu Ala Ile Leu Leu Ala Leu Tyr Leu Leu Arg Arg
            130                 135                 140

Asp Gln Arg Leu Pro Pro Asp Ala His Lys Pro Pro Gly Gly Gly Ser
145                 150                 155                 160

Phe Arg Thr Pro Ile Gln Glu Glu Gln Ala Asp Ala His Ser Thr Leu
                165                 170                 175

Ala Lys Ile

<210> SEQ ID NO 33
<211> LENGTH: 159
<212> TYPE: PRT
<213> ORGANISM: Artificial
<220> FEATURE:
```

<223> OTHER INFORMATION: Amino acid sequence of human CD134_CRD4
      truncated
<220> FEATURE:
<221> NAME/KEY: SIGNAL
<222> LOCATION: (1)..(28)
<220> FEATURE:
<221> NAME/KEY: TRANSMEM
<222> LOCATION: (97)..(117)

<400> SEQUENCE: 33

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Cys Thr Leu Ala
                20                  25                  30

Gly Lys His Thr Leu Gln Pro Ala Ser Asn Ser Ser Asp Ala Ile Cys
            35                  40                  45

Glu Asp Arg Asp Pro Pro Ala Thr Gln Pro Gln Glu Thr Gln Gly Pro
50                  55                  60

Pro Ala Arg Pro Ile Thr Val Gln Pro Thr Glu Ala Trp Pro Arg Thr
65                  70                  75                  80

Ser Gln Gly Pro Ser Thr Arg Pro Val Glu Val Pro Gly Gly Arg Ala
                85                  90                  95

Val Ala Ala Ile Leu Gly Leu Gly Leu Val Leu Gly Leu Leu Gly Pro
            100                 105                 110

Leu Ala Ile Leu Leu Ala Leu Tyr Leu Leu Arg Arg Asp Gln Arg Leu
        115                 120                 125

Pro Pro Asp Ala His Lys Pro Pro Gly Gly Gly Ser Phe Arg Thr Pro
    130                 135                 140

Ile Gln Glu Glu Gln Ala Asp Ala His Ser Thr Leu Ala Lys Ile
145                 150                 155

<210> SEQ ID NO 34
<211> LENGTH: 19
<212> TYPE: PRT
<213> ORGANISM: Homo sapiens

<400> SEQUENCE: 34

Arg Cys Arg Ala Gly Thr Gln Pro Leu Asp Ser Tyr Lys Pro Gly Val
1               5                   10                  15

Asp Cys Ala

<210> SEQ ID NO 35
<211> LENGTH: 107
<212> TYPE: PRT
<213> ORGANISM: Homo sapiens

<400> SEQUENCE: 35

Arg Cys Arg Ala Gly Thr Gln Pro Leu Asp Ser Tyr Lys Pro Gly Val
1               5                   10                  15

Asp Cys Ala Pro Cys Pro Pro Gly His Phe Ser Pro Gly Asp Asn Gln
            20                  25                  30

Ala Cys Lys Pro Trp Thr Asn Cys Thr Leu Ala Gly Lys His Thr Leu
        35                  40                  45

Gln Pro Ala Ser Asn Ser Ser Asp Ala Ile Cys Glu Asp Arg Asp Pro
    50                  55                  60

Pro Ala Thr Gln Pro Gln Glu Thr Gln Gly Pro Pro Ala Arg Pro Ile
65                  70                  75                  80

Thr Val Gln Pro Thr Glu Ala Trp Pro Arg Thr Ser Gln Gly Pro Ser
                85                  90                  95

Thr Arg Pro Val Glu Val Pro Gly Gly Arg Ala
            100                 105

<210> SEQ ID NO 36
<211> LENGTH: 68
<212> TYPE: PRT
<213> ORGANISM: Homo sapiens

<400> SEQUENCE: 36

Cys Thr Leu Ala Gly Lys His Thr Leu Gln Pro Ala Ser Asn Ser Ser
1               5                   10                  15

Asp Ala Ile Cys Glu Asp Arg Asp Pro Pro Ala Thr Gln Pro Gln Glu
            20                  25                  30

Thr Gln Gly Pro Pro Ala Arg Pro Ile Thr Val Gln Pro Thr Glu Ala
        35                  40                  45

Trp Pro Arg Thr Ser Gln Gly Pro Ser Thr Arg Pro Val Glu Val Pro
    50                  55                  60

Gly Gly Arg Ala
65

<210> SEQ ID NO 37
<211> LENGTH: 29
<212> TYPE: PRT
<213> ORGANISM: Homo sapiens

<400> SEQUENCE: 37

Thr Tyr Ser Ser Pro Glu Asp Gly Ile His Glu Leu Phe Pro Ala Pro
1               5                   10                  15

Asp Gly Glu Glu Asp Thr Ala Glu Leu Gln Gly Gly Cys
            20                  25

<210> SEQ ID NO 38
<211> LENGTH: 39
<212> TYPE: PRT
<213> ORGANISM: Homo sapiens

<400> SEQUENCE: 38

Arg Cys Arg Ala Gly Thr Gln Pro Leu Asp Ser Tyr Lys Pro Gly Val
1               5                   10                  15

Asp Cys Ala Pro Cys Pro Pro Gly His Phe Ser Pro Gly Asp Asn Gln
            20                  25                  30

Ala Cys Lys Pro Trp Thr Asn
        35

<210> SEQ ID NO 39
<211> LENGTH: 20
<212> TYPE: DNA
<213> ORGANISM: Artificial
<220> FEATURE:
<223> OTHER INFORMATION: mkappa antisense primer (primer no: 201)

<400> SEQUENCE: 39
gacagttggt gcagcatcag                                                   20

<210> SEQ ID NO 40
<211> LENGTH: 20
<212> TYPE: DNA
<213> ORGANISM: Artificial
<220> FEATURE:
<223> OTHER INFORMATION: mkappa antisense primer (primer no: 266)

<400> SEQUENCE: 40

```
cactggatgg tgggaagatg                                          20

<210> SEQ ID NO 41
<211> LENGTH: 20
<212> TYPE: DNA
<213> ORGANISM: Artificial
<220> FEATURE:
<223> OTHER INFORMATION: mIgG1 antisense primer (primer no: 203)

<400> SEQUENCE: 41
ggccagtgga tagacagatg                                          20

<210> SEQ ID NO 42
<211> LENGTH: 20
<212> TYPE: DNA
<213> ORGANISM: Artificial
<220> FEATURE:
<223> OTHER INFORMATION: mIgG1 antisense primer (primer no: 204)

<400> SEQUENCE: 42
tggacaggga tccagagttc                                          20

<210> SEQ ID NO 43
<211> LENGTH: 25
<212> TYPE: DNA
<213> ORGANISM: Artificial
<220> FEATURE:
<223> OTHER INFORMATION: 20E5HC sense primer (primer no: 259)
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 43
gcgaagtaca aytncarcar wsngg                                    25

<210> SEQ ID NO 44
<211> LENGTH: 25
<212> TYPE: DNA
<213> ORGANISM: Artificial
<220> FEATURE:
<223> OTHER INFORMATION: 20E5HC sense primer (primer no: 260)
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 44
gcgtacaatt acarcarwsn ggncc                                    25

<210> SEQ ID NO 45
<211> LENGTH: 22
<212> TYPE: DNA
<213> ORGANISM: Artificial
<220> FEATURE:
<223> OTHER INFORMATION: 20E5LC sense primer (primer no: 265)
<220> FEATURE:
<221> NAME/KEY: misc_feature
<222> LOCATION: (17)..(17)
<223> OTHER INFORMATION: n is a, c, g, or t
```

-continued

<400> SEQUENCE: 45
gcgatataca ratgacncar ac                                              22

<210> SEQ ID NO 46
<211> LENGTH: 21
<212> TYPE: DNA
<213> ORGANISM: Artificial
<220> FEATURE:
<223> OTHER INFORMATION: mIgG1 antisense primer (primer no: 416)

<400> SEQUENCE: 46
cagtggatag acagatgggg g                                               21

<210> SEQ ID NO 47
<211> LENGTH: 20
<212> TYPE: DNA
<213> ORGANISM: Artificial
<220> FEATURE:
<223> OTHER INFORMATION: mkappa antisense primer (primer no: 394)

<400> SEQUENCE: 47
actggatggt gggaagatgg                                                 20

<210> SEQ ID NO 48
<211> LENGTH: 26
<212> TYPE: DNA
<213> ORGANISM: Artificial
<220> FEATURE:
<223> OTHER INFORMATION: signal peptide sense primer (primer no: 405)

<400> SEQUENCE: 48
atgggatgga gctrtatcat sytctt                                          26

<210> SEQ ID NO 49
<211> LENGTH: 26
<212> TYPE: DNA
<213> ORGANISM: Artificial
<220> FEATURE:
<223> OTHER INFORMATION: signal peptide sense primer (primer no: 410)

<400> SEQUENCE: 49
atggratgga gckgggtctt tmtctt                                          26

<210> SEQ ID NO 50
<211> LENGTH: 24
<212> TYPE: DNA
<213> ORGANISM: Artificial
<220> FEATURE:
<223> OTHER INFORMATION: signal peptide sense primer (primer no: 389)

<400> SEQUENCE: 50
atgggcwtca aagatggagt caca                                            24

<210> SEQ ID NO 51
<211> LENGTH: 24
<212> TYPE: DNA
<213> ORGANISM: Artificial
<220> FEATURE:
<223> OTHER INFORMATION: CD134 leader sense primer (primer no: 362)

<400> SEQUENCE: 51
ctcggatccg ccaccatgtg cgtg                                            24

<210> SEQ ID NO 52
<211> LENGTH: 24

```
<210> SEQ ID NO 52
<211> LENGTH: 24
<212> TYPE: DNA
<213> ORGANISM: Artificial
<220> FEATURE:
<223> OTHER INFORMATION: RD2 sense primer (primer no: 364)

<400> SEQUENCE: 52
actgtcactg daccctgcgg tccc                                          24

<210> SEQ ID NO 53
<211> LENGTH: 24
<212> TYPE: DNA
<213> ORGANISM: Artificial
<220> FEATURE:
<223> OTHER INFORMATION: CRD2 antisense primer (primer no: 365)

<400> SEQUENCE: 53
gggaccgcag ggtccagtga cagt                                          24

<210> SEQ ID NO 54
<211> LENGTH: 24
<212> TYPE: DNA
<213> ORGANISM: Artificial
<220> FEATURE:
<223> OTHER INFORMATION: CRD3 sense primer (primer no: 366)

<400> SEQUENCE: 54
actgtcactg gaaggtgcag ggct                                          24

<210> SEQ ID NO 55
<211> LENGTH: 24
<212> TYPE: DNA
<213> ORGANISM: Artificial
<220> FEATURE:
<223> OTHER INFORMATION: CD134 end primer (primer no: 363)

<400> SEQUENCE: 55
agaattctta ttagatcttg gcca                                          24

<210> SEQ ID NO 56
<211> LENGTH: 24
<212> TYPE: DNA
<213> ORGANISM: Artificial
<220> FEATURE:
<223> OTHER INFORMATION: CRD3 antisense primer (primer no: 367)

<400> SEQUENCE: 56
agccctgcac cttccagtga cagt                                          24

<210> SEQ ID NO 57
<211> LENGTH: 24
<212> TYPE: DNA
<213> ORGANISM: Artificial
<220> FEATURE:
<223> OTHER INFORMATION: CRD4 sense primer (primer no: 368)

<400> SEQUENCE: 57
actgtcactg gaccctgccc ccct                                          24

<210> SEQ ID NO 58
<211> LENGTH: 24
<212> TYPE: DNA
<213> ORGANISM: Artificial
<220> FEATURE:
<223> OTHER INFORMATION: CRD4 antisense primer (primer no: 369)

<400> SEQUENCE: 58
```

```
agggggggcag ggtccagtga cagt                                          24
```

<210> SEQ ID NO 59
<211> LENGTH: 24
<212> TYPE: DNA
<213> ORGANISM: Artificial
<220> FEATURE:
<223> OTHER INFORMATION: CRD4 truncated sense primer (primer no: 370)

<400> SEQUENCE: 59

```
actgtcactg gatgcaccct ggct                                           24
```

<210> SEQ ID NO 60
<211> LENGTH: 24
<212> TYPE: DNA
<213> ORGANISM: Artificial
<220> FEATURE:
<223> OTHER INFORMATION: CRD4 truncated antisense primer (primer no: 371)

<400> SEQUENCE: 60

```
agccagggtg catccagtga cagt                                           24
```

<210> SEQ ID NO 61
<211> LENGTH: 11
<212> TYPE: PRT
<213> ORGANISM: Artificial
<220> FEATURE:
<223> OTHER INFORMATION: N-terminal amino acid sequence of clone 20E5
      light chain

<400> SEQUENCE: 61

Asp Ile Gln Met Thr Gln Thr Thr Ser Ser Leu
1               5                   10

<210> SEQ ID NO 62
<211> LENGTH: 108
<212> TYPE: PRT
<213> ORGANISM: Artificial Sequence
<220> FEATURE:
<223> OTHER INFORMATION: Amino acid sequence of PDL-humanized light
      chain variable region VL1 clone 20E5

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg
            100                 105

<210> SEQ ID NO 63
<211> LENGTH: 108
<212> TYPE: PRT
<213> ORGANISM: Artificial Sequence
<220> FEATURE:
<223> OTHER INFORMATION: Amino acid sequence of PDL-humanized light chain variable region VL2 clone 20E5

<400> SEQUENCE: 63

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gln Gly Thr Lys Val Glu Ile Lys Arg
            100                 105
```

<210> SEQ ID NO 64
<211> LENGTH: 119
<212> TYPE: PRT
<213> ORGANISM: Artificial Sequence
<220> FEATURE:
<223> OTHER INFORMATION: Amino acid sequence of PDL-humanized heavy
      chain variable region VH1 clone 20E5

<400> SEQUENCE: 64

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Asp Gly Thr Lys Tyr Asn Glu Lys Phe
50                  55                  60

Lys Gly Arg Val Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115
```

<210> SEQ ID NO 65
<211> LENGTH: 119
<212> TYPE: PRT
<213> ORGANISM: Artificial Sequence
<220> FEATURE:
<223> OTHER INFORMATION: Amino acid sequence of PDL-humanized heavy
      chain variable region VH2 clone 20E5

<400> SEQUENCE: 65

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45
```

```
Gly Tyr Ile Asn Pro Tyr Asn Asp Gly Thr Lys Tyr Asn Glu Lys Phe
            50                  55                  60

Lys Gly Arg Ala Thr Ile Thr Ser Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Asn Tyr Tyr Gly Ser Ser Leu Ser Met Asp Tyr Trp Gly Gln Gly
                100                 105                 110

Thr Leu Val Thr Val Ser Ser
            115

<210> SEQ ID NO 66
<211> LENGTH: 119
<212> TYPE: PRT
<213> ORGANISM: Artificial Sequence
<220> FEATURE:
<223> OTHER INFORMATION: Amino acid sequence of PDL-humanized heavy
      chain variable region VH3 clone 20E5

<400> SEQUENCE: 66

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Arg Leu Glu Trp Ile
             35                  40                  45

Gly Tyr Ile Asn Pro Tyr Asn Asp Gly Thr Lys Tyr Asn Glu Lys Phe
         50                  55                  60

Lys Gly Arg Ala Thr Leu Thr Ser Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Asn Tyr Tyr Gly Ser Ser Leu Ser Met Asp Tyr Trp Gly Gln Gly
                100                 105                 110

Thr Leu Val Thr Val Ser Ser
            115

<210> SEQ ID NO 67
<211> LENGTH: 108
<212> TYPE: PRT
<213> ORGANISM: Artificial Sequence
<220> FEATURE:
<223> OTHER INFORMATION: Amino acid sequence of PDL-humanized light
      chain variable region VL1 clone 12H3

<400> SEQUENCE: 67

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Gly Ala Ala
                20                  25                  30

Val Ala Trp Tyr Gln Gln Lys Pro Gly Lys Ala Pro Lys Leu Leu Ile
             35                  40                  45

Tyr Trp Ala Ser Thr Arg His Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ile Asn Tyr Pro Leu
                 85                  90                  95
```

Thr Phe Gly Gly Gly Thr Lys Val Glu Ile Lys Arg
            100                 105

<210> SEQ ID NO 68
<211> LENGTH: 108
<212> TYPE: PRT
<213> ORGANISM: Artificial Sequence
<220> FEATURE:
<223> OTHER INFORMATION: Amino acid sequence of PDL-humanized light
      chain variable region VL2 clone 12H3

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys Arg
            100                 105

<210> SEQ ID NO 69
<211> LENGTH: 121
<212> TYPE: PRT
<213> ORGANISM: Artificial Sequence
<220> FEATURE:
<223> OTHER INFORMATION: Amino acid sequence of PDL-humanized heavy
      chain variable region VH1 clone 12H3

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Met
        35                  40                  45

Gly Gly Ile Tyr Pro Asn Asn Gly Gly Ser Thr Tyr Asn Gln Asn Phe
50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 70
<211> LENGTH: 121
<212> TYPE: PRT
<213> ORGANISM: Artificial Sequence
<220> FEATURE:
<223> OTHER INFORMATION: Amino acid sequence of PDL-humanized heavy
      chain variable region VH2 clone 12H3

<400> SEQUENCE: 70

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 71
<211> LENGTH: 121
<212> TYPE: PRT
<213> ORGANISM: Artificial Sequence
<220> FEATURE:
<223> OTHER INFORMATION: Amino acid sequence of PDL-humanized heavy
      chain variable region VH3 clone 12H3

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 72
<211> LENGTH: 1398
<212> TYPE: DNA
<213> ORGANISM: Artificial Sequence
<220> FEATURE:
<223> OTHER INFORMATION: Cricetulus griseus-optimized cDNA sequence
      coding for humanized heavy IgG4 chain clone 20E5 containing PDL-
      humanized VH1

<400> SEQUENCE: 72
atggaatgga gcggcgtgtt catgttcctg ctgtccgtga ccgcgggagt gcacagtcag      60
gtgcagctgg tgcagtctgg cgccgaagtg aagaaacctg gcgcctccgt gaaggtgtcc     120
tgcaaggcct ccggctacac ctttaccagc tacgtgatgc actgggtgcg acaggcccct     180

```
ggccagagac tggaatggat gggctacatc aaccccctaca acgacggcac caagtacaac    240
gagaagttca agggcagagt gaccatcacc tccgacacct ccgcctccac cgcctacatg    300
gaactgtcct ccctgcggag cgaggacacc gccgtgtact actgcgccaa ctactacggc    360
tcctccctgt ctatggacta ctggggccag ggcaccctcg tgaccgtgtc ctctgctagc    420
accaagggcc cctccgtgtt cctctggcc ccttgctcca gatccacctc cgagtctacc    480
gccgctctgg gctgcctcgt gaaggactac ttccccgagc ccgtgacagt gtcttggaac    540
tctggcgccc tgacctccgg cgtgcacaca tttccagctg tgctgcagtc ctccggcctg    600
tactccctgt cctccgtcgt gactgtgcct cctctagcc tgggcaccaa gacctacacc    660
tgtaacgtgg accacaagcc ctccaacacc aaggtggaca gcgggtgga atctaagtac    720 ggccctcctt gcccaccctg ccctgcccct gaatttctgg gcggaccttc cgtgttcctg    780
tttcccccaa agcccaagga caccctgatg atctcccgga ccccgaagt gacctgcgtg    840 gtggtggatg tgtcccagga agatcccgag gtgcagttca attggtacgt ggacggcgtg    900
gaagtgcaca acgccaagac caagcccaga gaggaacagt tcaactccac ctaccgggtg    960
gtgtccgtgc tgaccgtgct gcaccaggat tggctgaacg gcaaagagta caagtgcaag   1020
gtgtccaaca agggcctgcc ctccagcatc gaaaagacca tctccaaggc caagggccag   1080
ccccgggaac ccaggtgta cacactgcct ccaagccagg aagagatgac caagaaccag   1140
gtgtccctga cctgtctcgt gaaaggcttc taccctccg atatcgccgt ggaatgggag   1200
tccaacggcc agcctgagaa caactacaag accacccccc ctgtgctgga ctccgacggc   1260
tccttcttcc tgtactctcg cctgaccgtg gacaagtccc ggtggcagga aggcaacgtg   1320
ttctcctgct ctgtgatgca cgaggccctg cacaaccact acacccagaa gtccctgtcc   1380
ctgtctctgg gcaagtag                                                 1398

<210> SEQ ID NO 73
<211> LENGTH: 1398
<212> TYPE: DNA
<213> ORGANISM: Artificial Sequence
<220> FEATURE:
<223> OTHER INFORMATION: Cricetulus griseus-optimized cDNA sequence
      coding for humanized heavy IgG4 chain clone 20E5 containing PDL-
      humanized VH2

<400> SEQUENCE: 73
atggaatgga gcggcgtgtt catgttcctg ctgtccgtga ccgcgggagt gcattctcag     60
gtgcagctgt gcagtctgg cgccgaagtg aagaaacctg gcgcctccgt gaaggtgtcc    120
tgcaaggcct ccggctacac ctttaccagc tacgtgatgc actgggtgcg acaggcccct    180
ggccagagac tggaatggat cggctacatc aaccccctaca acgacggcac caagtacaac    240
gagaagttca agggcagagc caccatcacc tccgacacct ctgcctccac cgcctacatg    300
gaactgtcct ccctgcggag cgaggacacc gccgtgtact actgcgccaa ctactacggc    360
tcctccctgt ctatggacta ctggggccag ggcaccctcg tgaccgtgtc ctctgctagc    420
accaagggcc cctccgtgtt cctctggcc ccttgctcca gatccacctc cgagtctacc    480
gccgctctgg gctgcctcgt gaaggactac ttccccgagc ccgtgacagt gtcttggaac    540
tctggcgccc tgacctccgg cgtgcacaca tttccagctg tgctgcagtc ctccggcctg    600
tactccctgt cctccgtcgt gactgtgcct cctctagcc tgggcaccaa gacctacacc    660
tgtaacgtgg accacaagcc ctccaacacc aaggtggaca gcgggtgga atctaagtac    720
```

```
ggccctcctt gcccaccctg ccctgcccct gaatttctgg gcggaccttc cgtgttcctg      780
tttcccccaa agcccaagga caccctgatg atctcccgga ccccgaagt gacctgcgtg      840 gtggtggatg tgtcccagga agatcccgag gtgcagttca attggtacgt ggacggcgtg      900
gaagtgcaca acgccaagac caagcccaga gaggaacagt tcaactccac ctaccgggtg     960
gtgtccgtgc tgaccgtgct gcaccaggat tggctgaacg gcaaagagta caagtgcaag    1020
gtgtccaaca agggcctgcc ctccagcatc gaaaagacca tctccaaggc caagggccag    1080
ccccgggaac ccaggtgta cacactgcct ccaagccagg aagagatgac caagaaccag    1140
gtgtccctga cctgtctcgt gaaaggcttc taccccctccg atatcgccgt ggaatgggag    1200
tccaacggcc agcctgagaa caactacaag accaccccc ctgtgctgga ctccgacggc    1260
tccttcttcc tgtactctcg cctgaccgtg gacaagtccc ggtggcagga aggcaacgtg    1320
ttctcctgct ctgtgatgca cgaggccctg cacaaccact acacccagaa gtccctgtcc    1380
ctgtctctgg gcaagtag                                                  1398
```

<210> SEQ ID NO 74
<211> LENGTH: 1398
<212> TYPE: DNA
<213> ORGANISM: Artificial Sequence
<220> FEATURE:
<223> OTHER INFORMATION: Cricetulus griseus-optimized cDNA sequence
      coding for humanized heavy IgG4 chain clone 20E5 containing PDL-
      humanized VH3

<400> SEQUENCE: 74

```
atggaatgga gcggcgtgtt catgttcctg ctgtccgtga ccgcgggagt gcattctcag     60
gtgcagctgg tgcagtctgg cgccgaagtg aagaaacctg gcgcctccgt gaaggtgtcc    120
tgcaaggcct ccggctacac ctttaccagc tacgtgatgc actgggtgcg acaggccct    180 ggccagagac tggaatggat cggctacatc aaccctaca cgacggcac caagtacaac    240 gagaagttca agggcagagc cacctgacc tccgacaagt ctgcctccac cgcctacatg    300
gaactgtcct ccctgcggag cgaggacacc gccgtgtact actgcgccaa ctactacggc    360 tcctcctgt ctatggacta ctggggccag ggcaccctcg tgaccgtgtc ctctgctagc    420
accaagggcc cctccgtgtt tcctctggcc ccttgctcca gatccacctc cgagtctacc    480
gccgctctgg gctgcctcgt gaaggactac ttccccgagc ccgtgacagt gtcttggaac    540
tctggcgccc tgacctccgg cgtgcacaca tttccagctg tgctgcagtc ctccggcctg    600
tactccctgt cctccgtcgt gactgtgcct cctctagcc tgggcaccaa gacctacacc    660
tgtaacgtgg accacaagcc ctccaacacc aaggtggaca agcgggtgga atctaagtac    720
ggccctcctt gcccaccctg ccctgcccct gaatttctgg gcggaccttc cgtgttcctg    780
tttcccccaa agcccaagga caccctgatg atctcccgga ccccgaagt gacctgcgtg    840 gtggtggatg tgtcccagga agatcccgag gtgcagttca attggtacgt ggacggcgtg    900
gaagtgcaca acgccaagac caagcccaga gaggaacagt tcaactccac ctaccgggtg    960
gtgtccgtgc tgaccgtgct gcaccaggat tggctgaacg gcaaagagta caagtgcaag   1020
gtgtccaaca agggcctgcc ctccagcatc gaaaagacca tctccaaggc caagggccag   1080
ccccgggaac ccaggtgta cacactgcct ccaagccagg aagagatgac caagaaccag   1140
gtgtccctga cctgtctcgt gaaaggcttc taccccctccg atatcgccgt ggaatgggag   1200
tccaacggcc agcctgagaa caactacaag accaccccc ctgtgctgga ctccgacggc   1260
tccttcttcc tgtactctcg cctgaccgtg gacaagtccc ggtggcagga aggcaacgtg   1320
```

```
ttctcctgct ctgtgatgca cgaggccctg cacaaccact acacccagaa gtccctgtcc    1380
ctgtctctgg gcaagtag                                                  1398

<210> SEQ ID NO 75
<211> LENGTH: 702
<212> TYPE: DNA
<213> ORGANISM: Artificial Sequence
<220> FEATURE:
<223> OTHER INFORMATION: Cricetulus griseus-optimized cDNA sequence
      coding for humanized light chain clone 20E5 containing PDL-
      humanized VL1

<400> SEQUENCE: 75
atggaatgga gcggcgtgtt catgttcctg ctgtccgtga ccgcgggagt gcacagcgac      60
atccagatga cccagtcccc ctccagcctg tctgcctctg tgggcgacag agtgaccatc     120
acctgtcggg cctcccagga catctccaac tacctgaact ggtatcagca gaagcccggc     180
aaggccccca gctgctgat  ctactacacc tcccggctgc actccggcgt gccctctaga     240
ttttccggct ctggctccgg caccgactat accctgacca tcagctccct gcagcccgag     300
gacttcgcca cctactactg ccagcagggc aacaccctgc cctggacctt tggccagggc     360
accaaggtgg aaatcaagcg gaccgtagcc gcccccttcg tgttcatctt ccacccctcc     420
gacgagcagc tgaagtctgg caccgcttcc gtcgtgtgcc tgctgaacaa cttctacccc     480
cgcgaggcca aggtgcagtg gaaggtggac aacgccctgc agtccggcaa ctcccaggaa     540
agcgtgaccg agcaggactc caaggacagc acctactccc tgtcctccac cctgaccctg     600
tccaaggccg actacgagaa gcacaaggtg tacgcctgcg aagtgaccca ccagggcctg     660
tctagccccg tgaccaagtc tttcaaccgg ggcgagtgct ag                        702

<210> SEQ ID NO 76
<211> LENGTH: 702
<212> TYPE: DNA
<213> ORGANISM: Artificial Sequence
<220> FEATURE:
<223> OTHER INFORMATION: Cricetulus griseus-optimized cDNA sequence
      coding for humanized light chain clone 20E5 containing PDL-
      humanized VL2

<400> SEQUENCE: 76
atggaatgga gcggcgtgtt catgttcctg ctgtccgtga ccgcgggagt gcacagcgac      60
atccagatga cccagtcccc ctccagcctg tctgcctctg tgggcgacag agtgaccatc     120
acctgtcggg cctcccagga catctccaac tacctgaact ggtatcagca gaaacccggc     180
aaggccgtga gctgctgat  ctactacacc tcccggctgc actccggcgt gccctctaga     240
ttttccggct ctggctccgg caccgactat accctgacca tcagctccct gcagcccgag     300
gacttcgcta cctacttctg tcagcaaggc aacaccctgc cctggacctt tggccagggc     360
accaaggtgg aaatcaagcg gaccgtagcc gcccccttcg tgttcatctt ccacccctcc     420
gacgagcagc tgaagtctgg caccgcttcc gtcgtgtgcc tgctgaacaa cttctacccc     480
cgcgaggcca aggtgcagtg gaaggtggac aacgccctgc agtccggcaa ctcccaggaa     540
agcgtgaccg agcaggactc caaggacagc acctactccc tgtcctccac cctgaccctg     600
tccaaggccg actacgagaa gcacaaggtg tacgcctgcg aagtgaccca ccagggcctg     660
tctagccccg tgaccaagtc tttcaaccgg ggcgagtgct ag                        702

<210> SEQ ID NO 77
```

<211> LENGTH: 1404
<212> TYPE: DNA
<213> ORGANISM: Artificial Sequence
<220> FEATURE:
<223> OTHER INFORMATION: Cricetulus griseus-optimized cDNA sequence coding for humanized heavy IgG4 chain clone 12H3 containing PDL-humanized VH1

<400> SEQUENCE: 77

```
atggagctgg gcctgtcctg gatcttcctg ctggccatcc tgaagggcgt gcagtgccag      60
gtgcagctgg tgcagtctgg cgccgaagtg aagaaacccg gctcctccgt gaaggtgtcc     120
tgcaaggctt ccggctacac cttcaaggac tacaccatgc actgggtgcg acaggcccct     180
ggacagggcc tggaatggat gggcggcatc taccctaaca cggcggctc cacctacaac      240
cagaacttca aggatagagt gaccatcacc gccgacaagt ccacctccac cgcctacatg     300
gaactgtcct ccctgcggag cgaggacacc gccgtgtact actgtgcccg gatgggctac     360
cacggccccc acctggattt tgacgtgtgg ggccagggca ccaccgtgac cgtgtcctct     420
gcttctacca agggcccctc cgtgttccct ctggcccctt gctccagatc cacctccgag     480
tctaccgccg ctctgggctg cctcgtgaag gactacttcc ccgagcctgt gacagtgtcc     540
tggaactctg gcgccctgac ctctggcgtg cacacctttc agctgtgtgct gcagtcctcc    600
ggcctgtact ccctgtcctc cgtcgtgaca gtgccctcca gctctctggg caccaagacc     660
tacacctgta acgtggacca caagccctcc aacaccaagg tggacaagcg gtggaatct     720
aagtacggcc ctcctgccc tccttgccca gcccctgaat ttctgggcgg acccagcgtg     780
ttcctgttcc cccaaagcc aaggacacc ctgatgatct cccggacccc cgaagtgacc       840
tgcgtggtgg tggatgtgtc ccaggaagat cccgaggtgc agttcaattg gtacgtggac     900
ggcgtggaag tgcacaacgc caagaccaag cctagagagg aacagttcaa cagcacctac     960
cgggtggtgt ccgtgctgac cgtgctgcac caggattggc tgaacggcaa agagtacaag    1020
tgcaaggtgt ccaacaaggg cctgccttcc agcatcgaaa agaccatctc caaggccaag    1080
ggccagcccc gggaacccca ggtgtacaca ctgcctccaa gccaggaaga gatgaccaag    1140
aaccaggtgt ccctgacctg tctcgtgaaa ggcttctacc cctccgatat cgccgtggaa    1200
tgggagtcca acggccagcc tgagaacaac tacaagacca ccccccctgt gctggactcc    1260
gacggctcct tcttcctgta ctctcgcctg accgtggaca gtccggtg caggaaggc       1320
aacgtgttct cctgctccgt gatgcacgag gccctgcaca accactacac ccagaagtcc    1380
ctgtccctgt ctctgggaaa gtaa                                           1404
```

<210> SEQ ID NO 78
<211> LENGTH: 1404
<212> TYPE: DNA
<213> ORGANISM: Artificial Sequence
<220> FEATURE:
<223> OTHER INFORMATION: Cricetulus griseus-optimized cDNA sequence coding for humanized heavy IgG4 chain clone 12H3 containing PDL-humanized VH2

<400> SEQUENCE: 78

```
atggagctgg gcctgtcctg gatcttcctg ctggccatcc tgaagggcgt gcagtgccag      60
gtgcagctgg tgcagtctgg cgccgaagtg aagaaacccg gctcctccgt gaaggtgtcc     120
tgcaaggctt ccggctacac cttcaaggac tacaccatgc actgggtgcg acaggcccct     180
ggacagggcc tggaatggat cggcggcatc taccctaaca cggcggctc cacctacaac      240
cagaacttca aggatagagt gaccctgacc gccgacaagt ccacctccac cgcctacatg     300
```

```
gaactgtcct ccctgcggag cgaggacacc gccgtgtact actgtgcccg gatgggctac    360
cacggccccc acctggattt tgacgtgtgg ggccagggca ccaccgtgac cgtgtcctct    420
gcttctacca agggcccctc cgtgttccct ctggccccct gctccagatc cacctccgag    480
tctaccgccg ctctgggctg cctcgtgaag gactacttcc ccgagcctgt gacagtgtcc    540
tggaactctg gcgccctgac ctctggcgtg cacacctttc cagctgtgct gcagtcctcc    600
ggcctgtact ccctgtcctc cgtcgtgaca gtgccctcca gctctctggg caccaagacc    660
tacacctgta acgtggacca caagccctcc aacaccaagg tggacaagcg ggtggaatct    720
aagtacggcc ctccctgccc tccttgccca gcccctgaat ttctgggcgg acccagcgtg    780
ttcctgttcc ccccaaagcc caaggacacc ctgatgatct cccggacccc cgaagtgacc    840
tgcgtggtgg tggatgtgtc ccaggaagat cccgaggtgc agttcaattg gtacgtggac    900
ggcgtggaag tgcacaacgc caagaccaag cctagagagg aacagttcaa cagcacctac    960
cgggtggtgt ccgtgctgac cgtgctgcac caggattggc tgaacggcaa agagtacaag   1020
tgcaaggtgt ccaacaaggg cctgccttcc agcatcgaaa agaccatctc caaggccaag   1080
ggccagcccc gggaaccccca ggtgtacaca ctgcctccaa gccaggaaga gatgaccaag   1140
aaccaggtgt ccctgacctg tctcgtgaaa ggcttctacc cctccgatat cgccgtggaa   1200
tgggagtcca acggccagcc tgagaacaac tacaagacca ccccccctgt gctggactcc   1260
gacggctcct tcttcctgta ctctcgcctg accgtggaca gagccggtg gcaggaaggc   1320 aacgtgttct cctgctccgt gatgcacgag gccctgcaca accactacac ccagaagtcc   1380
ctgtccctgt ctctgggaaa gtaa                                          1404

<210> SEQ ID NO 79
<211> LENGTH: 1404
<212> TYPE: DNA
<213> ORGANISM: Artificial Sequence
<220> FEATURE:
<223> OTHER INFORMATION: Cricetulus griseus-optimized cDNA sequence
      coding for humanized heavy IgG4 chain clone 12H3 containing PDL-
      humanized VH3

<400> SEQUENCE: 79
atggagctgg gcctgtcctg gatcttcctg ctggccatcc tgaagggcgt gcagtgccag     60
gtgcagctgt gcagtctgg cgccgaagtg aagaaacccg gctcctccgt gaaggtgtcc    120
tgcaaggctt ccggctacac cttcaaggac tacaccatgc actgggtgcg acaggcccct    180
ggacagggcc tggaatggat cggcggcatc taccctaaca cggcggctc cacctacaac    240 cagaacttca ggatcgggc caccctgacc gtggacaagt ccacctctac cgcctacatg    300
gaactgtcct ccctgcggag cgaggacacc gccgtgtact actgtgcccg gatgggctac    360
cacggccccc acctggattt tgacgtgtgg ggccagggca ccaccgtgac agtgtcctct    420
gcttccacca agggcccctc cgtgtttcct ctggccccct gctccagatc cacctccgag    480
tctaccgccg ctctgggctg cctcgtgaag gactacttcc ccgagcctgt gaccgtgtcc    540
tggaactctg gcgctctgac ctctggcgtg cacaccttcc ctgctgtgct gcagtctagc    600
ggcctgtact ccctgtcctc cgtcgtgacc gtgccttcca gctctctggg caccaagacc    660
tacacctgta acgtggacca caagccctcc aacaccaagg tggacaagcg ggtggaatct    720
aagtacggcc ctccctgccc tccttgccca gcccctgaat ttctgggcgg accttccgtg    780
ttcctgttcc ccccaaagcc caaggacacc ctgatgatct cccggacccc cgaagtgacc    840
```

| | |
|---|---|
| tgcgtggtgg tggatgtgtc ccaggaagat cccgaggtgc agttcaattg gtacgtggac | 900 |
| ggcgtggaag tgcacaacgc caagaccaag cctagagagg aacagttcaa cagcacctac | 960 |
| cgggtggtgt ccgtgctgac cgtgctgcac caggattggc tgaacggcaa agagtacaag | 1020 |
| tgcaaggtgt ccaacaaggg cctgcctagc tccatcgaaa agaccatctc caaggccaag | 1080 |
| ggccagcccc gggaacccca ggtgtacaca ctgcctccaa gccaggaaga gatgaccaag | 1140 |
| aaccaggtgt ccctgacctg tctcgtgaaa ggcttctacc cctccgatat cgccgtggaa | 1200 |
| tgggagtcca acggccagcc tgagaacaac tacaagacca ccccccctgt gctggactcc | 1260 |
| gacggctcct tcttcctgta ctctcggctg acagtggata gagccggtg gcaggaaggc | 1320 |
| aacgtgttct cctgctccgt gatgcacgag gccctgcaca accactacac ccagaagtcc | 1380 |
| ctgtccctgt ctctgggaaa gtaa | 1404 |

<210> SEQ ID NO 80
<211> LENGTH: 711
<212> TYPE: DNA
<213> ORGANISM: Artificial Sequence
<220> FEATURE:
<223> OTHER INFORMATION: Cricetulus griseus-optimized cDNA sequence coding for humanized light chain clone 12H3 containing PDL-humanized VL1

<400> SEQUENCE: 80

| | |
|---|---|
| atggacatgc gggtgcccgc tcagctgctg ggattgctgc tgctgtggtt cccaggcgcc | 60 |
| agatgcgaca tccagatgac ccagtccccc tccagcctgt ctgcctctgt gggcgacaga | 120 |
| gtgaccatca catgcaaggc ctcccaggac gtgggagccg ccgtggcttg gtatcagcag | 180 |
| aagcctggca aggcccccaa gctgctgatc tactgggcct ctaccagaca caccggcgtg | 240 |
| ccctccagat tctccggctc tggctctggc accgactta ccctgaccat cagctccctg | 300 |
| cagcccgagg acttcgccac ctactactgc cagcagtaca tcaactaccc cctgaccttc | 360 |
| ggcggaggca ccaaggtgga aatcaagcgg accgtggccg ctcccctccgt gttcatcttc | 420 |
| ccaccttccg acgagcagct gaagtccggc accgcttctg tcgtgtgcct gctgaacaac | 480 |
| ttctaccccc gcgaggccaa ggtgcagtgg aaggtggaca cgccctgca gtccggcaac | 540 |
| tcccaggaat ccgtgaccga gcaggactcc aaggacagca cctactccct gtcctccacc | 600 |
| ctgaccctgt ccaaggccga ctacgagaag cacaaggtgt acgcctgcga agtgacccac | 660 |
| cagggcctgt ctagccccgt gaccaagtct ttcaaccggg gcgagtgcta a | 711 |

<210> SEQ ID NO 81
<211> LENGTH: 711
<212> TYPE: DNA
<213> ORGANISM: Artificial Sequence
<220> FEATURE:
<223> OTHER INFORMATION: Cricetulus griseus-optimized cDNA sequence coding for humanized light chain clone 12H3 containing PDL-humanized VL2

<400> SEQUENCE: 81

| | |
|---|---|
| atggacatgc gggtgcccgc tcagctgctg ggattgctgc tgctgtggtt cccaggcgcc | 60 |
| agatgcgaca tccagatgac ccagtccccc tccagcctgt ctgcctctgt gggcgacaga | 120 |
| gtgaccatca catgcaaggc ctcccaggac gtgggagccg ccgtggcttg gtatcagcag | 180 |
| aagcctggca aggcccccaa gctgctgatc tactgggcct ctaccagaca caccggcgtg | 240 |
| cccgacagat tctctggcgg cggatctggc accgactta ccctgaccat cagctccctg | 300 |
| cagcccgagg acttcgccac ctactactgc cagcagtaca tcaactaccc cctgaccttc | 360 |

```
ggcggaggca ccaaggtgga aatcaagcgg accgtggccg ctccctccgt gttcatcttc    420
ccaccttccg acgagcagct gaagtccggc accgcttctg tcgtgtgcct gctgaacaac    480 ttctacccc gcgaggccaa ggtgcagtgg aaggtggaca acgccctgca gtccggcaac    540
tcccaggaat ccgtgaccga gcaggactcc aaggacagca cctactccct gtcctccacc    600
ctgaccctgt ccaaggccga ctacgagaag cacaaggtgt acgcctgcga agtgacccac    660
cagggcctgt ctagccccgt gaccaagtct ttcaaccggg gcgagtgcta a             711
```

<210> SEQ ID NO 82
<211> LENGTH: 465
<212> TYPE: PRT
<213> ORGANISM: Artificial Sequence
<220> FEATURE:
<223> OTHER INFORMATION: Amino acid sequence of humanized heavy IgG4
      chain clone 20E5 containing PDL-humanized VH1

<400> SEQUENCE: 82

```
Met Glu Trp Ser Gly Val Phe Met Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Val Met His Trp Val Arg Gln Ala Pro Gly Gln Arg Leu
    50                  55                  60

Glu Trp Met Gly Tyr Ile Asn Pro Tyr Asn Asp Gly Thr Lys Tyr Asn
65                  70                  75                  80

Glu Lys Phe Lys Gly Arg Val Thr Ile Thr Ser Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Asn Tyr Tyr Gly Ser Ser Leu Ser Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
```

-continued

```
            290                 295                 300
Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
                340                 345                 350

Thr Ile Ser Lys Ala Lys Gly Gln Pro Arg Glu Pro Gln Val Tyr Thr
                355                 360                 365

Leu Pro Pro Ser Gln Glu Glu Met Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
                420                 425                 430

Ser Arg Trp Gln Glu Gly Asn Val Phe Ser Cys Ser Val Met His Glu
                435                 440                 445

Ala Leu His Asn His Tyr Thr Gln Lys Ser Leu Ser Leu Ser Leu Gly
        450                 455                 460

Lys
465

<210> SEQ ID NO 83
<211> LENGTH: 465
<212> TYPE: PRT
<213> ORGANISM: Artificial Sequence
<220> FEATURE:
<223> OTHER INFORMATION: Amino acid sequence of humanized heavy IgG4
      chain clone 20E5 containing PDL-humanized VH2

<400> SEQUENCE: 83

Met Glu Trp Ser Gly Val Phe Met Phe Leu Leu Ser Val Thr Ala Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr Val Met His Trp Val Arg Gln Ala Pro Gly Gln Arg Leu
        50                  55                  60

Glu Trp Ile Gly Tyr Ile Asn Pro Tyr Asn Asp Gly Thr Lys Tyr Asn
65                  70                  75                  80

Glu Lys Phe Lys Gly Arg Ala Thr Ile Thr Ser Asp Thr Ser Ala Ser
                85                  90                  95

Thr Ala Tyr Met Glu Leu Ser Ser Leu Arg Ser Glu Asp Thr Ala Val
                100                 105                 110

Tyr Tyr Cys Ala Asn Tyr Tyr Gly Ser Ser Leu Ser Met Asp Tyr Trp
            115                 120                 125

Gly Gln Gly Thr Leu Val Thr Val Ser Ser Ala Ser Thr Lys Gly Pro
        130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175
```

```
Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys
465

<210> SEQ ID NO 84
<211> LENGTH: 465
<212> TYPE: PRT
<213> ORGANISM: Artificial Sequence
<220> FEATURE:
<223> OTHER INFORMATION: Amino acid sequence of humanized heavy IgG4
      chain clone 20E5 containing PDL-humanized VH3

<400> SEQUENCE: 84

Met Glu Trp Ser Gly Val Phe Met Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Val Met His Trp Val Arg Gln Ala Pro Gly Gln Arg Leu
    50                  55                  60
```

```
Glu Trp Ile Gly Tyr Ile Asn Pro Tyr Asn Asp Gly Thr Lys Tyr Asn
 65                  70                  75                  80

Glu Lys Phe Lys Gly Arg Ala Thr Leu Thr Ser Asp Lys Ser Ala Ser
                 85                  90                  95

Thr Ala Tyr Met Glu Leu Ser Ser Leu Arg Ser Glu Asp Thr Ala Val
            100                 105                 110

Tyr Tyr Cys Ala Asn Tyr Tyr Gly Ser Ser Leu Ser Met Asp Tyr Trp
            115                 120                 125

Gly Gln Gly Thr Leu Val Thr Val Ser Ser Ala Ser Thr Lys Gly Pro
            130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Leu Gly Thr Lys Thr Tyr Thr Cys Asn Val Asp
210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
            275                 280                 285

Pro Glu Val Gln Phe Asn Trp Tyr Val Asp Gly Val Glu Val His Asn
290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Gln Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
            450                 455                 460

Lys
465
```

<210> SEQ ID NO 85
<211> LENGTH: 233
<212> TYPE: PRT
<213> ORGANISM: Artificial Sequence
<220> FEATURE:
<223> OTHER INFORMATION: Amino acid sequence of humanized light chain
     clone 20E5 containing PDL-humanized VL1

<400> SEQUENCE: 85

Met Glu Trp Ser Gly Val Phe Met Phe Leu Leu Ser Val Thr Ala Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Ile
        35                  40                  45

Ser Asn Tyr Leu Asn Trp Tyr Gln Gln Lys Pro Gly Lys Ala Pro Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Thr Leu Thr Ile Ser Ser
                85                  90                  95

Leu Gln Pro Glu Asp Phe Ala Thr Tyr Tyr Cys Gln Gln Gly Asn Thr
            100                 105                 110

Leu Pro Trp Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 86
<211> LENGTH: 233
<212> TYPE: PRT
<213> ORGANISM: Artificial Sequence
<220> FEATURE:
<223> OTHER INFORMATION: Amino acid sequence of humanized light chain
     clone 20E5 containing PDL-humanized VL2

<400> SEQUENCE: 86

Met Glu Trp Ser Gly Val Phe Met Phe Leu Leu Ser Val Thr Ala Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Ile
        35                  40                  45

Ser Asn Tyr Leu Asn Trp Tyr Gln Gln Lys Pro Gly Lys Ala Val Lys
    50                  55                  60

```
Leu Leu Ile Tyr Tyr Thr Ser Arg Leu His Ser Gly Val Pro Ser Arg
 65                  70                  75                  80

Phe Ser Gly Ser Gly Ser Gly Thr Asp Tyr Thr Leu Thr Ile Ser Ser
                 85                  90                  95

Leu Gln Pro Glu Asp Phe Ala Thr Tyr Phe Cys Gln Gln Gly Asn Thr
            100                 105                 110

Leu Pro Trp Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 87
<211> LENGTH: 467
<212> TYPE: PRT
<213> ORGANISM: Artificial Sequence
<220> FEATURE:
<223> OTHER INFORMATION: Amino acid sequence of humanized heavy IgG4
      chain clone 12H3 containing PDL-humanized VH1

<400> SEQUENCE: 87

Met Glu Leu Gly Leu Ser Trp Ile Phe Leu Leu Ala Ile Leu Lys Gly
 1               5                  10                  15

Val Gln Cys Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Lys Asp Tyr Thr Met His Trp Val Arg Gln Ala Pro Gly Gln Gly Leu
    50                  55                  60

Glu Trp Met Gly Gly Ile Tyr Pro Asn Asn Gly Gly Ser Thr Tyr Asn
 65                  70                  75                  80

Gln Asn Phe Lys Asp Arg Val Thr Ile Thr Ala Asp Lys Ser Thr Ser
                 85                  90                  95

Thr Ala Tyr Met Glu Leu Ser Ser Leu Arg Ser Glu Asp Thr Ala Val
            100                 105                 110

Tyr Tyr Cys Ala Arg Met Gly Tyr His Gly Pro His Leu Asp Phe Asp
        115                 120                 125

Val Trp Gly Gln Gly Thr Thr Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190
```

-continued

Phe Pro Ala Val Leu Gln Ser Ser Gly Leu Tyr Ser Leu Ser Ser Val
                195                 200                 205

Val Thr Val Pro Ser Ser Ser Leu Gly Thr Lys Thr Tyr Thr Cys Asn
210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser Gln
                275                 280                 285

Glu Asp Pro Glu Val Gln Phe Asn Trp Tyr Val Asp Gly Val Glu Val
                290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Gln Glu Glu Met Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
                420                 425                 430

Asp Lys Ser Arg Trp Gln Glu Gly Asn Val Phe Ser Cys Ser Val Met
                435                 440                 445

His Glu Ala Leu His Asn His Tyr Thr Gln Lys Ser Leu Ser Leu Ser
                450                 455                 460

Leu Gly Lys
465

<210> SEQ ID NO 88
<211> LENGTH: 467
<212> TYPE: PRT
<213> ORGANISM: Artificial Sequence
<220> FEATURE:
<223> OTHER INFORMATION: Amino acid sequence of humanized heavy IgG4
      chain clone 12H3 containing PDL-humanized VH2

<400> SEQUENCE: 88

Met Glu Leu Gly Leu Ser Trp Ile Phe Leu Leu Ala Ile Leu Lys Gly
1               5                   10                  15

Val Gln Cys Gln Val Gln Leu Val Gln Ser Gly Ala Glu Val Lys Lys
                20                  25                  30

Pro Gly Ser Ser Val Lys Val Ser Cys Lys Ala Ser Gly Tyr Thr Phe
                35                  40                  45

Lys Asp Tyr Thr Met His Trp Val Arg Gln Ala Pro Gly Gln Gly Leu
                50                  55                  60

Glu Trp Ile Gly Gly Ile Tyr Pro Asn Asn Gly Gly Ser Thr Tyr Asn

```
                65                  70                  75                  80
Gln Asn Phe Lys Asp Arg Val Thr Leu Thr Ala Asp Lys Ser Thr Ser
                    85                  90                  95

Thr Ala Tyr Met Glu Leu Ser Ser Leu Arg Ser Glu Asp Thr Ala Val
                100                 105                 110

Tyr Tyr Cys Ala Arg Met Gly Tyr His Gly Pro His Leu Asp Phe Asp
                115                 120                 125

Val Trp Gly Gln Gly Thr Thr Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Lys Thr Tyr Thr Cys Asn
                210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser Gln
                275                 280                 285

Glu Asp Pro Glu Val Gln Phe Asn Trp Tyr Val Asp Gly Val Glu Val
                290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Gln Glu Glu Met Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
                420                 425                 430

Asp Lys Ser Arg Trp Gln Glu Gly Asn Val Phe Ser Cys Ser Val Met
                435                 440                 445

His Glu Ala Leu His Asn His Tyr Thr Gln Lys Ser Leu Ser Leu Ser
                450                 455                 460

Leu Gly Lys
465

<210> SEQ ID NO 89
```

```
<211> LENGTH: 467
<212> TYPE: PRT
<213> ORGANISM: Artificial Sequence
<220> FEATURE:
<223> OTHER INFORMATION: Amino acid sequence of humanized heavy IgG4
      chain clone 12H3 containing PDL-humanized VH3

<400> SEQUENCE: 89

Met Glu Leu Gly Leu Ser Trp Ile Phe Leu Leu Ala Ile Leu Lys Gly
1               5                   10                  15

Val Gln Cys Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Lys Asp Tyr Thr Met His Trp Val Arg Gln Ala Pro Gly Gln Gly Leu
    50                  55                  60

Glu Trp Ile Gly Gly Ile Tyr Pro Asn Asn Gly Ser Thr Tyr Asn
65                  70                  75                  80

Gln Asn Phe Lys Asp Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Met Gly Tyr His Gly Pro His Leu Asp Phe Asp
        115                 120                 125

Val Trp Gly Gln Gly Thr Thr Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
```

```
                370                 375                 380
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
                420                 425                 430

Asp Lys Ser Arg Trp Gln Glu Gly Asn Val Phe Ser Cys Ser Val Met
                435                 440                 445

His Glu Ala Leu His Asn His Tyr Thr Gln Lys Ser Leu Ser Leu Ser
                450                 455                 460

Leu Gly Lys
465

<210> SEQ ID NO 90
<211> LENGTH: 236
<212> TYPE: PRT
<213> ORGANISM: Artificial Sequence
<220> FEATURE:
<223> OTHER INFORMATION: Amino acid sequence of humanized light chain
      clone 12H3 containing PDL-humanized VL1

<400> SEQUENCE: 90

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
                20                  25                  30

Leu Ser Ala Ser Val Gly Asp Arg Val Thr Ile Thr Cys Lys Ala Ser
                35                  40                  45

Gln Asp Val Gly Ala Ala Val Ala Trp Tyr Gln Gln Lys Pro Gly Lys
50                  55                  60

Ala Pro Lys Leu Leu Ile Tyr Trp Ala Ser Thr Arg His Thr Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Tyr Ile Asn Tyr Pro Leu Thr Phe Gly Gly Gly Thr Lys Val Glu Ile
                115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
                210                 215                 220

Ser Pro Val Thr Lys Ser Phe Asn Arg Gly Glu Cys
225                 230                 235

<210> SEQ ID NO 91
<211> LENGTH: 236
```

```
<212> TYPE: PRT
<213> ORGANISM: Artificial Sequence
<220> FEATURE:
<223> OTHER INFORMATION: Amino acid sequence of humanized light chain
      clone 12H3 containing PDL-humanized VL2

<400> SEQUENCE: 91
```

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
                20                  25                  30

Leu Ser Ala Ser Val Gly Asp Arg Val Thr Ile Thr Cys Lys Ala Ser
            35                  40                  45

Gln Asp Val Gly Ala Ala Val Ala Trp Tyr Gln Gln Lys Pro Gly Lys
        50                  55                  60

Ala Pro Lys Leu Leu Ile Tyr Trp Ala Ser Thr Arg His Thr Gly Val
65                  70                  75                  80

Pro Asp Arg Phe Ser Gly Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Tyr Ile Asn Tyr Pro Leu Thr Phe Gly Gly Gly Thr Lys Val Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

```
<210> SEQ ID NO 92
<211> LENGTH: 88
<212> TYPE: PRT
<213> ORGANISM: Artificial Sequence
<220> FEATURE:
<223> OTHER INFORMATION: Amino acid sequence of CRD4 A1-B1-module

<400> SEQUENCE: 92
```

Pro Cys Pro Pro Gly His Phe Ser Pro Gly Asp Asn Gln Ala Cys Lys
1               5                   10                  15

Pro Trp Thr Asn Cys Thr Leu Ala Gly Lys His Thr Leu Gln Pro Ala
                20                  25                  30

Ser Asn Ser Ser Asp Ala Ile Cys Glu Asp Arg Asp Pro Pro Ala Thr
            35                  40                  45

Gln Pro Gln Glu Thr Gln Gly Pro Pro Ala Arg Pro Ile Thr Val Gln
        50                  55                  60

Pro Thr Glu Ala Trp Pro Arg Thr Ser Gln Gly Pro Ser Thr Arg Pro
65                  70                  75                  80

Val Glu Val Pro Gly Gly Arg Ala

<210> SEQ ID NO 93
<211> LENGTH: 108
<212> TYPE: PRT
<213> ORGANISM: Artificial Sequence
<220> FEATURE:
<223> OTHER INFORMATION: Amino acid sequence of PDL-humanized light
      chain variable region VL1 clone 20E5

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg
            100                 105

<210> SEQ ID NO 94
<211> LENGTH: 108
<212> TYPE: PRT
<213> ORGANISM: Artificial Sequence
<220> FEATURE:
<223> OTHER INFORMATION: Amino acid sequence of PDL-humanized light
      chain variable region VL2 clone 20E5

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gln Gly Thr Lys Val Glu Ile Lys Arg
            100                 105

<210> SEQ ID NO 95
<211> LENGTH: 108
<212> TYPE: PRT
<213> ORGANISM: Artificial Sequence
<220> FEATURE:
<223> OTHER INFORMATION: Amino acid sequence of PDL-humanized light
      chain variable region VL1 clone 12H3

<400> SEQUENCE: 95

Asp Ile Gln Met Thr Gln Ser Pro Ser Ser Leu Ser Ala Ser Val Gly
1               5                   10                  15

```
Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys Arg
            100                 105
```

<210> SEQ ID NO 96
<211> LENGTH: 108
<212> TYPE: PRT
<213> ORGANISM: Artificial Sequence
<220> FEATURE:
<223> OTHER INFORMATION: Amino acid sequence of PDL-humanized light
      chain variable region VL2 clone 12H3

<400> SEQUENCE: 96

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys Arg
            100                 105
```

<210> SEQ ID NO 97
<211> LENGTH: 119
<212> TYPE: PRT
<213> ORGANISM: Artificial Sequence
<220> FEATURE:
<223> OTHER INFORMATION: Humanized 20E5 antibody variable heavy chain
<220> FEATURE:
<221> NAME/KEY: VARIANT
<222> LOCATION: (48)..(48)
<223> OTHER INFORMATION: may also be Met
<220> FEATURE:
<221> NAME/KEY: VARIANT
<222> LOCATION: (68)..(68)
<223> OTHER INFORMATION: may also be Val
<220> FEATURE:
<221> NAME/KEY: VARIANT
<222> LOCATION: (70)..(70)
<223> OTHER INFORMATION: may also be Ile
<220> FEATURE:
<221> NAME/KEY: VARIANT
<222> LOCATION: (74)..(74)
<223> OTHER INFORMATION: may also be Thr

<400> SEQUENCE: 97

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
         20                  25                  30

Val Met His Trp Val Arg Gln Ala Pro Gly Gln Arg Leu Glu Trp Ile
         35                  40                  45

Gly Tyr Ile Asn Pro Tyr Asn Asp Gly Thr Lys Tyr Asn Glu Lys Phe
50                  55                  60

Lys Gly Arg Ala Thr Leu Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 98
<211> LENGTH: 108
<212> TYPE: PRT
<213> ORGANISM: Artificial Sequence
<220> FEATURE:
<223> OTHER INFORMATION: Humanized 20E5 antibody variable light chain
<220> FEATURE:
<221> NAME/KEY: VARIANT
<222> LOCATION: (44)..(44)
<223> OTHER INFORMATION: May also be Pro
<220> FEATURE:
<221> NAME/KEY: VARIANT
<222> LOCATION: (87)..(87)
<223> OTHER INFORMATION: May also be Tyr

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gln Gly Thr Lys Val Glu Ile Lys Arg
            100                 105

<210> SEQ ID NO 99
<211> LENGTH: 121
<212> TYPE: PRT
<213> ORGANISM: Artificial Sequence
<220> FEATURE:
<223> OTHER INFORMATION: Humanized 12H3 antibody variable heavy chain
<220> FEATURE:
<221> NAME/KEY: VARIANT
<222> LOCATION: (48)..(48)
<223> OTHER INFORMATION: May also be Met
<220> FEATURE:
<221> NAME/KEY: VARIANT
<222> LOCATION: (68)..(68)
<223> OTHER INFORMATION: May also be Val
<220> FEATURE:
<221> NAME/KEY: VARIANT
<222> LOCATION: (70)..(70)
```

<223> OTHER INFORMATION: May also be Ile
<220> FEATURE:
<221> NAME/KEY: VARIANT
<222> LOCATION: (72)..(72)
<223> OTHER INFORMATION: May also be Ala

<400> SEQUENCE: 99

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 100
<211> LENGTH: 108
<212> TYPE: PRT
<213> ORGANISM: Artificial Sequence
<220> FEATURE:
<223> OTHER INFORMATION: Humanized 12H3 antibody variable light chain
<220> FEATURE:
<221> NAME/KEY: VARIANT
<222> LOCATION: (60)..(60)
<223> OTHER INFORMATION: May also be Ser
<220> FEATURE:
<221> NAME/KEY: VARIANT
<222> LOCATION: (65)..(65)
<223> OTHER INFORMATION: May also be Ser

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys Arg
            100                 105

<210> SEQ ID NO 101
<211> LENGTH: 119
<212> TYPE: PRT
<213> ORGANISM: Artificial Sequence
<220> FEATURE:
<223> OTHER INFORMATION: antibody heavy chain sequence

```
<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Gly Gly Thr Lys Tyr Asn Glu Lys Phe
    50                  55                  60

Lys Gly Arg Val Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 102
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Gly Gly Thr Lys Tyr Asn Glu Lys Phe
    50                  55                  60

Lys Gly Arg Ala Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 103
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45
```

Gly Tyr Ile Asn Pro Tyr Asn Gly Gly Thr Lys Tyr Asn Glu Lys Phe
            50                  55                  60

Lys Gly Arg Ala Thr Leu Thr Ser Asp Lys Ser Ala Ser Thr Ala Tyr
 65                  70                  75                  80

Met Glu Leu Ser Ser Leu Arg Ser Glu Asp Thr Ala Val Tyr Tyr Cys
                    85                  90                  95

Ala Asn Tyr Tyr Gly Ser Ser Leu Ser Met Asp Tyr Trp Gly Gln Gly
                100                 105                 110

Thr Leu Val Thr Val Ser Ser
            115

<210> SEQ ID NO 104
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Arg Leu Glu Trp Met
            35                  40                  45

Gly Tyr Ile Asn Pro Tyr Asn Ala Gly Thr Lys Tyr Asn Glu Lys Phe
            50                  55                  60

Lys Gly Arg Val Thr Ile Thr Ser Asp Thr Ser Ala Ser Thr Ala Tyr
 65                  70                  75                  80

Met Glu Leu Ser Ser Leu Arg Ser Glu Asp Thr Ala Val Tyr Tyr Cys
                    85                  90                  95

Ala Asn Tyr Tyr Gly Ser Ser Leu Ser Met Asp Tyr Trp Gly Gln Gly
                100                 105                 110

Thr Leu Val Thr Val Ser Ser
            115

<210> SEQ ID NO 105
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Arg Leu Glu Trp Ile
            35                  40                  45

Gly Tyr Ile Asn Pro Tyr Asn Ala Gly Thr Lys Tyr Asn Glu Lys Phe
            50                  55                  60

Lys Gly Arg Ala Thr Ile Thr Ser Asp Thr Ser Ala Ser Thr Ala Tyr
 65                  70                  75                  80

Met Glu Leu Ser Ser Leu Arg Ser Glu Asp Thr Ala Val Tyr Tyr Cys
                    85                  90                  95

Ala Asn Tyr Tyr Gly Ser Ser Leu Ser Met Asp Tyr Trp Gly Gln Gly
                100                 105                 110

Thr Leu Val Thr Val Ser Ser
        115

<210> SEQ ID NO 106
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Ala Gly Thr Lys Tyr Asn Glu Lys Phe
    50                  55                  60

Lys Gly Arg Ala Thr Leu Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 107
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Ser Gly Thr Lys Tyr Asn Glu Lys Phe
    50                  55                  60

Lys Gly Arg Val Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 108
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Ser Gly Thr Lys Tyr Asn Glu Lys Phe
    50                  55                  60

Lys Gly Arg Ala Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 109
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Ser Gly Thr Lys Tyr Asn Glu Lys Phe
    50                  55                  60

Lys Gly Arg Ala Thr Leu Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 110
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Glu Gly Thr Lys Tyr Asn Glu Lys Phe
            50                  55                  60

Lys Gly Arg Val Thr Ile Thr Ser Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Asn Tyr Tyr Gly Ser Ser Leu Ser Met Asp Tyr Trp Gly Gln Gly
                100                 105                 110

Thr Leu Val Thr Val Ser Ser
            115

<210> SEQ ID NO 111
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 111

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Val Met His Trp Val Arg Gln Ala Pro Gly Gln Arg Leu Glu Trp Ile
             35                  40                  45

Gly Tyr Ile Asn Pro Tyr Asn Glu Gly Thr Lys Tyr Asn Glu Lys Phe
            50                  55                  60

Lys Gly Arg Ala Thr Ile Thr Ser Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Asn Tyr Tyr Gly Ser Ser Leu Ser Met Asp Tyr Trp Gly Gln Gly
                100                 105                 110

Thr Leu Val Thr Val Ser Ser
            115

<210> SEQ ID NO 112
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 112

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Val Met His Trp Val Arg Gln Ala Pro Gly Gln Arg Leu Glu Trp Ile
             35                  40                  45

Gly Tyr Ile Asn Pro Tyr Asn Glu Gly Thr Lys Tyr Asn Glu Lys Phe
            50                  55                  60

Lys Gly Arg Ala Thr Leu Thr Ser Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Asn Tyr Tyr Gly Ser Ser Leu Ser Met Asp Tyr Trp Gly Gln Gly

Thr Leu Val Thr Val Ser Ser
        115

<210> SEQ ID NO 113
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Leu Asp Tyr Trp Gly Gln Gly
            100                 105                 110

Thr Leu Val Thr Val Ser Ser
        115

<210> SEQ ID NO 114
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Leu Asp Tyr Trp Gly Gln Gly
            100                 105                 110

Thr Leu Val Thr Val Ser Ser
        115

<210> SEQ ID NO 115
<211> LENGTH: 119
<212> TYPE: PRT
<213> ORGANISM: Artificial Sequence
<220> FEATURE:

<223> OTHER INFORMATION: antibody heavy chain sequence

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Leu Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Leu Asp Tyr Trp Gly Gln Gly
            100                 105                 110

Thr Leu Val Thr Val Ser Ser
        115

<210> SEQ ID NO 116
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Ile Asp Tyr Trp Gly Gln Gly
            100                 105                 110

Thr Leu Val Thr Val Ser Ser
        115

<210> SEQ ID NO 117
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile

```
                    35                  40                  45
Gly Tyr Ile Asn Pro Tyr Asn Asp Gly Thr Lys Tyr Asn Glu Lys Phe
        50                  55                  60
Lys Gly Arg Ala Thr Ile Thr Ser Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Asn Tyr Tyr Gly Ser Ser Leu Ser Ile Asp Tyr Trp Gly Gln Gly
                100                 105                 110
Thr Leu Val Thr Val Ser Ser
        115

<210> SEQ ID NO 118
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 118

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Val Met His Trp Val Arg Gln Ala Pro Gly Gln Arg Leu Glu Trp Ile
            35                  40                  45
Gly Tyr Ile Asn Pro Tyr Asn Asp Gly Thr Lys Tyr Asn Glu Lys Phe
        50                  55                  60
Lys Gly Arg Ala Thr Leu Thr Ser Asp Lys Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Asn Tyr Tyr Gly Ser Ser Leu Ser Ile Asp Tyr Trp Gly Gln Gly
                100                 105                 110
Thr Leu Val Thr Val Ser Ser
        115

<210> SEQ ID NO 119
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 119

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Lys Asp Tyr
                20                  25                  30
Thr Met His Trp Val Arg Gln Ala Pro Gly Gln Gly Leu Glu Trp Met
            35                  40                  45
Gly Gly Ile Tyr Pro Asn Gln Gly Gly Ser Thr Tyr Asn Gln Asn Phe
        50                  55                  60
Lys Asp Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
```

```
Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 120
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 120

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Gln Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 121
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 121

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Gln Gly Gly Ser Thr Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 122
<211> LENGTH: 121
<212> TYPE: PRT
<213> ORGANISM: Artificial Sequence
```

```
<220> FEATURE:
<223> OTHER INFORMATION: antibody heavy chain sequence

<400> SEQUENCE: 122

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Met
        35                  40                  45

Gly Gly Ile Tyr Pro Asn Ala Gly Gly Ser Thr Tyr Asn Gln Asn Phe
    50                  55                  60

Lys Asp Arg Val Thr Ile Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 123
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 123

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Ala Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 124
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 124

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30
```

```
Thr Met His Trp Val Arg Gln Ala Pro Gly Gln Gly Leu Glu Trp Ile
        35                  40                  45

Gly Gly Ile Tyr Pro Asn Ala Gly Gly Ser Thr Tyr Asn Gln Asn Phe
 50                      55                  60

Lys Asp Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Met Gly Tyr His Gly Pro His Leu Asp Phe Asp Val Trp Gly
             100                 105                 110

Gln Gly Thr Thr Val Thr Val Ser Ser
        115                 120

<210> SEQ ID NO 125
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 125

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Lys Asp Tyr
                 20                  25                  30

Thr Met His Trp Val Arg Gln Ala Pro Gly Gln Gly Leu Glu Trp Met
        35                  40                  45

Gly Gly Ile Tyr Pro Asn Glu Gly Gly Ser Thr Tyr Asn Gln Asn Phe
 50                      55                  60

Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Met Gly Tyr His Gly Pro His Leu Asp Phe Asp Val Trp Gly
             100                 105                 110

Gln Gly Thr Thr Val Thr Val Ser Ser
        115                 120

<210> SEQ ID NO 126
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 126

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Lys Asp Tyr
                 20                  25                  30

Thr Met His Trp Val Arg Gln Ala Pro Gly Gln Gly Leu Glu Trp Ile
        35                  40                  45

Gly Gly Ile Tyr Pro Asn Glu Gly Gly Ser Thr Tyr Asn Gln Asn Phe
 50                      55                  60

Lys Asp Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 127
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 127

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Glu Gly Gly Ser Thr Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 128
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 128

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Met
        35                  40                  45

Gly Gly Ile Tyr Pro Asn Asn Gly Gly Ser Thr Tyr Asn Gln Asn Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Tyr His Gly Pro His Leu Asp Phe Asp Val Trp Gly
            100                 105                 110

Gln Gly Thr Thr Val Thr Val Ser Ser
        115                 120

<210> SEQ ID NO 129
<211> LENGTH: 121
<212> TYPE: PRT

<213> ORGANISM: Artificial Sequence
<220> FEATURE:
<223> OTHER INFORMATION: antibody heavy chain sequence

<400> SEQUENCE: 129

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Tyr His Gly Pro His Leu Asp Phe Asp Val Trp Gly
            100                 105                 110

Gln Gly Thr Thr Val Thr Val Ser Ser
        115                 120

<210> SEQ ID NO 130
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 130

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Tyr His Gly Pro His Leu Asp Phe Asp Val Trp Gly
            100                 105                 110

Gln Gly Thr Thr Val Thr Val Ser Ser
        115                 120

<210> SEQ ID NO 131
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 131

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Met
        35                  40                  45

Gly Gly Ile Tyr Pro Asn Asn Gly Gly Ser Thr Tyr Asn Gln Asn Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Gly Tyr His Gly Pro His Leu Asp Phe Asp Val Trp Gly
            100                 105                 110

Gln Gly Thr Thr Val Thr Val Ser Ser
            115                 120

<210> SEQ ID NO 132
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 132

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Gly Tyr His Gly Pro His Leu Asp Phe Asp Val Trp Gly
            100                 105                 110

Gln Gly Thr Thr Val Thr Val Ser Ser
            115                 120

<210> SEQ ID NO 133
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 133

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys

```
                85                  90                  95
Ala Arg Ile Gly Tyr His Gly Pro His Leu Asp Phe Asp Val Trp Gly
            100                 105                 110

Gln Gly Thr Thr Val Thr Val Ser Ser
        115                 120

<210> SEQ ID NO 134
<211> LENGTH: 119
<212> TYPE: PRT
<213> ORGANISM: Artificial Sequence
<220> FEATURE:
<223> OTHER INFORMATION: antibody heavy chain sequence
<220> FEATURE:
<221> NAME/KEY: VARIANT
<222> LOCATION: (11)..(11)
<223> OTHER INFORMATION: May also be Leu
<220> FEATURE:
<221> NAME/KEY: VARIANT
<222> LOCATION: (48)..(48)
<223> OTHER INFORMATION: May also be Ile
<220> FEATURE:
<221> NAME/KEY: VARIANT
<222> LOCATION: (56)..(56)
<223> OTHER INFORMATION: May also be Gly, Ala, Ser or Glu
<220> FEATURE:
<221> NAME/KEY: VARIANT
<222> LOCATION: (68)..(68)
<223> OTHER INFORMATION: May also be Ala
<220> FEATURE:
<221> NAME/KEY: VARIANT
<222> LOCATION: (70)..(70)
<223> OTHER INFORMATION: May also be Ile
<220> FEATURE:
<221> NAME/KEY: VARIANT
<222> LOCATION: (74)..(74)
<223> OTHER INFORMATION: May also be Lys
<220> FEATURE:
<221> NAME/KEY: VARIANT
<222> LOCATION: (106)..(106)
<223> OTHER INFORMATION: May also be Leu or Ile

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Leu Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 135
<211> LENGTH: 17
<212> TYPE: PRT
<213> ORGANISM: Artificial Sequence
<220> FEATURE:
<223> OTHER INFORMATION: antibody CDR2 sequence

<400> SEQUENCE: 135
```

Tyr Ile Asn Pro Tyr Asn Gly Gly Thr Lys Tyr Asn Glu Lys Phe
1               5                   10                  15

Lys Gly

<210> SEQ ID NO 136
<211> LENGTH: 17
<212> TYPE: PRT
<213> ORGANISM: Artificial Sequence
<220> FEATURE:
<223> OTHER INFORMATION: antibody CDR2 sequence

<400> SEQUENCE: 136

Tyr Ile Asn Pro Tyr Asn Ala Gly Thr Lys Tyr Asn Glu Lys Phe Lys
1               5                   10                  15

Gly

<210> SEQ ID NO 137
<211> LENGTH: 17
<212> TYPE: PRT
<213> ORGANISM: Artificial Sequence
<220> FEATURE:
<223> OTHER INFORMATION: antibody CDR2 sequence

<400> SEQUENCE: 137

Tyr Ile Asn Pro Tyr Asn Ser Gly Thr Lys Tyr Asn Glu Lys Phe Lys
1               5                   10                  15

Gly

<210> SEQ ID NO 138
<211> LENGTH: 17
<212> TYPE: PRT
<213> ORGANISM: Artificial Sequence
<220> FEATURE:
<223> OTHER INFORMATION: antibody CDR2 sequence

<400> SEQUENCE: 138

Tyr Ile Asn Pro Tyr Asn Glu Gly Thr Lys Tyr Asn Glu Lys Phe Lys
1               5                   10                  15

Gly

<210> SEQ ID NO 139
<211> LENGTH: 10
<212> TYPE: PRT
<213> ORGANISM: Artificial Sequence
<220> FEATURE:
<223> OTHER INFORMATION: antibody CDR3 sequence

<400> SEQUENCE: 139

Tyr Tyr Gly Ser Ser Leu Ser Leu Asp Tyr
1               5                   10

<210> SEQ ID NO 140
<211> LENGTH: 10
<212> TYPE: PRT
<213> ORGANISM: Artificial Sequence
<220> FEATURE:
<223> OTHER INFORMATION: antibody CDR3 sequence

<400> SEQUENCE: 140

Tyr Tyr Gly Ser Ser Leu Ser Ile Asp Tyr
1               5                   10

<210> SEQ ID NO 141

-continued

```
<211> LENGTH: 17
<212> TYPE: PRT
<213> ORGANISM: Artificial Sequence
<220> FEATURE:
<223> OTHER INFORMATION: antibody CDR2 sequence

<400> SEQUENCE: 141

Gly Ile Tyr Pro Asn Gln Gly Gly Ser Thr Tyr Asn Gln Asn Phe Lys
1               5                   10                  15

Asp

<210> SEQ ID NO 142
<211> LENGTH: 17
<212> TYPE: PRT
<213> ORGANISM: Artificial Sequence
<220> FEATURE:
<223> OTHER INFORMATION: antibody CDR2 sequence

<400> SEQUENCE: 142

Gly Ile Tyr Pro Asn Ala Gly Gly Ser Thr Tyr Asn Gln Asn Phe Lys
1               5                   10                  15

Asp

<210> SEQ ID NO 143
<211> LENGTH: 17
<212> TYPE: PRT
<213> ORGANISM: Artificial Sequence
<220> FEATURE:
<223> OTHER INFORMATION: antibody CDR2 sequence

<400> SEQUENCE: 143

Gly Ile Tyr Pro Asn Glu Gly Gly Ser Thr Tyr Asn Gln Asn Phe Lys
1               5                   10                  15

Asp

<210> SEQ ID NO 144
<211> LENGTH: 12
<212> TYPE: PRT
<213> ORGANISM: Artificial Sequence
<220> FEATURE:
<223> OTHER INFORMATION: antibody CDR3 sequence

<400> SEQUENCE: 144

Leu Gly Tyr His Gly Pro His Leu Asp Phe Asp Val
1               5                   10

<210> SEQ ID NO 145
<211> LENGTH: 12
<212> TYPE: PRT
<213> ORGANISM: Artificial Sequence
<220> FEATURE:
<223> OTHER INFORMATION: antibody CDR3 sequence

<400> SEQUENCE: 145

Ile Gly Tyr His Gly Pro His Leu Asp Phe Asp Val
1               5                   10

<210> SEQ ID NO 146
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 146
```

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Met
        35                  40                  45

Gly Gly Ile Tyr Pro Asn Asn Gly Gly Ser Thr Tyr Asn Gln Asn Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 147
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 147

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 148
<211> LENGTH: 121
<212> TYPE: PRT
<213> ORGANISM: Artificial Sequence
<220> FEATURE:
<223> OTHER INFORMATION: antibody heavy chain sequence

<400> SEQUENCE: 148

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 149
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 149

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 150
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 150

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser

115

<210> SEQ ID NO 151
<211> LENGTH: 119
<212> TYPE: PRT
<213> ORGANISM: Artificial Sequence
<220> FEATURE:
<223> OTHER INFORMATION: antibody heavy chain sequence

<400> SEQUENCE: 151

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Leu Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 152
<211> LENGTH: 121
<212> TYPE: PRT
<213> ORGANISM: Artificial Sequence
<220> FEATURE:
<223> OTHER INFORMATION: antibody heavy chain sequence
<220> FEATURE:
<221> NAME/KEY: VARIANT
<222> LOCATION: (11)..(11)
<223> OTHER INFORMATION: May also be Leu
<220> FEATURE:
<221> NAME/KEY: VARIANT
<222> LOCATION: (48)..(48)
<223> OTHER INFORMATION: May also be Ile
<220> FEATURE:
<221> NAME/KEY: VARIANT
<222> LOCATION: (55)..(55)
<223> OTHER INFORMATION: May also be Gln, Ala or Glu
<220> FEATURE:
<221> NAME/KEY: VARIANT
<222> LOCATION: (68)..(68)
<223> OTHER INFORMATION: May also be Ala
<220> FEATURE:
<221> NAME/KEY: VARIANT
<222> LOCATION: (70)..(70)
<223> OTHER INFORMATION: May also be Leu
<220> FEATURE:
<221> NAME/KEY: VARIANT
<222> LOCATION: (72)..(72)
<223> OTHER INFORMATION: May also be Val
<220> FEATURE:
<221> NAME/KEY: VARIANT
<222> LOCATION: (99)..(99)
<223> OTHER INFORMATION: May also be Leu or Ile

<400> SEQUENCE: 152

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

```
Thr Met His Trp Val Arg Gln Ala Pro Gly Gln Gly Leu Glu Trp Met
        35                  40                  45

Gly Gly Ile Tyr Pro Asn Asn Gly Gly Ser Thr Tyr Asn Gln Asn Phe
        50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120
```

HUMANIZED ANTI-CD134 (OX40) ANTIBODIES AND USES THEREOF

CROSS-REFERENCE TO RELATED APPLICATIONS

The present application is a divisional of U.S. application Ser. No. 14/221,212, filed Mar. 20, 2014, which is a continuation of PCT Application No. PCT/NL2014/050162, filed Mar. 18, 2014, which claims benefit of European Application No. EP13159794.0, filed Mar. 18, 2013. The contents of the above patent applications are incorporated by reference herein in their entirety.

SUBMISSION OF SEQUENCE LISTING ON ASCII TEXT FILE

The instant application contains a sequence listing which has been submitted electronically in ASCII format and is hereby incorporated by reference in its entirety. Said ASCII copy, created on Sep. 7, 2017, is named 103270000032SeqList and is 175,896 bytes in size.

FIELD OF THE INVENTION

The invention relates to antibodies, the use of such antibodies, and particularly to humanized antibodies that bind to CD134, for the treatment of cancer.

BACKGROUND OF THE INVENTION

Enhancing anti-tumour T-cell function represents a unique approach for treating cancer. There is considerable evidence that tumour cells 'escape' the immune system by induction of an active immune tolerance largely mediated by regulatory T lymphocytes (Tregs; Quezda et al. Immunol Rev 2011; 241:104-118). Therefore, the balance between effector (i.e., direct or indirect eradication of tumour cells) T lymphocytes (Teffs) and tolerogenic (i.e., suppression of Teffs effector function and survival) Tregs appears to be crucial for effective anti-tumour immunotherapy. In other words, an effective anti-tumour immune response can be obtained by enhancing effector function of tumour-specific Teffs and/or by attenuating suppressive function of tumour-specific Tregs. A key receptor that has been shown to mediate these responses is the CD134 (OX40) receptor. (Sugamura, K, Ishii, N, Weinberg, A. Therapeutic targeting of the effector T-cell co-stimulatory molecule OX40. Nature Rev Imm 2004; 4: 420-431).

CD134 (also known as OX40, TNFRSF4, and ACT35) is a member of the tumour necrosis factor receptor superfamily. This CD134 surface co-stimulatory receptor is expressed on activated T lymphocytes, and plays an important role in their survival and function. The presence of CD134 expressing T lymphocytes has been demonstrated in various human malignant tumours and in the draining lymph nodes of cancer patients (Ramstad et al. Am J Surg 2000; 179: 400-406; Vetto et al. Am J Surg 1997; 174: 258-265).

In vivo ligation of the mouse CD134 receptor (by either soluble mouse OX40 ligand (OX40L)-immunoglobulin fusion proteins or mouse OX40L mimetics, such as anti-mouse CD134-specific antibodies) in tumour-bearing mice enhances anti-tumour immunity, leads to tumour-free survival in mouse models of various murine malignant tumour cell lines, e.g., lymphoma, melanoma, sarcoma, colon cancer, breast cancer, and glioma (Sugamura et al. Nature Rev Imm 2004; 4: 420-431).

It has been proposed to enhance the immune response of a mammal to an antigen by engaging the OX40R through the use of an OX40R binding agent (Int. Pat. Publ. No. WO 99/42585). Although the document refers generally to OX40-binding agents, the emphasis is on the use of OX40L or parts thereof; the disclosure of anti-OX40 antibodies is in the context of their being equivalent to OX40L. Indeed, when the Weinberg team (Weinberg et al. J Immunther 2006; 29: 575-585) translated the research to a study with non-human primates, they again deliberately chose an antibody that binds to the OX40L-binding site and generally mimics OX40L.

Al-Shamkhani et al. (Eur J Chem 1996; 26: 1695-1699) used an anti-OX40 antibody called OX86, which did not block OX40L-binding, in order to explore differential expression of OX40 on activated mouse T-cells; and Hirschhom-Cymerman et al. (J Exp Med 2009; 206: 1103-1116) used OX86 together with cyclophosphamide in a mouse model as a potential chemoimmunotherapy. However, OX86 would not be expected to bind human OX40 and, when choosing an antibody that would be effective in humans, one would, in the light of the Weinberg work, choose an antibody that did bind at the OX40L-binding site.

In vivo ligation of the human CD134 receptor (by anti-human CD134-specific antibodies which interact with the OX40L binding domain on human CD134; US 2009/0214560 A1) in severe combined immunodeficient (SCID) mice enhances anti-tumour immunity, which leads to tumour growth inhibition of various human malignant tumour cell lines, e.g. lymphoma, prostate cancer, colon cancer, and breast cancer.

The exact mechanism of human CD134 ligation-mediated anti-tumour immune responses in humans is not yet elucidated, but is thought to be mediated via the CD134 transmembrane signalling pathway that is stimulated by the interaction with OX40L. This interaction is mediated by the binding of trimeric OX40L to CD134. In current anti-cancer therapies, the use of trimerized OX40 ligand is proposed as a more effective agent than anti-OX40 antibodies (Morris et al. Mol Immunol 2007; 44: 3112-3121).

SUMMARY OF THE INVENTION

The present invention provides a binding molecule comprising
(a) a heavy chain variable region comprising the amino acid sequence of FIG. 27, or a variant of that sequence having 1, 2 or 3 amino acid substitutions; and/or
(b) a light chain variable region comprising the amino acid sequence of FIG. 27, or a variant of that sequence having 1, 2 or 3 amino acid substitutions.

The invention further provides a binding molecule comprising
(a) a heavy chain variable region comprising the amino acid sequence of FIG. 26, or a variant of that sequence having 1, 2 or 3 amino acid substitutions; and/or
(b) a light chain variable region comprising the amino acid sequence of FIG. 26 or a variant of that sequence having 1, 2 or 3 amino acid substitutions.

In some embodiments, the isolated binding, molecules bind to human CD134. The binding molecules of the invention may not prevent human CD134 (OX40) receptor binding to OX40 ligand (OX40L).

Such binding molecules include suitable anti-CD134 antibodies, antigen-binding fragments of the anti-CD134 antibodies, and derivatives of the anti-CD134 antibodies. In some embodiments the binding molecule binds to human CD134 with a $K_d$ of $1\times10^{-7}$ M or less. The binding molecule has agonist activity on human CD134 on T-effector cells and/or antagonistic activity on human CD134 on T-regulator cells. In some further embodiments, the binding molecule is a human monoclonal antibody that specifically binds human CD134 with a $K_d$ of 100 nM or less, for example less than 50 nM, or less than 20 nM.

The present invention also provides a composition that comprises one or more of the binding molecules and a pharmaceutically acceptable carrier. In some embodiments, the binding molecule is a human monoclonal anti-CD134 antibody or an antigen-binding fragment thereof. The composition may further comprise additional pharmaceutical agents, such as immunotherapeutic agents, chemotherapeutic agents, and hormonal therapeutic agents.

The present invention further provides diagnostic and therapeutic methods of using the binding molecules. In some embodiments is provided a method of treating or preventing cancer in a mammal, comprising administering to the mammal a therapeutically effective amount of a binding molecule or a composition comprising a binding molecule as disclosed herein. In some other embodiments, the disclosure provides a method of enhancing an immune response in a mammal, comprising administering to the mammal a therapeutically effective amount of a binding molecule or a composition comprising a binding molecule. In some embodiments, the binding molecule used in the methods is a human monoclonal anti-CD134 antibody or an antigen-binding fragment thereof, which binds to human CD134, wherein the antibody does not prevent human CD134 (OX40) receptor binding to OX40 ligand (OX40L).

The present invention further provides nucleic acid molecules that encode an amino acid sequence of a binding molecule, vectors comprising such nucleic acids, host cells comprising the vectors, and methods of preparing the binding molecules.

The disclosure also provides other aspects, which will be apparent from the entire disclosure, including the claims.

DESCRIPTION OF THE FIGURES

FIGS. 12A and 12B. Effect of mouse anti-human CD134 antibody clone 12H3 on human OX40L mediated proliferation of anti-human CD3/anti-human CD28 antibody stimulator beads-stimulated human CD134 expressing human effector (A) and regulatory (B) T lymphocytes.

Figure 24:
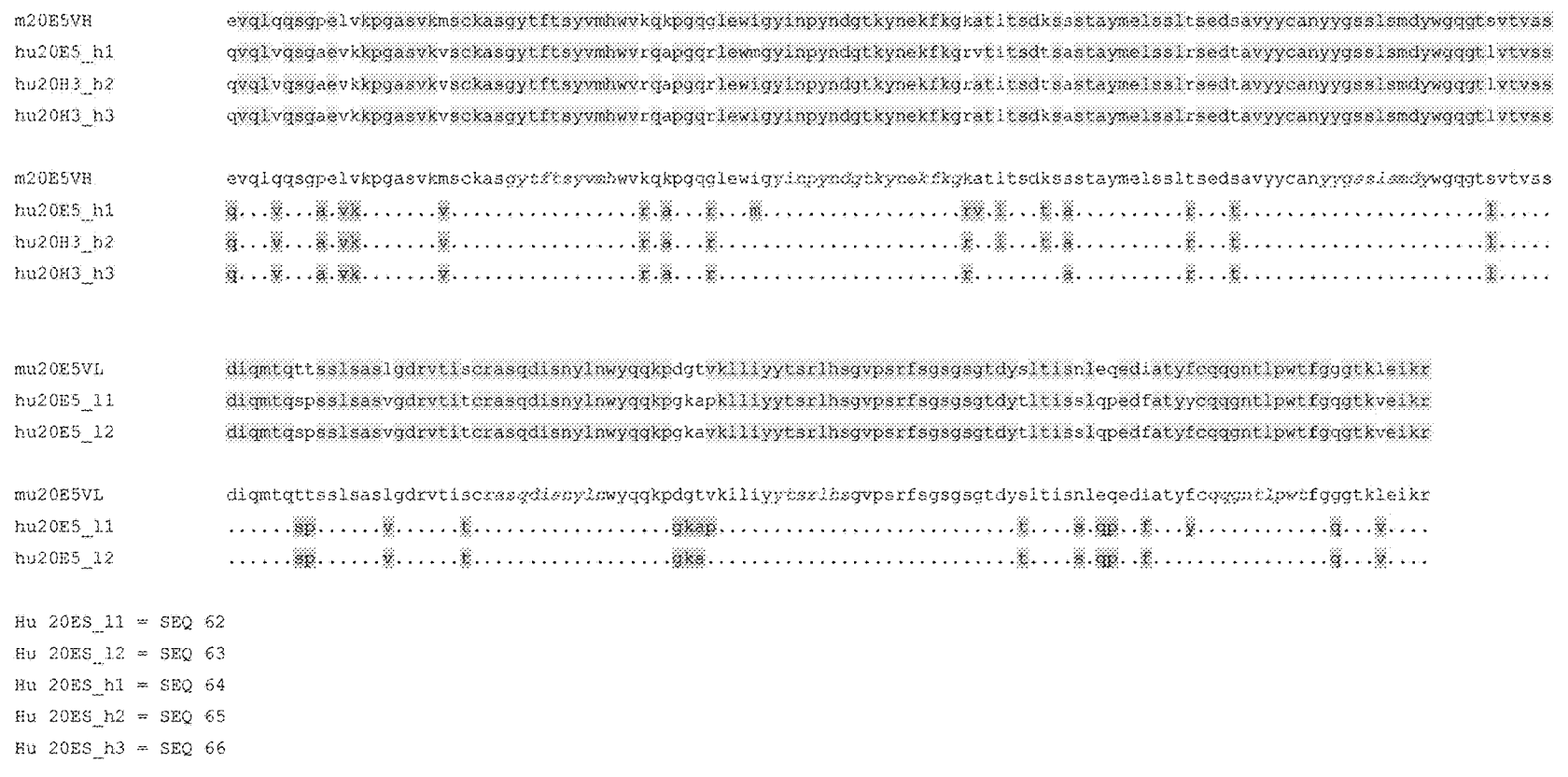

FIG. 24. Variable regions of monoclonal antibody 20E5. Murine variable regions (m20E5VH and m20E5VL); humanized 20E5 variable heavy chains (hu20E5_h1, hu20E5_h2 and hu20E5_h3) and humanized 20E5 variable light chains (hu20E5_l1 and hu20E5_l2). m20E5VH: SEQ ID NO: 4; m20E5VL: SEQ ID NO 5.

FIG. 25. Variable regions of monoclonal antibody 12H3. Murine variable regions (m12H3VH and m12H3VL); humanized 12H3 variable heavy chains (hu12H3_h1, hu12H3_h2 and hu12H3_h3) and humanized 12H3 variable light chains (hu12H3_l1 and hu12H3_l2). m12H3VH: SEQ ID NO: 12; m12H3VL: SEQ ID NO: 13.

FIG. 26. Humanized 20E5 variable regions.

FIG. 27. Humanized 12H3 variable regions.

FIG. 43. Alignment of humanized heavy chain variable regions (VH) derived from parental mouse anti-human CD134 20E5 antibody. SEQ ID NOs: are shown for each sequence at the end of the name of the sequence (20E5_VH1_64=amino acid sequence of SEQ ID NO: 64 etc.).

FIG. 44. Alignment of humanized heavy chain variable regions (VH) derived from parental mouse anti-human CD134 12H3 antibody. SEQ ID NO:s are shown for each sequence at the end of the name of the sequence (12H3_VH1_69=amino acid sequence of SEQ ID NO: 69 etc.).

DESCRIPTION OF THE INVENTION

Figure 1:
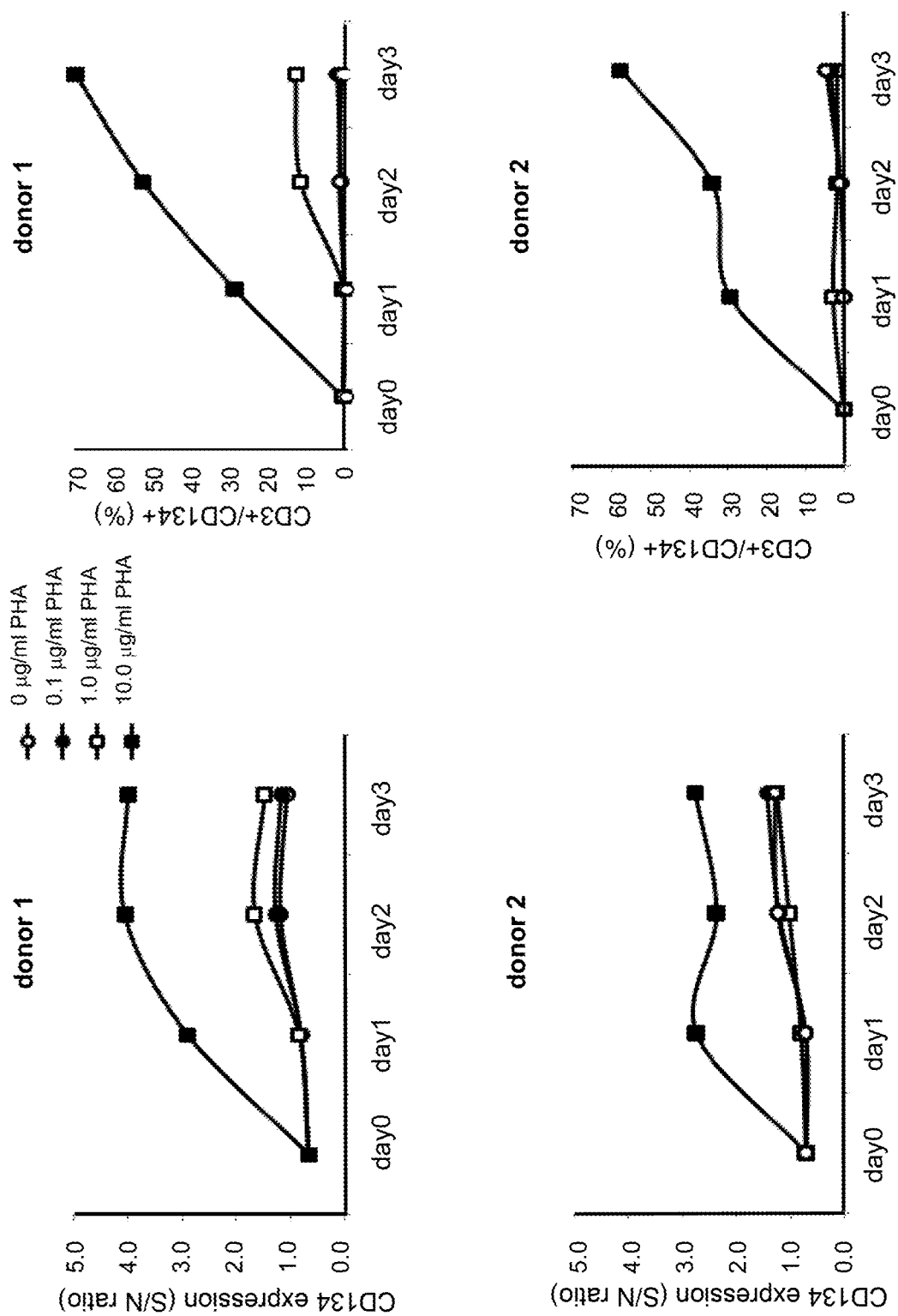
FIG. 1. Time course and dose effect of exposure to PHA-M on surface human CD134 expression of human T lymphocytes.

T-cell activation is mediated not only by antigen stimulation through T-cell receptors but also by co-stimulatory signals via co-stimulatory molecules. Among several co-stimulatory molecules, the tumour necrosis factor (TNF) receptor family member, OX40 (CD134) plays a key role in the survival and homeostasis of effector and memory T-cells. According to the conventional understanding of OX40 co-stimulation, an interaction between OX40 and OX40 ligand (OX40L) occurs when activated T-cells bind to professional antigen-presenting cells (APCs). The T-cell functions, including cytokine production, expansion, and survival, are then enhanced by the OX40 co-stimulatory signals. The interaction between OX40 and OX40L occurs during the T-cell-Dendritic cell (DC) interaction, 2-3 days after antigen recognition. The OX40-expressing T-cell may also interact with an OX40L-expressing cell other than DCs, and receive an OX40 signal from the cell, which may provide essential signals for the generation of memory T-cells, the enhancement of the Th2 response, and the prolongation of inflammatory responses. Thus, the optimal interaction between OX40 and OX40L might be formed in two steps: OX40L expressed on activated CD4 T-cells interacts with OX40 expressed on other responder CD4 T-cell, leading to the optimal generation of memory CD4 T cells (Soroosh et al. J Immunol 2006; 176: 5975-87) or OX40L expressed on CD4+ accessory cells may promote Th2 cell survival through the interaction with OX40 on Th2 cells (Kim et al. Immunity 2003; 18: 643-54). In addition, OX40L expression on B cells is required for in vivo Th2 development, but not Th1 development (Linton et al. J Exp Med 2003; 197: 875-83) and OX40L-expressing mast cells directly enhance effector T-cell function through the interaction between OX40 on T-cells and OX40L on mast cells (Kashiwakura et al. J Immunol 2004; 173: 5247-5257; Nakae et al. J Immunol 2006; 176: 2238-2248). In addition, as endothelial cells also express OX40L (Imura et al. J Exp Med 1996; 183: 2185-95), OX40 binding to endothelial cells might be involved in vascular inflammation. Excess OX40 signals, to both responder T-cells and T-regulatory cells, suppress Treg-mediated immune suppression. OX40 signals passing into responder T-cells render them resistant to Treg-mediated suppression. On the other hand, OX40 signals passing into Treg cells directly inhibit Treg-suppressive function, although it is controversial whether OX40 signals might control the Foxp3 expression level in Treg cells. In addition, deliberate OX40 stimulation inhibits the TGF-beta-dependent differentiation of iTreg cells (inducible Treg cells). The inhibition may be mediated in part by effector cytokines, such as IL-4 and IFN-gamma produced by effector T-cells stimulated with OX40. Importantly, blocking OX40L markedly promotes iTreg differentiation and induces graft tolerance, which might be mediated by Treg cells. Therefore, OX40 is a possible molecular target for controlling T-cell-mediated autoimmunity. Furthermore, recent studies reported that the interaction between OX40L expressed by mast cells and OX40 expressed by Treg cells may mutually suppress mast-cell function and Treg cell-suppressive function (Gri et al. Immunity 2008; 29: 771-81; Piconese et al. Blood 2009; 114: 2639-48).

Mice are the experimental tool of choice for immunologists, and the study of their immune responses has provided tremendous insight into the workings of the human immune system. The general structure of the mouse and human system seem to be quite similar; however, significant differences also exist. For example, in mice, CD134 is expressed on Teffs upon activation, whereas Tregs constitutively express CD134 (Piconese et al. J Exp Med 2008; 205: 825-839). In humans, CD134 is expressed on both Teffs and Tregs but only upon activation (see below, e.g., Example 2 (g), 'CD134 expression on human effector and regulatory T lymphocytes after stimulation with anti-human CD3/anti-human CD28 antibody stimulator beads'). Furthermore, mouse Tregs induce apoptosis of mouse Teffs to achieve suppression (Pandiyan et al. Nat Immunol 2007; 8: 1353; Scheffold et al. Nat Immunol 2007; 8: 1285-1287), whereas human Tregs do not induce apoptosis in human Teffs to achieve suppression (Vercoulen et al. Plos ONE 2009; 4: e7183). Collectively, these data indicate different roles of CD134 in the Tregs suppressive function between human and mouse immune systems.

The term "binding molecule" encompasses (1) an antibody, (2) an antigen-binding fragment of an antibody, and (3) a derivative of an antibody, each as defined herein. The term "binds to CD134" or "binding to CD134" refers to the binding of a binding molecule, as defined herein, to the CD134 receptor in an in vitro assay, such as a BIAcore assay or by Octet (surface plasmon resonance). The binding molecule has a binding affinity ($K_d$) of about $1\times10^{-6}$ M or less, for example about $5\times10^{-7}$ M or less, about $1\times10^{-7}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less.

The term "isolated antibody" or "isolated binding molecule" refers to an antibody or a binding molecule that: (1) is not associated with naturally associated components that accompany it in its native state; (2) is free of other proteins from the same species; (3) is expressed by a cell from a different species; or (4) does not occur in nature. Examples of isolated antibodies include an anti-CD134 antibody that has been affinity purified using CD134, an anti-CD134 antibody that has been generated by hybridomas or other cell lines in vitro, humanized anti-CD134 antibodies, and a human anti-CD134 antibody derived from a transgenic animal.

The term "agonist" refers to a binding molecule, as defined herein, which upon binding to CD134, (1) stimulates or activates CD134, (2) enhances, promotes, induces, increases or prolongs the activity, presence or function of CD134, or (3) enhances, promotes, increases or induces the expression of CD134. The term "antagonist" refers to a binding molecule, as defined herein, which upon binding to CD134, (1) inhibits or suppresses CD134, (2) inhibits or suppresses an activity, presence or function of CD134, or (3) inhibits or suppresses the expression of CD134.

The term "antibody" refers to an immunoglobulin molecule that is typically composed of two identical pairs of polypeptide chains, each pair having one "heavy" (H) chain and one "light" (L) chain. Human light chains are classified as kappa (κ) and lambda (λ). Heavy chains are classified as mu, delta, gamma, alpha, or epsilon, and define the antibody's isotype as IgM, IgD, IgG, IgA, and IgE, respectively. Each heavy chain is comprised of a heavy chain variable region (abbreviated herein as HCVR or VH) and a heavy chain constant region. The heavy chain constant regions of IgD, IgG, and IgA are comprised of three domains, CH1, CH2 and CH3, and the heavy chain constant regions of IgM and IgE are comprised of four domains, CH1, CH2, CH3, and CH4. Each light chain is comprised of a light chain variable region (abbreviated herein as LCVR or VL) and a light chain constant region. The light chain constant region is comprised of one domain, CL. The constant regions of the antibodies may mediate the binding of the immunoglobulin to host tissues or factors, including various cells of the immune system (e.g., effector cells). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from the amino-terminus to carboxy-terminus in the following order: FR1, CDR1, FR2, CDR2, FR3, CDR3, FR4. The variable regions of each heavy/light chain pair (VH and VL), respectively, typically form the antibody binding site. The assignment of amino acids to each region or domain is in accordance with the definitions of Kabat Sequences of Proteins of Immunological Interest (National Institutes of Health, Bethesda, Md. (1987 and 1991)) or in accordance with the definitions of Chothia et al. Conformations of immunoglobulin hypervariable regions (Nature 1989; 342(6252):877-83). The term "antibody" encompasses murine, humanized, human and chimeric antibodies, and an antibody that is a multimeric form of antibodies, such as dimers, trimers, or higher-order multimers of monomeric antibodies. Antibody also encompasses monospecific, bispecific or multispecific antibodies, and any other modified configuration of the immunoglobulin molecule that comprises an antigen recognition site of the required specificity. It also encompasses an antibody that is linked or attached to a non-antibody moiety. Further, the term "antibody" is not limited by any particular method of producing the antibody. For example, it includes monoclonal antibodies, recombinant antibodies and polyclonal antibodies.

The term "antibody derivative" or "derivative" of an antibody refers to a molecule that is capable of binding to the same antigen (i.e., human CD134) that the antibody binds to and comprises an amino acid sequence of the antibody linked to an additional molecular entity. The amino acid sequence of the antibody that is contained in the antibody derivative may be the full-length antibody, or may be any portion or portions of a full-length antibody. The additional molecular entity may be a biological or chemical molecule. Examples of additional molecular entities include chemical groups, peptides, proteins (such as enzymes, antibodies), amino acids, and chemical compounds. The additional molecular entity may be for use as a detection agent, marker label, therapeutic or pharmaceutical agent. The amino acid sequence of an antibody may be attached or linked to the additional entity by non-covalent association, chemical coupling, genetic fusion, or otherwise. The term "antibody derivative" also encompasses chimeric antibodies, humanized antibodies, and molecules that are derived from modifications of the amino acid sequences of a CD134 antibody, such as conservation amino acid substitutions, insertions and additions.

The term "antigen-binding fragment" of an antibody refers to one or more portions of a full-length antibody that retain the ability to bind to the same antigen (i.e., human CD134) that the antibody binds to. The term "antigen-binding fragment" also encompasses a portion of an antibody that is part of a larger molecule formed by non-covalent or covalent association or of the antibody portion with one or more additional molecular entities. Examples of additional molecular entities include amino acids, peptides, or proteins, such as the streptavidin core region, which may be used to make a tetrameric scFv molecule (Kipriyanov et al. Hum Antibodies Hybridomas 1995; 6(3): 93-101). An exemplary antigen-binding fragment is a VH and/or a VL of an antibody.

The term "chimeric antibody" refers to an antibody that comprises amino acid sequences derived from two different species such as human and mouse, typically a combination of mouse variable (from heavy and light chains) regions and human constant (heavy and light chains) regions.

The term "epitope" refers to the part of an antigen that is capable of specific binding to an antibody, or T-cell receptor or otherwise interacting with a molecule. "Epitope" is also referred to in the art as the "antigenic determinant". An epitope generally consists of chemically active surface groupings of molecules such as amino acids or carbohydrate or sugar side chains. An epitope may be "linear" or "non-linear/conformational". Once a desired epitope is determined (e.g., by epitope mapping), antibodies to that epitope can be generated. The generation and characterization of antibodies may also provide information about desirable epitopes. From this information, it is then possible to screen antibodies for those which bind to the same epitope e.g. by conducting cross-competition studies to find antibodies that competitively bind with one another, i.e., the antibodies compete for binding to the antigen.

The term "host cell" refers to a cell into which an expression vector has been introduced. The term encompasses not only the particular subject cell but also the progeny of such a cell. Because certain modifications may occur in successive generations due to either environmental influences or mutation, such progeny may not be identical to the parent cell, but are still included within the scope of the term "host cell."

The term "human antibody" refers to an antibody consisting of amino acid sequences of human immunoglobulin sequences only. A human antibody may contain murine carbohydrate chains if produced in a mouse, in a mouse cell or in a hybridoma derived from a mouse cell. Human antibodies may be prepared in a variety of ways known in the art.

The term "humanized antibody" refers to an antibody that contains some or all of the CDRs from a non-human animal antibody while the framework and constant regions of the antibody contain amino acid residues derived from human antibody sequences. Humanized antibodies are typically produced by grafting CDRs from a mouse antibody into human framework sequences followed by back substitution of certain human framework residues for the corresponding mouse residues from the source antibody. The term "humanized antibody" also refers to an antibody of non-human origin in which, typically in one or more variable regions, one or more epitopes have been removed, that have a high propensity of constituting a human T-cell and/or B-cell epitope, for purposes of reducing immunogenicity. The amino acid sequence of the epitope can be removed in full or in part. However, typically the amino acid sequence is altered by substituting one or more of the amino acids constituting the epitope for one or more other amino acids, thereby changing the amino acid sequence into a sequence that does not constitute a human T-cell and/or B-cell epitope. The amino acids are substituted by amino acids that are present at the corresponding position(s) in a corresponding human variable heavy or variable light chain as the case may be.

The term "mammal" refers to any animal species of the Mammalian class. Examples of mammals include: humans; laboratory animals such as rats, mice, simians and guinea pigs; domestic animals such as rabbits, cattle, sheep, goats, cats, dogs, horses, and pigs and the like.

The term "isolated nucleic acid" refers to a nucleic acid molecule of cDNA, or synthetic origin, or a combination thereof, which is separated from other nucleic acid molecules present in the natural source of the nucleic acid.

The term "$K_d$" refers to the equilibrium dissociation constant of a particular antibody-antigen interaction and is used to describe the binding affinity between a ligand (such as an antibody) and a protein (such as CD134). The smaller the equilibrium dissociation constant, the more tightly bound the ligand is, or the higher the affinity between ligand and protein. A $K_d$ can be measured by surface plasmon resonance, for example using the BIACORE 1 or the Octet system. The term "anti-CD134 antibody" refers to an antibody, as defined herein, capable of binding to the human CD134.

The terms "OX40 receptor", "CD134 receptor" and "CD134" are used interchangeably in the present application, and include the human CD134, as well as variants, isoforms, and species homologues thereof. Accordingly, human CD134 binding molecules disclosed herein may, in certain cases, also bind to the CD134 from species other than human. For example, the binding molecules of the invention may have cross-reactivity to other related antigens, for example to the CD134 from other species, such as human or monkey, for example Macacafascicularis (cynomolgus, cyno) or Pan troglodytes (chimpanzee, chimp). In other cases, the binding molecules may be completely specific for the human CD134 and may not exhibit species or other types of cross-reactivity. For example, they will not bind to the mouse or rat CD134.

The term "specifically bind to the human CD134" means that the $K_d$ of a binding molecule for binding to human CD134, is less than about 10 fold, 50 fold or 100 fold the $K_d$ for its binding to, e.g., the human CD40, as determined using an assay described herein or known to one of skill in the art (e.g. a BIAcore assay).

The determination that a particular agent binds specifically to the OX40 receptor may alternatively readily be made by using or adapting routine procedures. One suitable in vitro assay makes use of the Western blotting procedure (described in many standard texts, including "Antibodies, A Laboratory Manual" by Harlow and Lane). To determine that a given OX40 receptor binding agent binds specifically to the human OX40 protein, total cellular protein is extracted from mammalian cells that do not express the OX40 antigen, such as a non-lymphocyte cell (e.g., a COS cell or a CHO cell), transformed with a nucleic acid molecule encoding OX40. As a negative control, total cellular protein is also extracted from corresponding non-transformed cells. These protein preparations are then electrophorezed on a non-denaturing or denaturing polyacrylamide gel (PAGE). Thereafter, the proteins are transferred to a membrane (for example, nitrocellulose) by Western blotting, and the agent to be tested is incubated with the membrane. After washing the membrane to remove non-specifically bound agent, the presence of bound agent is detected by the use of an antibody raised against the test agent conjugated to a detection agent, such as the enzyme alkaline phosphatase; application of the substrate 5-bromo-4-chloro-3-indolyl phosphate/nitro blue tetrazolium results in the production of a dense blue compound by immuno-localized alkaline phosphatase. Agents which bind specifically to human OX40 will, by this technique, be shown to bind to the human OX40 band (which will be localized at a given position on the gel determined by its molecular mass) in the extract from OX40 transformed cells, whereas little or no binding will be observed in the extract from non-transformed cells. Non-specific binding of the agent to other proteins may occur and may be detectable as a weak signal on the Western blots. The nonspecific nature of this binding will be recognized by one skilled in the art by the weak signal obtained on the Western blot relative to the strong primary signal arising from the specific agent/human OX40 protein binding. Ideally, an OX40 receptor binding agent would not bind to the proteins extracted from the non-transformed cells. In addition to binding assays using extracted proteins, putative OX40 receptor binding agents may be tested to confirm their ability to bind substantially only OX40 receptor in vivo by conjugating the agent to a fluorescent tag (such as FITC) and analyzing its binding to antigen activated CD4+ T-cell and non-activated T-cell populations by Fluorescence Activated Cell Sorting (FACS). An agent which binds substantially only the OX40 receptor will stain only activated CD4+ T-cells.

The term "vector" refers to a nucleic acid molecule capable of transporting another nucleic acid molecule in a host cell. Examples of vectors include plasmids, viral vectors, cosmid or phage vectors, and naked DNA or RNA expression vectors. Some vectors are capable of autonomous replication in a host cell into which they are introduced. Some vectors can be integrated into the genome of a host cell upon introduction into the host cell, and thereby are replicated along with the host genome. Certain vectors are capable of directing the expression of genes to which they are operatively linked, and therefore may be referred to as "expression vectors."

As used herein, the twenty conventional amino acids and their abbreviations follow conventional usage.

The invention provides an isolated antibody that binds human CD134 comprising a light chain variable region (VL) of SEQ ID NO: 100 and a heavy chain variable region (VH) comprising heavy chain complementarity determining regions (HCDR)s HCDR1, HCDR2 and HCDR3, optionally having 1, 2 or 3 amino acid substitutions in the VL of SEQ ID NO: 100.

SEQ ID NO: 100:
DIQMTQSPSSLSASVGDRVTITCKASQDVGAAVAWYQQKPGKAPK

LLIYWASTRHTGVPX$_{11}$RFSGX$_{12}$GSGTDFTLTISSLQPEDFATYYCQQY

INYPLTFGG GTKVEIKR;

wherein
X$_{11}$ is D or S; and
X$_{12}$ is G or S.

In some embodiments described herein, the isolated antibody comprises the VH comprising the amino acid sequence of SEQ ID NO: 152, optionally having 1, 2 or 3 amino acid substitutions in the VH of SEQ ID NO: 152.

SEQ ID NO: 152:
QVQLVQSGAEX$_1$KKPGSSVKVSCKASGYTFKDYTMHWVRQAPGQGLEWX$_2$

GGIYPNX$_3$GGSTYNQNFKDRX$_4$TX$_5$TX$_6$DKSTSTAYMELSSLRSEDTAVY

YCARX$_7$GYHGPHLDFDVWGQGTTVTVSS;

wherein
X$_1$ is V or L;
X$_2$ is M or I;
X$_3$ is N, Q, A or E;
X$_4$ is V or A;
X$_5$ is I or L;
X$_6$ is A or V; and
X$_7$ is M, L or I.

In some embodiments described herein, the isolated antibody comprises the VH comprising the amino acid sequence of SEQ ID NO: 99, optionally having 1, 2 or 3 amino acid substitutions in the VH of SEQ ID NO: 99.

SEQ ID NO: 99:
QVQLVQSGAEVKKPGSSVKVSCKASGYTFKDYTMHWVRQAPGQGLEWX$_7$G

GIYPNNGGSTYNQNFKDRX$_8$TX$_9$TX$_{10}$DKSTSTAYMELSSLRSEDTAVYY

CARMGYHGPHLDFDVWGQGTTVTVSS;

wherein
X$_7$ is I or M;
X$_8$ is A or V;
X$_9$ is L OR I; and
X$_{10}$ is V or A.

In some embodiments described herein, the isolated antibody comprises the VL of SEQ ID NO: 100 and the VH of SEQ ID NO: 152.

In some embodiments described herein, the isolated antibody comprises the HCDR3 comprising the amino acid sequence of SEQ ID NOs: 16, 144 or 145.

In some embodiments described herein, the isolated antibody comprises the HCDR2 comprising the amino acid sequence of SEQ ID NOs: 15, 141, 142 or 143.

In some embodiments described herein, the isolated antibody comprises the HCDR1 comprising the amino acid sequence of SEQ ID NO: 14.

In some embodiments described herein, the isolated antibody comprises
a) the VL comprising the amino acid sequence of SEQ ID NOs: 67 or 68; and the VH comprising the amino acid sequence of SEQ ID NOs: 69, 70, 71, 119, 120, 121, 122, 123, 124, 125, 126, 127, 128, 129, 130, 131, 132, 133, 146, 147 or 148, optionally having 1, 2 or 3 amino acid substitutions at the VH linear amino acid residue positions 11, 55 or 99; or
b) the VL and the VH comprising the amino acid sequences of
  i. SEQ ID NOs: 67 and 69, respectively;
  ii. SEQ ID NOs: 67 and 70, respectively;
  iii. SEQ ID NOs: 67 and 71, respectively;
  iv. SEQ ID NO:s 68 and 69, respectively;
  v. SEQ ID NOs: 68 and 70, respectively; or
  vi. SEQ ID NOs: 68 and 71, respectively.

In some embodiments described herein, the isolated antibody comprises the VL and the VH of SEQ ID NOs: 67 and 119, 67 and 120, 67 and 121, 67 and 122, 67 and 123, 67 and 124, 67 and 125, 67 and 126, 67 and 127, 67 and 128, 67 and 129, 67 and 130, 67 and 131, 67 and 132, 67 and 133, 67 and 146, 67 and 147. 67 and 148, 68 and 119, 68 and 120, 68 and 121, 68 and 122, 68 and 123, 68 and 124, 68 and 125, 68 and 126, 68 and 127, 68 and 128, 68 and 129, 68 and 130, 68 and 131, 68 and 132, 68 and 133, 68 and 146, 68 and 147 or 68 and 148, respectively.

In some embodiments described herein, the antibody is an agonist of CD134.

In some embodiments described herein, the antibody comprises a substitution in an Fc region.

In some embodiments described herein, the substitution comprises a S267E/L328F substitution, an E233D/G237D/H268D/P271G/A330R substitution, a V234A/G237A/P238S/H268A/V309L/A330S/P331S substitution, or a M252Y/S254T/T256E substitution, wherein residue numbering is according to the EU Index.

Antibodies whose heavy chain, light chain, VH or VL amino acid sequences differ insubstantially from those described herein are encompassed within the scope of the invention. Insubstantial differences are substitutions of 1, 2, 3, 4, 5, 6, 7, 8, 9, 10, 11, 12, 13, 14, or 15 amino acids in an antibody variable region sequence that do not adversely affect antibody properties. Amino acid sequences substantially identical to the variable region sequences disclosed herein are within the scope of the invention. In some embodiments, the sequence identity can be about 90%, 91%, 92%, 93%, 94%, 95%, 96%, 97%, 98%, 99% or higher. Percent identity can be determined for example by pairwise alignment using the default settings of the AlignX module of Vector NTI v.9.0.0 (Invitrogen, Carlsbad, Calif.). The protein sequences of the present invention can be used as a query sequence to perform a search against public or patent databases to, for example, identify related sequences. Exemplary programs used to perform such searches are the XBLAST or BLASTP programs (http_//www ncbi_nlm/nih_gov), or the GenomeQuest™ (GenomeQuest, Westborough, Mass.) suite using the default settings.

Typically, this involves one or more conservative amino acid substitutions with an amino acid having similar charge, hydrophobic, or stereo chemical characteristics in the antigen-binding site or in the framework without adversely altering the properties of the antibody. Conservative substitutions may also be made to improve antibody properties, for example stability or affinity. 1, 2, 3, 4, 5, 6, 7, 8, 9, 10, 11, 12, 13, 14, or 15 amino acid substitutions can be made to the VH or VL sequence. In some embodiments, 1, 2 or 3 substitutions are made to the VH or the VL of the antibody described herein. Exemplary conservative amino acid substitutions are shown in Table 1. Furthermore, any native residue in the polypeptide may also be substituted with alanine, as has been previously described for alanine scanning mutagenesis (MacLennan et al (1998) *Act Physiol. Scand. Suppl.* 643:55-67; Sasaki et al (1998) *Adv. Biopsy's.* 35:1-24).

Anti-CD134 antibodies described herein that are modified to improve their stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and intermolecular forces (Worn et al., J. Mol. Biol., 305:989-1010, 2001). Potential structure destabilizing residues may be identified based upon the crystal structure of the antibody, and the effect of the residues on antibody stability can be tested by generating and evaluating variants having mutations in the identified residues.

In some embodiments described herein, the isolated antibody comprises 1, 2 or 3 amino acid substitutions at the VH linear residue positions 11, 55 or 99.

In some embodiments described herein, the 1, 2 or 3 amino acid substitutions at the VH linear residue positions are V11L, N55Q, N55A, N55E, M99L or M99I.

The substitutions at the VH linear residue positions 11, 55 or 99 may improve antibody stability and/or enhance its agonistic activity.

Amino acid substitutions can be done for example by PCR mutagenesis (U.S. Pat. No. 4,683,195). Libraries of variants can be generated using well known methods, for example using random (NNK) or non-random codons, for example DVK codons, which encode 11 amino acids (Ala, Cys, Asp, Glu, Gly, Lys, Asn, Arg, Ser, Tyr, Trp) and screening the libraries for variants with desired properties.

Although the embodiments illustrated in the Examples comprise pairs of variable regions, one from a heavy chain and one from a light chain, a skilled artisan will recognize that alternative embodiments may comprise single heavy or light chain variable regions. The single variable region can be used to screen for variable domains capable of forming a two-domain specific antigen-binding fragment capable of, for example, binding to human CD134 having the sequence of SEQ ID NO: 1. The screening may be accomplished by phage display screening methods using for example hierarchical dual combinatorial approach disclosed in Int. Pat. Publ. No. WO1992/01047. In this approach, an individual colony containing either a H or L chain clone is used to infect a complete library of clones encoding the other chain (L or H), and the resulting two-chain specific antigen-binding domain is selected in accordance with phage display techniques as described. Therefore, the individual VH and VL polypeptide chains are useful in identifying additional antibodies specifically binding human CD134 having the sequence of SEQ ID NO: 1 using the methods disclosed in Int. Pat. Publ. No. WO1992/01047.

In some embodiments described herein, the isolated antibody comprises the HCDR1, the HCDR2 and the HCDR3 amino acid sequences a. SEQ ID NOs: 14, 15 and 144, respectively;
b. SEQ ID NOs: 14, 15 and 145, respectively;
c. SEQ ID NOs: 14, 141, and 16, respectively;
d. SEQ ID NOs: 14, 141 and 144, respectively;
e. SEQ ID NO:s 14, 141 and 145, respectively;
f. SEQ ID NOs: 14, 142 and 16, respectively;
g. SEQ ID NOs: 14, 142 and 144, respectively;
h. SEQ ID NOs: 14, 142 and 145, respectively.
i. SEQ ID NOs: 14, 143 and 16, respectively;
j. SEQ ID NOs: 14, 143 and 144, respectively; or
k. SEQ ID NOs: 14, 143 and 145, respectively.

In some embodiments described herein, the antibodies comprising certain heavy chain and light chain CDR sequences as described herein are humanized, human or deimmunized antibodies.

Human or deimmunized antibodies can be made as described herein. Humanized antibodies typically refers to an antibody in which the antigen binding site is derived from non-human species and the variable region frameworks are derived from human immunoglobulin sequences. Humanized antibodies may include substitutions in the framework regions so that the framework may not be an exact copy of expressed human immunoglobulin or germline gene sequences. Humanized antibodies against CD134 may be generated for example in Balb/c mice using standard methods. The antibodies made in Balb/c mice or other non-human animals can be humanized using various technologies to generate more human-like sequences. Exemplary humanization techniques including selection of human acceptor frameworks are known to skilled in the art and include CDR grafting (U.S. Pat. No. 5,225,539), SDR grafting (U.S. Pat. No. 6,818,749), Resurfacing (Palin, Mol Immunol 28:489-499, 1991), Specificity Determining Residues Resurfacing (U.S. Pat. Publ. No. 2010/0261620), human-adaptation (or human framework adaptation) (U.S. Pat. Publ. No. US2009/0118127), Super humanization (U.S. Pat. No. 7,709,226) and guided selection (Osborn et al., Methods 36:61-68, 2005; U.S. Pat. No. 5,565,332).

Humanized antibodies can be further optimized to improve their selectivity or affinity to a desired antigen by incorporating altered framework support residues to preserve binding affinity (back mutations) by techniques such as those disclosed as described in Int. Pat. Publ. No. WO1990/007861 and in Int. Pat. Publ. No. WO1992/22653.

Immune effector properties of the antibodies of the invention may be modulated through Fc modifications by techniques known to those skilled in the art. For example, Fc effector functions such as C1q binding, complement dependent cytotoxicity (CDC), antibody-dependent cell-mediated cytotoxicity (ADCC), phagocytosis, down regulation of cell surface receptors (e.g., B cell receptor; BCR), etc. can be modulated by modifying residues in the Fc responsible for these activities through binding to activating Fc gamma receptors (FcγR) FcγRI, FcγRIIa or FcγRIII, or to inhibitory receptor FcγRIIb. Pharmacokinetic properties may also be enhanced by mutating residues in the Fc domain that extend antibody half-life by modulating Fc binding affinity to the neonatal Fc receptor FcRn. Exemplary Fc modifications are IgG4 S228P/L234A/L235A, IgG2 M252Y/S254T/T256E (Dall'Acqua et al., J Biol Chem 281:23514-24, 2006); or IgG2 V234A/G237A/P238S, V234A/G237A/H268Q, H268A/V309L/A330S/P331 or V234A/G237A/P238S/H268A/V309L/A330S/P331S (Intl. Pat. Publ. No. WO2011/066501), or those described in U.S. Pat. No. 6,737,056 (residue numbering according to the EU Index). Antibody Fc affinity to the inhibitory FcγRIIb may be augmented to enhance antibody cross-linking and agonistic signals. Exemplary Fc modifications that enhance Fc binding to the FcγRIIb are S267E/L328F and E233D/G237D/H268D/P271G/A330R (residue numbering according to the EU Index).

Another embodiment of the invention is an isolated antibody that binds human CD134, comprising a light chain variable region (VL) of SEQ ID NO: 98 and a heavy chain variable region (VH) comprising heavy chain complementarity determining regions (HCDR)s HCDR1, HCDR2 and HCDR3, optionally having 1, 2 or 3 amino acid substitutions in the VL of SEQ ID NO: 98.

SEQ ID NO: 98:
DIQMTQSPSSLSASVGDRVTITCRASQDISNYLNWYQQKPGKAX$_5$KLLIY

YTSRLHSGVPSRFSGSGSGTDYTLTISSLQPEDFATYX$_6$CQQGNTLPWTF

GQGTKVEIKR, wherein X$_5$ is V or P; and
X$_6$ is F or Y.

In some embodiments described herein, the isolated antibody comprises the VH comprising the amino acid sequence of SEQ ID NO: 134, optionally having 1, 2 or 3 amino acid substitutions in the VH of SEQ ID NO: 134.

SEQ ID NO: 134
QVQLVQSGAEX$_1$KKPGASVKVSCKASGYTFTSYVMHWVRQAPGQRLEWX$_2$

GYINPYNX$_3$GTKYNEKFKGRX$_4$TX$_5$TSDX$_6$SASTAYMELSSLRSEDTAVY

YCANYYGSSLSX$_7$DYWGQGTLVTVSS;

wherein
X1 is V or L;
X2 is M or I;
X3 is D, G, A, S or E;
X4 is V or A;
X5 is L or I;
X6 is T or K; and
X7 is M, L or I In some embodiments described herein, the isolated antibody comprises the VH comprising the amino acid sequence of SEQ ID NO: 97, optionally having 1, 2 or 3 amino acid substitutions in the VH of SEQ ID NO: 97.

SEQ ID NO: 97:
QVQLVQSGAEVKKPGASVKVSCKASGYTFTSYVMHWVRQAPGQRLEWX₁G

YINPYNDGTKYNEKFKGRX₂TX₃TSDX₄SASTAYMELSSLRSEDTAVYYC

ANYYGSSLSMDYWGQGTLVTVSS;

wherein

X₁ is I or M;
X₂ is A or V;
X₃ is L or I; and
X₄ is K or T.

In some embodiment described herein, the isolated antibody comprises the VL of SEQ ID NO: 99 and the VH of SEQ ID NO: 134.

In some embodiments described herein, the isolated antibody comprises the HCDR3 comprising the amino the amino acid sequence of SEQ ID NOs: 8, 139 or 140.

In some embodiments described herein, the isolated antibody comprises the HCDR2 comprising the amino the amino acid sequence of SEQ ID NOs: 7, 135, 136, 137 or 138.

In some embodiments described herein, the isolated antibody comprises the HCDR1 comprises the amino acid sequence of SEQ ID NO: 6.

In some embodiments described herein, the isolated antibody comprises a. the VL comprising the amino acid sequence of SEQ ID NOs: 62 or 63; and
the VH comprising the amino acid sequence of SEQ ID NOs: 64, 65, 66, 101, 102, 103, 104, 105, 106, 107, 108, 109, 110, 111, 112, 113, 114, 115, 116, 117, 118, 149, 150 or 151, optionally having 1, 2 or 3 amino acid substitutions at the VH linear amino acid residue positions 11, 56 or 106; or
b. the VL and the VH comprising the amino acid sequences of
i. SEQ ID NOs: 62 and 64, respectively;
ii. SEQ ID NOs: 62 and 65, respectively;
iii. SEQ ID NOs: 62 and 66, respectively;
iv. SEQ ID NOs: 63 and 64, respectively;
v. SEQ ID NOs: 63 and 65, respectively; or
vi. SEQ ID NOs: 63 and 66, respectively.

In some embodiments described herein, the isolated antibody comprises the VL and the VH of SEQ ID NOs: 62 and 64, 62 and 65, 62 and 66, 62 and 101, 62 and 102, 62 and 103, 62 and 104, 62 and 105, 62 and 106, 62 and 107, 62 and 108, 62 and 109, 62 and 110, 62 and 111, 62 and 112, 62 and 113, 62 and 114, 62 and 115, 62 and 116, 62 and 117, 62 and 118, 62 and 149, 62 and 150, 62 and 151. 63 and 64, 63 and 65, 63 and 66, 63 and 101, 63 and 102, 63 and 103, 63 and 104, 63 and 105, 63 and 106, 63 and 107, 63 and 108, 63 and 109, 63 and 110, 63 and 111, 63 and 112, 63 and 113, 63 and 114, 63 and 115, 63 and 116, 63 and 117, 63 and 118, 63 and 149, 63 and 150, 63 and 151, In some embodiments described herein, the isolated antibody comprises 1, 2 or 3 amino acid substitutions at the VH linear residue positions 11, 56 or 106.

In some embodiments described herein, the 1, 2 or 3 amino acid substitutions at the VH linear residue positions are V11L, D56G, D56A, D56S, D56E, M106L or M106I.

The 1, 2 or 3 amino acid substitutions at the VH linear residue positions 11, 55 or 99 may improve antibody stability and/or enhance its agonistic activity.

The invention provides a binding molecule comprising (a) a heavy chain variable region comprising the amino acid sequence of FIG. 27 (SEQ ID NO: 99), or a variant of that sequence having 1, 2 or 3 amino acid substitutions; and/or
(b) a light chain variable region comprising the amino acid sequence of FIG. 27 (SEQ ID NO: 100), or a variant of that sequence having 1, 2 or 3 amino acid substitutions.

The invention also provides a binding molecule comprising (a) a heavy chain variable region comprising the amino acid sequence of FIG. 26 (SEQ ID NO: 97), or a variant of that sequence having 1, 2 or 3 amino acid substitutions; and/or
(b) a light chain variable region comprising the amino acid sequence of FIG. 26 (SEQ ID NO: 98) or a variant of that sequence having 1, 2 or 3 amino acid substitutions.

In some embodiments the binding molecule binds to human CD134. In some embodiments the binding molecule does not prevent human CD134 (OX40) receptor binding to OX40 ligand (OX40L).

In some embodiments the effect on binding of OX40L to CD134 is reduced by not more than 50% on human CD134 expressing T-cells, at or above the concentration at which binding to said CD134 molecule is saturated.

In some embodiments, at a concentration of 70 nM of the binding molecule, the effect on binding of OX40L to CD134 is reduced by not more than 70% on human CD134 expressing T-cells.

In some embodiments the binding molecule binds to an epitope of the extracellular domain of human CD134 comprising the amino acid sequence of SEQ ID NO: 34, SEQ ID NO: 35; SEQ ID NO: 36, SEQ ID NO: 38 and/or SEQ ID NO: 92.

In some embodiments the binding molecule is a Fab-fragment, a single chain Fv (scFv) fragment, or an antibody.

In some embodiments the antibody is an IgG, IgA, IgD, IgE or IgM antibody, such as IgG1, IgG2, IgG3 or IgG4 antibody. In some embodiments the antibody is an IgG1 or an IgG4 antibody.

The invention further provides a nucleic acid molecule encoding a binding molecule or an antibody according to the invention. Further provided is a nucleic acid molecule encoding a heavy chain variable region, a heavy chain, a light chain variable region, or a light chain of a humanized antibody of the invention. Exemplary humanized antibodies are humanized 12H3 or humanized 20E5 antibodies of the invention.

In some embodiments the nucleic acid molecule encodes a (a) a heavy chain variable region comprising the amino acid sequence of FIG. 27 (SEQ ID NO: 99), or a variant of that sequence having 1, 2 or 3 amino acid substitutions; and/or
(b) a light chain variable region comprising the amino acid sequence of FIG. 27 (SEQ ID NO: 100), or a variant of that sequence having 1, 2 or 3 amino acid substitutions.

In another embodiment, the nucleic acid molecule encodes a variable region of a humanized antibody of the 12H3 parental mouse antibody. The variable region is selected from the variable regions of the antibodies 12H3_VL1VH1; the 12H3_VL1VH2; the 12H3_VL1VH3; the 12H3_VL2VH1; the 12H3_VL2VH2; or the 12H3_VL2VH3. The amino acid sequences of exemplary variable regions are depicted in SEQ ID NO: 67, 68, 69, 70, and 71.

In another embodiment the invention provides a nucleic acid molecule that encodes the amino acid sequence of a humanized 12H3 heavy chain variable region shown in SEQ ID NOs: 69, 70 and 71. In another embodiment the invention provides a nucleic acid molecule that encodes the amino acid sequence of a humanized 12H3 light chain variable region shown in SEQ ID NOs: 67 and 68.

In another embodiment the nucleic acid molecule encodes a variable region of a humanized antibody of the 20E5 parental mouse antibody. Exemplary variable regions are the variable regions of the antibodies 20E5_VL1VH1; the 20E5_VL1VH2; the 20E5_VL1VH3; the 20E5_VL2VH1; the 20E5_VL2VH2; and the 20E_VL2VH3. The amino acid sequences of the exemplary variable regions are depicted in SEQ ID NO: 62, 63, 64, 65, and 66.

In another embodiment, the invention provides a nucleic acid molecule that encodes the amino acid sequence of a humanized 20E5 heavy chain variable region shown in SEQ ID NOs: 64, 65 and 66. In another embodiment the invention provides a nucleic acid molecule that encodes the amino acid sequence of a humanized 20E5 light chain variable region shown in SEQ ID NOs: 62 or 63.

The invention also provides a nucleic acid molecule that encodes an antibody heavy or light chain or a humanized antibody heavy or light chain variable region comprising a humanized variable region selected from the humanized variable regions of antibodies 12H3_VL1VH1; the 12H3_VL1VH2; the 12H3_VL1VH3; the 12H3_VL2VH1; the 12H3_VL2VH2; the 12H3_VL2VH3; the 20E5_VL1VH1; the 20E5_VL1VH2; the 20E5_VL1VH3; the 20E5_VL2VH1; the 20E5_VL2VH2; or the 20E_VL2VH3 (as indicated in the previous paragraph and the examples).

In some embodiments, the nucleic acid molecule that codes for a humanized antibody heavy or light chains or a humanized antibody heavy or light chain variable regions is a nucleic acid molecule that codes for the humanized 12H3 antibody light chain of SEQ ID NO: 90 (minus the N-terminal signal sequence "MDMRVPAQLLGLLLLWFPGARC") or the humanized heavy chain of SEQ ID NO: 87 (minus the signal sequence "MELGLSWIFLLAILKGVQC".

In some embodiments, the nucleic acid molecule that codes for a humanized antibody heavy or light chain or a humanized antibody heavy or light chain variable region is a nucleic acid molecule that codes for the humanized 12H3 light chain of SEQ ID NO: 90 (minus the N-terminal signal sequence "MDMRVPAQLLGLLLLWFPGARC") or the humanized heavy chain of SEQ ID NO: 88 (minus the signal sequence "MELGLSWIFLLAILKGVQC".

In some embodiments, the nucleic acid molecule that codes for a humanized antibody heavy or light chain or a humanized antibody heavy or light chain variable region is a nucleic acid molecule that codes for the humanized 12H3 light chain of SEQ ID NO: 90 (minus the N-terminal signal sequence "MDMRVPAQLLGLLLLWFPGARC") or the heavy chain of SEQ ID NO: 89 (minus the signal sequence "MELGLSWIFLLAILKGVQC".

In some embodiments, the nucleic acid molecule that codes for a humanized antibody heavy or light chain or a humanized antibody heavy or light chain variable region is a nucleic acid molecule that codes for the humanized 12H3 light chain of SEQ ID NO: 91 (minus the N-terminal signal sequence "MDMRVPAQLLGLLLLWFPGARC") or the heavy chain of SEQ ID NO: 87 (minus the signal sequence "MELGLSWIFLLAILKGVQC".

In some embodiments, the nucleic acid molecule that codes for a humanized antibody heavy or light chain or a humanized antibody heavy or light chain variable region is a nucleic acid molecule that codes for the humanized 12H3 light chain of SEQ ID NO: 91 (minus the N-terminal signal sequence "MDMRVPAQLLGLLLLWFPGARC") or the heavy chain of SEQ ID NO: 88 (minus the signal sequence "MELGLSWIFLLAILKGVQC".

In some embodiments, the nucleic acid molecule that codes for a humanized antibody heavy or light chain or a humanized antibody heavy or light chain variable region is a nucleic acid molecule that codes for the humanized 12H3 light chain of SEQ ID NO: 91 (minus the N-terminal signal sequence "MDMRVPAQLLGLLLLWFPGARC") or the heavy chain of SEQ ID NO: 89 (minus the signal sequence "MELGLSWIFLLAILKGVQC".

In some embodiments, the nucleic acid molecule that codes for a humanized antibody heavy or light chain or a humanized antibody heavy or light chain variable region is a nucleic acid molecule that codes for the humanized 20E5 light chain of SEQ ID NO: 85 (minus the N-terminal signal sequence "MEWSGVFMFLLSVTAGVHS") or the heavy chain of SEQ ID NO: 82 (minus the signal sequence "MEWSGVFMFLLSVTAGVHS".

In some embodiments, the nucleic acid molecule that codes for a humanized antibody heavy or light chain or a humanized antibody heavy or light chain variable region is a nucleic acid molecule that codes for the humanized 20E5 light chain of SEQ ID NO: 85 (minus the N-terminal signal sequence "MEWSGVFMFLLSVTAGVHS") or the heavy chain of SEQ ID NO: 83 (minus the signal sequence "MEWSGVFMFLLSVTAGVHS".

In some embodiments, the nucleic acid molecule that codes for a humanized antibody heavy or light chain or a humanized antibody heavy or light chain variable region is a nucleic acid molecule that codes for the humanized 20E5 light chain of SEQ ID NO: 85 (minus the N-terminal signal sequence "MEWSGVFMFLLSVTAGVHS") or the heavy chain of SEQ ID NO: 84 (minus the signal sequence "MEWSGVFMFLLSVTAGVHS".

In some embodiments, the nucleic acid molecule that codes for a humanized antibody heavy or light chain or a humanized antibody heavy or light chain variable region is a nucleic acid molecule that codes for the humanized 20E5 light chain of SEQ ID NO: 86 (minus the N-terminal signal sequence "MEWSGVFMFLLSVTAGVHS") or the heavy chain of SEQ ID NO: 82 (minus the signal sequence "MEWSGVFMFLLSVTAGVHS".

In some embodiments, the nucleic acid molecule that codes for a humanized antibody heavy or light chain or a humanized antibody heavy or light chain variable region is a nucleic acid molecule that codes for the humanized 20E5 light chain of SEQ ID NO: 86 (minus the N-terminal signal sequence "MEWSGVFMFLLSVTAGVHS") or the heavy chain of SEQ ID NO: 83 (minus the signal sequence "MEWSGVFMFLLSVTAGVHS".

In some embodiments, the nucleic acid molecule that codes for a humanized heavy or light chain or a humanized antibody heavy or light chain variable region antibody is a nucleic acid molecule that codes for the humanized 20E5 light chain of SEQ ID NO: 86 (minus the N-terminal signal sequence "MEWSGVFMFLLSVTAGVHS") or the heavy chain of SEQ ID NO: 84 (minus the signal sequence "MEWSGVFMFLLSVTAGVHS".

Nucleic acid molecules that encode the amino acid sequences depicted in SEQ ID NO: 62-71 and/or SEQ ID NO: 82-91 are the nucleic acid molecules having a sequence as shown in SEQ ID NO: 72-81.

The nucleic acid sequence shown in SEQ ID NO: 72 codes for the amino acid sequence shown in SEQ ID NO: 82.

Nucleic acids 58-414 of SEQ ID NO: 72 codes for the amino acid sequence shown in SEQ ID NO: 64.

The nucleic acid sequence depicted in SEQ ID NO: 73 codes for the amino acid sequence shown in SEQ ID NO: 83. Nucleic acids 58-414 of SEQ ID NO: 73 codes for the amino acid sequence shown in SEQ ID NO: 65.

The nucleic acid sequence depicted in SEQ ID NO: 74 codes for the amino acid sequence shown in SEQ ID NO: 84. Nucleic acids 58-414 of SEQ ID NO: 74 codes for the amino acid sequence shown in SEQ ID NO: 66.

The nucleic acid sequence depicted in SEQ ID NO: 75 codes for the amino acid sequences shown in SEQ ID NO: 85. Nucleic acids 58-381 of SEQ ID NO: 75 codes for the amino acid sequence shown in SEQ ID NO: 62.

The nucleic acid sequence depicted in SEQ ID NO: 76 codes for the amino acid sequence shown in SEQ ID NO: 86. Nucleic acids 58-381 of SEQ ID NO: 76 codes for the amino acid sequence shown in SEQ ID NO: 63.

The nucleic acid sequence depicted in SEQ ID NO: 77 codes for the amino acid sequence shown in SEQ ID NO: 87. Nucleic acids 58-420 of SEQ ID NO: 77 codes for the amino acid sequence shown in SEQ ID NO: 69.

The nucleic acid sequence depicted in SEQ ID NO: 78 codes for the amino acid sequence shown in SEQ ID NO: 88. Nucleic acids 58-420 of SEQ ID NO: 78 codes for the amino acid sequence shown in SEQ ID NO: 70.

The nucleic acid sequence depicted in SEQ ID NO: 79 codes for the amino acid sequence shown in SEQ ID NO: 89. Nucleic acids 58-420 of SEQ ID NO: 79 codes for the amino acid sequence shown in SEQ ID NO: 71.

The nucleic acid sequence depicted in SEQ ID NO: 80 codes for the amino acid sequence shown in SEQ ID NO: 90. Nucleic acids 67-390 of SEQ ID NO: 80 codes for the amino acid sequence shown in SEQ ID NO: 67.

The nucleic acid sequence depicted in SEQ ID NO: 81 codes for the amino acid sequence shown in SEQ ID NO: 91. Nucleic acids 67-390 of SEQ ID NO: 81 codes for the amino acid sequence shown in SEQ ID NO: 68.

Some embodiments of the invention provide a nucleic acid molecule comprising the nucleic acid sequence depicted in SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, and/or SEQ ID NO: 81. In a preferred embodiment the nucleic acid molecule comprises the sequence without the nucleic acid sequence encoding the signal peptide. This is because many different signal peptides can be used. The invention thus provides a nucleic acid molecule comprising the nucleic acid sequence depicted in SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, and/or SEQ ID NO: 81, wherein the nucleic acid sequence encoding the signal peptide is absent or replaced by a nucleic acid sequence encoding a different signal peptide suitable for directing excretion of the encoded polypeptide.

In some embodiments, the invention provides a nucleic acid molecule comprising
nucleic acid residues 58-414 of SEQ ID NO: 72;
nucleic acid residues 58-414 of SEQ ID NO: 73;
nucleic acid residues 58-414 of SEQ ID NO: 74;
nucleic acid residues 58-381 of SEQ ID NO: 75;
nucleic acid residues 58-381 of SEQ ID NO: 76;
nucleic acid residues 58-420 of SEQ ID NO: 77;
nucleic acid residues 58-420 of SEQ ID NO: 78;
nucleic acid residues 58-420 of SEQ ID NO: 79;
nucleic acid residues 67-390 of SEQ ID NO: 80; or
nucleic acid residues 67-390 of SEQ ID NO: 81.

In some embodiments, the invention provides a nucleic acid molecule encoding the heavy chain variable region comprising the amino acid sequence of SEQ ID NOs: 101-133 or 146-148.

The invention further provides a gene delivery vehicle or vector comprising a nucleic acid according to the invention.

Further provided is an isolated or recombinant cell, or in vitro cell culture cell comprising a nucleic acid or vector according to the invention. The cell is preferably a host cell as defined herein. In some embodiments, the cell is a cell commonly used for the production of antibodies, such as a CHO cell, a CHO-K1 SV cell (Lonza Biologics, Walkersville, Md.), a CHO-K1 cell (ATCC CRL-61), aNSO cell (European Collection of Cell Cultures (ECACC), Salisbury, Wiltshire, UK, ECACC N. 85110503), a SP2/0 cell (American Type Culture Collection (ATCC), Manassas, Va., CRL-1581) a HEK 293-F cell, a PER.C6 cell, a FO cell (ATCC CRL-1646) an Ag653 cell (ATCC CRL-1580), or a hybridoma. In another embodiment the cell is an insect cell.

The invention further provides a method for producing a binding molecule characterised in that a binding molecule according to the claims or an antibody according to claims is produced. The produced antibody is collected from the cell culture, the cell culture supernatant/medium or a combination thereof. The collected antibody is purified and packaged into a container, preferably a storage or shipping container.

The invention further provides a binding molecule or an antibody according to the invention for use in the treatment of an individual in need of enhancement of an immune response.

Also provided is a binding molecule or an antibody according to the invention for use in preventing or treating cancer in an individual in need thereof.

Further provided is a binding molecule or an antibody according to the invention for use in the treatment of an individual suffering from or at risk of suffering from a chronic viral and/or intracellular bacterial infection.

The invention further provides a pharmaceutical composition comprising a binding molecule or an antibody according to the invention, and a pharmaceutically acceptable carrier.

The present invention provides isolated binding molecules that bind to the human CD134, including anti-CD134 antibodies, antigen-binding fragments of the anti-CD134 antibodies, and derivatives of the anti-CD134 antibodies. The binding molecules are characterized by at least one of the following functional properties: (a) bind to the human CD134 with a $K_d$ of $1\times10^{-6}$ M or less and (b) do not prevent human CD134 (OX40) receptor binding to OX40 ligand (OX40L); (c) have agonist activity on the human CD134 on T-effector cells and/or antagonistic activity on the human CD134 on T-regulatory cells; (d) do not bind to CD40 receptor at concentration up to 500 nM; (e) do not bind to CD137 receptor at concentrations up to 500 nM; (f) do not bind to CD271 receptor at concentrations up to 500 nM; (g) are capable of enhancing IL-2 production by isolated human T cells; (h) are capable of enhancing immune response; (i) are capable of inhibiting tumour cell growth; and (j) have therapeutic effect on a cancer. In some embodiments the binding molecule binds to the human CD134 with a $K_d$ of $1\times10^{-7}$ M or less, or $1\times10^{-8}$ M or less, or $5\times1\times10^{-9}$ M or less.

Antibodies and other binding molecules of the invention may be prepared by conventional techniques and then screened in order to identify and obtain binding molecules that do not prevent binding of OX40L to CD134. For example, binding molecules that bind CD134 even when the CD134 has been exposed to a saturating concentration of OX40L may be selected.

Some embodiments of the present invention provide a mouse, human or humanized antibody that binds to the human CD134. In some embodiments, the mouse, human or humanized antibody is a monoclonal antibody that specifically binds to the human CD134 with a $K_d$ of 100 nM or less or 10 nM or less, and/or has agonist activity on human CD134 resulting in stimulation of T-effector cells and/or suppression of T-regulatory cells. An exemplary such antibody is the monoclonal antibody clone 12H3. The amino acid sequence of the whole heavy chain variable region and the amino acid sequences of the three CDRs of the variable region of the heavy chain (VH) of antibody clone 12H3 are shown in SEQ ID NOs: 12 and 14-16, respectively. The amino acid sequence of the whole light chain variable region and the amino acid sequences of the three CDRs of the variable region of the light chain (VL) of antibody clone 12H3 are shown in SEQ ID NOs: 13 and 17-19, respectively. Another exemplary antibody is the monoclonal antibody clone 20E5. The amino acid sequence of the whole heavy chain variable region and the amino acid sequences of the three CDRs of the variable region of the heavy chain (VH) of antibody clone 20E5 are shown in SEQ ID NOs: 4 and 6-8, respectively. The amino acid sequence of the whole light chain variable region and the amino acid sequences of the three CDRs of the variable region of the light chain (VL) of antibody clone 20E5 are shown in SEQ ID NOs: 5 and 9-11, respectively. Yet other exemplary antibodies are humanized antibodies 12H3_VL1VH1, 12H3_VL1VH2, 12H3_VL1VH3, 12H3_VL2VH1, 12H3_VL2VH2, 12H3_VL2VH3 and humanized antibodies 20E5_VL1VH1, 20E5_VL1VH2, 20E5_VL1VH3, 20E5_VL2VH1, 20E5_VL2VH2, 20E5_VL2VH3, and optimized variants of those comprising heavy chain variable regions as described in Example 14. These antibodies comprise variable region sequences of SEQ ID NO: 67 (12H3_VL1), SEQ ID NO: 68 (12H3_VL2), SEQ ID NO: 69 (12H3_VH1), SEQ ID NO: 70 (12H3_VH2), SEQ ID NO: 71 (12H3_VH3), SEQ ID NO: 62 (20E5_VL1), SEQ ID NO: 63 (20E5_VL2), SEQ ID NO: 64 (20E5_VH1), SEQ ID NO: 65 (20E5_VH2), SEQ ID NO: 66 (20E5_VH3), and variable regions shown in Tables 6 and 9 having the amino acid sequence shown in SEQ ID NOs: 101-133 and 146-151.

The invention also provides antibodies comprising a humanized variable region selected from the humanized variable regions of antibodies 12H3_VL1VH1; the 12H3_VL1VH2; the 12H3_VL1VH3; the 12H3_VL2VH1; the 12H3_VL2VH2; the 12H3_VL2VH3; the 20E5_VL1VH1; the 20E5_VL1VH2; the 20E5_VL1VH3; the 20E5_VL2VH1; the 20E5_VL2VH2; or the 20E_VL2VH3 (as indicated in the previous paragraph and the examples), or heavy chain variable regions of SEQ ID NOs: 101-133 and 146-151.

In some embodiments, the humanized antibody is the humanized 12H3 antibody comprising the light chain of SEQ ID NO: 90 (minus the N-terminal signal sequence "MDMRVPAQLLGLLLLWFPGARC") and the heavy chain of SEQ ID NO: 87 (minus the signal sequence "MELGLSWIFLLAILKGVQC".

In some embodiments, the humanized antibody is the humanized 12H3 antibody comprising the light chain of SEQ ID NO: 90 (minus the N-terminal signal sequence "MDMRVPAQLLGLLLLWFPGARC") and the heavy chain of SEQ ID NO: 88 (minus the signal sequence "MELGLSWIFLLAILKGVQC".

In some embodiments, the humanized antibody is the humanized 12H3 antibody comprising the light chain of SEQ ID NO: 90 (minus the N-terminal signal sequence "MDMRVPAQLLGLLLLWFPGARC") and the heavy chain of SEQ ID NO: 89 (minus the signal sequence "MELGLSWIFLLAILKGVQC".

In some embodiments, the humanized antibody is the humanized 12H3 antibody comprising the light chain of SEQ ID NO: 91 (minus the N-terminal signal sequence "MDMRVPAQLLGLLLLWFPGARC") and the heavy chain of SEQ ID NO: 87 (minus the signal sequence "MELGLSWIFLLAILKGVQC".

In some embodiments, the humanized antibody is the humanized 12H3 antibody comprising the light chain of SEQ ID NO: 91 (minus the N-terminal signal sequence "MDMRVPAQLLGLLLLWFPGARC") and the heavy chain of SEQ ID NO: 88 (minus the signal sequence "MELGLSWIFLLAILKGVQC".

In some embodiments, the humanized antibody is the humanized 12H3 antibody comprising the light chain of SEQ ID NO: 91 (minus the N-terminal signal sequence "MDMRVPAQLLGLLLLWFPGARC") and the heavy chain of SEQ ID NO: 89 (minus the signal sequence "MELGLSWIFLLAILKGVQC".

In some embodiments, the humanized antibody is the humanized 20E5 antibody comprising the light chain of SEQ ID NO: 85 (minus the N-terminal signal sequence "MEWSGVFMFLLSVTAGVHS") and the heavy chain of SEQ ID NO: 82 (minus the signal sequence "MEWSGVFMFLLSVTAGVHS".

In some embodiments, the humanized antibody is the humanized 20E5 antibody comprising the light chain of SEQ ID NO: 85 (minus the N-terminal signal sequence "MEWSGVFMFLLSVTAGVHS") and the heavy chain of SEQ ID NO: 83 (minus the signal sequence "MEWSGVFMFLLSVTAGVHS".

In some embodiments the humanized antibody is the humanized 20E5 antibody comprising the light chain of SEQ ID NO: 85 (minus the N-terminal signal sequence "MEWSGVFMFLLSVTAGVHS") and the heavy chain of SEQ ID NO: 84 (minus the signal sequence "MEWSGVFMFLLSVTAGVHS".

In some embodiments, the humanized antibody is the humanized 20E5 antibody comprising the light chain of SEQ ID NO: 86 (minus the N-terminal signal sequence "MEWSGVFMFLLSVTAGVHS") and the heavy chain of SEQ ID NO: 82 (minus the signal sequence "MEWSGVFMFLLSVTAGVHS".

In some embodiments, the humanized antibody is the humanized 20E5 antibody comprising the light chain of SEQ ID NO: 86 (minus the N-terminal signal sequence "MEWSGVFMFLLSVTAGVHS") and the heavy chain of SEQ ID NO: 83 (minus the signal sequence "MEWSGVFMFLLSVTAGVHS".

In some embodiments, the humanized antibody is the humanized 20E5 antibody comprising the light chain of SEQ ID NO: 86 (minus the N-terminal signal sequence "MEWSGVFMFLLSVTAGVHS") and the heavy chain of SEQ ID NO: 84 (minus the signal sequence "MEWSGVFMFLLSVTAGVHS".

The antibodies of the invention can comprise one or more of these CDRs, or one or more of these CDRS with 1, 2 or 3 amino acid substitutions per CDR. The substitutions may be 'conservative' substitutions. Conservative substitutions providing functionally similar amino acids are well known in the art, and are described for example in Table 1 of WO 2010/019702, which is incorporated herein by reference.

Exemplary conservative substitutions are shown in Table 1. Amino acids are indicated using the well known three-letter code.

TABLE 1

| Original amino acid | Exemplary conservative substitution |
|---|---|
| Ala | Val, Ile, Leu, Gly, Ser |
| Arg | Lys, His, Glu, Asn |
| Asn | Glu, His, Lys, Arg |
| Asp | Glu, Asn |
| Cys | Ser, Ala |
| Gln | Asn |
| Glu | Asp, Glu |
| Gly | Pro, Ala |
| His | Asn, Gln, Lys, Arg |
| Ile | Leu, Val, Met, Ala, Phe, Nle |
| Leu | Nle, Ile, Val, Met, Ala, Phe |
| Lys | Arg, Glu, Asn, His |
| Met | Leu, Phe, Ile |
| Phe | Leu, Val, Ile, Ala, Tyr |
| Pro | Ala, Gly |
| Ser | Thr |
| Thr | Ser |
| Trp | Tyr, Phe |
| Tyr | Trp, Phe, Thr, Ser |
| Val | Ile, Met, leu, Phe, Ala, Nle |

Given that clone 12H3 and clone 20E5 bind to the human CD134, the VH and VL sequences of each of them can be "mixed and matched" with other anti-CD134 antibodies to create additional antibodies. The binding of such "mixed and matched" antibodies to the human CD134 can be tested using the binding assays known in the art, including an assay described in the Examples. In one case, when VH and VL regions are mixed and matched, a VH sequence from a particular VH/VL pairing is replaced with a structurally similar VH sequence. Likewise, in another case a VL sequence from a particular VH/VL pairing is replaced with a structurally similar VL sequence.

Molecules containing only one or two CDR regions (in some cases, even just a single CDR or a part thereof, especially CDR3) are capable of retaining the antigen-binding activity of the antibody from which the CDR(s) are derived. See, for example, Laune et al. JBC 1997; 272: 30937-44; Monnet et al. JBC 1999; 274:3789-96; Qiu et al. Nature Biotechnology 2007; 25: 921-9; Ladner et al. Nature Biotechnology 2007; 25: 875-7; Heap et al. J Gen Virol 2005; 86: 1791-1800; Nicaise et al. Protein Science 2004; 13: 1882-91; Vaughan and Sollazzo Combinatorial Chemistry & High Throughput Screening 2001; 4:417-430; Quiocho Nature 1993; 362: 293-4; Pessi et al. Nature 1993; 362: 367-9; Bianchi et al. J Mol Biol 1994; 236: 649-59; and Gao et al. J Biol Chem 1994; 269: 32389-93.

Accordingly, one embodiment of the present invention is an isolated anti-human CD134 antibody that comprises: (a) a heavy chain variable region comprising the amino acid sequence of SEQ ID NO: 12; (b) a light chain variable region comprising the amino acid sequence of SEQ ID NO: 13.

In a further embodiment according to the invention is provided an isolated CD134 binding molecule that comprises: (a) a heavy chain CDR1 comprising the amino acid sequence of SEQ ID NO: 14; and/or (b) a heavy chain CDR2 comprising the amino acid sequence of SEQ ID NO: 15; and/or (c) heavy chain CDR3 comprising the amino acid sequence of SEQ ID NO: 16.

In a further embodiment according to the invention is provided an isolated CD134 binding molecule that comprises (a) a light chain CDR1 comprising the amino acid sequence of SEQ ID NO: 17; and/or (b) a light chain CDR2 comprising the amino acid sequence of SEQ ID NO: 18; and/or (c) a light chain CDR3 comprising the amino acid sequence of SEQ ID NO: 19.

Accordingly, one embodiment of the present invention is an isolated anti-human CD134 antibody that comprises: (a) a heavy chain variable region comprising the amino acid sequence of SEQ ID NO: 4; (b) a light chain variable region comprising the amino acid sequence of SEQ ID NO: 5.

In a further embodiment according to the invention is provided an isolated CD134 binding molecule that comprises: (a) a heavy chain CDR1 comprising the amino acid sequence of SEQ ID NO: 6; and/or (b) a heavy chain CDR2 comprising the amino acid sequence of SEQ ID NO: 7; and/or (c) heavy chain CDR3 comprising the amino acid sequence of SEQ ID NO: 8.

In a further embodiment according to the invention is provided an isolated CD134 binding molecule that comprises (a) a light chain CDR1 comprising the amino acid sequence of SEQ ID NO: 9; and/or (b) a light chain CDR2 comprising the amino acid sequence of SEQ ID NO: 10; and/or (c) a light chain CDR3 comprising the amino acid sequence of SEQ ID NO: 11.

Given that clone 12H3 and clone 20E5 bind to the human CD134 and that antigen-binding specificity is provided primarily by the CDR1, CDR2, and CDR3 regions, the VH CDR1, CDR2, and CDR3 sequences and VL CDR1, CDR2, and CDR3 sequences can be "mixed and matched" to create additional anti-CD134 antibodies. For example, CDRs from different anti-CD134 antibodies can be mixed and matched, although each antibody will typically contain a VH CDR1, CDR2, and CDR3 and a VL CDR1, CDR2, and CDR3. The binding of such "mixed and matched" antibodies to the CD134 can be tested using the binding assays described above and in the Examples (e.g., ELISAs, Biacore analysis). In one case, when VH CDR sequences are mixed and matched, the CDR1, CDR2 and/or CDR3 sequence from a particular VH sequence is replaced with structurally similar CDR sequence(s). Likewise, when VL CDR sequences are mixed and matched, the CDR1, CDR2 and/or CDR3 sequence from a particular VL sequence typically is replaced with a structurally similar CDR sequence(s). It will be readily apparent to an ordinarily skilled artisan that novel VH and VL sequences can be created by replacing one or more VH and/or VL CDR region sequences with structurally similar sequences from the CDR sequences disclosed herein.

The class (e.g., IgG, IgM, IgE, IgA, or IgD) and subclass (e.g., IgG1, IgG2, IgG3, or IgG4) of the anti-CD134 antibodies may be determined by any suitable method such as by ELISA or Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies. The anti-CD134 antibodies can be an IgG, an IgM, an IgE, an IgA, or an IgD molecule. For example, the anti-CD134 antibodies can be an IgG that is an IgG1, IgG2, IgG3, or an IgG4 subclass. Thus, another aspect of the invention provides a method for converting the class or subclass of an anti-CD134 antibody to another class or subclass.

In some embodiments, the anti-CD134 antibody is of IgG4 isotype. The binding molecules according to an embodiment of the invention include monoclonal antibodies, fragments thereof, peptides and other chemical entities. Monoclonal antibodies can be made by the conventional method of immunization of a mammal, followed by isolation of plasma B cells producing the monoclonal antibodies of interest and fusion with a myeloma cell.

In various embodiments, instead of being an actual antibody, the binding moiety may be an antibody mimic (for example, based upon a non-antibody scaffold), an RNA aptamer, a small molecule or a CovX-body.

It will be appreciated that antibody mimics (for example, non-antibody scaffold structures that have a high degree of stability yet allow variability to be introduced at certain positions) may be used to create molecular libraries from which binding moieties can be derived. Those skilled in the arts of biochemistry will be familiar with many such molecules. Such molecules may be used as a binding moiety in the agent of the present invention.

Exemplary antibody mimics are discussed in Skerra et al. (2007, Curr. Opin. Biotech., 18: 295-304) and include: affibodies (also called Trinectins; Nygren et al., 2008, FEBS J, 275, 2668-2676); CTLDs (also called Tetranectins; Thogersen et al., Innovations Pharmac. Technol. (2006), 27-30; adnectins (also called monobodies; Koide et al., Meth. Mol. Biol., 352 (2007), 95-109); anticalins (Schlehuber et al., Drug Discovery Today (2005), 10, 23-33); DARPins (ankyrins; Binz et al., Nat. Biotechnol. (2004), 22, 575-582); avimers (Silverman et al., Nat. Biotechnol. (2005), 23, 1556-1561); microbodies (Krause et al., FEBS J, (2007), 274, 86-95); peptide aptamers (Borghouts et al., Expert. Opin. Biol. Ther. (2005), 5, 783-797); Kunitz domains (Attucci et al., J. Pharmacol. Exp. Ther. (2006) 318, 803-809); affilins (Hey et al., Trends. Biotechnol. (2005), 23, 514-522).

Accordingly, it is preferred that the antibody mimic is selected from the group comprising or consisting of affibodies, tetranectins (CTLDs), adnectins (monobodies), anticalins, DARPins (ankyrins), avimers, iMabs, microbodies, peptide aptamers, Kunitz domains, aptamers and affilins.

By "small molecule" is meant a low molecular weight organic compound of 900 Daltons or less. Although large biopolymers such as nucleic acids, proteins, and polysaccharides (such as starch or cellulose) are not included as "small molecules", their constituent monomers (ribo- or deoxyribonucleotides, amino acids, and monosaccharides, respectively) and oligomers (i.e. short polymers such as dinucleotides, peptides such as the antioxidant glutathione, and disaccharides such as sucrose) are included. The production of small molecules is described in Mayes & Whitcombe, 2005, Adv. Drug Deliv. Rev. 57:1742-78 and Root-Bernstein & Dillon, 2008, Curr. Pharm. Des. 14:55-62.

CovX-Bodies are created by covalently joining a pharmacophore via a linker to the binding site of a specially-designed antibody, effectively reprogramming the antibody (Tryder et al., 2007, Bioorg. Med. Chem. Lett., 17:501-6). The result is a new class of chemical entities that is formed where each component contributes desirable traits to the intact CovX-Body—in particular, the entity has the biologic actions of the peptide and the extended half-life of the antibody.

Human antibodies can be made by several different methods, including by use of human immunoglobulin expression libraries (Stratagene Corp., La Jolla, Calif.; Cambridge Antibody Technology Ltd., London, England) to produce fragments of human antibodies (VH, VL, Fv, Fd, Fab, or (Fab')2), and use of these fragments to construct whole human antibodies by fusion of the appropriate portion thereto, using techniques similar to those for producing chimeric antibodies. For example, human antibodies may be isolated from phage display libraries expressing antibody heavy and light chain variable regions as fusion proteins with bacteriophage pIX coat protein as described in Shi et al (2010) J. Mol. Biol. 397:385-96 and PCT Intl. Publ. No. WO09/085462). Human antibodies can also be produced in transgenic mice with a human immunoglobulin genome. Such mice are available from e.g. Abgenix, Inc., Fremont, Regeneron (http://_www_regeneroncom), Harbour Antibodies (http://_www_harbourantibodies_com), Open Monoclonal Technology, Inc. (OMT) (http://_www_omtinc_net), KyMab (http://_www_kymab_com), Trianni (http://_www.trianni_com) and Ablexis (http:_//_www_ablexis.com). In addition to connecting the heavy and light chain Fv regions to form a single chain peptide, Fab can be constructed and expressed by similar means (M. J. Evans et al. J Immunol Meth 1995; 184: 123-138).

Deimmunized antibodies are antibodies in which potentially immunogenic T cell epitopes have been eliminated, as described in International Patent Application PCT/GB98/01473. Therefore, immunogenicity in humans is expected to be eliminated or substantially reduced when they are applied in vivo. The immunoglobulin-based binding molecules of the invention may have their immunogenic T cell epitopes (if present) eliminated by means of such methods.

All of the wholly and partially human antibodies described above are less immunogenic than wholly murine or non-human-derived antibodies, as are the fragments and single chain antibodies. All these molecules (or derivatives thereof) are therefore less likely to evoke an immune or allergic response. Consequently, they are better suited for in vivo administration in humans than wholly non-human antibodies, especially when repeated or long-term administration is necessary.

Bispecific antibodies can be used as cross-linking agents between human CD134 of the same human target cell, or human CD134 on two different human target cells. Such bispecific antibodies have specificity for each of two different epitopes on human CD134. These antibodies and the method of making them are described in U.S. Pat. No. 5,534,254 (Creative Biomolecules, Inc.). Different embodiments of bispecific antibodies described in the patent include linking single chain Fv with peptide couplers, including Ser-Cys, $(Gly)_4$-Cys, $(His)_6$-$(Gly)_4$-Cys, chelating agents, and chemical or disulfide couplings including bismaleimidohexane and bismaleimidocaproyl.

The VL and/or the VH regions of the antibodies of the invention can be engineered into other embodiments of bispecific full length antibodies, where each antibody arm binds a distinct antigen or epitope. Such bispecific antibodies may be made for example by modulating the CH3 interactions between the two antibodies heavy chains to form bispecific antibodies using technologies such as those described in U.S. Pat. No. 7,695,936; Int. Pat. Publ. No. WO2004/111233; U.S. Pat. Publ. No. US2010/0015133; U.S. Pat. Publ. No. US2007/0287170; Int. Pat. Publ. No. WO2008/119353; U.S. Pat. Publ. No. US2009/0182127; U.S. Pat. Publ. No. US2010/0286374; U.S. Pat. Publ. No. US2011/0123532; Int. Pat. Publ. No. WO2011/131746; Int. Pat. Publ. No. WO2011/143545; or U.S. Pat. Publ. No. US2012/0149876. Additional bispecific structures into which the VL and/or the VH regions of the antibodies of the invention can be incorporated are for example Dual Variable Domain Immunoglobulins (Int. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441).

Non-antibody molecules can be isolated or screened from compound libraries by conventional means. An automated system for generating and screening a compound library is described in U.S. Pat. Nos. 5,901,069 and 5,463,564. A more focused approach involves three-dimensional modelling of the binding site, and then making a family of molecules which fit the model. These are then screened for those with optimal binding characteristics.

Another approach is to generate recombinant peptide libraries, and then screen them for those which bind to the epitope of human CD134 of interest. See, for example, U.S. Pat. No. 5,723,322. This epitope is the same as that bound by the monoclonal antibodies described in the examples below. Molecules can be generated or isolated with relative ease in accordance with techniques well known in the art once the epitope is known.

A further embodiment provides derivatives of any of the anti-CD134 antibodies as described above. In one particular aspect, the antibody derivative is derived from modifications of the amino acid sequences of clone 12H3 and/or clone 20E5. Amino acid sequences of any regions of the antibody chains may be modified, such as framework regions, CDR regions, or constant regions. The modifications can be introduced by standard techniques known in the art, such as site-directed mutagenesis and random PCR-mediated mutagenesis, and may comprise natural as well as non-natural amino acids. Types of modifications include insertions, deletions, substitutions, or combinations thereof, of one or more amino acids of an anti-CD134 antibody. In some embodiments, the antibody derivative comprises 1, 2, 3, or 4 amino acid substitutions in the heavy chain CDRs and/or one amino acid substitution in the light chain CDRs. In some embodiments, a derivative of an anti-CD134 antibody comprises one or more amino acid substitutions relative to the germ line amino acid sequence of the human gene. In a particular embodiment, one or more of those substitutions from germ line is in the CDR2 region of the heavy chain. In another particular embodiment, the amino acid substitutions relative to the germline are at one or more of the same positions as the substitutions relative to germ line in antibodies clone 12H3 and clone 20E5. In another embodiment, the amino acid substitution is to change one or more cysteines in an antibody to another residue, such as, without limitation, alanine or serine. The cysteine may be a canonical or non-canonical cysteine. The substitution can be made in a CDR or framework region of a variable domain or in the constant domain of an antibody. Another type of amino acid substitution is to eliminate asparagine-glycine pairs, which form potential deamidation sites, by altering one or both of the residues. In still other embodiments, the amino acid substitution is a conservative amino acid substitution. In one embodiment, the antibody derivative has 1, 2, 3, or 4 conservative amino acid substitutions in the heavy chain CDR regions relative to the amino acid sequences of clone 12H3 and/or clone 20E5. Another type of modification of an anti-CD134 antibody is the alteration of the original glycosylation pattern of the antibody. The term "alteration" refers to deletion of one or more carbohydrate moieties found in the antibody, and/or adding one or more glycosylation sites that are not present in the antibody.

Glycosylation of antibodies is typically N-linked. N-linked refers to the attachment of the carbohydrate moiety to the side chain of an asparagine residue. Examples of other modifications include acylation, amidation, acetylation, cross-linking, cyclization, formylation, hydroxylation, iodination, methylation, myristoylation, disulfide bond formation, demethylation, formation of covalent cross-links, formation of cysteine, oxidation, phosphorylation, prenylation, pegylation, proteolytic processing and sulfation.

A further embodiment provides an antibody derivative that comprises an anti-CD134 antibody, or antigen-binding fragment thereof, as described herein, linked to an additional molecular entity. Examples of additional molecular entities include pharmaceutical agents, peptides or proteins, and detection agents or labels. Specific examples of pharmaceutical agents that may be linked to an anti-CD134 antibody include cytotoxic agents or other cancer therapeutic agents, and radioactive isotopes. Specific examples of peptides or proteins that may be linked to an anti-CD134 antibody include antibodies, which may be the same anti-CD134 antibody or a different antibody. Specific examples of detection agents or labels that may be linked to an anti-CD134 antibody include (1) fluorescent compounds, such as fluorescein, fluorescein isothiocyanate, phycoerythrin, rhodamine, 5-dimethylamine-1-naphthalene-sulfonyl chloride and lanthanide phosphors; (2) enzymes, such as horseradish peroxidase, alkaline phosphatase, luciferase, and glucose oxidase; (3) biotin; (4) a predetermined polypeptide epitope recognized by a secondary reporter, such as leucine zipper pair sequences, metal binding domains, epitope tags and binding sites for secondary antibodies. A further embodiment provides an antibody derivative which is a multimeric form of an anti-CD134 antibody, such as antibody dimers, trimers, or higher-order multimers of monomeric antibodies. Individual monomers within an antibody multimer may be identical or different, i.e., they may be heteromeric or homomeric antibody multimers. Multimerization of antibodies may be accomplished through natural aggregation. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. Suitable crosslinkers include those that are heterobifunctional, such as m-maleimidobenzoyl-N-hydroxysuccinimide ester, N-succinimidyl S-acethylthio-acetate and succinimidyl 4-(maleimidomethyl)cyclohexane-1-carboxylate) or homobifunctional (such as disuccinimidyl suberate). Such linkers are commercially available. Antibodies can also be made to multimerize through recombinant DNA techniques known in the art.

A yet further embodiment provides an antibody derivative which is a chimeric antibody, comprising an amino acid sequence of a anti-human CD134 antibody described herein above. In another example, all of the CDRs of the chimeric antibody are derived from anti-human CD134 antibodies. In another example, the CDRs from more than one anti-human CD134 antibody are combined in a chimeric antibody. Further, a chimeric antibody may comprise the framework regions derived from one anti-human CD134 antibody and one or more CDRs from one or more different human antibodies. Chimeric antibodies can be generated using conventional methods known in the art. In some particular embodiments, the chimeric antibody comprises one, two, or three CDRs from the heavy chain variable region or from the light chain variable region of an antibody selected from antibody clone 12H3 and/or clone 20E5.

Examples of other antibody derivatives provided by the present invention include single chain antibodies, diabodies, domain antibodies, nanobodies, and unibodies. In some embodiments, the monoclonal antibodies may be chimeric antibodies, humanized antibodies, human antibodies, deimmunized antibodies, bispecific antibodies, single-chain antibodies, fragments, including Fab, F(ab')2, Fv or other fragments which retain the antigen binding function of the parent antibody. Single chain antibodies ("ScFv") and the method of their construction are described in U.S. Pat. No. 4,946,778.

A "single-chain antibody" (scFv) consists of a single polypeptide chain comprising a VL domain linked to a VH domain wherein VL domain and VH domain are paired to form a monovalent molecule. Single chain antibody can be prepared according to method known in the art (see, for example, Bird et al., (1988) Science 242:423-426 and Huston et al., (1988) Proc. Natl. Acad. Sci. USA 85:5879-5883). A "diabody" consists of two chains, each chain comprising a heavy chain variable region connected to a light chain variable region on the same polypeptide chain connected by a short peptide linker, wherein the two regions on the same chain do not pair with each other but with complementary domains on the other chain to form a bispecific molecule. Methods of preparing diabodies are known in the art (See, e.g., Holliger P. et al., (1993) Proc. Natl. Acad. Sci. USA 90:6444-6448, and Poljak R. J. et al., (1994) Structure 2:1121-1123). Domain antibodies (dAbs) are small functional binding units of antibodies, corresponding to the variable regions of either the heavy or light chains of antibodies. Domain antibodies are well expressed in bacterial, yeast, and mammalian cell systems. Further details of domain antibodies and methods of production thereof are known in the art (see, for example, U.S. Pat. Nos. 6,291,158; 6,582,915; 6,593,081; WO04/003019 and WO03/002609). Nanobodies are derived from the heavy chains of an antibody. A nanobody typically comprises a single variable domain and two constant domains (CH2 and CH3) and retains antigen-binding capacity of the original antibody. Nanobodies can be prepared by methods known in the art (see e.g., U.S. Pat. Nos. 6,765,087, 6,838,254, WO 06/079372). Unibodies consist of one light chain and one heavy chain of an IgG4 antibody. Unibodies may be made by the removal of the hinge region of IgG4 antibodies. Further details of unibodies and methods of preparing them may be found in WO2007/059782.

In addition to the binding moiety, the molecules of the invention may further comprise a moiety for increasing the in vivo half-life of the molecule, such as but not limited to polyethylene glycol (PEG), human serum albumin, glycosylation groups, fatty acids and dextran. Such further moieties may be conjugated or otherwise combined with the binding moiety using methods well known in the art.

A further aspect of the invention provides a nucleic acid molecule encoding an amino acid sequence of a CD134-binding binding molecule according to the first aspect of the invention. The amino acid sequence encoded by the nucleic acid molecule may be any portion of an intact antibody, such as a CDR, a sequence comprising one, two, or three CDRs, or a variable region of a heavy chain or light chain, or may be a full-length heavy chain or light chain. In some embodiments, the nucleic acid molecule encodes an amino acid sequence that comprises (1) a CDR3 region, particularly a heavy chain CDR3 region, of antibodies clone 12H3 and/or clone 20E5; (2) a variable region of a heavy chain or variable region of a light chain of antibodies clone 12H3 and/or clone 20E5; or (3) a heavy chain or a light chain of antibodies clone 12H3 and/or clone 20E5. In other embodiments, the nucleic acid molecule encodes a polypeptide that comprises an amino acid sequence selected from the group consisting of SEQ ID NOs: 12, 13, 14, 15, 16, 17, 18 or 19, or from the group consisting of SEQ ID NOs: 4, 5, 6, 7, 8, 9, 10 or 11.

The nucleic acid molecules provided by the disclosure may be obtained from any source that produces a CD134 antibody in accordance with the invention. mRNA from anti-CD134 antibody-producing cells may be isolated by standard techniques, cloned and/or amplified using PCR and library construction techniques, and screened using standard protocols to obtain nucleic acid molecules encoding an amino acid sequence of an anti-CD134 antibody. The mRNA may be used to produce cDNA for use in the polymerase chain reaction (PCR) or cDNA cloning of antibody genes. In one embodiment, the nucleic acid molecule is obtained from a hybridoma that expresses an anti-CD134 antibody, as described above, preferably a hybridoma that has as one of its fusion partners a non-human transgenic animal cell that expresses human immunoglobulin genes. In another embodiment, the hybridoma is derived from a non-human, non-transgenic animal.

A nucleic acid molecule encoding the heavy chain of an anti-CD134 antibody may be constructed by fusing a nucleic acid molecule encoding the heavy variable region with a nucleic acid molecule encoding a constant region of a heavy chain. Similarly, a nucleic acid molecule encoding the light chain of an anti-CD134 antibody may be constructed by fusing a nucleic acid molecule encoding the light chain variable region with a nucleic acid molecule encoding a constant region of a light chain. The nucleic acid molecules encoding the VH and VL chain may be converted to full-length antibody genes by inserting them into expression vectors already encoding heavy chain constant and light chain constant regions, respectively, such that the VH segment is operatively linked to the heavy chain constant region (CH) segment(s) within the vector and the VL segment is operatively linked to the light chain constant region (CL) segment within the vector. Alternatively, the nucleic acid molecules encoding the VH or VL chains are converted into full-length antibody genes by linking, e.g., ligating, the nucleic acid molecule encoding a VH chain to a nucleic acid molecule encoding a CH chain using standard molecular biological techniques. The same may be achieved using nucleic acid molecules encoding the VL and the CL chains. Nucleic acid molecules encoding the full-length heavy and/or light chains may then be expressed from a cell into which they have been introduced and the anti-CD134 antibody isolated.

The nucleic acid molecules may be used to recombinantly express large quantities of anti-CD134 antibodies, as described below. The nucleic acid molecules may also be used to produce other binding molecules provided by the disclosure, such as chimeric antibodies, single chain antibodies, immunoadhesins, diabodies, mutated antibodies, bispecific antibodies, and antibody derivatives, as described elsewhere herein. In one embodiment, a nucleic acid molecule is used as probe or PCR primer for specific antibody sequences. For instance, a nucleic acid molecule probe may be used in diagnostic methods or a nucleic acid molecule PCR primer may be used to amplify regions of DNA that could be used, inter alia, to isolate nucleic acid sequences for use in producing variable regions of the anti-CD134 antibodies.

Once DNA molecules encoding the VH and VL segments of an anti-CD134 antibody are obtained, these DNA molecules can be further manipulated by recombinant DNA techniques, for example to convert the variable region genes to full-length antibody chain genes, to Fab fragment genes, to a scFv gene, or they can be incorporated into bispecific antibodies.

A further aspect of the invention provides a vector, which comprises a nucleic acid molecule described herein above. The nucleic acid molecule may encode a portion of a light chain or heavy chain (such as a CDR or a variable region), a full-length light or heavy chain, polypeptide that comprises a portion or full-length of a heavy or light chain, or an amino acid sequence of an antibody derivative or antigen-binding fragment.

An example of a suitable expression vector is one that encodes a functionally complete human CH or CL immunoglobulin sequence, with appropriate restriction sites engineered so that any VH or VL sequence can be inserted and expressed. The expression vector can encode a signal peptide that facilitates secretion of the amino acid sequence of the antibody chain from a host cell. The DNA encoding the amino acid sequence of an antibody chain may be cloned into the vector such that the signal peptide is linked in-frame to the amino terminus of the amino acid sequence of the antibody chain. The signal peptide can be an immunoglobulin signal peptide or a heterologous signal peptide (i.e., a signal peptide from a non-immunoglobulin protein). In addition to the nucleic acid sequence encoding an amino acid sequence of an anti-CD134 antibody (antibody VH, VL, full length heavy and/or full length light chain genes), the expression vectors carry regulatory sequences that control the expression of the antibody chain genes in a host cell. The design of the expression vector, including the selection of regulatory sequences, may depend on such factors as the choice of the host cell to be transformed, the level of expression of protein desired, and so forth. Regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters.

The host cell may be a mammalian, insect, plant, bacterial, or yeast cell. Examples of mammalian cell lines suitable as host cells include Chinese hamster ovary (CHO) cells, NS0 cells, PER-C6 cells, SP2/0 cells, HEK-293T cells, NIH-3T3 cells, HeLa cells, baby hamster kidney (BHK) cells, African green monkey kidney cells (COS), human hepatocellular carcinoma cells (e.g., Hep G2), human lung cells, A549 cells, and a number of other cell lines. Examples of insect cell lines include Sf9 or Sf21 cells.

Examples of plant host cells include *Nicotiana, Arabidopsis*, duckweed, corn, wheat, potato, and so forth. Bacterial host cells include *E. coli* and *Streptomyces* species.

Examples of yeast host cells include *Saccharomyces cerevisiae* and *Pichia pastoris*.

Amino acid sequences of a binding molecule expressed by different cell lines or in transgenic animals may have different glycosylation. However, all binding molecules encoded by the nucleic acid molecules provided herein, or comprising the amino acid sequences provided herein are part of the present invention, regardless of the glycosylation of the binding molecules.

Another aspect of the invention provides a method for producing a CD134-binding molecule as defined above using phage display. The method comprises (a) synthesizing a library of human antibodies on phage, (b) screening the library with the CD134 or a portion thereof, (c) isolating phage that binds the CD134 or a portion thereof, and (d) obtaining the antibody from the phage. One exemplary method for preparing the library of antibodies comprises the step of: (a) immunizing a non-human animal comprising human immunoglobulin loci with CD134 or an antigenic portion thereof to create an immune response; (b) extracting antibody-producing cells from the immunized animal; (c) isolating RNA encoding heavy and light chains of the anti-CD134 antibodies from the extracted cells; (d) reverse transcribing the RNA to produce cDNA; (e), amplifying the cDNA; and (f) inserting the cDNA into a phage display vector such that antibodies are expressed on the phage. Recombinant anti-human CD134 antibodies or antigen binding fragments thereof can be isolated by screening a recombinant combinatorial antibody library. The library may be a scFv phage display library, generated using human VL and VH cDNAs prepared from mRNA isolated from B cells. Methods for preparing and screening such libraries are known in the art. Kits for generating phage display libraries are commercially available.

In some embodiments of the invention is provided a composition, e.g., a pharmaceutical composition, containing one or a combination of binding molecules as described herein, and optionally a pharmaceutically acceptable carrier. The compositions can be prepared by conventional methods known in the art. In some embodiments, the composition comprises an anti-CD134 antibody or an antigen-binding fragment thereof. In a particular embodiment, the composition comprises antibody clone 12H3 and/or clone 20E5, or an antigen-binding fragment of either antibody. In still other embodiments, the composition comprises a derivative of antibody clone 12H3 and/or clone 20E5. In other embodiments, the pharmaceutical composition comprises a humanized antibody 12H3_VL1VH1, 12H3_VL1VH2, 12H3_VL1VH3, 12H3_VL2VH1, 12H3_VL2VH2, 12H3_VL2VH3, 20E5_VL1VH1, 20E5_VL1VH2, 20E5_VL1VH3, 20E5_VL2VH1, 20E5_VL2VH2 or 20E5_VL2VH3. In other embodiments, the pharmaceutical composition comprises a variant of the humanized antibodies described above, comprising the heavy chain variable regions of SEQ ID NOs: 101-133 or 146-151. The term "pharmaceutically acceptable carrier" refers to any inactive substance that is suitable for use in a formulation for the delivery of a binding molecule. A carrier may be an antiadherent, binder, coating, disintegrant, filler or diluent, preservative (such as antioxidant, antibacterial, or antifungal agent), sweetener, absorption delaying agent, wetting agent, emulsifying agent, buffer, and the like.

Non-peptide molecules of the invention could be administered orally, including by suspension, tablets and the like. Liquid formulations could be administered by inhalation of lyophilized or aerosolized microcapsules. Suppositories could also be used. Additional pharmaceutical vehicles could be used to control the duration of action of the molecules of the invention. The dosage and scheduling for the formulation, which is selected can be determined by standard procedures, well known in the art. Such procedures involve extrapolating an estimated dosing schedule from animal models, and then determining the optimal dosage in a human clinical dose ranging study.

The compositions may be in any suitable forms, such as liquid, semi-solid, and solid dosage forms. The various dosage forms of the compositions can be prepared by conventional techniques known in the art.

The relative amount of a binding molecule included in the composition will vary depending upon a number of factors, such as the desired release and pharmacodynamic characteristics, the specific binding molecule and carriers used and dosage form. The amount of a binding molecule in a single dosage form will generally be that amount which produces a therapeutic effect, but may also be a lesser amount. Generally, this amount will range from about 0.001 percent to about 99 percent, from about 0.1 percent to about 70 percent, or from about 1 percent to about 30 percent relative to the total weight of the dosage form.

In addition to the binding molecule, one or more additional therapeutic agents may be included in the composition or separately as part of the same treatment regime. Examples of the additional therapeutic agents are described herein below. The suitable amount of the additional therapeutic agent to be included in the composition can be readily selected by a person skilled in the art, and will vary depending on a number of factors, such as the particular agent and carriers used, dosage form, and desired release and pharmacodynamic characteristics. The amount of the additional therapeutic agent included in a single dosage form will generally be that amount of the agent which produces a therapeutic effect, but may be a lesser amount as well.

Binding molecules and pharmaceutical compositions comprising a binding molecule provided by the present disclosure are useful for therapeutic, diagnostic, or other purposes, such as enhancing an immune response, treating cancer, enhancing efficacy of other cancer therapy, or enhancing vaccine efficacy, and have a number of utilities, such as for use as medicaments or diagnostic agents. Thus, in preferred aspect, of the invention is provided methods of using the binding molecules or pharmaceutical compositions.

A further aspect of the invention provides a method for modulation of human CD134-mediated anti-tumour immune responses, including enhancement of human CD134 expressing human Teffs effector function and/or attenuation of human CD134 expressing human Tregs suppressive function, using binding molecules that bind to human CD134, including anti-human CD134 antibodies, which (1) circumvent the interaction of naturally occurring human OX40L with the human CD134 receptor and/or (2) do not block human CD134-mediated cell signalling after occupancy with its natural occurring human OX40L.

A further aspect of the invention provides a method for modulation of human CD134-mediated anti-tumour immune responses, including enhancement of human CD134 expressing human Teffs effector function and/or attenuation of human CD134 expressing human Tregs suppressive function, using binding molecules that bind to human CD134 described herein.

Another aspect of the invention provides a method of modulation of human CD134-mediated anti-tumour immune responses, whereby said method does not include binding molecules that bind to human CD134, including anti-human CD134 antibodies, such as human OX40L mimetics, which interact with human OX40L binding domain on the human CD134 receptor and/or block human OX40L-human CD134 cell signalling.

The present invention discloses binding molecules that bind to human CD134, including anti-human CD134 antibodies, for anti-tumour therapeutic purposes. The anti-human CD134 antibodies bind to the extracellular domain of human CD134. In some embodiments, the anti-human CD134 antibodies bind to non-OX40L-binding regions (i.e. the anti-human CD134 antibodies do not completely block the binding of human OX40L to human CD134) on the extracellular domain of human CD134 on activated human Teffs and human Tregs.

In one particular aspect, methods are provided for enhancing immune response in a mammal, comprising administering to the mammal a therapeutically effective amount of a binding molecule as described herein. In some embodiments, the binding molecule is an anti CD134 antibody or antigen-binding fragment thereof and the mammal is a human. In a further embodiment, the binding molecule is antibody clone 12H3 and/or clone 20E5, or an antigen-binding fragment of either antibody, of a humanized 12H3 or humanized 20E5 antibody. The term "enhancing immune response", means stimulating, evoking, increasing, improving, or augmenting any response of a mammal's immune system. The immune response may be a cellular response (i.e. cell-mediated, such as cytotoxic T lymphocyte mediated) or a humoral response (i.e. antibody mediated response), and may be a primary or secondary immune response. Examples of enhancement of immune response include increased CD4+ helper T cell activity and generation of cytolytic T cells. The enhancement of immune response can be assessed using a number of in vitro or in vivo measurements known to those skilled in the art, including, but not limited to, cytotoxic T lymphocyte assays, release of cytokines (for example IL-2 production), regression of tumours, survival of tumour bearing animals, antibody production, immune cell proliferation, expression of cell surface markers, and cytotoxicity. In one embodiment, the method enhances a cellular immune response, particularly a cytotoxic T cell response.

One aspect of the invention provides a binding molecule that binds to human CD134, wherein at or above the saturation concentration of said binding molecule, the effect on binding of OX40L to CD134 is reduced by not more than 70%, on human CD134 expressing T-cells, as measured by a fluorescence-based flow cytometric assay, as described in Example 2(f). More preferably, the effect on binding of OX40L to CD134 is reduced by not more than about 60%, or about 50%, or about 40%, or about 30%, or about 20%, or about 10% or less, or preferably no reduction in binding at all.

Another aspect of the invention provides a binding molecule wherein at a concentration of 70 nM of the binding molecule, the effect on binding of OX40L to CD134 is reduced by not more than 70% on human CD134 expressing T-cells, as measured by a fluorescence-based flow cytometric assay, as described in Example 2(f). More preferably, the effect on binding of OX40L to CD134 is reduced by not more than about 60%, or about 50%, or about 40%, or about 30%, or about 20%, or about 10% or less, or preferably no reduction in binding at all.

Another aspect of the invention provides a binding molecule that competes for human CD134 binding with an antibody comprising (1) a heavy chain variable region comprising the amino acid sequence of SEQ ID NO: 12 and (2) a light chain variable region comprising the amino acid sequence of SEQ ID NO: 13, as shown by cross-competition between an un-labelled said binding molecule and a fluorescent-labelled said antibody on PHA-stimulated human CD134-expressing T-lymphocytes, as measured by flow cytometry (further described in Example 2(e)). The binding of said antibody, at or above its saturation concentration, is reduced by at least about 50%, or about 60%, or about 70%, or about 80%, or about 90% or more, or is abolished, when assayed by cross-competition against said binding molecule.

Another aspect of the invention provides a binding molecule that competes for human CD134 binding with an antibody comprising (1) a heavy chain variable region comprising the amino acid sequence of SEQ ID NO: 4 and (2) a light chain variable region comprising the amino acid sequence of SEQ ID NO: 5, as shown by cross-competition between an un-labelled said binding molecule and a fluorescent-labelled said antibody on PHA-stimulated human CD134 expressing T-lymphocytes, as measured by flow cytometry (further described in Example 2(e)). The binding of said antibody, at or above its saturation concentration, is reduced by at least about 50%, or about 60%, or about 70%, or about 80%, or about 90% or more, or is abolished, when assayed by cross-competition against said binding molecule.

Another aspect of the invention provides a binding molecule that binds to human CD134, wherein the effect on binding of OX40L to CD134 on human CD134 expressing T-cells is reduced by not more than about 70%, or about 60%, or about 50%, or about 40%, or about 30%, or about 20%, or about 10% or less by the binding molecule, and wherein said binding molecule further does not impede the immunostimulatory and/or proliferative responses of human OX40L on human CD134 expressing T-effector cells.

Another aspect of the invention provides a binding molecule that binds to human CD134, wherein the binding molecule does not prevent human CD134 (OX40) receptor binding to OX40 ligand (OX40L) and wherein said binding molecule further does not impede the immunostimulatory and/or proliferative responses of human OX40L on human CD134 expressing T-effector cells.

Another aspect of the invention provides a binding molecule that binds to human CD134, wherein the effect on binding of OX40L to CD134 on human CD134 expressing T-cells is reduced by not more than about 70%, or about 60%, or about 50%, or about 40%, or about 30%, or about 20%, or about 10% or less by the binding molecule, and wherein said binding molecule enhances the immunostimulatory and/or proliferative responses of human OX40L on human CD134 expressing T-effector cells.

Another aspect of the invention provides a binding molecule that binds to human CD134, wherein the binding molecule does not prevent human CD134 (OX40) receptor binding to OX40 ligand (OX40L) and wherein said binding molecule enhances the immunostimulatory and/or proliferative responses of human OX40L on human CD134 expressing T-effector cells.

Another aspect of the invention provides a binding molecule that binds to human CD134, wherein the effect on binding of OX40L to CD134 on human CD134 expressing human T cells is reduced by not more than about 70%, or about 60%, or about 50%, or about 40%, or about 30%, or about 20%, or about 10% or less by the binding molecule, and wherein said binding molecule further does not impede suppressor function responses of human OX40L on human CD134 expressing T-regulatory cells.

Another aspect of the invention provides a binding molecule that binds to human CD134, wherein the binding molecule does not prevent human CD134 (OX40) receptor binding to OX40 ligand (OX40L) and wherein said binding molecule further does not impede suppressor function responses of human OX40L on human CD134 expressing T-regulatory cells.

Another aspect of the invention provides a binding molecule that binds to human CD134, wherein the effect on binding of OX40L to CD134 on human CD134 expressing human T cells is reduced by not more than about 70%, or about 60%, or about 50%, or about 40%, or about 30%, or about 20%, or about 10% or less by the binding molecule, and wherein said binding molecule enhances the suppressor function responses of human OX40L on human CD134 expressing T-regulatory cells.

Another aspect of the invention provides a binding molecule that binds to human CD134, wherein the binding molecule does not prevent human CD134 (OX40) receptor binding to OX40 ligand (OX40L) and wherein said binding molecule enhances the suppressor function responses of human OX40L on human CD134 expressing T-regulatory cells Another aspect of the invention provides a binding molecule that binds to human CD134, wherein the effect on binding of OX40L to CD134 on human CD134 expressing T-cells is reduced by not more than about 70%, or about 60%, or about 50%, or about 40%, or about 30%, or about 20%, or about 10% or less by the binding molecule, and wherein said binding molecule further does not impede the proliferative responses of human OX40L on human CD134 expressing T regulatory cells.

Another aspect of the invention provides a binding molecule that binds to human CD134, wherein the binding molecule does not inhibit or prevent human CD134 (OX40) receptor binding to OX40 ligand (OX40L) and wherein said binding molecule further does not impede the proliferative responses of human OX40L on human CD134 expressing T regulatory cells.

Another aspect of the invention provides a binding molecule that binds to human CD134, wherein the effect on binding of OX40L to CD134 on human CD134 expressing T-cells is reduced by not more than about 70%, or about 60%, or about 50%, or about 40%, or about 30%, or about 20%, or about 10% or less by the binding molecule, and wherein said binding molecule inhibits the proliferative responses of human OX40L on human CD134 expressing T-regulatory cells.

Another aspect of the invention provides a binding molecule that binds to human CD134, wherein the binding molecule does not inhibit or prevent human CD134 (OX40) receptor binding to OX40 ligand (OX40L) and wherein said binding molecule inhibits the proliferative responses of human OX40L on human CD134 expressing T regulatory cells.

A suitable method for measuring the simultaneous binding of OX40L and anti-CD134 antibody is described as follows. FITC fluorescent signal (geomean or mean fluorescent intensity (MFI)) of human OX40L binding on PHA-stimulated human CD134 expressing PBMCs in absence of anti-human CD134 antibody is set at 100%. PE fluorescent signal (MFI) of anti-human CD134 antibody binding on PHA-stimulated human CD134 expressing PBMCs in absence of human OX40L is set at 100%. Reduction of this FITC fluorescent signal and PE fluorescent signal when both human OX40L and anti-human CD134 antibody are added simultaneously to PHA-stimulated human CD134 expressing PBMCs preferably does not exceed about 70%, or about 60%, or about 50%, or about 40%, or about 30%, or about 20%, or about 10% or less.

A suitable method for measuring the lack of impediment on OX40L-mediated proliferative responses of Teffs is as follows. Tritiated thymidine or BrdU incorporation in human CD134 expressing Teffs after human OX40L treatment is set at 100%. Change (i.e. decrement or increment) of this tritiated thymidine or BrdU incorporation when both human OX40L and anti-human CD134 antibody are added simultaneously to activated (e.g., PHA-stimulated or anti-CD3/anti-CD28 beads-stimulated) human CD134 expressing Teffs preferably does not exceed about 30%, or about 20%, or about 10% or less.

A suitable method for measuring enhancement on OX40L-mediated proliferative responses of Teffs, is as follows. Tritiated thymidine or BrdU incorporation in human CD134 expressing Teffs after human OX40L treatment is set at 100%. Enhancement of this tritiated thymidine or BrdU incorporation when both human OX40L and anti-human CD134 antibody are added simultaneously to activated (e.g., PHA-stimulated or anti-CD3/anti-CD28 beads-stimulated) human CD134 expressing Teffs is preferably greater than about 30%, or about 40%, or about 50%, or about 60%, or about 70%, or higher.

A suitable method for measuring the lack of impediment on OX40L-mediated suppression function of Tregs is as follows. Tritiated thymidine or BrdU incorporation in human CD134 expressing Teffs, which are co-cultured with human CD134 expressing Tregs (e.g., Teff/Treg ratio=1:1), after human OX40L treatment is set at 100%. Change (i.e. decrement or increment) of this tritiated thymidine or BrdU incorporation when both human OX40L and anti-human CD134 antibody are added simultaneously to activated (e.g., PHA-stimulated or anti-CD3/anti-CD28 beads-stimulated) human CD134 expressing Teffs, which are co-cultured with human CD134 expressing Tregs (e.g., Teff/Treg ratio=1:1), preferably does not exceed about 30%, or about 20%, or about 10% or less.

A suitable method for measuring enhancement on OX40L-mediated suppression function of Tregs is as follows. Tritiated thymidine or BrdU incorporation in human CD134 expressing Teffs, which are co-cultured with human CD134 expressing Tregs (e.g., Teff/Treg ratio=1:1), after human OX40L treatment is set at 100%. Enhancement of this tritiated thymidine or BrdU incorporation when both human OX40L and anti-human CD134 antibody are added simultaneously to activated (e.g., PHA-stimulated or anti-CD3/anti-CD28 beads-stimulated) human CD134 expressing Teffs, which are co-cultured with human CD134 expressing Tregs (e.g., Teff/Treg ratio=1:1), is preferably greater than about 30%, or about 40%, or about 50%, or about 60%, or about 70%, or higher.

A suitable method for measuring the lack of impediment on OX40L-mediated proliferative responses of Tregs is as follows. Tritiated thymidine or BrdU incorporation in human CD134 expressing Tregs after human OX40L treatment is set at 100%. Change (i.e. decrement or increment) of this tritiated thymidine or BrdU incorporation when both human OX40L and anti-human CD134 antibody are added simultaneously to activated (e.g., PHA-stimulated or anti-CD3/anti-CD28 beads-stimulated) human CD134 expressing Tregs preferably does not exceed about 30%, or about 20%, or about 10% or less.

A suitable method for measuring the inhibition of OX40L-mediated proliferative responses of Tregs, is as follows. Tritiated thymidine or BrdU incorporation in human CD134 expressing Tregs after human OX40L treatment is set at 100%. Reduction of this tritiated thymidine or BrdU incorporation when both human OX40L and anti-human CD134 antibody are added simultaneously to activated (e.g., PHA-stimulated or anti-CD3/anti-CD28 beads-stimulated) human CD134 expressing Tregs is preferably greater than about 30%, or about 40%, or about 50%, or about 60%, or about 70%, or higher.

Another aspect of the invention provides a method of treating cancer in a mammal, comprising administering to the mammal a therapeutically effective amount of a binding molecule as described herein.

In some embodiment of the invention, the binding molecule is antibody clone 12H3 and/or clone 20E5, or an antigen-binding fragment of either antibody. In a further embodiment, the mammal is a human.

In some embodiments of the invention, the binding molecule is the antibody 12H3_VL1VH1 having the VH of SEQ ID NO: 69 and the VL of SEQ ID NO: 67.

In some embodiments of the invention, the binding molecule is the antibody 12H3_VL1VH2 having the VH of SEQ ID NO: 70 and the VL or SEQ ID NO: 67

In another preferred embodiment of the invention is provided a method of preventing cancer in a mammal, comprising administering to the mammal a therapeutically effective amount of a binding molecule as described herein.

The term "preventing cancer" or "prevention of cancer" refers to delaying, inhibiting, or preventing the onset of a cancer in a mammal in which the onset of oncogenesis or tumorigenesis is not evidenced but a predisposition for cancer is identified whether determined by genetic screening, for example, or otherwise. The term also encompasses treating a mammal having premalignant conditions to stop the progression of, or cause regression of, the premalignant conditions towards malignancy. Examples of premalignant conditions include hyperplasia, dysplasia, and metaplasia. In some embodiments, the binding molecule is an anti-CD134 antibody or a fragment thereof as described herein. In a further embodiment of the invention is provided a binding molecule selected from antibody clone 12H3 and/or clone 20E5, or an antigen-binding fragment of either antibody. In a further embodiment, the mammal is a human.

The terms "treat" or "treatment" refers to both therapeutic treatment and prophylactic or preventative measures, wherein the object is to prevent or slow down (lessen) an undesired physiological change or disorder, such as the development or spread of tumor or tumor cells. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those already with the condition or disorder as well as those prone to have the condition or disorder or those in which the condition or disorder is to be prevented. Any of the antibodies of the invention may be used in the methods of the invention.

Another embodiment of the invention is a method of treating cancer, comprising administering to a patient in need thereof an anti-CD134 antibody comprising the VH of SEQ ID NO: 152 and the VL of SEQ ID NO: 100 for a time sufficient to treat the cancer.

Another embodiment of the invention is a method of treating cancer, comprising administering to a patient in need thereof an anti-CD134 antibody comprising the VH of SEQ ID NO: 134 and the VL of SEQ ID NO: 98 for a time sufficient to treat the cancer.

Another embodiment of the invention is a method of treating cancer, comprising administering to a patient in need thereof an anti-CD134 antibody comprising the
VH of SEQ ID NO: 67 and the VL of SEQ ID NO: 69;
VH of SEQ ID NO: 67 and the VL of SEQ ID NO: 70;
VH of SEQ ID NO: 67 and the VL of SEQ ID NO: 71;
VH of SEQ ID NO: 68 and the VL of SEQ ID NO: 69;
VH of SEQ ID NO: 68 and the VL of SEQ ID NO: 70; or
VH of SEQ ID NO: 68 and the VL of SEQ ID NO: 71;
for a time sufficient to treat the cancer.

A variety of cancers, including malignant or benign and/or primary or secondary, may be treated or prevented with a method according to the invention. Examples of such cancers are known to those skilled in the art and listed in standard textbooks such as the Merck Manual of Diagnosis and Therapy (published by Merck). In some embodiments, the cancer is cancer that typically is responsive to immunotherapy, but also cancer that has not hitherto been associated with immunotherapy. Exemplary cancers are melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. The cancer may be refractory or recurrent malignancy carcinoma, lymphoma, blastoma, sarcoma, and leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; multiple myeloma and post-transplant lymphoproliferative disorder (PTLD).

In another embodiment of the invention, the binding molecules may be administered alone as monotherapy, or administered in combination with one or more additional therapeutic agents or therapies. Thus, in another embodiment of the invention is provided a method of treating or preventing cancer by a combination therapy, which method comprises administering a binding molecule as disclosed herein, in combination with one or more additional therapies or therapeutic agents. The term "additional therapy" refers to a therapy which does not employ a binding molecule provided by the disclosure as a therapeutic agent. The term "additional therapeutic agent" refers to any therapeutic agent other than a binding molecule provided by the disclosure. In some embodiments, the binding molecule is anti-human CD134 antibody clone 12H3 and/or clone 20E5, an antigen-binding fragment of either antibody, or humanized 12H3 or humanized 20E5 antibody. In one particular aspect, the present disclosure provides a combination therapy for treating cancer in a mammal, which comprises administering to the mammal a therapeutically effective amount of a binding molecule provided by the disclosure in combination with one or more additional therapeutic agents. In a further embodiment, the mammal is a human.

In some embodiments, the cancer is prostate cancer, colon cancer, lung cancer, hematological malignancy, melanoma or bladder cancer.

In some embodiments, the cancer is prostate cancer.
In some embodiments, the cancer is colon cancer.
In some embodiments, the cancer is lung cancer.

In some embodiments, the cancer is a haematological malignancy.

In some embodiment, the cancer is melanoma.
In some embodiments, the cancer is bladder cancer.
In some embodiments, the lung cancer is small-cell lung cancer, non-small cell lung cancer, adenocarcinoma of the lung, or squamous carcinoma of the lung.

A wide variety of cancer therapeutic agents may be used in combination with a binding molecule. One of ordinary skill in the art will recognize the presence and development of other cancer therapies which can be used in combination with the methods and binding molecules of the present disclosure, and will not be restricted to those forms of therapy set forth herein. Examples of categories of additional therapeutic agents that may be used in the combination therapy for treating cancer include (1) chemotherapeutic agents, (2) immunotherapeutic agents, and (3) hormone therapeutic agents.

The term "chemotherapeutic agent" refers to a chemical or biological substance that can cause death of cancer cells, or interfere with division, repair, growth, and/or function of cancer cells. Examples of chemotherapeutic agents include those that are disclosed in WO 2006/088639, WO 2006/129163, and US 20060153808, the disclosures of which are incorporated herein by reference.

The term "immunotherapeutic agents" refers to a chemical or biological substance that can enhance an immune response of a mammal. Examples of immunotherapeutic agents include: *bacillus* Calmette-Guerin (BCG); cytokines such as interferons; vaccines such as MyVax personalized immunotherapy, Onyvax-P, Oncophage, GRNVAC1, Favld, Provenge, GVAX, Lovaxin C, BiovaxID, GMXX, and NeuVax; and antibodies such as alemtuzumab (CAMPATH®), bevacizumab (AVASTIN®), cetuximab (ERBITUX®), gemtuzunab ozogamicin (MYLOTARG®), ibritumomab tiuxetan (ZEVALIN®), panitumumab (VECTIBIX®), rituximab (RITUXAN®, MABTHERA®), trastuzumab (HERCEPTIN®), tositumomab (BEXXAR®), tremelimumab, CAT-3888, and agonist antibodies to CD40 receptor that are disclosed in WO2003/040170.

The term "hormone therapeutic agent" refers to a chemical or biological substance that inhibits or eliminates the production of a hormone, or inhibits or counteracts the effect of a hormone on the growth and/or survival of cancerous cells. Examples of such agents suitable for the methods herein include those that are disclosed in US20070117809. Examples of particular hormone therapeutic agents include tamoxifen (NOLVADEX®), toremifene (Fareston), fulvestrant (FASLODEX®), anastrozole (ARIMIDEX®), exemestane (AROMASIN®), letrozole (FEMARA®), megestrol acetate (MEGACE®), goserelin (ZOLADEX®), and leuprolide (LUPRON®). The binding molecules of this disclosure may also be used in combination with non-drug hormone therapies such as (1) surgical methods that remove all or part of the organs or glands which participate in the production of the hormone, such as the ovaries, the testicles, the adrenal gland, and the pituitary gland, and (2) radiation treatment, in which the organs or glands of the patient are subjected to radiation in an amount sufficient to inhibit or eliminate the production of the targeted hormone.

In another embodiment of the invention is provided a method of treating or preventing cancer by a combination therapy, which method comprises administering a binding molecule as disclosed herein, and surgery to remove a tumour. The binding molecule may be administered to the mammal before, during, or after said surgery.

The combination therapy for treating cancer also encompasses combination of a binding molecule provided by the disclosure with radiation therapy, such as ionizing (electromagnetic) radiotherapy (e.g., X-rays or gamma rays) and particle beam radiation therapy (e.g., high linear energy radiation). The source of radiation can be external or internal to the mammal. The binding molecule may be administered to the mammal before, during, or after the radiation therapy.

The binding molecules and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. The suitable route and method of administration may vary depending on a number of factors such as the specific antibody being used, the rate of absorption desired, specific formulation or dosage form used, type or severity of the disorder being treated, the specific site of action, and conditions of the patient, and can be readily selected by a person skilled in the art.

The term "therapeutically effective amount" of a binding molecule refers to an amount that is effective for an intended therapeutic purpose. For example, in the context of enhancing an immune response, a "therapeutically effective amount" is any amount that is effective in stimulating, evoking, increasing, improving, or augmenting any response of a mammal's immune system. In the context of treating cancer, a "therapeutically effective amount" is any amount that is sufficient to cause any desirable or beneficial effect in the mammal being treated, such as inhibition of further growth or spread of cancer cells, death of cancer cells, inhibition of reoccurrence of cancer, reduction of pain associated with the cancer, or improved survival of the mammal. In a method of preventing cancer, a "therapeutically effective amount" is any amount that is effective in delaying, inhibiting, or preventing the onset of a cancer in the mammal to which the binding molecule is administered.

The therapeutically effective amount of a binding molecule usually ranges from about 0.001 to about 500 mg/kg, and more usually about 0.05 to about 100 mg/kg, of the body weight of the mammal. For example, the amount can be about 0.3 mg/kg, 1 mg/kg, 3 mg/kg, 5 mg/kg, 10 mg/kg, 50 mg/kg, or 100 mg/kg of body weight of the mammal. In some embodiments, the therapeutically effective amount of an anti-human CD134 antibody is in the range of about 0.1-30 mg/kg of body weight of the mammal. The precise dosage level to be administered can be readily determined by a person skilled in the art and will depend on a number of factors, such as the type, and severity of the disorder to be treated, the particular binding molecule employed, the route of administration, the time of administration, the duration of the treatment, the particular additional therapy employed, the age, sex, weight, condition, general health and prior medical history of the patient being treated, and like factors well known in the art.

A binding molecule or composition is usually administered on multiple occasions. Intervals between single doses can be, for example, weekly, monthly, every three months or yearly. An exemplary treatment regimen entails administration once per week, once every two weeks, once every three weeks, once every four weeks, once a month, once every 3 months or once every three to 6 months. Typical dosage regimens for an anti-human CD134 antibody include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks.

The invention provides a binding molecule that binds to human CD134, wherein the binding molecule does not prevent human CD134 (OX40) receptor binding to OX40 ligand (OX40L). In some embodiments, at or above the saturation concentration of said molecule, the effect on binding of OX40L to CD134 is reduced by not more than 50% on human CD134 expressing T-cells. In some embodiments, at a concentration of 70 nM of the binding molecule, the effect on binding of OX40L to CD134 is reduced by not more than 70% on human CD134 expressing T-cells. The invention further provides a binding molecule comprising:

(a) a heavy chain variable region comprising the amino acid sequence of SEQ ID NO: 12 or a variant of that sequence having 1, 2 or 3 amino acid substitutions; and/or (b) a light chain variable region comprising the amino acid sequence of SEQ ID NO: 13 or a variant of that sequence having 1, 2 or 3 amino acid substitutions.

In some embodiments the binding molecule comprises
(a) a heavy chain CDR1 comprising the amino acid sequence of SEQ ID NO: 14 or a variant of that sequence having 1, 2 or 3 amino acid substitutions;

(b) a heavy chain CDR2 comprising the amino acid sequence of SEQ ID NO: 15 or a variant of that sequence having 1, 2 or 3 amino acid substitutions; and/or (c) a heavy chain CDR3 comprising the amino acid sequence of SEQ ID NO: 16 or a variant of that sequence having 1, 2 or 3 amino acid substitutions.

In a preferred embodiment the binding molecule comprises
(a) a light chain CDR1 comprising the amino acid sequence of SEQ ID NO: 17 or a variant of that sequence having 1, 2 or 3 amino acid substitutions;

(b) a light chain CDR2 comprising the amino acid sequence of SEQ ID NO: 18 or a variant of that sequence having 1, 2 or 3 amino acid substitutions; and/or (c) a light chain CDR3 comprising the amino acid sequence of SEQ ID NO: 19 or a variant of that sequence having 1, 2 or 3 amino acid substitutions.

The invention further provides a binding molecule that competes for human CD134 binding with an antibody comprising:
(a) a heavy chain variable region comprising the amino acid sequence of SEQ ID NO:12; and (b) a light chain variable region comprising the amino acid sequence of SEQ ID NO:13.

Also provided is a binding molecule comprising:
(a) a heavy chain variable region comprising the amino acid sequence of SEQ ID NO:4 or a variant of that sequence having 1, 2 or 3 amino acid substitutions; and/or (b) a light chain variable region comprising the amino acid sequence of SEQ ID NO:5 or a variant of that sequence having 1, 2 or 3 amino acid substitutions.

In one embodiment, the binding molecule according to the invention comprises
(a) a heavy chain CDR1 comprising the amino acid sequence of SEQ ID NO:6 or a variant of that sequence having 1, 2 or 3 amino acid substitutions;

(b) a heavy chain CDR2 comprising the amino acid sequence of SEQ ID NO:7 or a variant of that sequence having 1, 2 or 3 amino acid substitutions; and/or (c) a heavy chain CDR3 comprising the amino acid sequence of SEQ ID NO:8 or a variant of that sequence having 1, 2 or 3 amino acid substitutions.

In one embodiment, the binding molecule according to the invention comprises (a) a light chain CDR1 comprising the amino acid sequence of SEQ ID NO:9 or a variant of that sequence having 1, 2 or 3 amino acid substitutions;

(b) a light chain CDR2 comprising the amino acid sequence of SEQ ID NO: 10 or a variant of that sequence having 1, 2 or 3 amino acid substitutions; and/or (c) a light chain CDR3 comprising the amino acid sequence of SEQ ID NO: 11 or a variant of that sequence having 1, 2 or 3 amino acid substitutions.

In one embodiment, the binding molecule competes for human CD134 binding with an antibody comprising:

(a) a heavy chain variable region comprising the amino acid sequence of SEQ ID NO:4; and (b) a light chain variable region comprising the amino acid sequence of SEQ ID NO:5.

In one embodiment, the binding molecule specifically binds to an epitope in an amino acid sequence of the extracellular domain of human CD134. In some embodiments, the binding molecule binds to an epitope of the extracellular domain of human CD134 comprising the amino acid sequence of:

(a) SEQ ID NO:34;
(b) SEQ ID NO:35
(c) SEQ ID NO:36;
(d) SEQ ID NO:38; and/or
(d) SEQ ID NO:92.

In some embodiments, the binding molecule does not prevent human CD134 receptor binding to OX40 ligand (OX40L) on human CD134 expressing human immunocompetent cells (e.g. activated Teffs and/or activated Tregs) that are involved in inhibiting growth of human tumor cells.

In some embodiments, the binding molecule enhances the binding and/or immunostimulatory responses of human OX40 ligand (OX40L) on human CD134 expressing human immunocompetent cells (e.g. activated Teffs and/or activated Tregs) that are involved in inhibiting growth of human tumor cells In some embodiments, the binding molecule does not prevent human CD134 binding to OX40 ligand (OX40L) and does not impede the immunostimulatory and/or proliferative responses of human OX40L on human CD134 expressing T-effector cells.

The invention also provides a binding molecule that binds to human CD134, wherein the binding molecule does not prevent human CD134 binding to OX40 ligand (OX40L) and does enhance the immunostimulatory and/or proliferative responses of human OX40L on human CD134 expressing T-effector cells.

The invention further provides a binding molecule that binds to human CD134, wherein the binding molecule does not prevent human CD134 binding to OX40 ligand (OX40L) and does not impede suppressor function responses of human OX40L on human CD134 expressing T regulatory cells.

Also provided is a binding molecule that binds to human CD134, wherein the binding molecule does not prevent human CD134 binding to OX40 ligand (OX40L) and does enhance suppressor function responses of human OX40L on human CD134 expressing T regulatory cells.

Also provided is a binding molecule that binds to human CD134, wherein the binding molecule does not prevent human CD134 binding to OX40 ligand (OX40L) but does not impede the proliferative responses of human OX40L on human CD134 expressing T-regulatory cells Yet further provided is a binding molecule that binds to human CD134, wherein the binding molecule does not prevent human CD134 binding to OX40 ligand (OX40L) but does inhibit the proliferative responses of human OX40L on human CD134 expressing T-regulatory cells.

A binding molecule of the invention is preferably a binding molecule wherein at or above the saturation concentration of said molecule, the effect on binding of OX40L to CD134 is reduced by not more than 50% on human CD134 expressing T-cells.

A binding molecule of the invention is preferably a binding molecule wherein a concentration of 70 nM of the binding molecule, the effect on binding of OX40L to CD134 is reduced by not more than 70% on human CD134 expressing T-cells.

In one embodiment a binding molecule according to the invention is a humanized antibody. In another embodiment the binding molecule according to the invention is a chimeric, humanized or deimmunized antibody, or a fragment thereof.

In yet another embodiment a binding molecule according to the invention is an antibody, an antibody mimic (for example, based upon a non-antibody scaffold), an RNA aptamer, a small molecule or a CovX-body.

In some embodiments the binding molecule according to the invention is an IgG, IgA, IgD, IgE, or IgM antibody, such as an IgG1, IgG2, IgG3 or IgG4 antibody.

In some embodiments, the binding molecule is an IgG4 antibody.

In some embodiments the antibody is an antigen-binding fragment of an antibody, for example selected from the group consisting of: Fv fragments (e.g. single chain Fv and disulphide-bonded Fv); Fab like fragments (e.g., Fab fragments, Fab' fragments and F(ab')2 fragments); and domain antibodies. In some embodiments, the antigen binding fragment or binding moiety is an scFv. In some embodiments, the binding moiety is a recombinant antibody. In some embodiments, the binding moiety is a monoclonal antibody.

The invention also provides a nucleic acid molecule encoding a binding molecule according to any one of the preceding claims, provided that the binding moiety is a polypeptide.

Also provided is a vector comprising at least one nucleic acid molecule according to the invention.

Further provided is a host cell comprising a vector or a nucleic acid according to the invention. The host cell is preferably derived from a mammal or insect.

The invention further provides a process for preparing a binding molecule according to the invention, comprising the steps of (i) preparing CD134-binding molecules and (ii) screening the said molecules in order to identify and obtain binding molecules that do not prevent binding of OX40L to CD134. Step (ii) preferably comprises identifying binding molecules that bind CD134 following exposure of the CD134 to a saturating concentration of OX40L. When the binding molecule is a monoclonal antibody, the process for preparing a binding molecule comprises immunizing an animal with human CD134, preparing hybridomas secreting anti-CD134 antibodies and screening for hybridomas producing anti-CD134 antibodies. The invention further provides a binding molecule according to invention or produced according to the invention for use in preventing or treating cancer in a subject in need thereof. In some embodiments, the cancer is lung cancer, prostate cancer, breast cancer, head and neck cancer, oesophageal cancer, stomach cancer, colon cancer, colorectal cancer, bladder cancer, cervical cancer, uterine cancer, ovarian cancer, liver cancer, hematological cancer, melanoma, or any other disease or disorder characterized by uncontrolled cell growth.

Further provided is a method of enhancing an immune response in a human subject, comprising administering to the human subject a therapeutically effective amount of a binding molecule according to the invention or produced according to the invention, and optionally a pharmaceutically acceptable carrier. The enhanced immune response can comprise an increase in the immunostimulator/effector function of T-effector cells, optionally as a result of proliferation of those cells, and/or a down-regulation of the immunosuppressor function of T-regulatory cells, optionally without expansion in numbers of those cells.

Also provided is a method of treating cancer in a human subject in need thereof, comprising administering to the human subject a therapeutically effective amount of a binding molecule according to the invention or produced according to the invention. In some embodiments, the cancer is lung cancer, prostate cancer, breast cancer, head and neck cancer, oesophageal cancer, stomach cancer, colon cancer, colorectal cancer, bladder cancer, cervical cancer, uterine cancer, ovarian cancer, liver cancer, hematological cancer, melanoma, or any disease or disorder characterized by uncontrolled cell growth.

Also provided is a method of reducing the size of a tumour or inhibiting the growth of cancer cells in a subject or reducing or inhibiting the development of metastatic cancer in a subject suffering from cancer, comprising administering to the human subject a binding molecule according to the invention or produced according to the invention.

The invention further provides the use of a binding molecule according to the invention or produced according to the invention in the preparation of a medicament for the treatment or prevention of cancer.

Also provided is a pharmaceutical composition comprising a binding moiety according to the invention or produced according to the invention together with one or more pharmaceutically acceptable diluents or excipients. The composition is preferably suitable for parenteral administration into the human body, for example by intravenous, intramuscular, intradermal, intraperitoneal, intratumour, intravesical, intra-arterial, intrathecal, intra-capsular, intra-orbital, intracardiac, transtracheal, intra-articular, subcapsular, subarachnoid, intraspinal, epidural, intrasternal or subcutaneous administration.

Further Embodiments of the Invention

Set out below are certain further numbered embodiments of the invention according to the disclosures elsewhere herein. Features from embodiments of the invention set out above described as relating to the invention disclosed herein also relate to each and every one of these further numbered embodiments.

1. An isolated antibody that binds human CD134 comprising a light chain variable region (VL) of SEQ ID NO: 100 and a heavy chain variable region (VH) comprising heavy chain complementarity determining regions (HCDR)s HCDR1, HCDR2 and HCDR3, optionally having 1, 2 or 3 amino acid substitutions in the VL of SEQ ID NO: 100.
2. The antibody according to embodiment 1, wherein the VH comprises the amino acid sequence of SEQ ID NO: 152, optionally having 1, 2 or 3 amino acid substitutions in the VH of SEQ ID NO: 152.
3. The antibody according to embodiment 1 or 2, wherein the VH comprises the amino acid sequence of SEQ ID NO: 99, optionally having 1, 2 or 3 amino acid substitutions in the VH of SEQ ID NO: 99.
4. The antibody according to any one of embodiments 1-3, wherein the HCDR3 comprises the amino acid sequence of SEQ ID NOs: 16, 144 or 145.
5. The antibody according to embodiment 4, wherein the HCDR2 comprises the amino acid sequence of SEQ ID NOs: 15, 141, 142 or 143.
6. The antibody according to embodiment 5, wherein the HCDR1 comprises the amino acid sequence of SEQ ID NO: 14.
7. The antibody according to any one of embodiments 1-6, wherein:
   a. the VL comprises the amino acid sequence of SEQ ID NOs: 67 or 68; and
   b. the VH comprises the amino acid sequence of SEQ ID NOs: 69, 70, 71, 119, 120, 121, 122, 123, 124, 125, 126, 127, 128, 129, 130, 131, 132, 133, 146, 147 or 148, optionally having substitutions at linear amino acid residue positions 11, 55 or 99; or
   c. the VL and the VH comprise the amino acid sequences of
      i. SEQ ID NOs: 67 and 69, respectively;
      ii. SEQ ID NOs: 67 and 70, respectively;
      iii. SEQ ID NOs: 67 and 71, respectively;
      iv. SEQ ID NO:s 68 and 69, respectively;
      v. SEQ ID NOs: 68 and 70, respectively; or
      vi. SEQ ID NOs: 68 and 71, respectively.
8. The antibody according to any one of embodiments 1-7, wherein the substitutions at linear amino acid residue positions are V11L, N55Q, N55A, N55E, M99L or M99I.
9. The antibody according to any one of embodiments 1-8, wherein the binding molecule binds to an epitope of the extracellular domain of human CD134 comprising the amino acid sequence of SEQ ID NO: 34, SEQ ID NO: 35; SEQ ID NO: 36, SEQ ID NO: 38 or SEQ ID NO: 92.
10. The antibody according to any one of embodiments 1-9, wherein the antibody is humanized or deimmunized.
11. The antibody according to any one of embodiments 1-10, wherein the antibody is an agonist of CD134.
12. The antibody according to any one of embodiments 1-11, wherein the antibody is of IgG1, IgG2, IgG3 or IgG4 isotype.
13. The antibody according to any one of embodiments 1-12, wherein the antibody comprises a substitution in an Fc region.
14. The antibody of according to embodiment 13, wherein the substitution modulates binding of the antibody to an Fc gamma receptor (FcγR) or to a neonatal Fc receptor (FcRn).
15. The antibody according to embodiment 14, wherein the substitution comprises a S267E/L328F substitution, an E233D/G237D/H268D/P271G/A330R substitution, a V234A/G237A/P238S/H268A/V309L/A330S/P331S substitution, or a M252Y/S254T/T256E substitution, wherein residue numbering is according to the EU Index.
16. An isolated nucleic acid molecule encoding the VH or the VL of any one of embodiments 1-3 or 7.
17. A vector comprising the nucleic acid molecule of embodiment 16.
18. A host cell comprising the vector of embodiment 17.
19. The antibody according to any one of embodiments 1-15, 23-37, 41-45 or 49 for use in the treatment of a subject in need of enhancement of an immune response.
20. The antibody according to any one of embodiments 1-15, 23-37, 41-45 or 49 for use in the treatment of cancer.
21. The antibody according to embodiment 20 for use of treatment of cancer, wherein the cancer is prostate cancer, colon cancer, lung cancer, hematological malignancy, melanoma or bladder cancer.

22. A pharmaceutical composition comprising the antibody of any one of embodiments 1-15, 23-37 or 41-45 and a pharmaceutically acceptable carrier.

23. An isolated antibody that binds human CD134, comprising a light chain variable region (VL) of SEQ ID NO: 98 and a heavy chain variable region (VH) comprising heavy chain complementarity determining regions (HCDR)s HCDR1, HCDR2 and HCDR3, optionally having 1, 2 or 3 amino acid substitutions in the VL of SEQ ID NO: 98.

24. The antibody according to embodiment 23, wherein the VH comprises the amino acid sequence of SEQ ID NO: 134, optionally having 1, 2 or 3 amino acid substitutions in the VH of SEQ ID NO: 134.

25. The antibody according to embodiments 23 or 24, wherein the VH comprises the amino acid sequence of SEQ ID NO: 97, optionally having 1, 2 or 3 amino acid substitutions in the VH of SEQ ID NO: 97.

26. The antibody according to any one of embodiments 23-25, wherein the HCDR3 comprises the amino acid sequence of SEQ ID NOs: 8, 139 or 140.

27. The antibody according to embodiment 26, wherein the HCDR2 comprises the amino acid sequence of SEQ ID NOs: 7, 135, 136, 137 or 138.

28. The antibody according to embodiment 27, wherein the HCDR1 comprises the amino acid sequence of SEQ ID NO: 6.

29. The antibody according to any one of embodiments 23-29, wherein:
a. the VL comprises the amino acid sequence of SEQ ID NOs: 62 or 63; and
b. the VH comprises the amino acid sequence of SEQ ID NOs: 64, 65, 66, 101, 102, 103, 104, 105, 106, 107, 108, 109, 110, 111, 112, 113, 114, 115, 116, 117, 118, 149, 150 or 151, optionally having substitutions at linear amino acid residue positions 11, 56 or 106; or
c. the VL and the VH comprise the amino acid sequences of
  i. SEQ ID NOs: 62 and 64, respectively;
  ii. SEQ ID NOs: 62 and 65, respectively;
  iii. SEQ ID NOs: 62 and 66, respectively;
  iv. SEQ ID NOs: 63 and 64, respectively;
  v. SEQ ID NOs: 63 and 65, respectively; or
  vi. SEQ ID NOs: 63 and 66, respectively.

30. The antibody according to any one of embodiments 23-29, wherein the substitutions at linear amino acid residue positions are V11L, D56G, D56A, D56S, D56E, M106L or M106I.

31. The antibody according to any one of embodiments 23-30, wherein the antibody binds to an epitope of the extracellular domain of human CD134 comprising the amino acid sequence of SEQ ID NO: 34, SEQ ID NO: 35; SEQ ID NO: 36, SEQ ID NO: 38 or SEQ ID NO: 92.

32. The antibody according to any one of embodiments 23-31, wherein the antibody is humanized or deimmunized.

33. The antibody according to any one of embodiments 23-32, wherein the antibody is an agonist of CD134.

34. The antibody according to any one of embodiments 23-33, wherein the antibody is of IgG1, IgG2, IgG3 or IgG4 isotype.

35. The antibody according to any one of embodiments 23-34, wherein the antibody comprises a substitution an Fc region.

36. The antibody according to embodiment 35, wherein the substitution modulates binding of the antibody to an Fc gamma receptor (FcγR) or to a neonatal Fc receptor (FcRn).

37. The antibody according to embodiment 36, wherein the substitution comprises a S267E/L328F substitution, an E233D/G237D/H268D/P271G/A330R substitution, a V234A/G237A/P238S/H268A/V309L/A330S/P331S substitution, or a M252Y/S254T/T256E substitution, wherein residue numbering is according to the EU Index.

38. An isolated nucleic acid molecule encoding the VH or the VL of any one of embodiments 23-37.

39. A vector comprising the nucleic acid molecule according to embodiment 38.

40. A host cell comprising the vector according to embodiment 39.

41. An isolated agonistic antibody that binds human CD134, comprising a light chain variable region (VL) and a heavy chain variable region (VH) comprising heavy chain complementarity determining regions (HCDR)s HCDR1, HCDR2 and HCDR3, and light chain complementarity determining regions (LCDR)s LCDR1, LCDR2 and LCDR3, wherein
a. the HCDR1 comprises the amino acid sequence of SEQ ID NO: 14;
b. the HCDR2 comprises the amino acid sequence of SEQ ID NOs: 15, 141, 142 or 143;
c. the HCDR3 comprises the amino acid sequence of SEQ ID NOs: 16, 144 or 145;
d. the LCDR1 comprises the amino acid sequence of SEQ ID NO: 17;
e. the LCDR2 comprises the amino acid sequence of SEQ ID NO: 18; and
f. the LCDR3 comprises the amino acid sequence of SEQ ID NO: 19;
with the proviso that the antibody does not comprise the VH comprising the HCDR1, the HCDR2 and the HCDR3 amino acid sequences of SEQ ID NOs: 14, 15 and 16, and the VL comprising the LCDR1, the LCDR2 and the LCDR3 amino acid sequences of SEQ ID NOs: 17, 18 and 19.

42. The isolated antibody according to embodiment 41, wherein the antibody comprises the HCDR1, the HCDR2 and the HCDR3 sequences of
a. SEQ ID NOs: 14, 15, 144, respectively,
b. SEQ ID NOs: 14, 141, 16, respectively;
c. SEQ ID NOs: 14, 142, 16, respectively;
d. SEQ ID NOs: 14, 141, 144, respectively; or
e. SEQ ID NOs: 14, 142, 144, respectively.

43. The isolated antibody according to embodiments 41 or 42, wherein the antibody is humanized, deimmunized, or human.

44. The isolated antibody according to any one of embodiments 41-43, wherein the antibody is of IgG1, IgG2, IgG3 or IgG4 isotype.

45. The isolated antibody according to any one of embodiments 41-44, wherein the antibody comprises a substitution in an Fc region that modulates binding of the antibody to an Fc gamma receptor (FcγR) or to a neonatal Fc receptor (FcRn), wherein the substitution comprises a S267E/L328F substitution, an E233D/G237D/H268D/P271 G/A330R substitution, a V234A/G237A/P238S/H268A/V309L/A330S/P331S substitution, or a M252Y/S254T/T256E substitution, wherein residue numbering is according to the EU Index.

46. An isolated nucleic acid molecule encoding the VH or the VL of embodiment 41.

47. A vector comprising the nucleic acid molecule according to embodiment 46.

48. A host cell comprising the vector according to embodiment 47.

49. An isolated agonistic antibody that binds human CD134, comprising a light chain variable region (VL) and a heavy chain variable region (VH) comprising heavy chain complementarity determining regions (HCDR)s HCDR1, HCDR2 and HCDR3, and light chain complementarity determining regions (LCDR)s LCDR1, LCDR2 and LCDR3, wherein
a. the HCDR1 comprises the amino acid sequence of SEQ ID NO: 6;
b. the HCDR2 comprises the amino acid sequence of SEQ ID NOs:7, 135, 136, 137 or 138;
c. the HCDR3 comprises the amino acid sequence of SEQ ID NOs: 8, 139 or 140;
d. the LCDR1 comprises the amino acid sequence of SEQ ID NO: 9;
e. the LCDR2 comprises the amino acid sequence of SEQ ID NO: 10; and
f. the LCDR3 comprises the amino acid sequence of SEQ ID NO: 11;
g. with the proviso that the antibody does not comprise the VH comprising the HCDR1, the HCDR2 and the HCDR3 amino acid sequences of SEQ ID NO:s 6, 7 and 8, and the VL comprising the LCDR1, the LCDR2 and the LCDR3 amino acid sequences of SEQ ID NOs: 9, 10 and 11.

The invention further provides embodiments

Z1. A binding molecule comprising
(a) a heavy chain variable region comprising the amino acid sequence of FIG. 27, or a variant of that sequence having 1, 2 or 3 amino acid substitutions; and/or
(b) a light chain variable region comprising the amino acid sequence of FIG. 27, or a variant of that sequence having 1, 2 or 3 amino acid substitutions.

Z2. A binding molecule comprising
(a) a heavy chain variable region comprising the amino acid sequence of FIG. 26, or a variant of that sequence having 1, 2 or 3 amino acid substitutions; and/or
(b) a light chain variable region comprising the amino acid sequence of FIG. 26 or a variant of that sequence having 1, 2 or 3 amino acid substitutions.

Z3. A binding molecule according to embodiment Z1 or embodiment Z2, that binds to human CD134. Z4. A binding molecule according to any one of embodiments Z1-3, wherein the binding molecule does not prevent human CD134 (OX40) receptor binding to OX40 ligand (OX40L). Z5. A binding molecule according to any one of embodiments Z1-4, wherein at or above the concentration at which binding to said CD134 molecule is saturated, the effect on binding of OX40L to CD134 is reduced by not more than 50% on human CD134 expressing T-cells. Z6. A binding molecule according to any one of embodiments Z1-5, wherein at a concentration of 70 nM of the binding molecule, the effect on binding of OX40L to CD134 is reduced by not more than 70% on human CD134 expressing T-cells. Z7. A binding molecule according to any one of embodiments Z1-6, wherein the binding molecule binds to an epitope of the extracellular domain of human CD134 comprising the amino acid sequence of SEQ ID NO: 34, SEQ ID NO: 35; SEQ ID NO: 36, SEQ ID NO: 38 and/or SEQ ID NO: 92. Z8. A binding molecule according to any one of embodiments Z1-7, that is a Fab-fragment, a single chain Fv (scFv) fragment, or an antibody. Z9. An antibody according to embodiment Z8, which is an humanized or deimmunized IgG, IgA, IgD, IgE or IgM antibody, such as IgG1, IgG2, IgG3 or IgG4 antibody. Z10. A nucleic acid molecule encoding a binding molecule or an antibody according to any one of embodiments Z1-9. Z11. A gene delivery vehicle or vector comprising a nucleic acid according to embodiment Z10. Z12. An isolated or recombinant cell, or in vitro cell culture cell comprising a nucleic acid or vector according to embodiment Z10 or Z11. Z13. A method for producing a binding molecule characterised in that a binding molecule according to any one of embodiments Z1-8, or an antibody according to embodiment Z9 is produced. Z14. A binding molecule or an antibody according to any one of embodiments Z1-9 for use in the treatment of an individual in need of enhancement of an immune response. Z15. A binding molecule or an antibody according to any one of embodiments Z1-9 for use in preventing or treating cancer in an individual in need thereof. Z16. A pharmaceutical composition comprising a binding molecule or an antibody according to any one of embodiments Z1-9, and a pharmaceutically acceptable carrier.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1. Generation of Mouse Anti-Human CD134 (=OX40) Monoclonal Antibodies (a). Generation of Sf9 Insect Cells Expressing Surface CD134 cDNA encoding for human CD134 protein (GenBank ref CAB96543.1; see SEQ ID NO:1) was optimized for Sf9 insect cell (*Spodotera frugiperda*) expression and synthesized by GENEART, Regensburg, Germany (see SEQ ID NO: 2; cat. no. 0904551 (BC internal code V076)). This cDNA was subcloned in baculovirus transfer plasmid pVL1393 (BD transfection kit cat no. 560129; BD Biosciences). Subsequently, Sf9 insect cells (ATCC) were co-transfected with transfer plasmid pVL1393 containing cDNA encoding human CD134 together with BaculoGold Baculovirus DNA (BD transfection kit), and then incubated at 27° C. for 4-5 days. After this co-transfection step, supernatant was collected and stored at 4° C., and used to infect more Sf9 insect cells for virus amplification. For this purpose, Sf9 insect cells were transfected with amplified recombinant baculovirus, and then incubated at 27° C. for 3-5 days. These Sf9 insect cells were harvested, washed with sterile PBS, and aliquoted at ≈2×106 cells/250 µl in PBS and stored at −80° C. to obtain cell lysates. Prior to storage, human CD134 surface expression on transfected Sf9 insect cells were confirmed using 1:10 phycoerythrin (PE)-conjugated mouse anti-human CD134 (clone ACT35; BD Biosciences) and flow cytometry.

(b). Immunization and Generation of Mouse Anti-Human CD134 Monoclonal Antibodies BALB/c mice (females, 6 weeks of age; Charles River Laboratories) were subcutaneously injected with ≈400 µL human CD134-transfected Sf9 insect cell lysates (250 µL cell lysate aliquot+250 µL Complete Freund's adjuvant; Sigma) on Day 0. Similar subcutaneous injections using human CD134-transfected Sf9 insect cell lysates and Incomplete Freund's adjuvant (Sigma) were given on Day 21 and Day 42. Intraperitoneal booster injections with human CD134-transfected Sf9 insect cell lysates (250 µL/mouse) without adjuvant were given on Day 61 and on Day 62. On day 65, splenocytes from immunized mice were fused with SP2/0 myeloma cells (DSMZ) using standard hybridoma technology initially described by Kohler and Milstein (Nature 1975; 256: p 495-497). Briefly, immunized mice were sacrificed. Splenocytes were teased from spleens, and washed in serum-free opti-MEM I with GlutaMax medium (SF medium; Invitrogen). Logarithmically growing SP2/0-Ag14 myeloma cells were washed in SF medium, and added to the splenocytes yielding a 5:1 ratio of splenocytes to myeloma cells. The cells were then pelleted, and the supernatant was removed. One ml of a 37% (v/v) solution of polyethylene glycol 4000 (Merck) was then added dropwise over a 60 sec period, after which the cells were incubated for another 60 sec at 37° C. Eight ml SF medium, followed by 5 ml opti-MEM I with GlutaMax/10% (v/v) fetal calf serum (FCS; Bodinco), was then slowly added with gentle agitation. After 30 minutes at RT, the cells were pelleted, washed in opti-MEM I with GlutaMax/10% FCS to remove residual polyethylene glycol, and finally plated at a concentration of $10^5$ cells/200 µl per well in opti-MEM I with GlutaMax/10% FCS/50× Hybri-Max™ aminopterin (de novo DNA synthesis inhibitor; Sigma). From day 7, aminopterin selection medium was replenished every 2-3 days, and at day 14 it was replaced by opti-MEM I with GlutaMax/10% FCS. Hybridomas, which produced antibodies (mouse IgG class) against human CD134 (screened with conventional ELISA and flow cytometric techniques using a recombinant human CD134:human Fcγ fusion protein (R&D Systems; see Example 11 (a) below) and human CD134 expressing PHA (Roche)-stimulated CD4 T cell blasts (see Example 2 (a) below) as targets, respectively) were expanded, cryopreserved, and subcloned by limiting dilution. Anti-human CD134 specific monoclonal antibodies were purified using protein G columns (GE Healthcare), and resulted in mouse anti-human CD134 monoclonal antibodies clone 12H3 and clone 20E5.

Example 2. Flow Cytometric Characterization of Mouse Anti-Human CD134 Monoclonal Antibodies Clones 12H3 and 20E5

(a). CD134 Expression on PHA-Stimulated Human T Lymphocytes

Human peripheral blood mononuclear cells (PBMC) from healthy donors (informed consent) were isolated by density centrifugation on Lymphoprep (1.077 g/mL; Nycomed). Subsequently, 1-2×10⁶ PBMC/mL in RPMI-1640 culture medium (Gibco) containing 10% fetal calf serum (Bodinco) and 50 µg/mL gentamycin (Gibco) were stimulated with 0, 0.1, 1.0 or 10.0 µg/mL phytohemagglutinin-M (PHA-M; Roche) at 37° C./5% $CO_2$ for 1-3 days. After culture, PBMC were harvested and put at 1-2×10⁶ cells/mL in ice-chilled phosphate-buffered saline containing 0.1% bovine serum albumin (Sigma)/0.05% $NaN_3$ (PBS/BSA/$NaN_3$) supplemented with 10% human pooled serum (HPS; blocking Fcγ receptors; BioWhittaker). Cells were incubated with µg/mL commercially available mouse anti-human CD134 antibody clone ACT35 (mouse IgG1 isotype; BD Biosciences, Alphen aan de Rijn, The Netherlands) for 30 minutes at 4° C. After extensive washing in PBS/BSA/$NaN_3$, cells were subsequently incubated with 1:200 diluted PE-conjugated goat anti-mouse IgG antibodies (Jackson ImmunoResearch) for 30 minutes at 4° C. After extensive washing in PBS/BSA/$NaN_3$, cells were incubated with 1:20 diluted Fluorescein isothiocyanate (FITC) conjugated mouse anti-human CD3 antibody (BD Biosciences) to detect T lymphocytes for 30 minutes at 4° C. After extensive washing in PBS/BSA/$NaN_3$, cells were fixed in 2% formaldehyde in PBS/BSA/$NaN_3$ for 30 minutes at 4° C. Binding of antibodies was measured using flow cytometry (FACSCalibur; BD Biosciences).

As shown in FIG. 1 (n=1 from each donor), peripheral blood-derived non-stimulated/resting human T lymphocytes did not express any CD134, however, PHA dose-dependently stimulated human $CD3^{positive}$ T lymphocytes to express surface CD134. When exposed to 10 µg/mL PHA, CD134 expression levels on activated human $CD3^{positive}$ T lymphocytes seemed to reach a plateau between 'day 1' and 'day 2', however, the percentage of human $CD134^{positive}$/$CD3^{positive}$ T lymphocytes time-dependently increased during experimentation.

(b). CD134 Expression on PHA-Stimulated Human CD4 T Lymphocyte Subpopulation

PHA-stimulated (at 0 and 10 µg/mL for 1 day; see above) human CD134 expressing T lymphocytes were generated. Cells were harvested and put at 1-2×10⁶ cells/mL in ice chilled PBS/BSA/$NaN_3$ supplemented with 10% HPS (blocking Fcγ receptors; BioWhittaker). Cells were incubated with 1:10 diluted FITC-conjugated mouse anti-human CD4 antibody (BD Biosciences) or 1:10 diluted FITC-conjugated mouse anti-human CD8 antibody (BD Biosciences) in combination with 1:10 diluted commercially available PE conjugated mouse anti-human CD134 clone ACT35 (BD Biosciences) for 30 minutes at 4° C. After extensive washing in PBS/BSA/$NaN_3$, cells were fixed in 2% formaldehyde in PBS/BSA/$NaN_3$ for 30 minutes at 4° C. Binding of antibodies was measured using flow cytometry (FACSCalibur; BD Biosciences).

Figure 2:
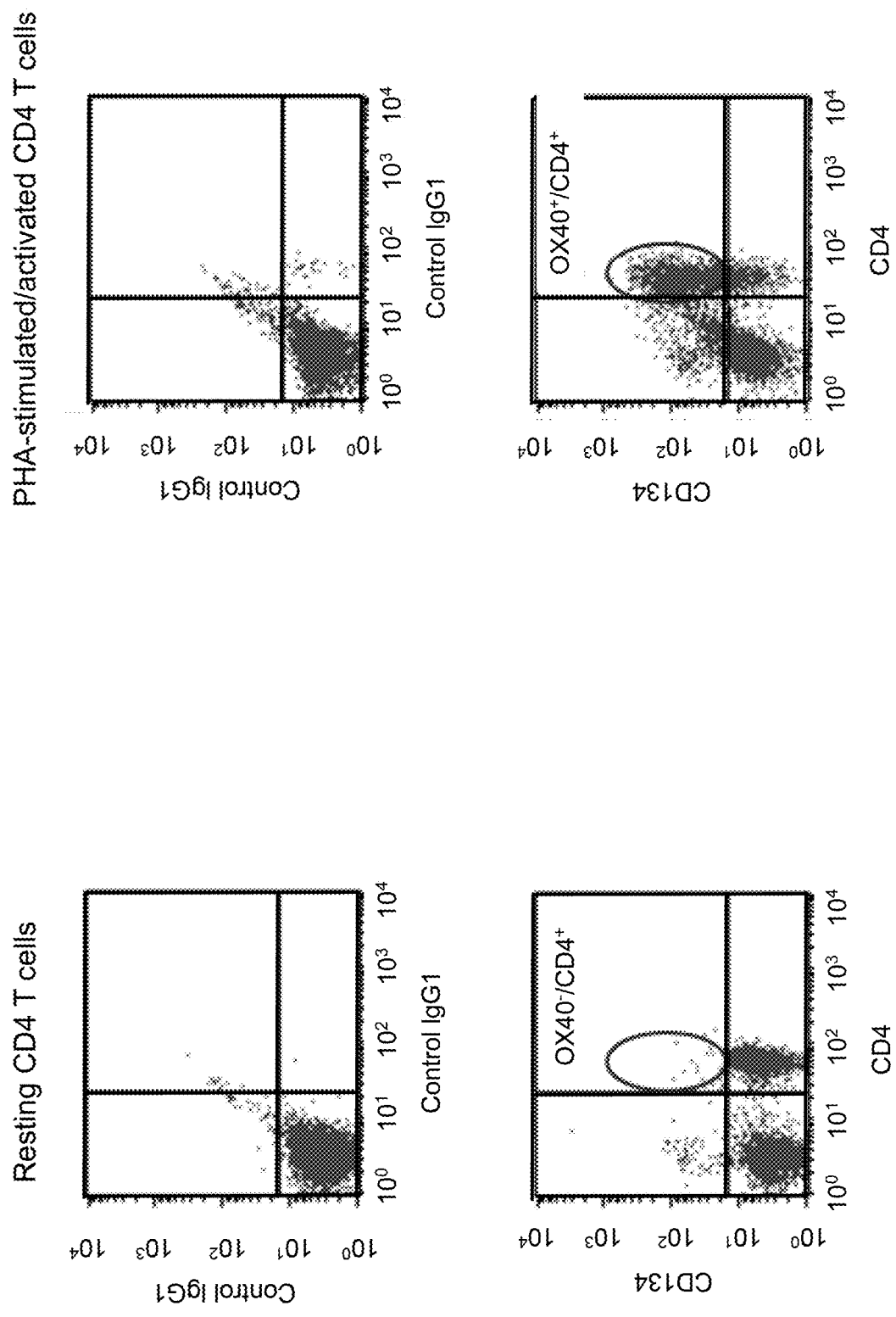
FIG. 2. Human CD134 expression on resting and on PHA-M-activated human CD4 T lymphocytes.

As shown in FIG. 2, CD134 expression was observed on PHA-stimulated human $CD4^{positive}$ T lymphocytes and not on resting human $CD4^{positive}$ T lymphocytes. Low CD134 expression was found on PHA-activated human $CD8^{positive}$ T lymphocytes and not on resting human $CD8^{positive}$ T lymphocytes (data not shown).

(c). Binding of Mouse Anti-Human CD134 Monoclonal Antibodies Clones 12H3 and 20E5 on PHA-Stimulated Human CD134 Expressing T Lymphocytes PHA-stimulated (at 10 µg/mL for 2 days; see above) human CD134 expressing T lymphocytes were generated. Cells were harvested and put at 1-2×10⁶ cells/mL in ice chilled PBS/BSA/$NaN_3$ supplemented with 10% HPS (blocking Fcγ receptors; BioWhittaker). Cells were incubated with 0, 0.007, 0.02, 0.07, 0.2, 0.6, 1.9, 5.6, 16.7, 50.0 µg/mL commercially available mouse anti-human CD134 antibody clone ACT35 (mouse IgG1 isotype; BD Biosciences) and mouse anti-human CD134 antibody clone 12H3 or clone 20E5 for 30 minutes at 4° C. After extensive washing in PBS/BSA/$NaN_3$, cells were subsequently incubated with 1:200 diluted PE-conjugated goat anti-mouse IgG antibodies (Jackson ImmunoResearch) for 30 minutes at 4° C. After extensive washing in PBS/BSA/$NaN_3$, cells were incubated with 1:20 diluted FITC-conjugated mouse anti-human CD3 antibody (BD Biosciences) to detect T lymphocytes for 30 minutes at 4° C. After extensive washing in PBS/BSA/$NaN_3$, cells were fixed in 2% formaldehyde in PBS/BSA/$NaN_3$ for 30 minutes at 4° C. Binding of antibodies was measured using flow cytometry (FACSCalibur; BD Biosciences).

Figure 3:
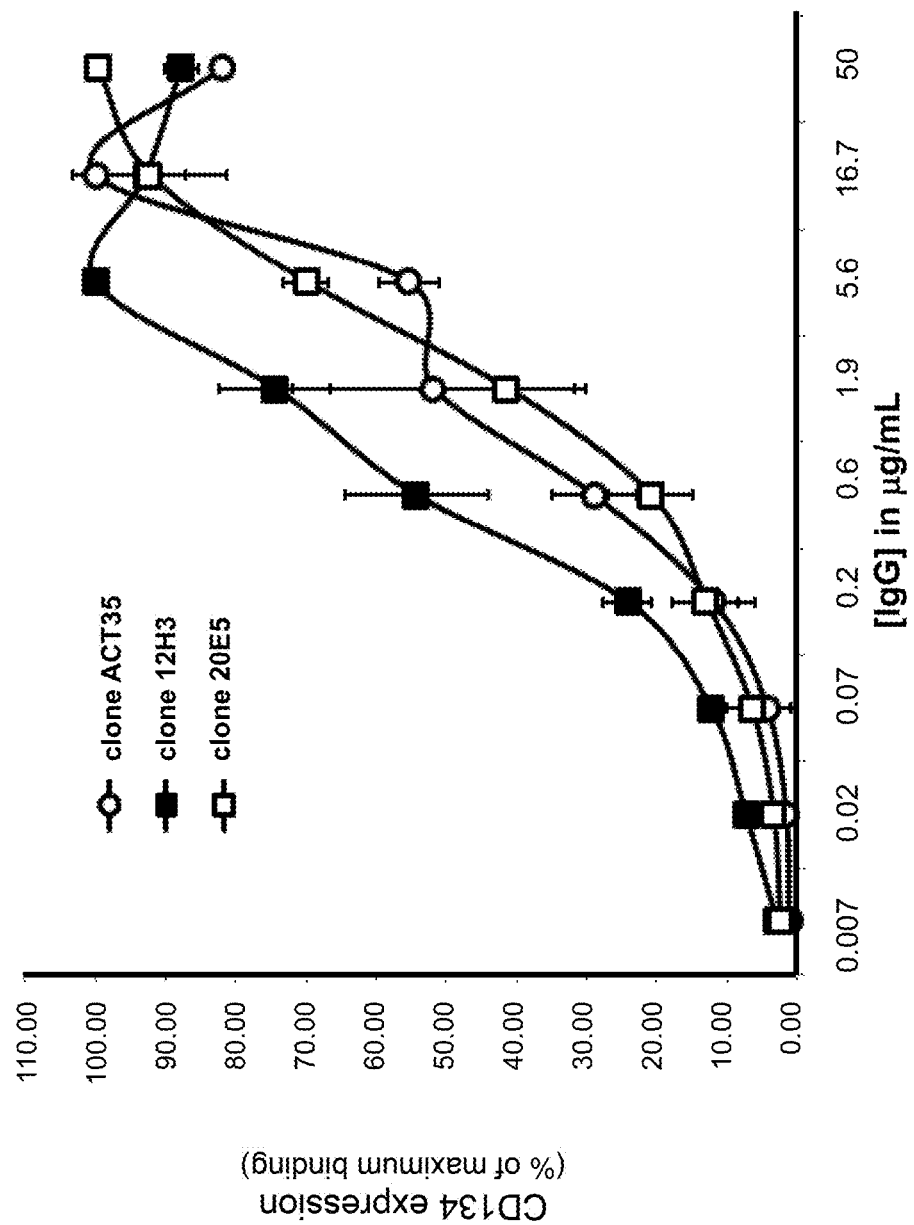
FIG. 3. Binding characteristics of mouse anti-human CD134 antibodies clone ACT35, clone 12H3, and clone 20E5 on PHA-M-stimulated human CD134 expressing T lymphocytes.

As shown in FIG. 3 (mean±SD; results observed in two donors), mouse anti-human CD134 antibody clone ACT35, clone 12H3, and clone 20H5 saturated human CD134 surface molecules on PHA-stimulated CD3$^{positive}$ T lymphocytes at approximately 5.0-10.0 µg/mL. Using these two donors, half maximal binding was observed at ≈0.5 µg/mL for mouse anti human CD134 antibody clone 12H3, and at ≈2.5 µg/mL for mouse anti-human CD134 antibody clone ACT35 and clone 20E5.

(d). Binding of Mouse Anti-Human CD134 Monoclonal Antibodies Clones 12H3 and 20E5 on PHA-Stimulated Human CD134 Expressing CD4 Positive and CD8 Positive T Lymphocytes PHA-stimulated (at 20 µg/mL for 1 day; see above) human CD134 expressing T lymphocytes were generated. Cells were harvested and put at 1-2×10$^6$ cells/mL in ice-chilled PBS/BSA/NaN$_3$ supplemented with 10% HPS (blocking Fcγ receptors; BioWhittaker). Cells were incubated with 20.0 µg/mL mouse IgG1κ isotype control (BD Biosciences), or with 20.0 µg/mL mouse anti-human CD134 monoclonal antibody clone 12H3 or clone 20E5 for 30 minutes at 4° C. After extensive washing in PBS/BSA/NaN$_3$, cells were subsequently incubated with 1:100 diluted PE-conjugated goat anti-mouse IgG antibodies (Jackson ImmunoResearch) for 30 minutes at 4° C. After extensive washing in PBS/BSA/NaN$_3$, cells were incubated for 30 minutes at 4° C. with 1:20 diluted FITC-conjugated mouse anti-human CD4 antibody (BD Biosciences) or with 1:20 diluted FITC-conjugated mouse anti-human CD8 antibody (BD Biosciences) to detect T lymphocyte subpopulations. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Figure 4:
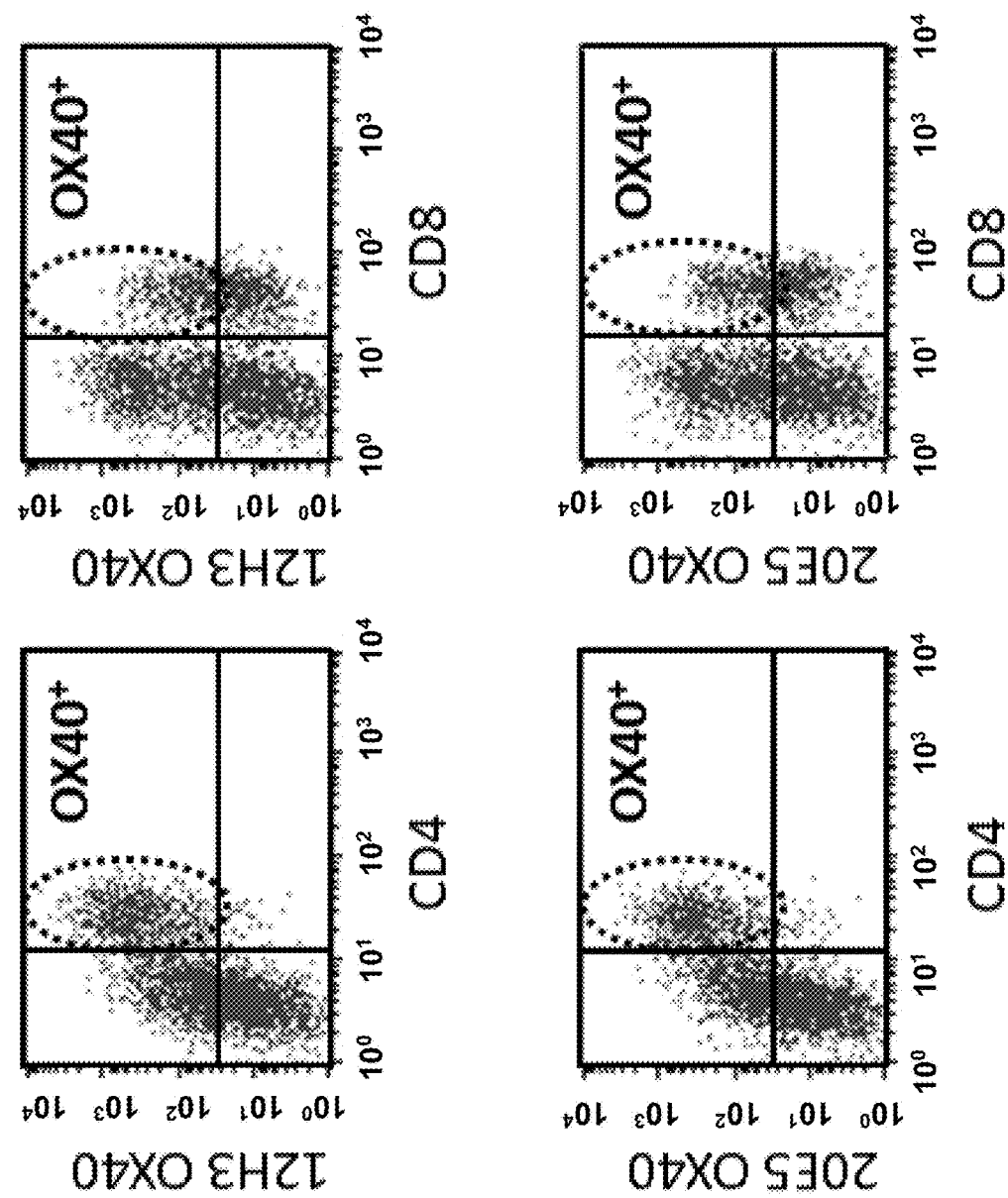
FIG. 4. Binding of mouse anti-human CD134 antibodies clone 12H3 and clone 20E5 on PHA-M-stimulated human CD134 expressing CD4 T lymphocytes and CD8 T lymphocytes.

As shown in FIG. 4, mouse anti-human CD134 monoclonal antibody clone 12H3 and clone 20E5 demonstrated positive staining on the activated human CD4$^{positive}$ T lymphocyte subpopulation, and low positive staining on the activated human CD8$^{positive}$ T lymphocyte subpopulation.

(e). Cross-Competition of Non-Labeled Mouse Anti-Human CD134 Antibodies Clones 12H3 and 20E5 with PE-Conjugated Commercial Mouse Anti-CD134 Antibodies on PHA-Stimulated Human CD134 Expressing T Lymphocytes PHA (at 10 µg/mL or at 20 µg/mL for 4 days or for 1 day, respectively; see above) stimulated human CD134 expressing T lymphocytes were generated. Cells were harvested and put at 1-2×10$^6$ cells/mL in ice-chilled PBS/BSA/NaN$_3$ supplemented with 10% HPS (blocking Fcγ receptors; BioWhittaker). Cells were incubated with 20 µg/mL non-labeled mouse anti-human CD134 monoclonal antibody clone 12H3 or with 10 µg/mL non-labeled clone 20E5 for 30 minutes at 4° C. Cells were subsequently incubated with 1:20 diluted PE-conjugated commercially available mouse anti-human CD134 antibody clone ACT35 (BD Biosciences) or clone L106 (BD Biosciences; see also Godfrey patent) for 30 minutes at 4° C. After extensive washing in PBS/BSA/NaN$_3$, cells were fixed in 2% formaldehyde in PBS/BSA/NaN$_3$ for 30 minutes at 4° C. Binding of PE-conjugated commercial available anti-CD134 antibodies was measured using flow cytometry (FACSCalibur; BD Biosciences).

Figure 5:
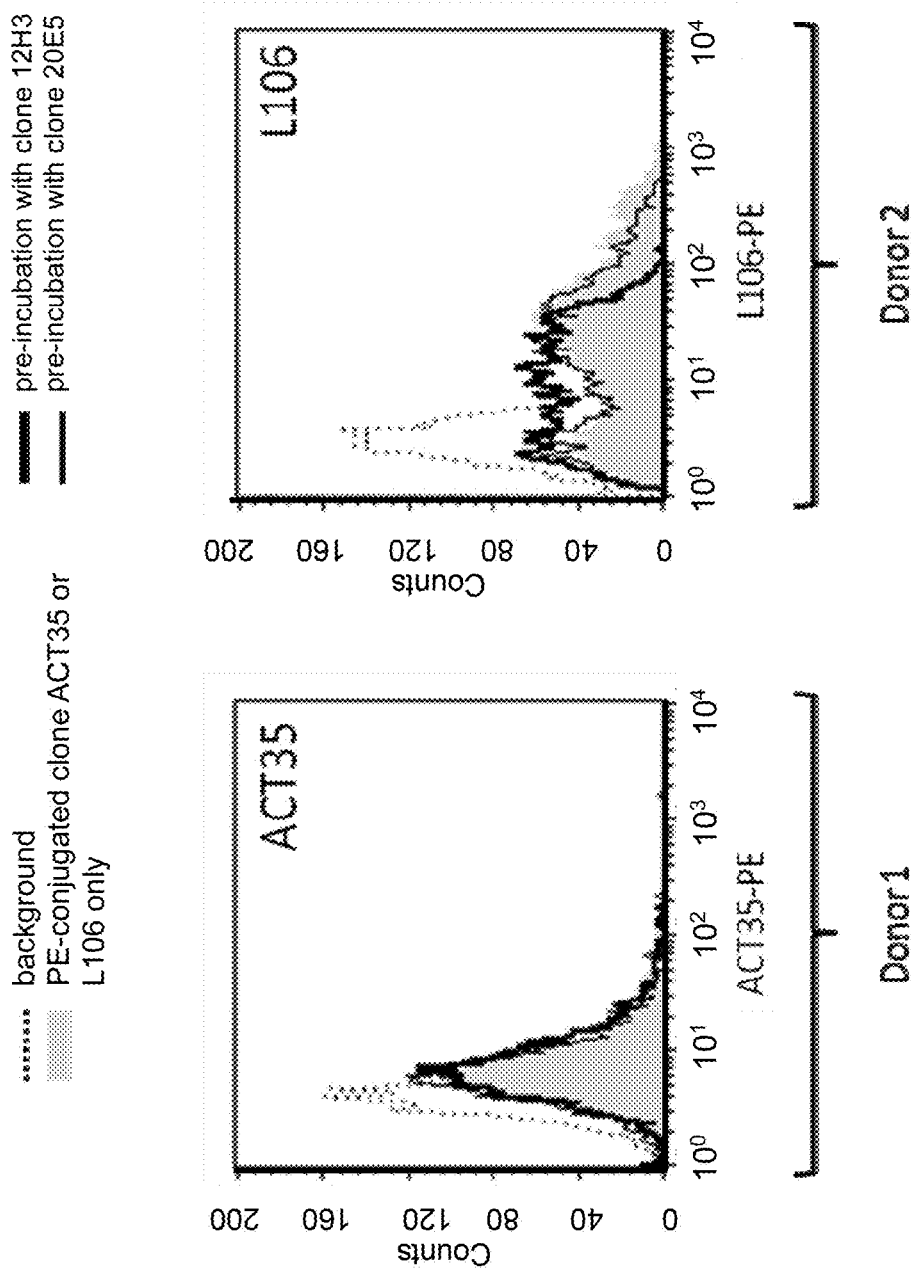
FIG. 5. Cross-competition of non-labeled mouse anti-human CD134 antibodies clone 12H3 or clone 20E5 with PE-conjugated commercial mouse anti-CD134 antibodies clone ACT35 or clone L106 on PHA-M-stimulated human CD134 expressing T lymphocytes.

As shown in FIG. 5, pre-incubation with non-labeled mouse anti-human CD134 antibody clone 12H3 partially blocked the binding of commercial PE-conjugated mouse anti-human CD134 antibody clone L106 against human CD134 on PHA-stimulated T lymphocytes. Pre incubation with non-labelled mouse anti-human CD134 antibody clone 20E5 slightly blocked the binding of commercial PE-conjugated mouse anti-human CD134 antibody clone L106 against human CD134 on PHA-stimulated T lymphocytes. Pre-incubation with non labelled mouse anti-human CD134 antibody clone 12H3 and clone 20E5 showed no effect on the binding of commercial PE-conjugated mouse anti-human CD134 antibody clone ACT35 against human CD134 on PHA-stimulated T lymphocytes.

These results demonstrated that mouse anti-human CD134 antibody clone 12H3 specifically recognized human CD134 (partial blocking of clone L106 binding) on PHA-stimulated T lymphocytes, and bound (ii) to a non-identical epitope on human CD134, which was recognized by commercial mouse anti-human CD134 antibody clone L106. These results also demonstrated that mouse anti-human CD134 antibody clone 20E5 (i) specifically recognized human CD134 (slight blocking of clone L106 binding) on PHA-stimulated T lymphocytes, and (ii) bound to a non-identical epitope, which was recognized by commercial mouse anti-human CD134 antibody clone L106. Moreover, these results demonstrated that mouse anti-human CD134 antibody clone 12H3 and clone 20E5 seemed to recognize human CD134 epitopes on PHA-stimulated T lymphocytes, which were different to the epitope recognized by commercial mouse anti-human CD134 antibody clone ACT35. In addition, these results demonstrated that mouse anti-human CD134 antibody clone 12H3 and clone 20E5 seemed to recognize dissimilar human CD134 epitopes (evidenced by partial blocking vs slight blocking of L106 binding, respectively) on PHA-stimulated T lymphocytes.

(f). Simultaneous Binding of Recombinant Human OX40 Ligand and Mouse Anti-Human CD134 Antibodies Clones 12H3 and 20E5 on PHA-Stimulated Human CD134 Expressing T Lymphocytes PHA-stimulated (at 10 µg/mL for 1 day; see above) human CD134 expressing T lymphocytes were generated. Cells were harvested and put at 1-2×10$^6$ cells/mL in ice-chilled PBS/BSA/NaN$_3$ supplemented with 10% HPS (blocking Fcγ receptors; BioWhittaker). Cells were incubated with 10.0 µg/mL polyhistidine-tagged recombinant human OX40 ligand (OX40L; R&D Systems) in combination with 50.0 µg/mL anti-polyhistidine antibody (mouse IgG1, clone AD1.1.10; R&D Systems) for 30 minutes at 4° C. After extensive washing in PBS/BSA/NaN$_3$, cells were subsequently incubated with 1:100 diluted FITC-conjugated goat anti-mouse IgG antibodies (Jackson ImmunoResearch) for 30 minutes at 4° C. After extensive washing in PBS/BSA/NaN$_3$, cells were incubated with 10.0 µg/mL biotinylated (using N-hydroxysuccinimido-biotin from Pierce) mouse anti-human CD134 monoclonal antibody clone 12H3 or clone 20E5 for 30 minutes at 4° C. After extensive washing in PBS/BSA/NaN$_3$, cells were incubated with 1:100 diluted PE-conjugated streptavidin (Jackson ImmunoResearch) for 30 minutes at 4° C. After extensive washing in PBS/BSA/NaN$_3$, cells were fixed in 2% formaldehyde in PBS/BSA/NaN$_3$ for 30 minutes at 4° C. Binding of human OX40L and anti-human CD134 antibodies was measured using flow cytometry (FACSCalibur; BD Biosciences).

Figure 6:
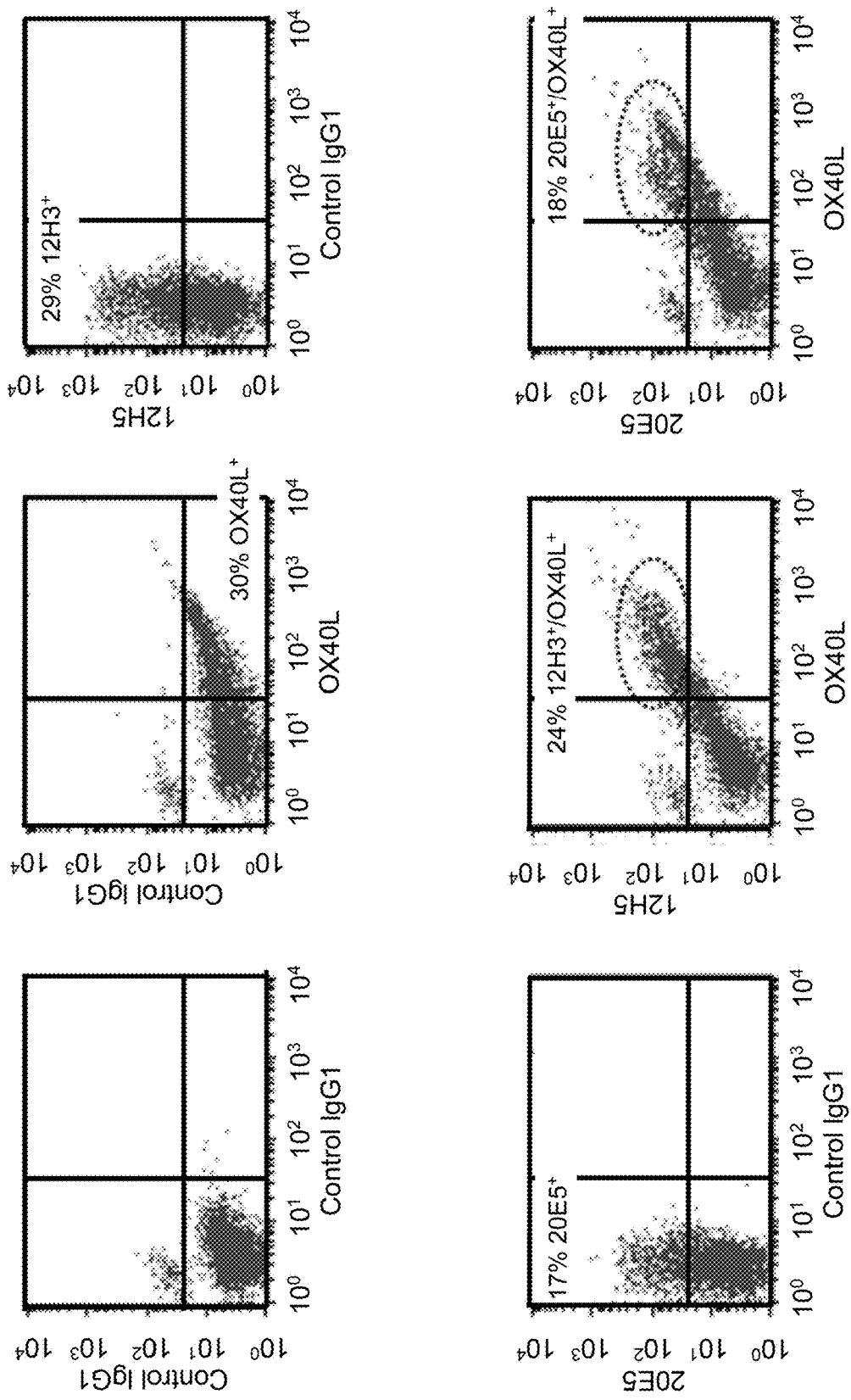
FIG. 6. Simultaneous binding of mouse anti-human CD134 antibodies clone 12H3 or clone 20E5 with human OX40L on PHA-M-stimulated human CD134 expressing T lymphocytes.

As shown in FIG. 6, both mouse anti-human CD134 monoclonal antibody clone 12H3 and mouse anti-human CD134 monoclonal antibody clone 20E5 bound simultaneously with human OX40L on PHA-stimulated human CD134 expressing T lymphocytes. This indicated that mouse anti-human CD134 monoclonal antibody clone 12H3 and clone 20E5 do not interact with epitopes within the OX40L binding region on human CD134 receptors. This finding is in contrast with commercially available mouse anti-human CD134 monoclonal antibody clone L106 (Stanford University/Godfrey patent EP 0 726 952 B1), which recognized an epitope within the human OX40L binding region of human CD134 receptors (Taylor and Schwarz. J Immunol Methods 2001; 255: 67-72; Kirin & La Jolla Institute/Croft patent WO 2007/062235 A2).

(g). CD134 Expression on Human Effector and Regulatory T Lymphocytes after Stimulation with Anti-Human CD3/Anti-Human CD28 Antibody Stimulator Beads Human CD4 T lymphocytes were purified from PBMCs by positive selection using microbeads-conjugated mouse anti-human CD4 antibodies (Miltenyi Biotec) and VarioMACS™ Magnet/LS columns (Miltenyi Biotec). Subsequently, these CD4 T lymphocytes were stained with FITC-conjugated mouse anti-human CD4 antibodies (Dako) and PE conjugated mouse anti-human CD25 antibodies (BD Biosciences). $CD4^{positive}/CD25^{negative}$ conventional effector T lymphocytes (Teffs) and $CD4^{positive}/CD25^{high}$ regulatory T lymphocytes (Tregs) were sorted using an Altra flow cytometric cell sorter (Beckman Coulter). This resulted in enrichments of >95% Teffs and of >95% Tregs. Teffs and Tregs were put on $2.5 \times 10^5$ cells/mL in RPMI-1640/glutamax culture medium (Gibco) supplemented with 0.02 mM pyruvate (Gibco), 100 U/mL penicillin (Gibco), 100 µg/mL streptomycin (Gibco), and 10% heat inactivated HPS (HPSi; from LMI). Then, cells were seeded at $2.5 \times 10^4$ cells/200 µL/well in 96-well round-bottom plates (Greiner), and stimulated with mouse anti-human CD3/mouse anti-human CD28 antibody stimulator beads (CD3/CD28 beads; Invitrogen) at 1 bead/2 cells in the presence of 25 U/mL recombinant human interleukin-2 (Proleukin® from Novartis Pharmaceuticals UK Ltd) at 37° C./5% CO2 for 2-8 days. After culture, cells were harvested and put at $1-2 \times 10^6$ cells/mL in ice-chilled PBS/0.2% BSA, and were simultaneously stained with 1:50 diluted FITC-conjugated mouse anti-human CD4 antibody (Dako), 1:10 diluted PE-conjugated mouse anti-human CD25 antibody (BD Biosciences), 1:50 diluted ECD™-conjugated mouse anti-human CD3 antibody (Beckman-Coulter), 1:10 diluted PE-Cy™5-conjugated mouse anti-human CD134 antibody (clone ATC35; BD Biosciences), and 1:10 diluted PE-Cy™7-conjugated mouse anti-human CD127 antibody (eBiosciences). Binding of antibodies was measured using flow cytometry (FACSCalibur; BD Biosciences).

Figure 7:
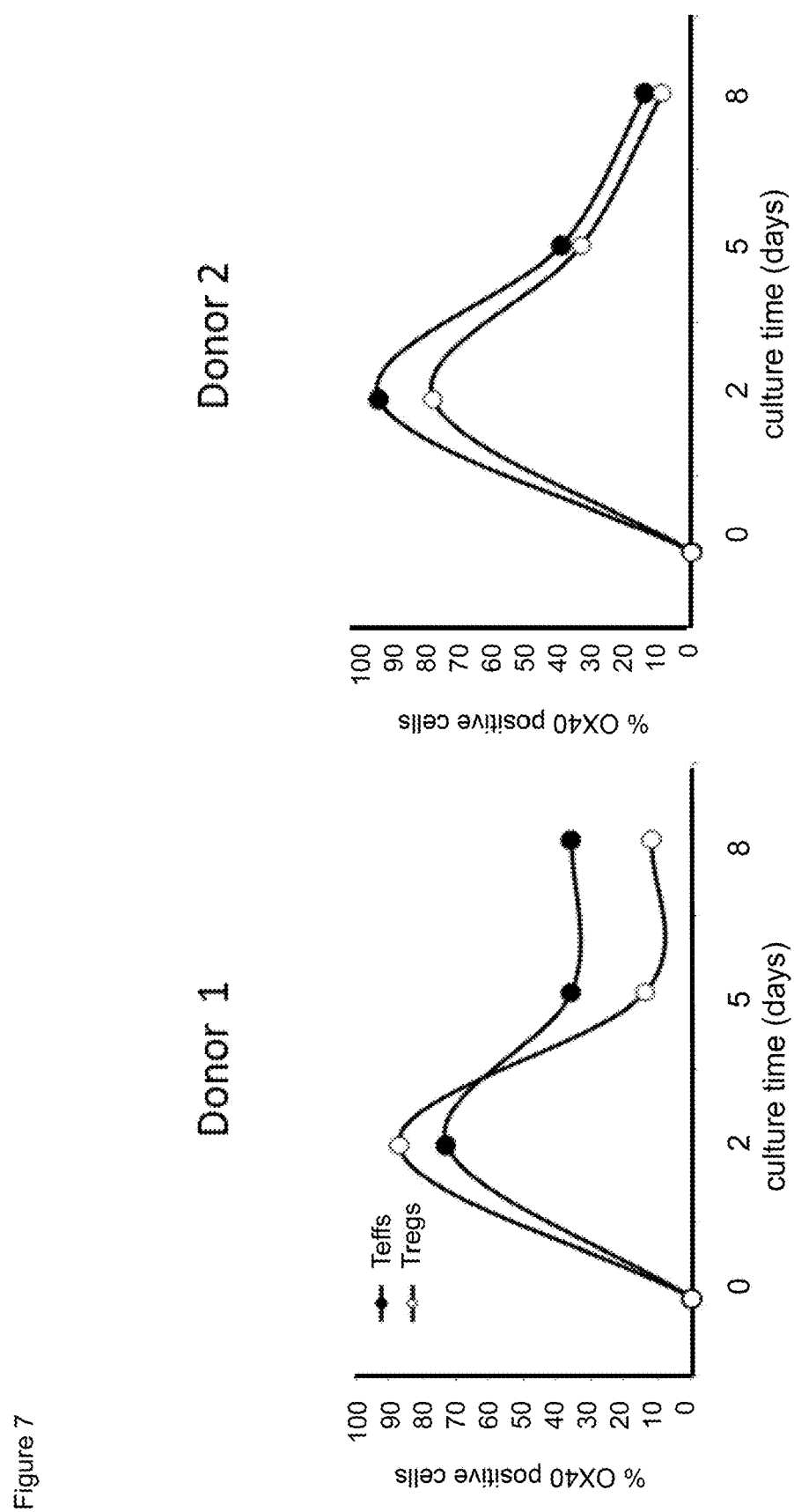
FIG. 7. Time course effect of exposure to anti-human CD3/anti-human CD28 antibody stimulator beads on surface human CD134 expression of human effector T lymphocytes (Teffs) and of regulatory T lymphocytes (Tregs).

As shown in FIG. 7 (n=1 from each donor), peripheral blood-purified non-stimulated/resting (day 0) human Teffs and human Tregs did not express any CD134, however, CD3/CD28 beads-stimulated human Teffs and human Tregs expressed surface CD134. CD134 expression on activated human Teffs and human Tregs peaked after 2 days in culture, and attenuated after 5 and 8 days in culture.

Example 3. Biological Characterization of Mouse Anti-Human CD134 Monoclonal Antibodies Clones 12H3 and 20E5

(a). Proliferation of PHA-Stimulated Human CD134 Expressing T Lymphocytes after Treatment with Mouse Anti-Human CD134 Antibodies Clones 12H3 and 20E5

PHA-stimulated (at 0 and 10 µg/mL for 1 day; see above) human CD134 expressing T lymphocytes were generated. Cells were harvested and suspended at $2 \times 10^6$ cells/mL in RPMI culture medium (Gibco) containing 10% fetal calf serum (Bodinco) and 50 µg/mL gentamycin (Gibco). Cells were seeded at $0.1 \times 10^6$ cells/100 L/well (i.e., $1 \times 10^6$ cells/mL) in 96-wells flat-bottom plates (Corning), and were exposed to 0, 0.025, 0.25, 2.5, or 25.0 µg/mL mouse anti-human CD134 monoclonal antibody clone 12H3 or mouse anti-human CD134 monoclonal antibody clone 20E5, or/and in combination with 0, 0.01, 0.1, or 1.0 µg/mL polyhistidine-tagged recombinant human OX40L (in the presence of 1:5 molar ratio mouse anti-polyhistidine antibody; R&D Systems) at 37° C./5% CO2 for 6 days. After 6 days, cell proliferation was measured using the colorimetric (BrdU incorporation) Cell Proliferation ELISA™ (Roche) and an ELISA reader (BioRad) at A450 nm.

Figure 8:
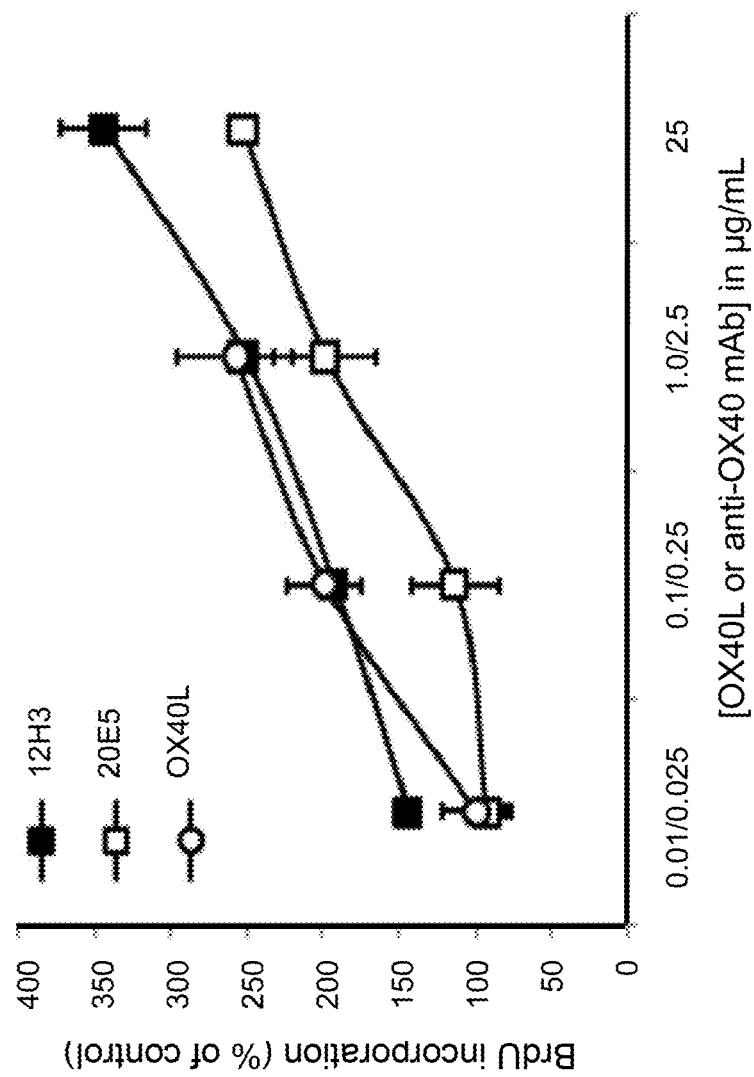
FIG. 8. Dose effect of exposure to mouse anti-human CD134 antibodies clone 12H3 or clone 20E5, or to human OX40L on proliferation of PHA-M-stimulated human CD134 expressing T lymphocytes.

As shown in FIG. 8 (mean±SD, n=4 using one donor), mouse anti-human CD134 monoclonal antibody clone 12H3 and mouse anti-human CD134 monoclonal antibody clone 20E5 dose-dependently induced proliferation in PHA-stimulated human CD134 expressing T lymphocytes. Mouse anti-human CD134 monoclonal antibody clone 12H3 induced proliferation at 0.25, 2.5, and 25 µg/mL. Mouse anti-human CD134 monoclonal antibody clone 12H3 induced proliferation at 2.5 and 25 µg/mL. In addition, human OX40L also dose dependently induced proliferation in PHA-stimulated human CD134 expressing T lymphocytes. Human OX40L induced proliferation at 0.1 and 1.0 µg/mL. Resting (without PHA stimulation) human $CD134^{negative}$ T lymphocytes did not show any proliferative responses after treatment with mouse anti-human CD134 monoclonal antibody clone 12H3, mouse anti-human CD134 monoclonal antibody clone 20E5, or human OX40L (data not shown).

Figure 9:
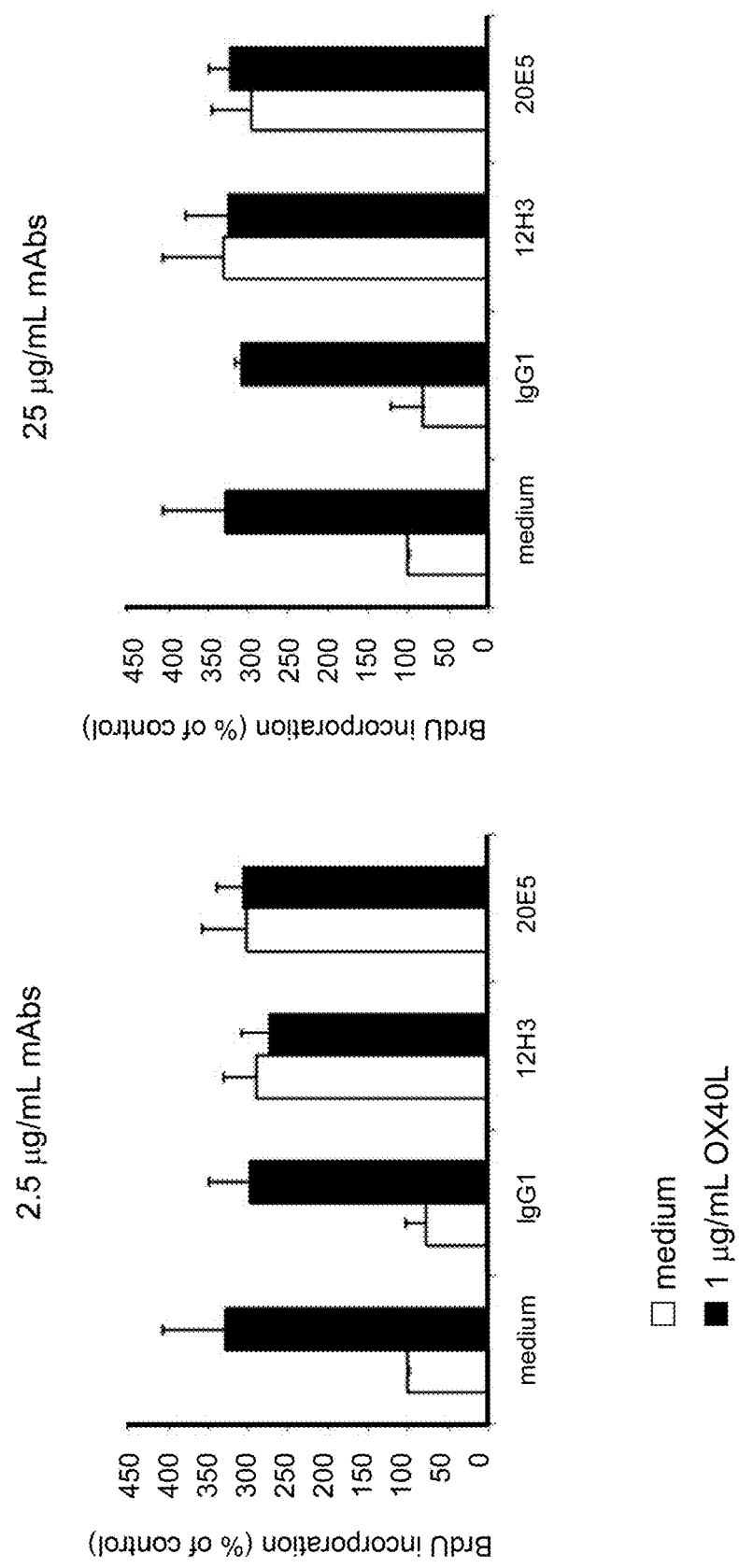
FIG. 9. Effect of combining mouse anti-human CD134 antibodies clone 12H3 with human OX40L, or mouse anti-human CD134 antibodies clone 20E5 with human OX40L on proliferation of PHA-M-stimulated human CD134 expressing T lymphocytes.

As shown in FIG. 9 (mean±SD, n=2 using one donor), mouse anti-human CD134 monoclonal antibody clone 12H3 (at 2.5 and 25 µg/mL), mouse anti-human CD134 monoclonal antibody clone 20E5 (at 2.5 and 25 µg/mL), and human OX40L (at 1.0 µg/mL) induced proliferation in PHA-stimulated human CD134 expressing T lymphocytes. Non treated (medium only) or treatment with mouse IgG1K isotype control (at 2.5 and 25 µg/mL; BD Biosciences) did not demonstrate any effect on PHA-stimulated human CD134 expressing T lymphocyte proliferation. The combination of mouse anti-human CD134 monoclonal antibody clone 12H3 at 2.5 and µg/mL (or at lower concentrations; data not shown)) or mouse anti-human CD134 monoclonal antibody clone 20E5 at 2.5 and 25 µg/mL (or at lower concentrations; data not shown) with human OX40L at 1.0 µg/mL (or at lower concentrations; data not shown) did not demonstrate any reciprocal (i.e., synergistic or additive, or even inhibitory) effects on proliferation in PHA-stimulated human CD134 expressing T lymphocytes.

(b). Proliferation of Anti-Human CD3/Anti-CD28 Beads-Stimulated Human CD134 Expressing T Effector and T Regulator Lymphocytes after Treatment with Mouse Anti-Human CD134 Antibodies Clones 12H3 and 20E5

Human CD4 T lymphocytes were purified from PBMCs by negative selection using a cocktail of mouse antibodies (BD BioSciences) directed against human CD8 (clone RPA-T8), CD14 (clone M5E2), CD16 (clone 3G8), CD19 (clone 4G7), CD33 (clone P67.6), CD56 (clone B159), and CD235a (HIR2). After incubation with Dynabeads®-conjugated sheep anti-mouse IgG (Invitrogen), unbound CD4 T lymphocytes were collected from the Dynal Magnetic Particle Concentrator, MPC™-6 (Invitrogen). From these enriched CD4 T lymphocytes, $CD25^{high}$ Tregs and $CD25^{negative}$ Teffs were separated by MACS-sorting using 10 µL microbeads-conjugated mouse anti-human CD25 antibodies (Miltenyi Biotec)/$10^7$ cells and MiniMACS™ Magnet/MS columns (Miltenyi Biotec VarioMACS™ Magnet/LS columns (Miltenyi Biotec). This resulted in enrichments of >90% Teffs and of >90% Tregs. Teffs and Tregs were put on $0.25 \times 10^6$ cells/mL in RPMI-1640/glutamax culture medium (Gibco) supplemented with 0.02 mM pyruvate (Gibco), 100 U/mL penicillin (Gibco), 100 µg/mL streptomycin (Gibco), and 10% HPSi. Then, Teffs and Tregs were seeded at 2.5×10⁴ cells/200 L/well (i.e., 0.125×10⁶ cells/mL) in 96-wells round-bottom plates (Greiner), and were stimulated with CD3/CD28 beads (Invitrogen) at 1 bead/5 cells with or without 5.0 g/mL mouse anti-human CD134 monoclonal antibody clone 12H3, 5.0 µg/mL mouse anti human CD134 monoclonal antibody clone 20E5, 1.0 µg/mL polyhistidine-tagged recombinant human OX40L (in the presence of 1:5 molar ratio mouse anti-polyhistidine antibody; R&D Systems), a combination of 5.0 µg/mL mouse anti-human CD134 monoclonal antibody clone 12H3 with 1.0 µg/mL polyhistidine-tagged recombinant human OX40L (in the presence of 1:5 molar ratio mouse anti-polyhistidine antibody), or a combination of 5.0 µg/mL mouse anti-human CD134 monoclonal antibody clone 20E5 with 1.0 µg/mL polyhistidine tagged recombinant human OX40L (in the presence of 1:5 molar ratio mouse anti-polyhistidine antibody) at 37° C./5% $CO_2$ for 4 or 5 days. After 4 or 5 days, cell proliferation was measured using 0.5 µCi tritiated thymidine (Perkin & Elmer) incorporation and a β-counter (Canberra-Packard).

Figure 10:
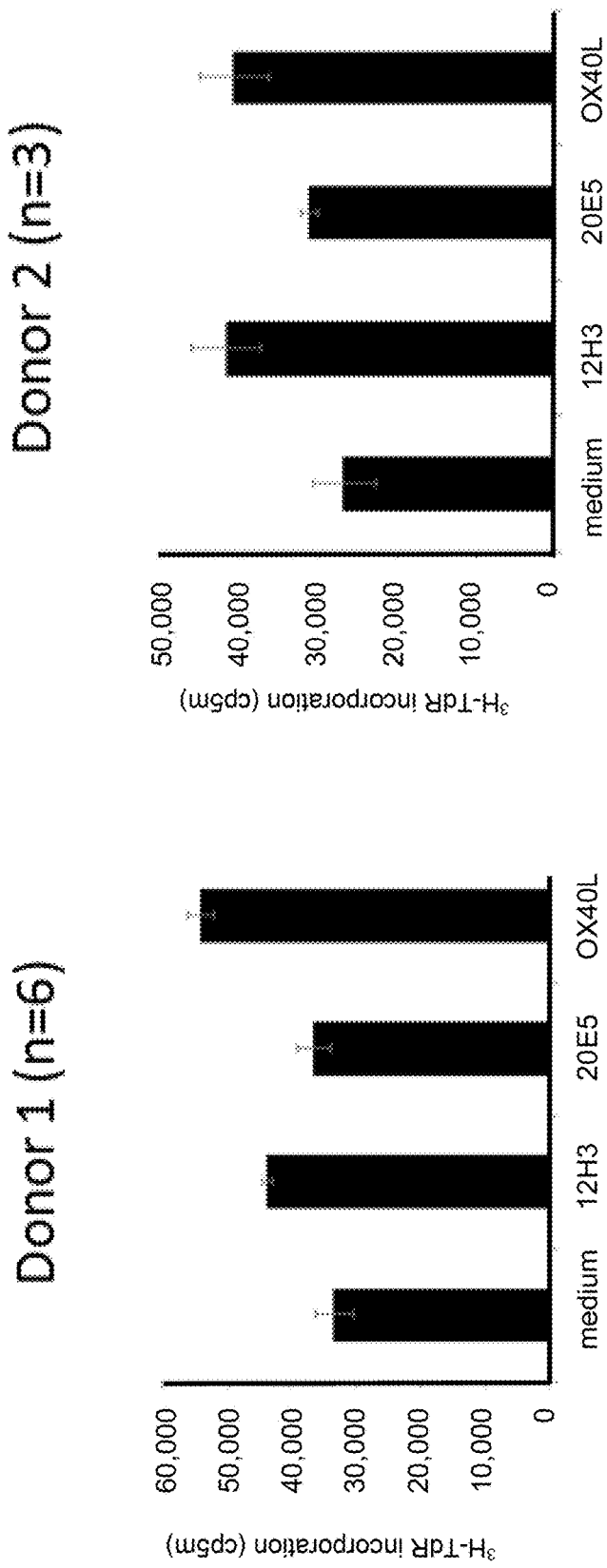
FIG. 10. Effect of exposure to mouse anti-human CD134 antibodies clone 12H3 or clone 20E5, or to human OX40L on proliferation of anti-human CD3/anti-human CD28 antibody stimulator beads-stimulated human CD134 expressing human effector T lymphocytes.
Figure 10:
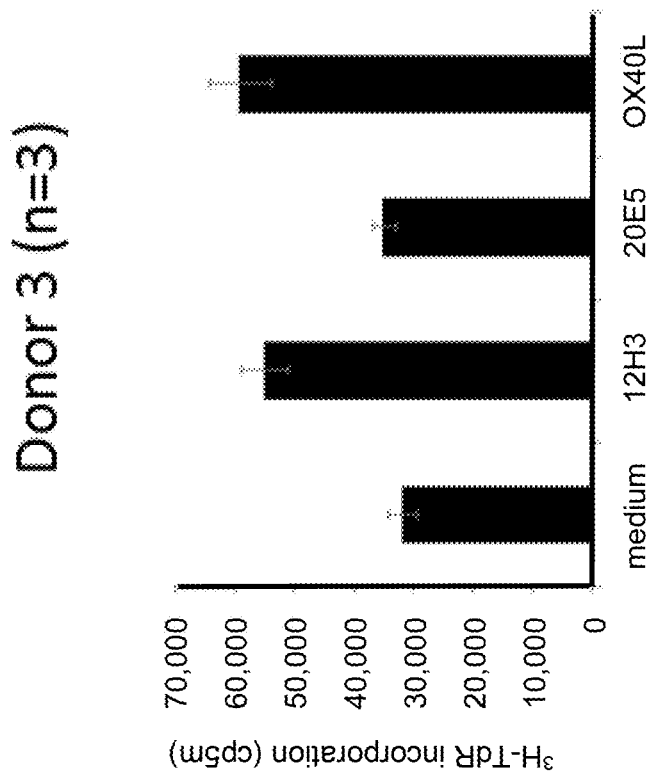

As shown in FIG. 10 (mean±SD), although CD3/CD28 stimulator beads alone induced considerable proliferation in human CD134 expressing Teffs (i.e. medium), mouse anti human CD134 monoclonal antibody clone 12H3 or human OX40L induced additional proliferation in CD3/CD28 beads-stimulated human CD134 expressing Teffs. Mouse anti human CD134 monoclonal antibody clone 20E5 did not induce additional proliferation in CD3/CD28 beads-stimulated human CD134 expressing Teffs.

Figure 11:
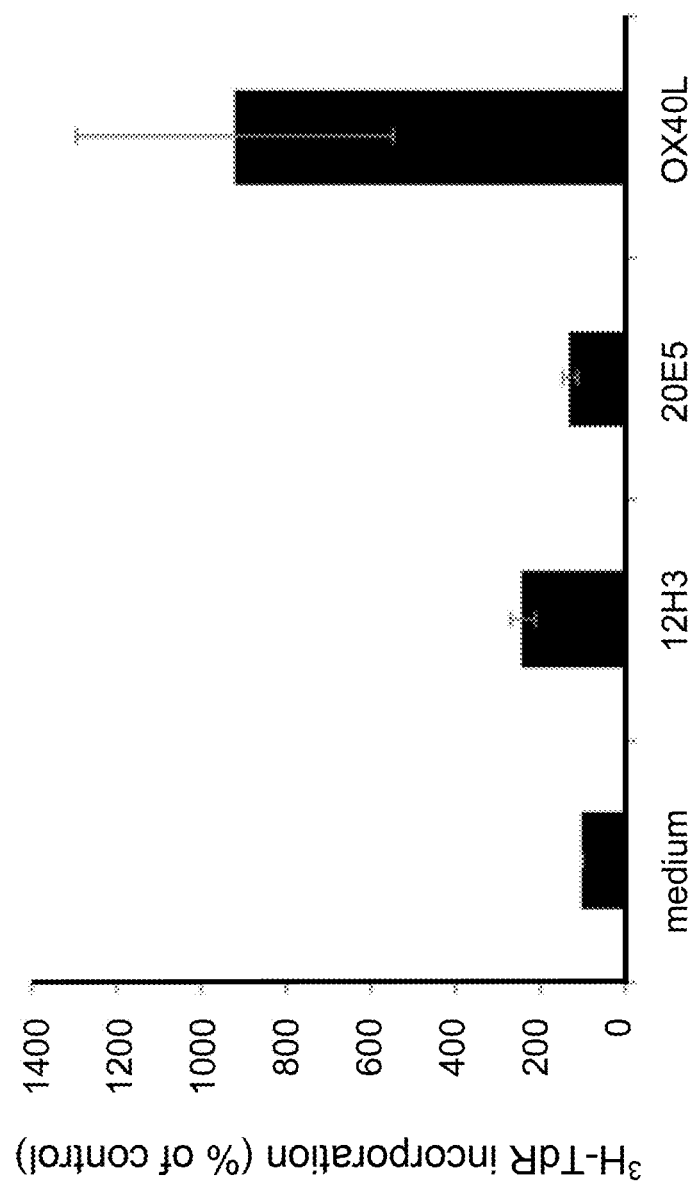
FIG. 11. Effect of exposure to mouse anti-human CD134 antibodies clone 12H3 or clone 20E5, or to human OX40L on proliferation of anti-human CD3/anti-human CD28 antibody stimulator beads-stimulated human CD134 expressing human regulatory T lymphocytes.

As shown in FIG. 11 (mean±SEM from 5 donors), mouse anti-human CD134 monoclonal antibody clone 12H3 and mouse anti-human CD134 monoclonal antibody clone 20E5 did not induce or induced low proliferation in CD3/CD28 beads-stimulated human CD134 expressing Tregs, whereas human OX40L induced very strong proliferation in CD3/CD28 beads stimulated human CD134 expressing Tregs.

As shown in FIG. 12A (mean±SD), mouse anti-human CD134 monoclonal antibody clone 12H3 in combination with human OX40L did not demonstrate any reciprocal (i.e., inhibitory, synergistic or additive) effects in CD3/CD28 beads-stimulated human CD134 expressing Teffs. Furthermore, mouse anti-human CD134 monoclonal antibody clone 20E5 in combination with human OX40L did not demonstrate any reciprocal (i.e., inhibitory, synergistic or additive) effects in CD3/CD28 beads-stimulated human CD134 expressing Teffs (data not shown).

As shown in FIG. 12B (mean±SD), in contrast to the (lack of any) effect observed with human OX40L-mediated proliferative responses in CD3/CD28 beads-stimulated human CD134 expressing Teffs, mouse anti-human CD134 monoclonal antibody clone 12H3 strongly suppressed human OX40L-mediated proliferative responses in CD3/CD28 beads stimulated human CD134 expressing Tregs.

(c). Suppression Function of Anti-Human CD3/Anti-CD28 Beads-Stimulated Human CD134 Expressing T Regulator Lymphocytes after Treatment with Mouse Anti-Human CD134 Antibodies Clones 12H3 and 20E5

Human CD4 T lymphocytes were purified from PBMCs, and Teffs and Tregs were enriched as described in Example 3(b) above. Teffs and Tregs were put on 0.25×10⁶ cells/mL in RPMI 1640/glutamax culture medium (Gibco) supplemented with 0.02 mM pyruvate (Gibco), 100 U/mL penicillin (Gibco), 100 µg/mL streptomycin (Gibco), and 10% HPSi. Then, Teffs were seeded at 2.5×10⁴ cells/200 µL/well (i.e., 0.125×10⁶ Teffs/mL) and co-cultured with 2.5×10⁴ suppressive Tregs/200 µL/well (i.e., 0.125×10⁶ Tregs/mL; Teffs/Tregs ratio=1:1) in 96-wells round-bottom plates (Greiner). These Teffs/Tregs co-cultures were stimulated with CD3/CD28 beads (Invitrogen) at 1 bead/10 cells with or without 5.0 µg/mL mouse anti-human CD134 monoclonal antibody clone 12H3, 5.0 µg/mL mouse anti-human CD134 monoclonal antibody clone 20E5, and 1.0 µg/mL polyhistidine-tagged recombinant human OX40L (in the presence of 1:5 molar ratio mouse anti-polyhistidine antibody; R&D Systems) at 37° C./5% CO2 for 5 days. After 5 days, cell proliferation was measured using 0.5 µCi tritiated thymidine (Perkin & Elmer) incorporation and a β-counter (Canberra-Packard).

Figure 13:
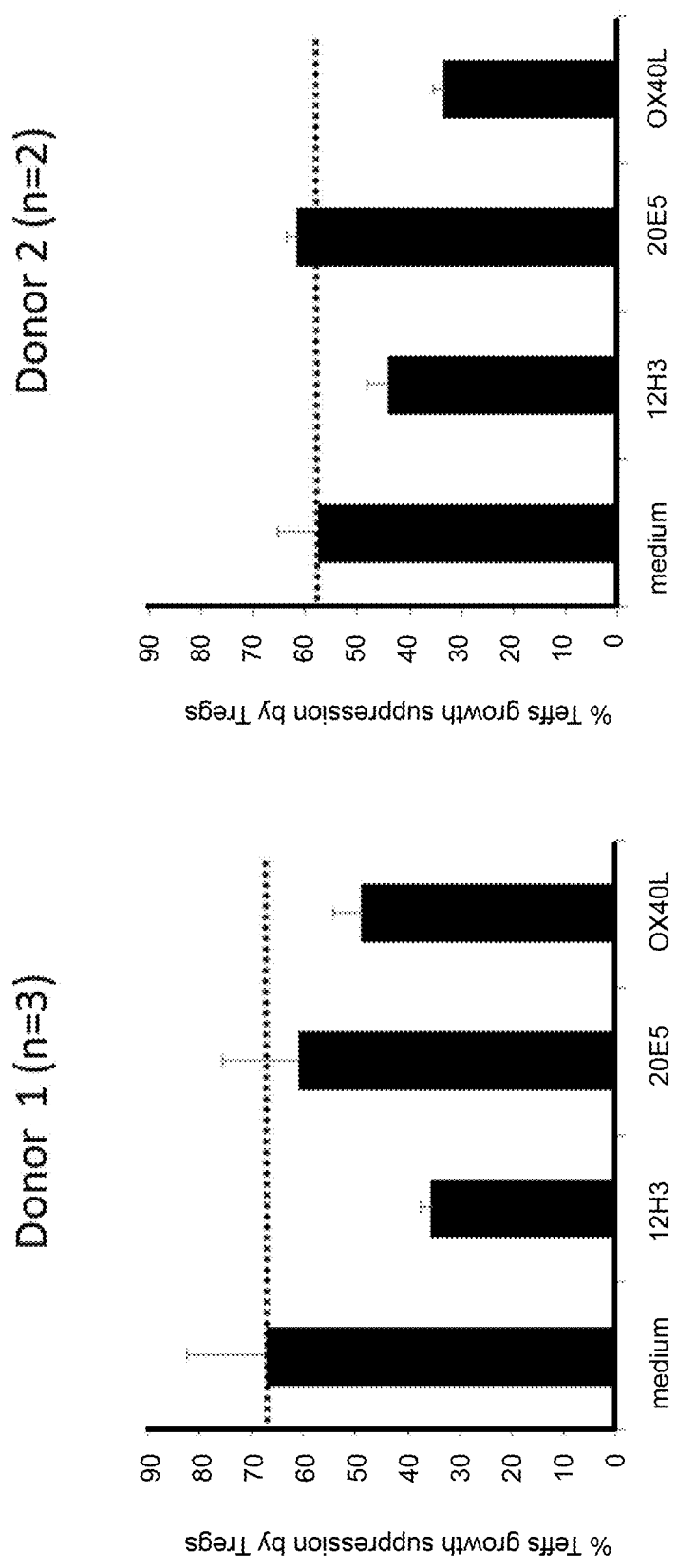
FIG. 13. Effect of exposure to mouse anti-human CD134 antibodies clone 12H3 or clone 20E5, or to human OX40L on human CD134 expressing human regulatory T lymphocyte-mediated suppression of human CD134 expressing human effector T lymphocyte proliferation.

As shown in FIG. 13 (mean±SD), human Tregs suppressed CD3/CD28 beads-induced human Teffs proliferative responses (i.e., medium). This suppressive function of human Tregs was dampened in the presence of mouse anti-human CD134 monoclonal antibody clone 12H3 or in the presence of human OX40L. Mouse anti-human CD134 monoclonal antibody clone 20E5 showed no effect on human Tregs suppressive function.

Example 4. Molecular Genetic Characterization of Mouse Anti-Human CD134 Monoclonal Antibodies Clones 20E5 and 12H3

(a). Isotyping and Edman Degradation

Mouse immunoglobulin class, isotype, and light chain type of Protein G-purified mouse anti-human CD134 monoclonal antibodies clones 20E5 and 12H3 were determined using the IsoStrip™ Mouse Monoclonal Antibody Isotype Kit (Roche), and showed that both mouse anti-human CD134 monoclonal antibodies clones 20E5 and 12H3 consisted of IgG1 heavy chains and kappa (κ) light chains.

After standard SDS-PAGE electrophoresis, using the precast gel NuPage® Novex® system (Invitrogen) under reduced (DTT and 70° C. heating) conditions, mouse anti-human CD134 monoclonal antibody clone 20E5 was electro-blotted onto a polyvinylidene fluoride (PDVF/Immobilon-P) transfer membrane (Millipore), and stained with Coomassie brilliant blue (BioRad). Then, heavy and light chains bands (50 kDa and 25 kDa, respectively) were excised from the PVDF membrane, and used for Edman degradation analysis (performed by EuroSequence, Groningen, The Netherlands) to determine the N-terminal amino acid sequences. The results are shown in SEQ ID NO. 3 and SEQ ID NO. 61 for mouse anti-human CD134 monoclonal antibody clone 20E5. Eleven amino acids of the N-terminus from heavy chains and 11 amino acids of the N-terminus from light chains were determined.

(b). RT PCR

Hybridoma cells of clone 20E5 and 12H3 were harvested from cell culture. Cells were washed with PBS, aliquoted in vials containing 5×10⁶ cells, and stored as pellets at −80° C. Cell pellets were used to isolate RNA by using RNeasy Mini Isolation Kit (QIAGEN). RNA concentration was determined (A260 nm) and RNA was stored at −80° C. Total yield of isolated RNA: 27.3 µg and 58.4 µg for clone 20E5 and clone 12H3, respectively (A260/A280 ratio for both 1.9). By reverse transcriptase, cDNA was synthesized from 1 µg of RNA using the RevertAid™ H Minus First Strand cDNA Synthesis Kit (Fermentas), and stored at −20° C.

Based on the isotype (mouse kappa/IgG1) and Edman degradation analysis of mouse anti-human CD134 monoclonal antibody clone 20E5, following primers were designed to amplify V-regions of mouse anti-human CD134 monoclonal antibody clone 20E5:

| Primer No.* | Sequence** | SEQ ID No. | Direction | Gene |
|---|---|---|---|---|
| 201 | GACAGTTGGTGCAGCATCAG | 39 | antisense | mkappa |
| 266 | CACTGGATGGTGGGAAGATG | 40 | antisense | mkappa |
| 203 | GGCCAGTGGATAGACAGATG | 41 | antisense | mIgG1 |
| 204 | TGGACAGGGATCCAGAGTTC | 42 | antisense | mIgG1 |
| 259 | GCGAAGTACAAYTNCARCARWSNGG | 43 | sense | 20E5HC |
| 260 | GCGTACAATTACARCARWSNGGNCC | 44 | sense | 20E5HC |
| 265 | GCGATATACARATGACNCARAC | 45 | sense | 20E5LC |

*no. according to Bioceros internal coding system;
**degenerated primers: N = A, C, G, or T, Y = C or T, R = A or G, W = A or T, and S = G or C.

Based on the isotype (mouse kappa/IgG1) of mouse anti-human CD134 monoclonal antibody clone 12H3 and sense primers annealing to cDNAs encoding mouse signal peptides (partially based on Antibody Engineering Volume 1 Kontermann, Roland E.; Dtibel, Stefan (Eds.), Springer Lab Manuals, 2nd ed., 2010), following primers were designed to amplify V-regions of mouse anti-human CD134 monoclonal antibody clone 12H3:

| Primer No.* | Sequence** | SEQ ID No. | Direction | Gene |
|---|---|---|---|---|
| 416 | CAGTGGATAGACAGATGGGGG | 46 | antisense | mIgG1 |
| 394 | ACTGGATGGTGGGAAGATGG | 47 | antisense | mkappa |
| 405 | ATGGGATGGAGCTRTATCATSYTCTT | 48 | sense | signal peptide |
| 410 | ATGGRATGGAGCKGGGTCTTTMTCTT | 49 | sense | signal peptide |
| 389 | ATGGGCWTCAAAGATGGAGTCACA | 50 | sense | signal peptide |

*no. according to Bioceros internal coding system;
**degenerated primers: N = A, C, G, or T, Y = C or T, R = A or G, W = A or T, and S = G or C, M = C or A and K = G or T.

Primers 201 and 266 are antisense designed to anneal within the constant region of the mouse kappa gene at position 214-232 and 236-255 respectively (based on accession number V00807 [version V00807.1]).

Primers 203 and 204 are antisense designed to anneal within the constant region of mouse IgG1 at position 115-134 and 221-240 respectively (based on accession number J00453 [version J00453.1]).

Primers 259 and 260 are sense degenerate primers (degeneracy respectively 512 and 256) annealing at the N-terminus (amino acid 1-8 and 2-9 respectively) of the heavy chain of mouse anti-human CD134 antibody clone 20E5 based on Edman degradation.

Primer 265 is a sense degenerate primer (degeneracy of 16) annealing at the N-terminus (amino acid 1-7) of the light chain of mouse anti-human CD134 antibody clone 20E5 based on Edman degradation.

Primer 416 is antisense designed to anneal within the constant region of mouse IgG1 at position 111-131 (based on accession number J00453 [version J00453.1]).

Primer 394 is antisense designed to anneal within the constant region of the mouse kappa gene at position 235-254 (based on accession number V00807 [version V00807.1]).

Primers 389, 405 and 410 are degenerated primers (degeneracy respectively 2, 8 and 8) annealing with signal peptide sequences of murine antibodies. Primer 389 was designed for the light chain, primers 405 and 410 for the heavy chain.

Primers 201, 266, 203, 204, 259, 260, and 265 were used in various combinations to amplify variable regions of mouse anti-human CD134 antibody clone 20E5, and primers 416, 394, 405, 410, and 389 were used in various combinations to amplify variable regions of mouse anti-human CD134 antibody clone 12H3. Various different PCRs were done using generated cDNA of both clones as template.

Accuprime™ Pfx DNA Polymerase (Invitrogen) was used to amplify variable regions of heavy and light chains of both mouse anti-human CD134 antibody clone 20E5 and clone 12H3. The PCR products were analyzed on a 1% agarose gel. Products of PCR reactions were gel-purified and cloned in the pCR-Blunt II-TOPO® vector for sequence analysis. From plasmids containing a PCR insert, cloned inserts were analysed by DNA sequencing (performed by ServicXS B.V., Leiden, The Netherlands or Macrogen, Amsterdam, The Netherlands) using T7 to obtain the consensus sequence for V-regions of mouse anti-human CD134 antibodies clones 20E5 and 12H3. Eleven informative sequences heavy chain reactions and 3 informative light chain sequence reactions were obtained for mouse anti-CD134 antibody clone 20E5. Five informative sequences heavy chain reactions and 3 informative light chain sequence reactions were obtained for mouse anti-CD134 antibody clone 12H3. Based on this information, consensus sequences of V-regions of both antibodies were determined (see SEQ ID NO. 4, 5, 12 and 13).

Example 5. Generation of Chimeric Human IgG4/Kappa and/or Human IgG1/Kappa (i.e., Swapping Mouse Constant Domains for Constant Human IgG/Kappa Domains) Anti-Human CD134 Monoclonal Antibodies Clones 20E5 an 12H3

Based on determined murine V-regions (see Example 4 (b) above) of mouse anti-CD134 antibodies clones 20E5 and 12H3, a design was made to generate chimeric human antibody versions. To this end, CHO cell-optimized cDNA sequences (see SEQ ID NO. 20 (coding for chimeric human heavy IgG4 chain clone 20E5), SEQ ID NO. 21 (coding for chimeric human light K chain clone 20E5), SEQ ID NO. 22 (coding for chimeric human heavy IgG1 chain clone 20E5), SEQ ID NO. 23 (coding for chimeric human heavy IgG4 chain clone 12H3), and SEQ ID NO. 24 (coding for chimeric human light K chain clone 12H3)), were ordered at GENEART (Regensburg, Germany), which encoded for a murine signal peptide followed by either the variable light chain linked to human kappa constant region, or followed by the variable heavy chain linked to human IgG constant region. This design was done for both antibodies; for clone 20E5, the variable heavy chain was linked to human IgG4 or to human IgG1 constant region; for clone 12H3, the variable heavy chain region was linked to human IgG4 constant region. Using suitable restriction enzymes, generated cDNAs were subcloned in pcDNA3.1-derived expression plasmids. Chimeric antibodies were expressed using FreeStyle™ MAX CHO (CHO-S cells) Expression System (Invitrogen). Expressed antibodies were purified using affinity chromatography protein A columns (GE Healthcare). For chimeric amino acid sequences, see SEQ ID NO. 25, 26, 27, 28, and 29.

Example 6. Binding Characterization of Chimeric Human IgG4/Kappa and/or IgG1/Kappa Anti-Human CD134 Monoclonal Antibody Clone 20E5

(a). Binding Characteristics of Human IgG4κ Anti-Human CD134 Monoclonal Antibody Clone 20E5 on PHA-Stimulated Human CD134 Expressing CD4 Positive T Lymphocytes PHA-stimulated (at 10 μg/mL for 1 day; see above) human CD134 expressing T lymphocytes were generated. Cells were harvested and put at $1-2 \times 10^6$ cells/mL in ice chilled PBS/BSA/NaN$_3$. Cells were incubated with 0, 0.007, 0.02, 0.07, 0.2, 0.6, 1.9, 5.6, 16.7, 50.0 μg/mL chimeric human IgG4κ anti-human CD134 antibody clone 20E5 for 30 minutes at 4° C. After extensive washing in PBS/BSA/NaN$_3$, cells were subsequently incubated with 1:50 diluted FITC-conjugated mouse anti-human IgG4 antibodies (Sigma) for 30 minutes at 4° C. After extensive washing in PBS/BSA/NaN$_3$, cells were incubated with 1:10 diluted PE-conjugated mouse anti-human CD4 antibody (BD Biosciences) for 30 minutes at 4° C. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Chimeric human IgG4κ anti-human CD134 antibody clone 20E5 saturated human CD134 surface molecules on PHA-stimulated CD4$^{positive}$ T lymphocytes at approximately 5.0-10.0 μg/mL (data not shown). Half maximal binding was observed at ≈1.0 μg/mL for chimeric human IgG4κ anti-human CD134 antibody clone 20E5 (data not shown).

(b). Binding of Chimeric Human IgG4κ Anti-Human CD134 Monoclonal Antibody Clone 20E5 on PHA-Stimulated Human CD134 Expressing CD4 Positive and CD8 Positive T Lymphocytes PHA-stimulated (at 10 μg/mL for 1 day; see above) human CD134 expressing T lymphocytes were generated. Cells were harvested and put at $1-2 \times 10^6$ cells/mL in ice-chilled PBS/BSA/NaN$_3$. Cells were incubated with or without 20.0 g/mL chimeric human IgG4κ anti-human CD134 antibody clone 20E5 for 30 minutes at 4° C. After extensive washing in PBS/BSA/NaN$_3$, cells were subsequently incubated for 30 minutes at 4° C. with 1:200 diluted PE-conjugated goat anti-human IgG (Fcγ specific) antibodies (Jackson ImmunoResearch) for 30 minutes at 4° C. After extensive washing in PBS/BSA/NaN$_3$, cells were incubated with 1:10 diluted FITC-conjugated mouse anti-human CD4 antibody (BD Biosciences) or with 1:10 diluted FITC-conjugated mouse anti-human CD8 antibody (BD Biosciences) to detect T lymphocyte subpopulations. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Chimeric human IgG4κ anti-human CD134 antibody clone 20E5 demonstrated positive staining on the PHA-activated human CD4positive T lymphocyte subpopulation, and low positive staining on the PHA-activated human CD8positive T lymphocyte subpopulation (data not shown).

(c). Binding of Chimeric Human IgG4κ Anti-Human CD134 Monoclonal Antibody Clone 20E5 on Anti-Human CD3/Anti-Human CD28 Antibody Stimulator Beads-Stimulated Human CD134 Expressing CD4 Positive and CD8 Positive T Lymphocytes Human peripheral blood mononuclear cells (PBMC) from healthy donors (informed consent) were isolated by density centrifugation on Lymphoprep (1.077 g/mL; Nycomed). Subsequently, $1 \times 10^6$ PBMC/mL in RPMI-1640 culture medium (Gibco) containing 10% fetal calf serum (Bodinco) and 50 μg/mL gentamycin (Gibco) were stimulated with mouse anti human CD3/mouse anti-human CD28 antibody stimulator beads (CD3/CD28 beads; Invitrogen) at 1 bead/4 cells in the absence or presence of 25 U/mL recombinant human interleukin-2 (PeproTech) at 37° C./5% CO2 for 1 day. After culture, PBMC were harvested and put at $1-2 \times 10^6$ cells/mL in ice-chilled PBS/BSA/NaN$_3$. Cells were incubated with or without 20.0 g/mL chimeric human IgG4κ anti-human CD134 antibody clone 20E5 for 30 minutes at 4° C. After extensive washing in PBS/BSA/NaN$_3$, cells were subsequently incubated with 1:200 diluted PE-conjugated goat anti-human IgG (Fcγ specific) antibodies (Jackson ImmunoResearch) for 30 minutes at 4° C. After extensive washing in PBS/BSA/NaN$_3$, cells were incubated for 30 minutes at 4° C. with 1:10 diluted FITC-conjugated mouse anti-human CD4 antibody (BD Biosciences) or with 1:10 diluted FITC-conjugated mouse anti-human CD8 antibody (BD Biosciences) to detect T lymphocyte subpopulations. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Figure 14:
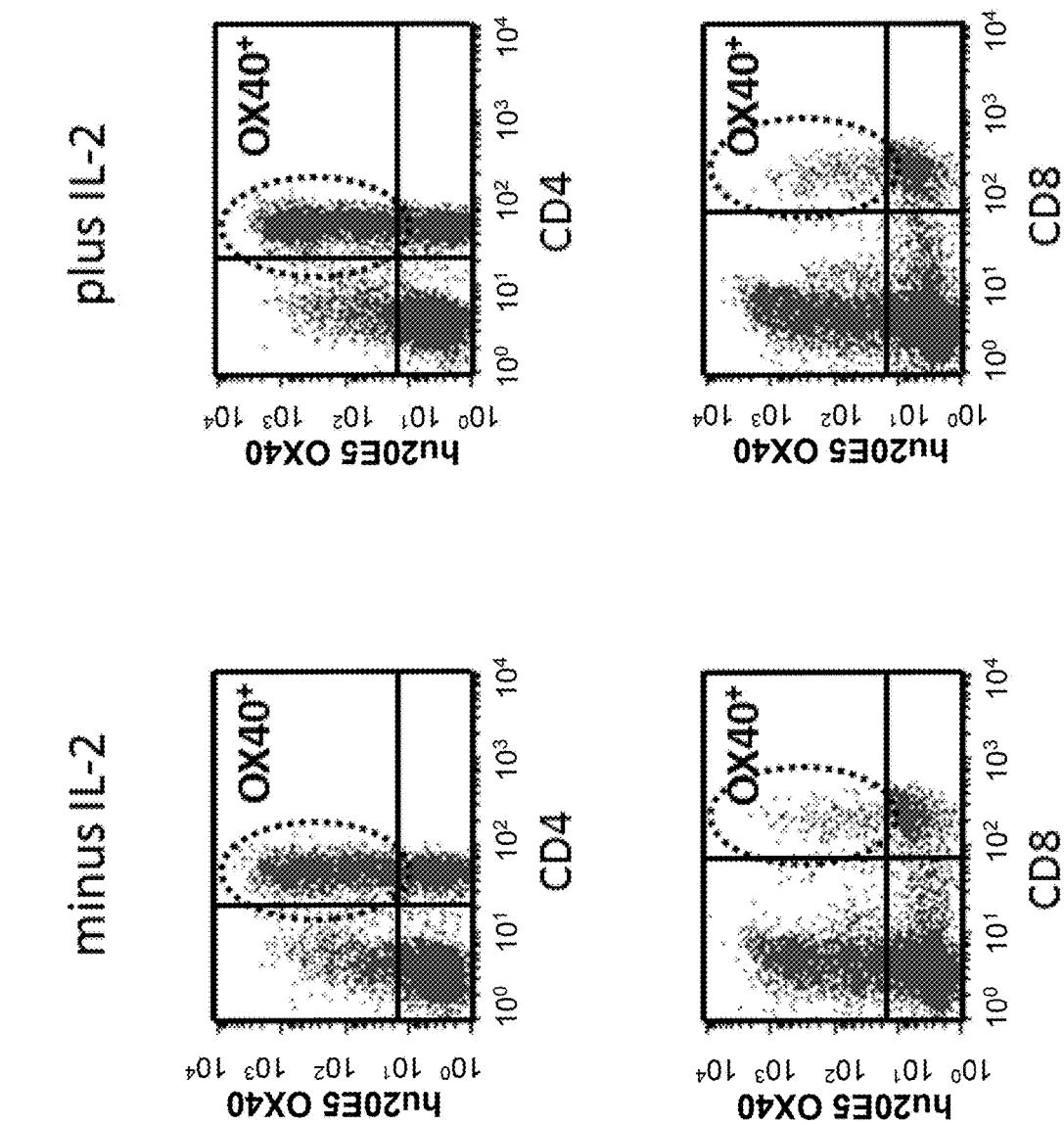
FIG. 14. Binding of chimeric human IgG4κ anti-human CD134 antibody clone 20E5 on (minus and plus IL-2) CD3/CD28 beads-stimulated human CD134 expressing CD4 T lymphocytes and CD8 T lymphocytes.

As shown in FIG. 14, chimeric human IgG4κ anti-human CD134 antibody clone 20E5 demonstrated positive staining on the CD3/CD28 beads-activated human CD4$^{positive}$ T lymphocyte subpopulation, and low positive staining on the CD3/CD28 beads-activated human CD8$^{positive}$ T lymphocyte subpopulation. No apparent effect was observed using recombinant human IL-2 supplement.

Example 7. Biological Characterization of Chimeric Human IgG4/Kappa Anti-Human CD134 Monoclonal Antibody Clone 20E5

(a). Proliferation of PHA-Stimulated Human CD134 Expressing T Lymphocytes after Treatment with Chimeric Human IgG4κ Anti-Human CD134 Monoclonal Antibody Clone 20E5

PHA-stimulated (10 μg/mL for 1 day; see above) human CD134 expressing T lymphocytes were generated. Cells were harvested and suspended at $2 \times 10^6$ cells/mL in RPMI culture medium (Gibco) containing 10% fetal calf serum (Bodinco) and 50 μg/mL gentamycin (Gibco). Cells were seeded at $0.1 \times 10^6$ cells/100 μL/well (i.e., $1 \times 10^6$ cells/mL) in 96-wells flat bottom plates (Corning), and were exposed to 25.0 g/mL chimeric human IgG4κ anti-human CD134 antibody clone 20E5 or to 25.0 g/mL control human IgG4κ anti-human CD40 antibody (PG102; Pangenetics), or to 1.0 μg/mL polyhistidine-tagged recombinant human OX40L (in the presence of 1:5 molar ratio mouse anti-polyhistidine antibody; R&D Systems) at 37° C./5% C02 for 6 days. After 6 days, cell proliferation was measured using the colorimetric (BrdU incorporation) Cell Proliferation ELISA™ (Roche) and an ELISA reader (BioRad) at A450 nm.

Figure 15:
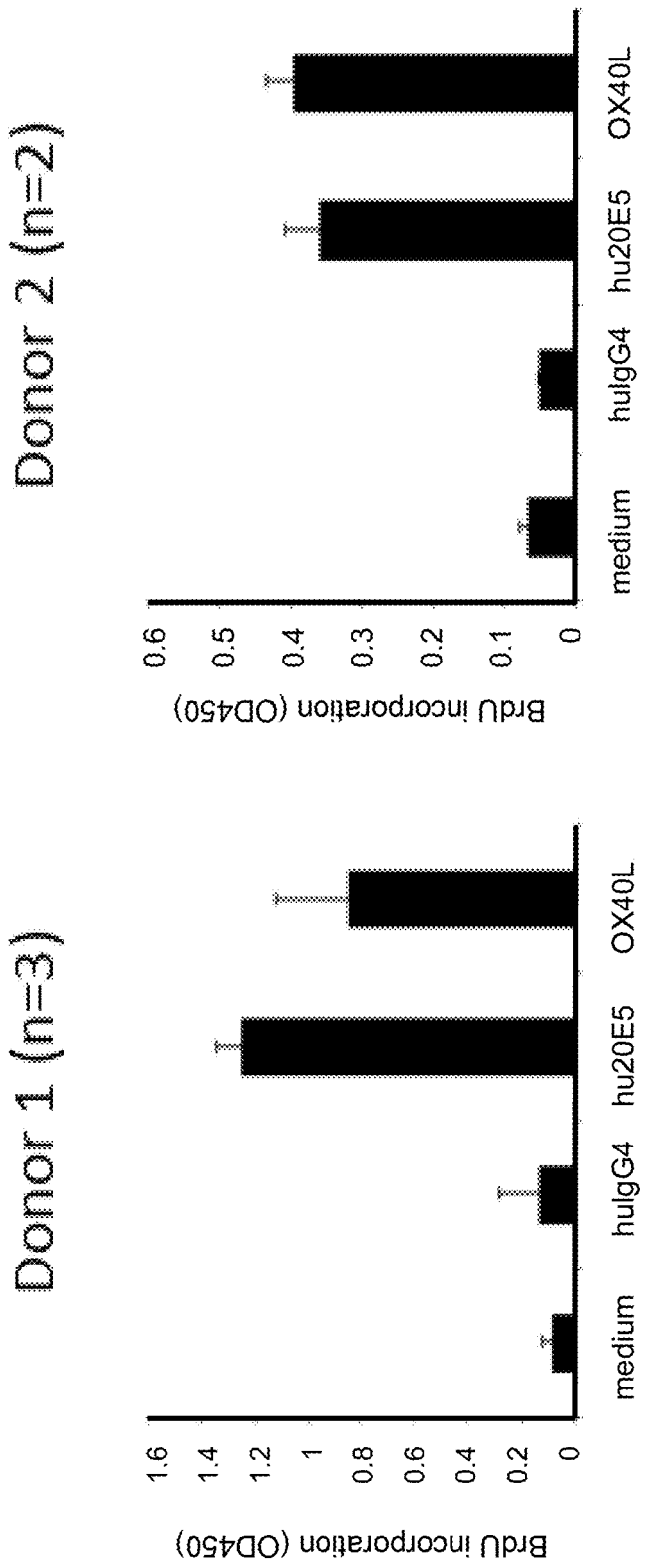
FIG. 15. Effect of chimeric human IgG4κ anti-human CD134 antibody clone 20E5 or human OX40L on proliferation of PHA-M-stimulated human CD134 expressing T lymphocytes.
Figure 15:
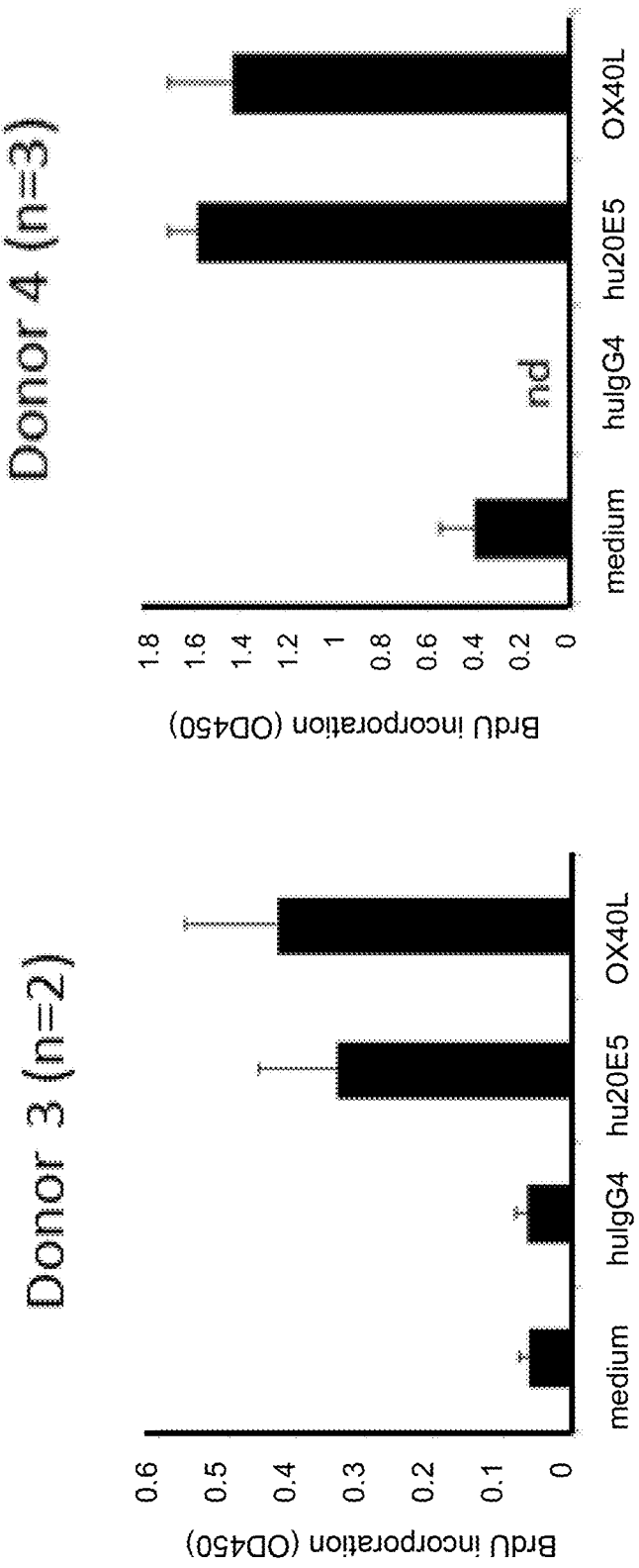
Figure 15:
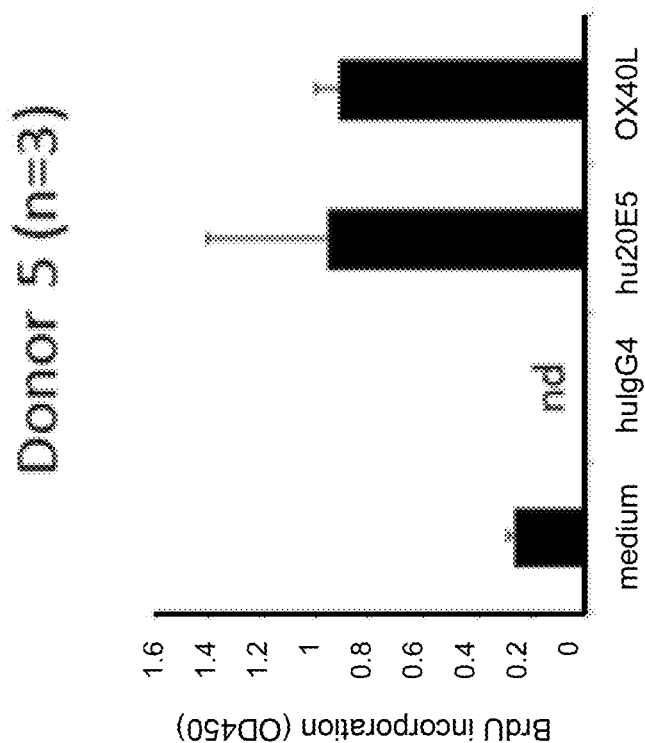

As shown in FIG. 15 (mean±SD), chimeric human IgG4κ anti-human CD134 antibody clone 20E5 (hu20E5) and human OX40L induced proliferation in PHA-stimulated human CD134 expressing T lymphocytes. Non-treated (medium only) or treatment with control human IgG4κ anti-human CD40 antibody (huIgG4) did not demonstrate any effect on PHA stimulated human CD134 expressing T lymphocyte proliferation.

(b). Proliferation of PHA-Stimulated Human CD134 Expressing T Lymphocytes after Treatment with Chimeric Human IgG4κ Anti-Human CD134 Monoclonal Antibody Clone 20E5 in Combination with Recombinant Human OX40L PHA-stimulated (10 µg/mL for 1 day; see above) human CD134 expressing T lymphocytes were generated. Cells were harvested and suspended at $2 \times 10^6$ cells/mL in RPMI culture medium (Gibco) containing 10% fetal calf serum (Bodinco) and 50 µg/mL gentamycin (Gibco). Cells were seeded at $0.1 \times 10^6$ cells/100 µL/well (i.e., $1 \times 10^6$ cells/mL) in 96-wells flat-bottom plates (Corning), and were exposed to 0, 0.025, 0.25, 2.5, or 25.0 µg/mL chimeric human IgG4κ anti-human CD134 antibody clone 20E5, or/and in combination with 0, 0.01, 0.1, or 1.0 µg/mL polyhistidine-tagged recombinant human OX40L (in the presence of 1:5 molar ratio mouse anti-polyhistidine antibody; R&D Systems) at 37° C./5% C02 for 6 days. After 6 days, cell proliferation was measured using the colorimetric (BrdU incorporation) Cell Proliferation ELISA™ (Roche) and an ELISA reader (BioRad) at A450 nm.

Figure 16:
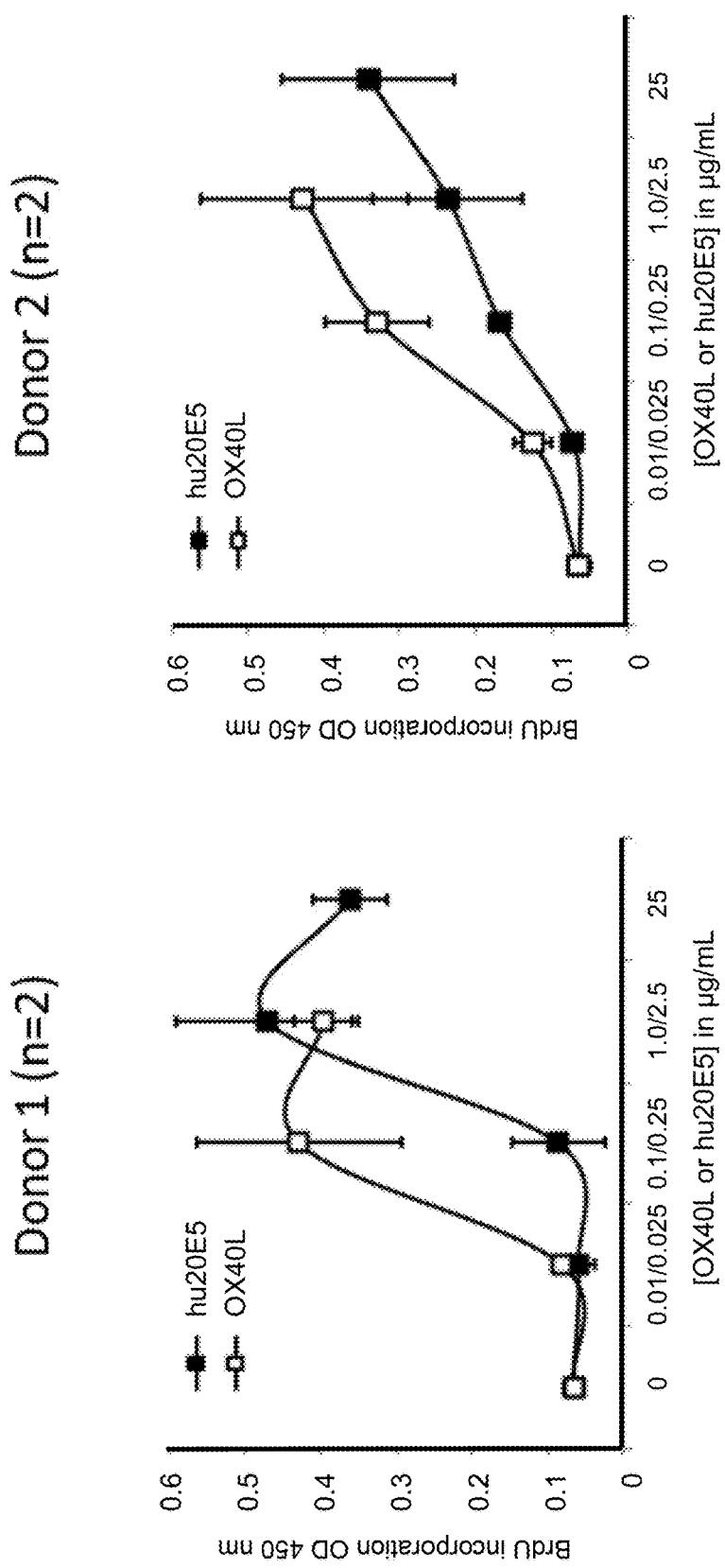
FIG. 16. Dose effect of exposure to chimeric human IgG4κ anti-human CD134 antibody clone 20E5 or to human OX40L on proliferation of PHA-M-stimulated human CD134 expressing T lymphocytes FIG. 17. Effect of combining chimeric human IgG4κ anti-human CD134 antibody clone 20E5 with human OX40L on proliferation of PHA-M-stimulated human CD134 expressing T lymphocytes.

As shown in FIG. 16 (mean±SD), chimeric human IgG4κ anti-human CD134 antibody clone 20E5 (hu20E5) and human OX40L dose-dependently induced proliferation in PHA-stimulated human CD134 expressing T lymphocytes. Chimeric human IgG4κ anti-human CD134 antibody clone 20E5 donor-dependently induced proliferation at either 2.5 and 25 µg/mL (donor 1) or at 0.25, 2.5, and 25 µg/mL (donor 2). In addition, human OX40L donor dependently induced proliferation at either 0.1 and 1.0 µg/mL (donor 1) or at 0.01, 0.1, and 1.0 µg/mL (donor 2).

As shown in FIG. 17 (mean±SD), the combination of chimeric human IgG4κ anti-human CD134 antibody clone 20E5 (hu20E5) at 2.5 and 25 µg/mL (or at lower concentrations; data not shown) with human OX40L at 0.1 and 1.0 µg/mL (or at lower concentrations; data not shown) did not demonstrate any reciprocal (i.e., synergistic or additive, or even inhibitory) effects on proliferation in PHA-stimulated human CD134 expressing T lymphocytes.

(c). Proliferation of Anti-Human CD3/Anti-Human CD28 Antibody Stimulator Beads-Stimulated Human CD134 Expressing T Lymphocytes after Treatment with Chimeric Human IgG4κ Anti-Human CD134 Monoclonal Antibody Clone 20E5

Human peripheral blood mononuclear cells (PBMC) from healthy donors (informed consent) were isolated by density centrifugation on Lymphoprep (1.077 g/mL; Nycomed). Subsequently, PBMC were seeded at $0.1 \times 10^6$ cells/100 µL/well (i.e., $1 \times 10^6$ cells/mL) in 96-wells flat-bottom plates (Corning) in RPMI-1640 culture medium (Gibco) containing 10% fetal calf serum (Bodinco) and 50 µg/mL gentamycin (Gibco), and were stimulated with mouse anti-human CD3/mouse anti-human CD28 antibody stimulator beads (CD3/CD28 beads; Invitrogen) at 1 bead/2 cells in the absence or presence of 25 U/mL recombinant human interleukin-2 (PeproTech) at 37° C./5% C02. After 1 day or after 2 days, these (minus and plus interleukin-2) CD3/CD28 beads-stimulated human CD134 expressing T lymphocytes were exposed to 25.0 µg/mL chimeric human IgG4κ anti-human CD134 antibody clone 20E5 or to 1.0 g/mL polyhistidine-tagged recombinant human OX40L (in the presence of 1:5 molar ratio mouse anti-polyhistidine antibody; R&D Systems) at 37° C./5% CO2 for 6 days or for 5 days, respectively. Cells, which were initially stimulated with combination of CD3/CD28 beads plus recombinant human interleukin-2, were re-stimulated 1 day prior to cell proliferation measurements with 25 U/mL of recombinant human interleukin-2. After 6 days or after 5 days exposure to chimeric human IgG4κ anti-human CD134 antibody clone 20E5 or to human OX40L, cell proliferation was measured using the colorimetric (BrdU incorporation) Cell Proliferation ELISA™ (Roche) and an ELISA™ reader (BioRad) at A450 nm.

Figure 18:
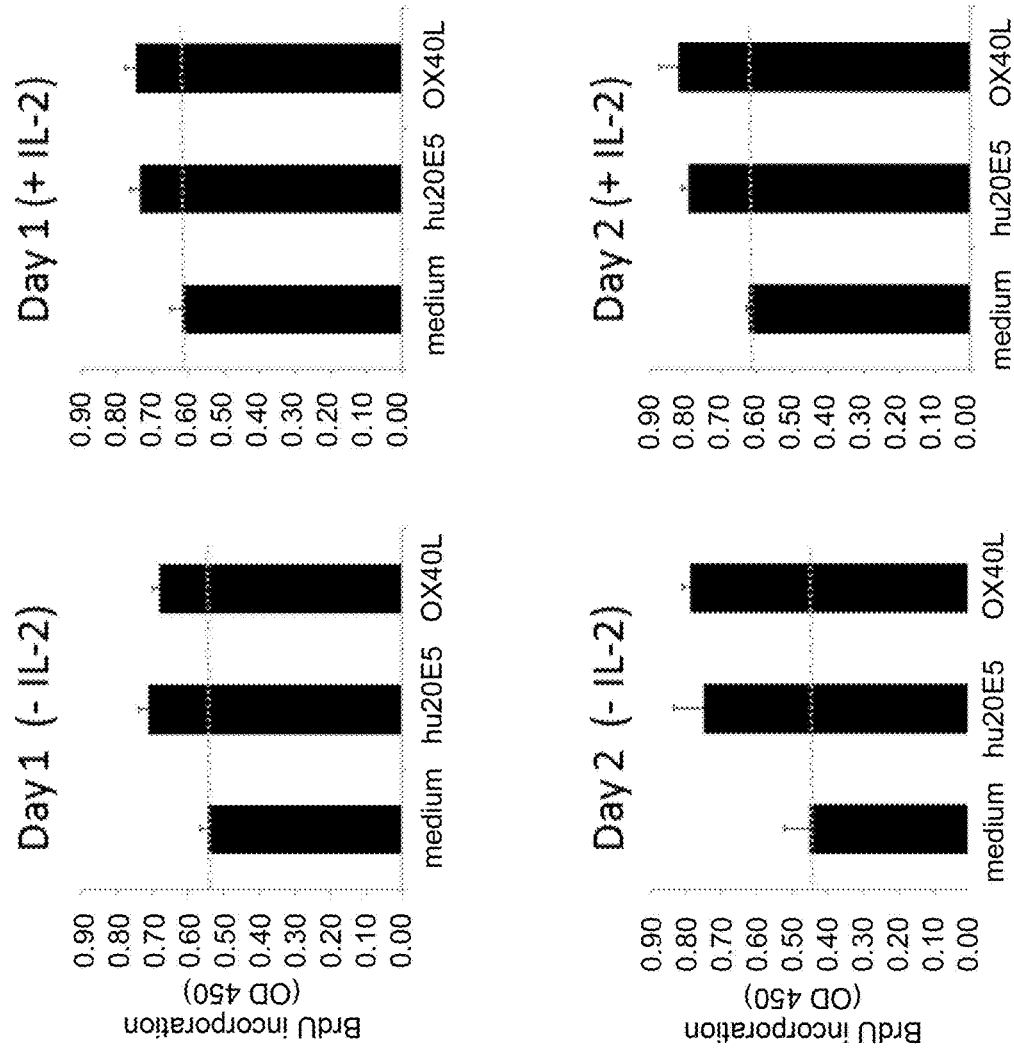
FIG. 18. Effect of chimeric human IgG4κ anti-human CD134 antibody clone 20E5 or human OX40L on proliferation of (minus and plus IL-2) CD3/CD28 beads-stimulated human CD134 expressing T lymphocytes.

As shown in FIG. 18 (mean±SD, n=3 using one donor), although CD3/CD28 stimulator beads alone induced considerable proliferation in human CD134 expressing T lymphocytes (i.e., medium), chimeric human IgG4κ anti-human CD134 antibody clone 20E5 (hu20E5) and human OX40L induced additional proliferation in CD3/CD28 beads-stimulated human CD134 expressing T lymphocytes. Addition of interleukin-2 only seemed to enhance basal (i.e., medium) proliferation in CD3/CD28 beads-stimulated human CD134 expressing T lymphocytes.

(d). Immunostimulatory Responses in Rhesus Macaque Monkeys after Treatment with Human (Chimeric) Anti-Human CD134 Antibodies Clones 12H3 and 20E5

Non-human primates rhesus macaque monkeys may be immunized with the simian immunodeficiency virus protein, gp130, as described by Weinberg et al. (J Immunother 2006; 29: 575-585).

The draining lymph nodes from immunized monkeys treated with human (e.g., chimeric or humanized or deimmunized; e.g., subclass human IgG1 or IgG4) anti-human CD134 antibodies clones 12H3 and 20E5 are expected to show enlarged lymph nodes compared with control immunized monkeys. Animals treated with mouse or humanized 12H3 or 20E5 antibodies are expected to show increased gp130-specific antibody titres, and increased long-lived T-cell responses, compared with controls. There should be no overt signs of toxicity in the treated monkeys.

Example 8. Characterization of Human CD134 Domains and Epitopes Recognized by Mouse Anti-Human CD134 Monoclonal Antibody Clones 12H3 and 20E5

(a). Binding of Mouse Anti-Human CD134 Monoclonal Antibodies Clones 12H3 and 20E5 with Non-Reduced and Reduced Recombinant Human CD134:Human Fcγ Fusion Protein (Western Blotting).

Thirteen hundred or 650 ng/lane (for Coomassie brilliant blue staining) or 250 ng/lane (for western blotting) recombinant human CD134:human Fcγ (IgG1) fusion protein (R&D Systems) was electrophorized using 4-12% Tris-Bis gels and MOPS running buffer (Invitrogen) under a variety of non-reducing and reducing conditions (see FIG. 19-A) in pre cast LDS-PAGE denaturing electrophoresis NuPage® Novex® system. Then, recombinant human CD134:human Fcγ fusion protein was either stained with Coomassie brilliant blue (BioRad) or electro-blotted onto a polyvinylidene fluoride (PDVF) transfer membrane (Millipore). After blocking with PBS/0.05% Tween 20/1% BSA fraction V (Roche) for 20 min at RT, PDVF membranes were incubated with 100 ng/mL mouse anti-human CD134 monoclonal antibody clone 12H3 or 20E5 for 1 hour at RT. In parallel, 100 ng/mL mouse IgG1κ isotype control antibody (BD Biosciences) was used as a negative control. After extensive washing in PBS/0.05% Tween 20, binding of mouse anti-human CD134 monoclonal antibody clone 12H3 or 20E5 was determined with 1:5000 diluted horseradish peroxidase-conjugated goat anti-mouse Fcγ-specific antibodies (Jackson ImmunoResearch) for 1 hour at RT, followed by a ready-to-use solution of TMB substrate (Sigma) for colorimetric detection.

Figures 19A, 19B:
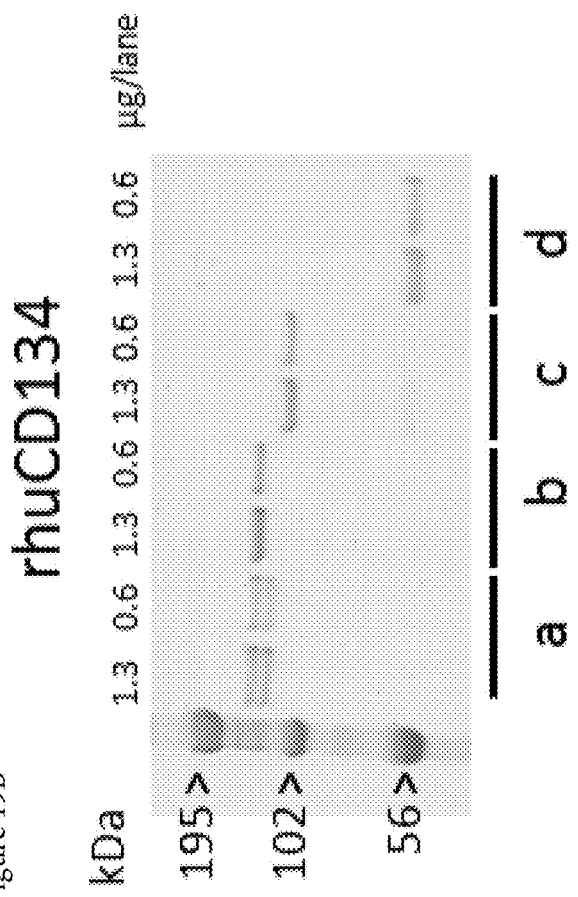
FIGS. 19A, 19B, and 19C. Binding of mouse anti-human CD134 antibodies clones 12H3 and 20E5 with non-reduced and reduced recombinant human CD134:human Fcγ fusion protein. (A) Examined non-reducing (a, b) and reducing (c, d) conditions. (B) Electrophoretic migration patterns of recombinant human CD134:human Fcγ fusion protein (rhuCD134) under non-reducing (a, b) and reducing (c, d) conditions using Coomassie brilliant blue staining. (C) Western blot of non-reducing (a,b) and reducing (c, d) recombinant human CD134:human Fcγ fusion protein exposed to mouse IgG1κ isotype control antibody (mIgG1) or to mouse anti-human CD134 antibodies clones 12H3 and 20E5 (m12H3 and m20E5, respectively).
Figure 19C:
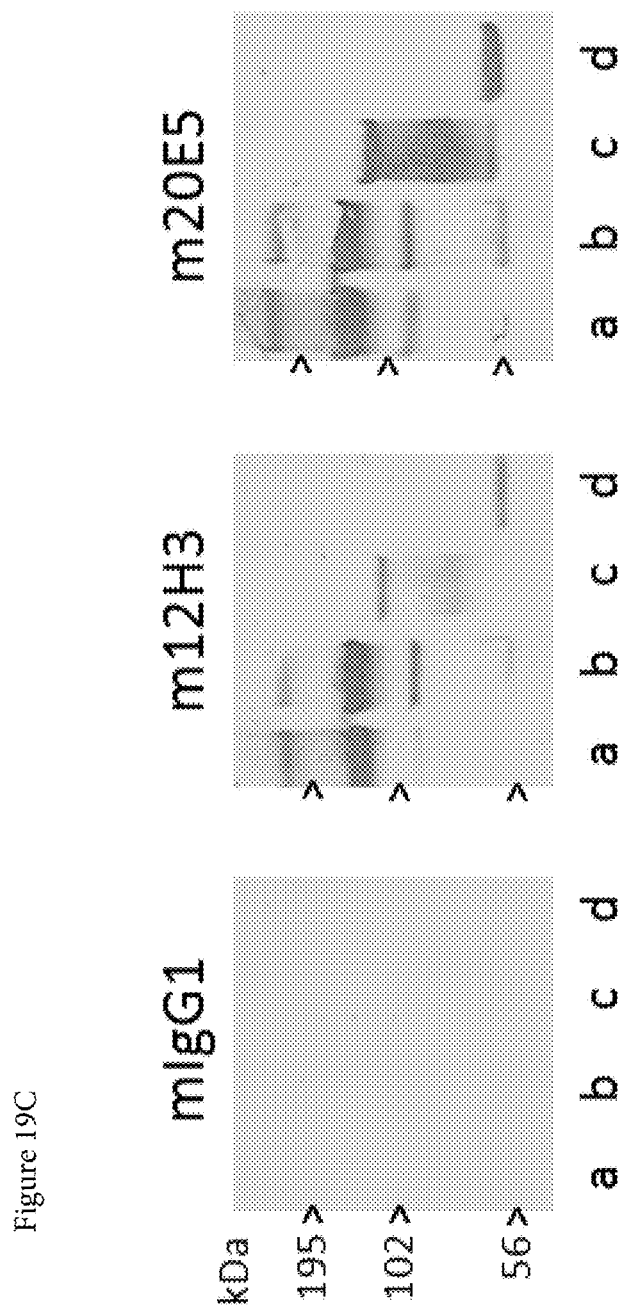

As shown in FIG. 19-B, recombinant human CD134:human Fcγ fusion protein under non reducing (and LDS denaturing without and with heat denaturing, condition a and b, respectively) conditions demonstrated a molecular mass of ≈130-140 kDa. Non-reduction without heating (condition a) showed two bands at close proximity, which suggested that a fraction of recombinant human CD134:human Fcγ fusion protein was incompletely denatured/unfolded. Non-reduction with heating (condition b) showed one band, which suggested that recombinant human CD134:human Fcγ fusion protein was completely denatured/unfolded. Recombinant human CD134:human Fcγ fusion protein under reducing (and LDS denaturing without and with heat denaturing, condition c and d, respectively) conditions resulted in bands at ≈110 kDa (condition c) and at ≈60-65 kDa (condition d). Former observation suggested incomplete reduction of recombinant human CD134:human Fcγ fusion protein, and latter observation suggested complete reduction/breakage of disulfide bridges joining two human IgG1-derived Fcγ-fragments within each recombinant human CD134:human Fcγ fusion protein molecule.

As shown in FIG. 19-C, both mouse anti-human CD134 antibodies clone 12H3 and clone 20E5 recognized recombinant human CD134:human Fcγ fusion protein under non-reducing (and LDS denaturing without and with heat denaturing, condition a and b, respectively) conditions at predominantly ≈130 kDa. In contrast, mouse anti-human CD134 antibody clone 12H3 showed only a slight binding with recombinant human CD134:human Fcγ fusion protein under reducing (and LDS denaturing without and with heat denaturing, condition c and d, respectively) conditions, whereas mouse anti-human CD134 antibody clone 20E5 showed a strong binding to recombinant human CD134:human Fcγ fusion protein under reducing (and LDS denaturing without and with heat denaturing, condition c and d, respectively) conditions.

These results demonstrated that mouse anti-human CD134 antibodies clone 12H3 and clone 20E5 specifically recognized human CD134. Furthermore, these results demonstrated that mouse anti-human CD134 antibodies clone 12H3 and clone 20E5 seemed to recognize dissimilar human CD134 epitopes, which is evidenced by respective slight binding (clone 12H3) vs. strong binding (clone 20E5) with recombinant human CD134:human Fcγ fusion protein under reducing (and LDS denaturing with and without heat denaturing) conditions. These results suggested that mouse anti-human CD134 antibody clone 12H3 recognized an epitope on human CD134, which is not sensitive to denaturation (LDS and heat treatment) and sensitive to reduction (i.e., breakage of disulphide bridge(s)—most likely, cysteine-rich domains (CRD)-related—by DTT). These results suggested that mouse anti-human CD134 antibody clone 20E5 recognized an epitope on human CD134, which is not sensitive to denaturation (LDS and heat treatment) and not sensitive to reduction (i.e., breakage of disulphide bridge(s)—most likely, CRD-related—by DTT).

(b). Binding of Mouse Anti-Human CD134 Monoclonal Antibodies Clones 12H3 and 20E5 with Full-Length Human CD134 Construct and Various Truncated Human CD134 Constructs Expressed on 293-F Cell Line (Domain Mapping)

In order to analyze the fine specificity of mouse anti-human CD134 monoclonal antibodies clones 12H3 and 20E5, the location of epitope(s) recognized by mouse anti-human CD134 monoclonal antibodies clones 12H3 and 20E5 was determined by domain mapping. The ability of mouse anti-human CD134 monoclonal antibodies clones 12H3 and 20E5 to bind to truncated human CD134 constructs, expressed on the surface of (HEK-derived) 297-F cells, was determined by FACS analysis.

Figure 20:
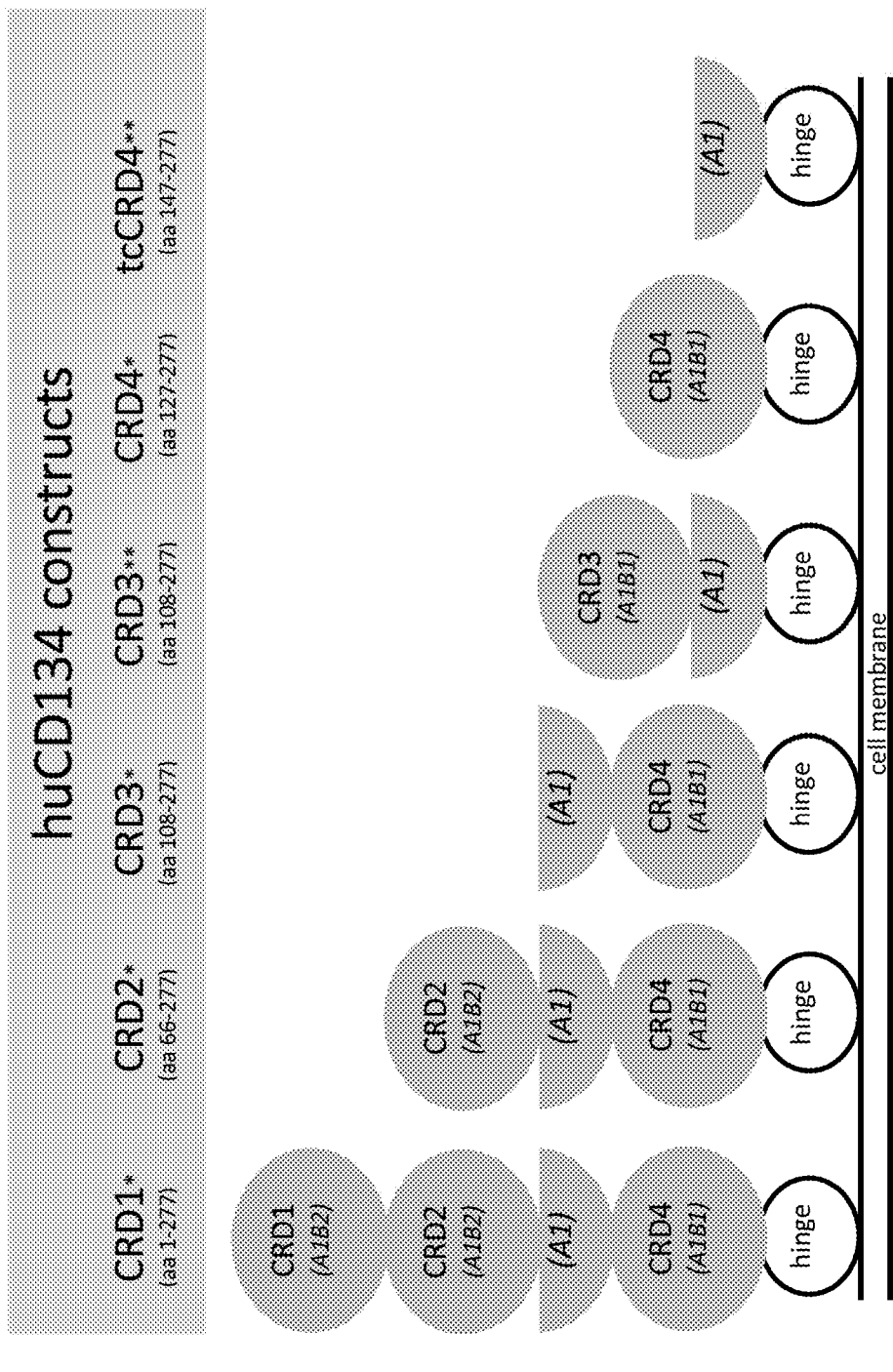
FIG. 20. Schematic representation of cysteine-rich domains (CRD) in full-length human CD134 (denoted as 'CRD1') and in various truncated human CD134 forms (denoted as 'CRD2', 'CRD3', 'CRD4', and 'truncated (tc) CRD4').

Based on literature (Swiss-Prot: P43489.1; Latza et al. Eur J Immunol 1994; 24: 677-683; Bodmer et al. Trends Biochem Sci 2002; 27: 19-26; Compaan et al. Structure 2006; 14: 1321-1330; US Patent Publ. No. 2011/0028688 A1), cysteine-rich domains (CRD) and a hinge-like structure in the extracellular region of human CD134 were identified. CRDs are coded CRD1, CRD2, (truncated) CRD3, (truncated) CRD4 (see FIG. 20). CRDs contain topologically distinct types of modules, called an A-module and a B-module (see also FIG. 20). A modules are C-shaped structures, and B-modules are S-shaped structures. A typical CRD is usually composed of A1-B2-modules or A2-B1-modules (or, less frequently, a different pair of modules, like A1-B1) with 6 conserved cysteine residues, wherein the numeral denotes the number of disulphide bridges within each module (see also FIG. 20). As shown in FIG. 20, 5 different human CD134 constructs were generated and expressed: (1) full-length human CD134 construct, which starts with N-terminal CRD1 (i.e., CRD1 A1-B2-module covers amino acids 29-65), and therefore denoted as 'CRD1', and comprised amino acids 1-277 (see SEQ ID NO. 1), (2) 'CRD2' construct, which starts with N-terminal CRD2 (i.e., CRD2 A1 B2-module covers amino acids 66-107), and comprised amino acids 66-277 linked to signal peptide amino acids 1-28 (see SEQ ID NO. 30), (3) 'CRD3' construct, which starts with N terminal CRD3 (i.e., CRD3 A1-B1-module covers amino acids 108-146 (according to Compaan et al. Structure 2006; 14: 1321-1330) or truncated CRD3 A1-module covers amino acids 108-126 (according to Latza et al. Eur J Immunol 1994; 24: 677-683)), and comprised amino acids 108-277 linked to signal peptide amino acids 1-28 (see SEQ ID NO. 31), (4) 'CRD4' construct, which consists of N-terminal CRD4 or CRD3 subdomain B1 module/truncated CRD4 A1-module (i.e., CRD4 A1-B1-module covers amino acids 127 167 (Latza et al. Eur J Immunol 1994; 24: 677-683) or a combination (not shown in FIG. 20) of CRD3 subdomain B1-module with truncated CRD4 A1-module covers amino acids 127-146 with amino acids 147-167, respectively (Compaan et al. Structure 2006; 14: 1321-1330)), and comprised amino acids 127-277 linked to signal peptide amino acids 1-28 (see SEQ ID NO. 32), and (5) 'truncated (tc) CRD4' construct, which consists of N-terminal truncated CRD4 or CRD4 subdomain B1-module (i.e., truncated CRD4 A1 module covers amino acids 147-167 (Compaan et al. Structure 2006; 14: 1321-1330) or CRD4 subdomain B1-module (not shown in FIG. 20; Latza et al. Eur J Immunol 1994; 24: 677-683) covers amino acids 147-167), and comprised amino acids 147-277 linked to signal peptide amino acids 1-28 (see SEQ ID NO. 33). By assembly PCR using Accuprime™ Pfx DNA Polymerase (Invitrogen), these 5 human CD134 constructs were generated using primers shown in the following table:

| Primer No.* | Sequence | SEQ ID No. | Direction | Gene |
|---|---|---|---|---|
| 362 | CTCGGATCCGCCACCATGTGCGTG | 51 | sense | CD134 leader |
| 363 | AGAATTCTTATTAGATCTTGGCCA | 55 | antisense | CD134 end |
| 364 | ACTGTCACTGGACCCTGCGGTCCC | 52 | sense | CRD2 |
| 365 | GGGACCGCAGGGTCCAGTGACAGT | 53 | antisense | CRD2 |
| 366 | ACTGTCACTGGAAGGTGCAGGGCT | 54 | sense | CRD3 |
| 367 | AGCCCTGCACCTTCCAGTGACAGT | 56 | antisense | CRD3 |
| 368 | ACTGTCACTGGACCCTGCCCCCCT | 57 | sense | CRD4 |
| 369 | AGGGGGGCAGGGTCCAGTGACAGT | 58 | antisense | CRD4 |
| 370 | ACTGTCACTGGATGCACCCTGGCT | 59 | sense | CRD4 truncated |
| 371 | AGCCAGGGTGCATCCAGTGACAGT | 60 | antisense | CRD4 truncated |

*Primer No. according to Bioceros internal coding system

Briefly, cDNA encoding amino acids 1-28 of signal peptide and cDNA encoding amino acids 66-277 of human CD134 were amplified using respectively primer pair 362/365 and 364/363 in a PCR reaction with full-length human CD134 as a template. Subsequently, 'CRD2' construct was generated by using these two PCR products in an assembly PCR using primer pair 362/363. The cDNA encoding 'CRD2' construct was subcloned into a pcDNA3.1-derived expression plasmid using suitable restriction sites. Similarly, 'CRD3' construct (amino acids 1-28 of signal peptide linked to amino acids 108-277 of human CD134), 'CRD4' construct (amino acids 1-28 of signal peptide linked to amino acid 127-277), and 'truncated CRD4' construct (amino acids 1-28 of signal peptide linked to amino acid 147-277) were generated and subcloned in pcDNA3.1-derived expression plasmids using the corresponding primers shown in above-mentioned table. Furthermore, full-length human CD134 (SEQ ID NO. 1) was also re-cloned in a pcDNA3.1-derived expression plasmid.

Using the FreeStyle™ 293 Expression System (Invitrogen), FreeStyle™ 293-F cells (Invitrogen) were transiently transfected with the 5 generated variants of human CD134. After 48-72 h, surface human CD134 expression on transfected cells was analyzed by FACS analysis. To this end, transfected cells were harvested and put at 1-2×10⁶ cells/mL in ice chilled PBS/BSA/NaN₃. Cells were incubated with 20.0 µg/mL mouse anti-human CD134 monoclonal antibodies clones 12H3 and 20E5 for 30 minutes at 4° C. In parallel, 20.0 µg/mL mouse IgG1κ isotype control antibody (BD Biosciences) was used as a negative control. After extensive washing in PBS/BSA/NaN₃, cells were subsequently incubated with 1:200 diluted PE-conjugated goat anti-mouse IgG (Fcγ specific) antibodies (Jackson ImmunoResearch) for 30 minutes at 4° C. After extensive washing in PBS/BSA/NaN₃, cells were fixed in 2% formaldehyde in PBS/BSA/NaN₃ for 30 minutes at 4° C. Binding of antibodies was measured using flow cytometry (FACSCalibur; BD Biosciences).

Figure 21:
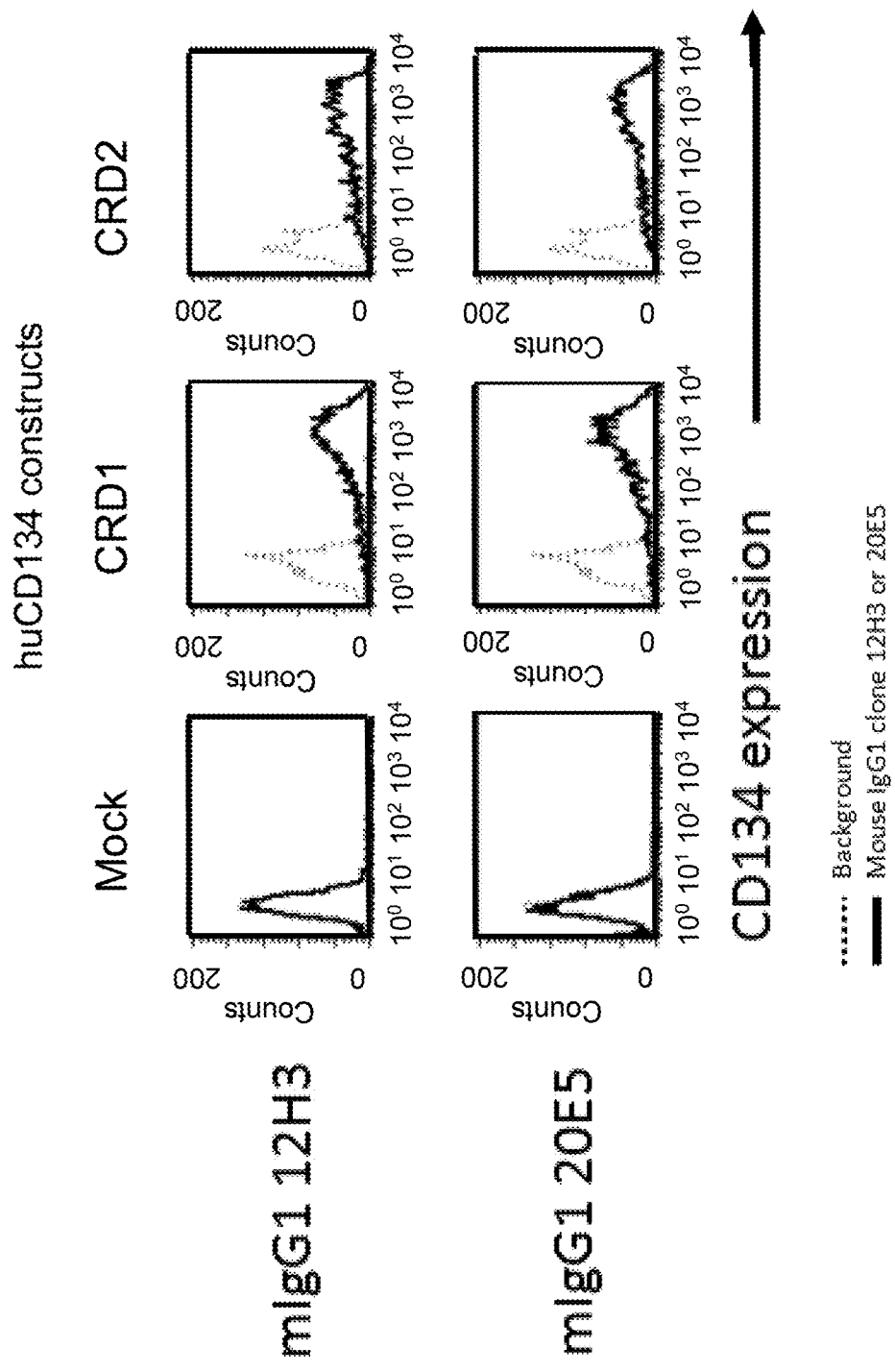
FIG. 21. Binding of mouse anti-human CD134 antibodies clones 12H3 and 20E5 on 293-F cell line transiently transfected with full-length human CD134 construct (denoted 'CRD1') or with various truncated human CD134 constructs (denoted 'CRD2', 'CRD3', 'CRD4', and 'truncated (tc) CRD4').
Figure 21:
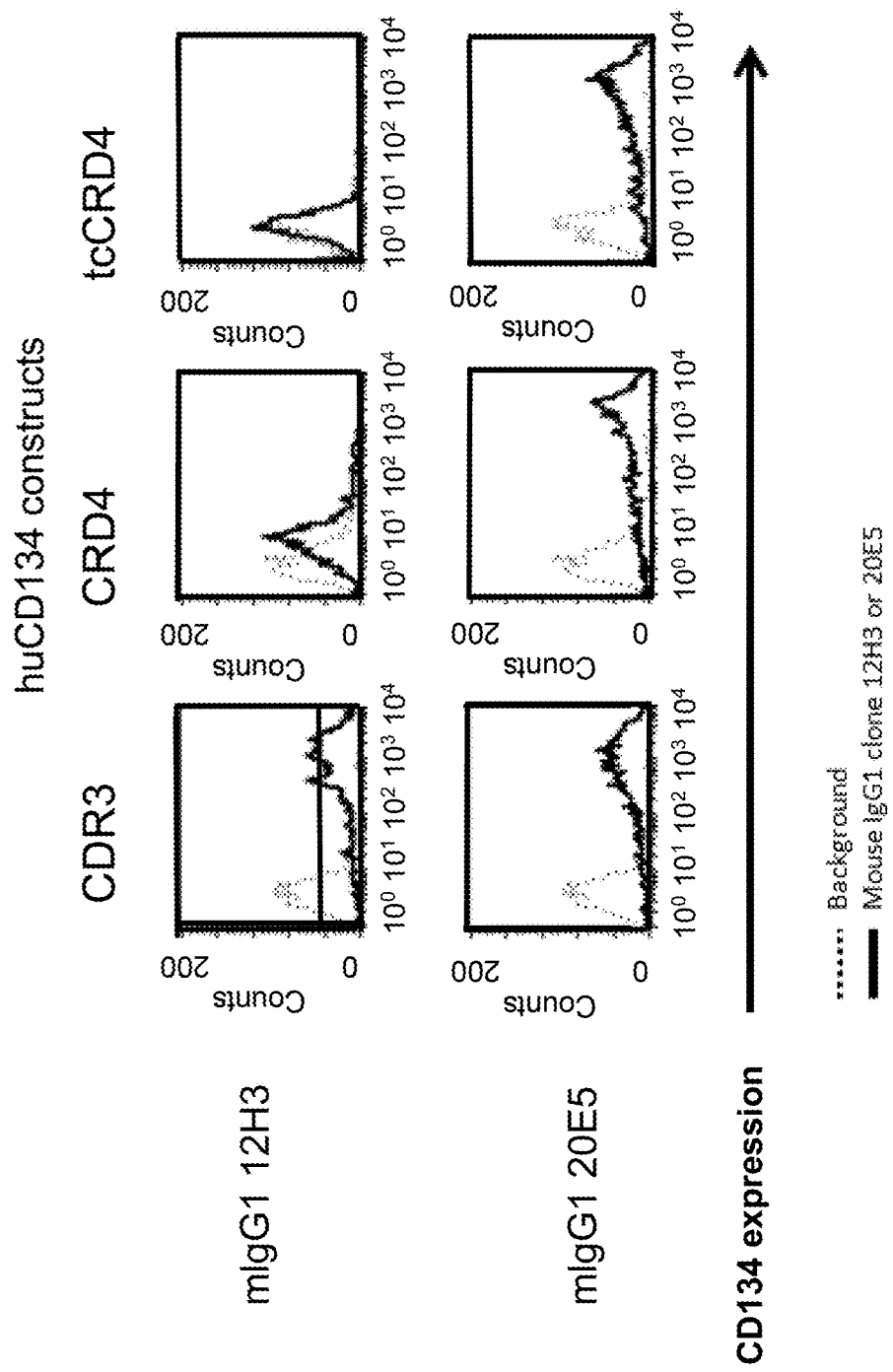

As shown in FIG. 21, both mouse anti-human CD134 antibodies clones 12H3 and 20E5 recognized full-length (denoted as 'CRD1' construct) human CD134 on transfected 293-F cells, whereas both mouse anti-human CD134 antibodies clones 12H3 and 20E5 showed no binding on mock-transfected 293-F cells. Moreover, mouse anti-human CD134 antibodies clones 12H3 and 20E5 recognized truncated human CD134 variants that lacked CRD1 and CRD1-CRD2 (denoted as 'CRD2' construct and 'CRD3' construct, respectively) on transfected 293-F cells. In contrast, binding of mouse anti-human CD134 antibody clone 12H3 against truncated human CD134 variant that lacked CRD1-CRD2-truncated CRD3 A1 module (denoted as 'CRD4' construct) was very weak, and binding of mouse anti-human CD134 antibody clone 12H3 against truncated human CD134 variant that lacked CRD1-CRD2-truncated CRD3 A1-module-CRD4 subdomain A1-module (according to definition of Latza et al. Eur J Immunol 1994; 24: 677-683) or alternatively CRD1-CRD2-CRD3 A1 B1 module (according to definition of Compaan et al. Structure 2006; 14: 1321-1330; denoted as 'tcCRD4' construct) was completely absent, whereas mouse anti-human CD134 antibody clone 20E5 showed a strong binding against truncated human CD134 variant that lacked CRD1-CRD2-truncated CRD3 A1-module (denoted as 'CRD4' construct) and against truncated human CD134 variant that lacked CRD1-CRD2-truncated CRD3 A1-module-CRD4 subdomain A1-module (according to definition of Latza et al. Eur J Immunol 1994; 24: 677 683) or alternatively CRD1-CRD2-CRD3 A1-B1-module (according to definition of Compaan et al. Structure 2006; 14: 1321-1330; denoted as 'tcCRD4' construct).

These results demonstrated that mouse anti-human CD134 antibodies clones 12H3 and 20E5 specifically recognized human CD134 (comparison of full-length human CD134 transfection vs mock transfection). Furthermore, these results demonstrated that mouse anti human CD134 antibodies clones 12H3 and 20E5 seemed to recognize dissimilar human CD134 epitopes, which is evidenced by respective lack of binding (using clone 12H3) vs strong binding (using clone 20E5) with truncated human CD134 variant that lacked CRD1 CRD2-truncated CRD3 A1-module (denoted as 'CRD4' construct) and with truncated human CD134 variant that lacked CRD1-CRD2-truncated CRD3 A1-module-CRD4 subdomain A1-module (according to definition of Latza et al. Eur J Immunol 1994; 24: 677 683) or alternatively CRD1-CRD2-CRD3 A1-B1-module (according to definition of Compaan et al. Structure 2006; 14: 1321-1330; denoted as 'tcCRD4' construct). These results demonstrated that mouse anti-human CD134 antibody clone 12H3 did not seem to recognize a human CD134 epitope in CRD1 and CRD2, and mouse anti-human CD134 antibody clone 20E5 did not seem to recognize a human CD134 epitope in CRD1, CRD2, and truncated CRD3 A1-module-CRD4 subdomain A1-module (according to definition of Latza et al. Eur J Immunol 1994; 24: 677-683) or alternatively CRD1-CRD2-CRD3 A1 B1 module (according to definition of Compaan et al. Structure 2006; 14: 1321-1330). These results demonstrated that mouse anti-human CD134 antibody clone 12H3 seemed to recognize a linear or non-linear/conformational epitope in truncated CRD3 A1-module (according to definition of Latza et al. Eur J Immunol 1994; 24: 677-683) with amino acid sequence 108-126 (i.e., 19-meric peptide RCRAGTQPLDSYKPGVDCA; see SEQ ID NO: 34) on extracellular human CD134, or amino acid sequence 108-126 (i.e., 19-meric peptide RCRAGTQ-PLDSYKPGVDCA; see SEQ ID NO: 34) formed a part for binding to a non-linear/conformational epitope in truncated CRD3 A1-module/CRD4 A1-B1-module (according to definition of Latza et al. Eur J Immunol 1994; 24: 677-683), and possibly in the hinge-like structure, with amino acid sequence 108-214 (see SEQ ID NO: 35) on extracellular human CD134. These results demonstrated that mouse anti-human CD134 antibody clone 20E5 seemed to recognize a linear or non-linear/conformational epitope in truncated CRD4 A1-module (according to definition of Compaan et al. Structure 2006; 14: 1321-1330), and possibly in the hinge-like structure, with amino acid sequence 147-214 (SEQ ID NO:36) on extracellular human CD134.

Using a crystallography, Compaan et al. (Structure 2006; 14: 1321-1330) recently discovered critical involvement of CRD1, CRD2 (especially A1 loop and immediately following residues), and CRD3 (primarily A1 loop) on human CD134 during OX40Ligand (CD252)/CD134 (=OX40) interaction. This discovery is in good agreement with our findings that (1, see above) mouse anti-human CD134 antibody clone 20E5 did not seem to recognize a human CD134 epitope in CRD1, CRD2, and truncated CRD3 A1-module-CRD4 subdomain A1 module (according to definition of Latza et al. Eur J Immunol 1994; 24: 677-683) or alternatively CRD1-CRD2-CRD3 A1-B11-module (according to definition of Compaan et al. Structure 2006; 14: 1321-1330) on extracellular human CD134, and (2, see above) mouse anti-human CD134 antibody clone 20E5 bound simultaneously with human OX40L on PHA stimulated human CD134 expressing T lymphocytes. This suggested that mouse anti human CD134 antibody clone 20E5 recognized an epitope on human CD134, which was not critically involved in interaction of human CD134 with human OX40L. Moreover, our findings that (1, see above) mouse anti-human CD134 antibody clone 12H3 seemed to recognize a linear or non-linear/conformational epitope in truncated CRD3 A1-module (according to definition of Latza et al. Eur J Immunol 1994; 24: 677-683) with amino acid sequence 108-126 (i.e., 19-meric peptide RCRAGTQ-PLDSYKPGVDCA; see SEQ ID NO: 34) on extracellular human CD134, or amino acid sequence 108-126 (i.e., 19-meric peptide RCRAGTQPLDSYKPGVDCA; see SEQ ID NO: 34) formed a part for binding to a non-linear/conformational epitope in truncated CRD3 A1-module/CRD4 A1-B1-module (according to definition of Latza et al. Eur J Immunol 1994; 24: 677-683), and possibly in the hinge-like structure, with amino acid sequence 108-214 (see SEQ ID NO: 35) on extracellular human CD134, and (2, see above) mouse anti-human CD134 antibody clone 12H3 bound simultaneously with human OX40L on PHA-stimulated human CD134 expressing T lymphocytes, substantiated the idea that the epitope (as described above) on human CD134 that was recognized by mouse anti-human CD134 antibody clone 12H3 was not critically involved in interaction of human CD134 with human OX40L.

(c). Epitope Mapping (1) of Mouse Anti-Human CD134 Monoclonal Antibody Clone 12H3 Using Human CD134-Derived Peptide ELISA In order to further analyze the fine specificity of mouse anti-human CD134 monoclonal antibody clone 12H3, the location of the epitope recognized by mouse anti-human CD134 monoclonal antibody clone 12H3 was determined by epitope mapping. The ability of mouse anti-human CD134 monoclonal antibody clone 12H3 to bind with a human CD134-derived peptide, which corresponded to amino acid sequence of truncated CRD3 A1-module-CRD4 subdomain A1-module (according to definition of Latza et al. Eur J Immunol 1994; 24: 677 683), was determined by ELISA.

Ninety six-wells flat-bottom ELISA plates (Corning) were coated with 10 ng/well human CD134-derived peptide (synthesized by Pepscan Presto, Lelystad, The Netherlands), which corresponded to amino acid sequence of truncated CRD3 A1-module-CRD4 subdomain A1 module (see SEQ ID NO: 38) or with 10 ng/well human fibronectin-derived control peptide (synthesized by Pepscan Presto, Lelystad, The Netherlands), which corresponded to amino acid sequence of extra type III structural domain (see SEQ ID NO: 37) in PBS o/n at 4° C. After extensive washing in PBS/0.05% Tween 20, plates were blocked in PBS/0.05% Tween 20/1% BSA fraction V (Roche) for 1 hour at RT. Subsequently, plates were incubated with 0, 0.00005-50.0 (10-fold dilution steps in block buffer) µg/mL mouse anti-human CD134 monoclonal antibody clone 12H3 or mouse IgG1K isotype control antibody (BD Biosciences) for 1 hour at RT. After extensive washing in PBS/0.05% Tween 20, binding of antibodies was determined with 1:5000 diluted horseradish peroxidase-conjugated goat anti-mouse IgG Fcγ specific antibodies (Jackson ImmunoResearch) for 1 hour at RT, followed by a ready-to-use solution of TMB substrate (Invitrogen) for colorimetric detection. After adding 1 M $H_2SO_4$, optical densities was measured at a wavelength of 450 nm (reference wavelength of 655 nm) using a microplate reader (BioRad).

Figure 23A:
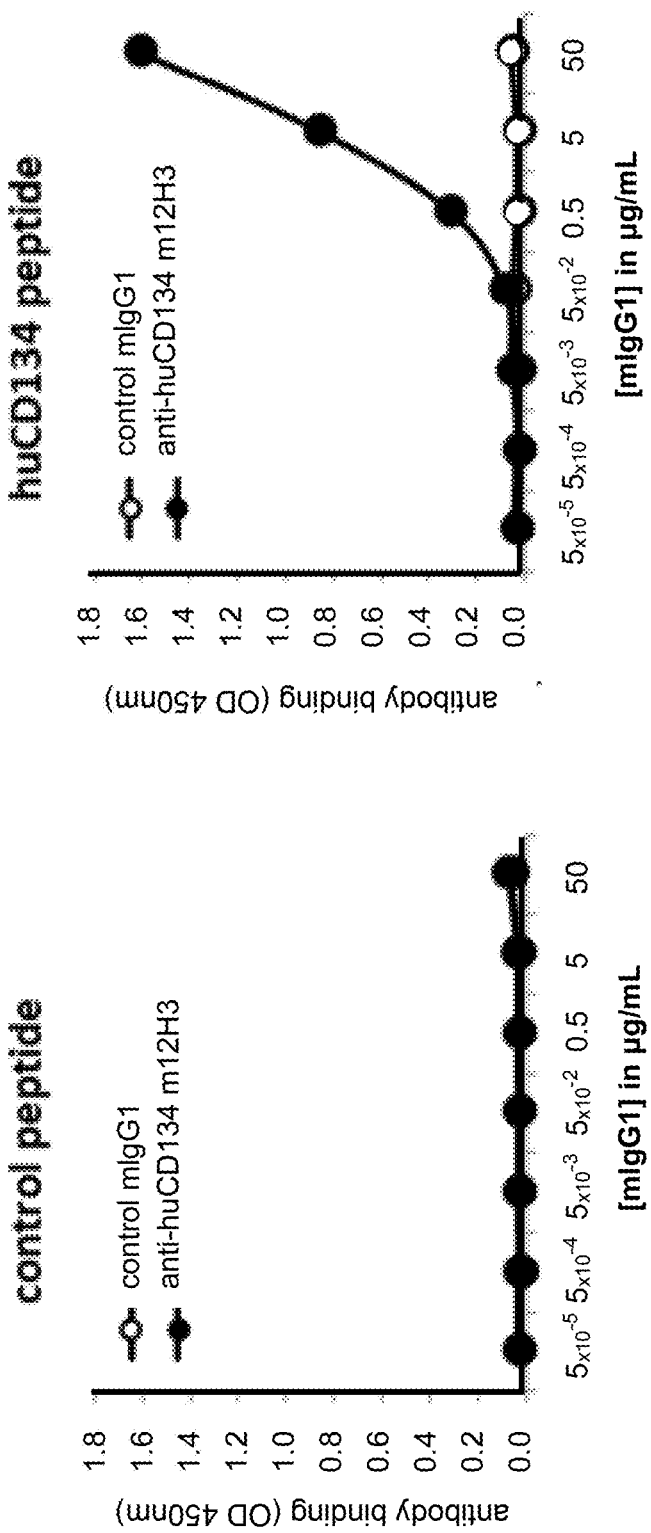
FIGS. 23A and 23B. Binding of mouse anti-human CD134 antibody clone 12H3 (A) and chimeric human IgG4κ anti-human CD134 antibody clone 12H3 (B) with human CD134-derived peptide, which corresponds to amino acid sequence of truncated CRD3 A1-module-CRD4 subdomain A1-module (according to definition of Latza et al. Eur J Immunol 1994; 24: 677 683).

As shown in FIG. 23A (n=1), mouse anti-human CD134 monoclonal antibody clone 12H3 dose-dependently and specifically bound human CD134-derived peptide, whereas mouse IgG1K isotype control antibody demonstrated no binding to human CD134-derived peptide. Both mouse anti-human CD134 monoclonal antibody clone 12H3 and IgG1K isotype control antibody demonstrated no binding to human fibronectin-derived control peptide.

These results demonstrated that mouse anti-human CD134 antibody clone 12H3 specifically recognized an epitope on human CD134 (comparison of human CD134-derived peptide vs. human fibronectin-derived control peptide). Furthermore, these results demonstrated that mouse anti-human CD134 antibody clone 12H3 seemed to recognize a linear or non-linear/conformational epitope in truncated CRD3 A1-module-CRD4 subdomain A1-module (according to definition of Latza et al. Eur J Immunol 1994; 24: 677-683) with amino acid sequence 108-146 (i.e., 39-meric peptide RCRAGTQPLDSYKPGVDCAPCPPGHFSPGDN-QACKPWTN; see SEQ ID NO: 38) on extracellular human CD134.

(d) Epitope Mapping (2) of Mouse Anti-Human CD134 Monoclonal Antibodies Clones 12H3 and 20E5 Using CLIPS Epitope Mapping Technology by Pepscan CLIPS Epitope Mapping Technology by Pepscan (Lelystad, The Netherlands) may be used to determine the epitopes recognized by mouse anti-human CD134 antibodies clones 12H3 and 20E5. This CLIPS technology enables the determination of linear, conformational, discontinuous, and complex epitopes involving dimeric or multimeric protein complexes. For this purpose, the linear amino acid sequence of human CD134=OX40 (SEQ ID NO: 1) is used as the target protein.

Example 9. Characterization of Human CD134 Domains and Epitopes Recognized by Chimeric Human IgG4/Kappa and/or IgG1/Kappa Anti-Human CD134 Monoclonal Antibodies Clones 12H3 and 20E5

(a). Binding Chimeric Human IgG4κ and/or IgG1K Anti-Human CD134 Monoclonal Antibodies Clones 12H3 and 20E5 with Full-Length Human CD134 Construct and Various Truncated Human CD134 Constructs Expressed on 293-F Cell Line (Domain Mapping)

In order to analyze the fine specificity of chimeric human IgG4κ and/or IgG1K anti-human CD134 monoclonal antibodies clones 12H3 and 20E5, the location of epitope(s) recognized by chimeric human IgG4κ and/or IgG1K anti-human CD134 monoclonal antibodies clones 12H3 and 20E5 was determined by domain mapping. The ability of chimeric human IgG4κ and/or IgG1K anti-human CD134 monoclonal antibodies clones 12H3 and 20E5 to bind to truncated human CD134 constructs (see Example 8 (b) above), expressed on the surface of (HEK-derived) 297-F cells, was determined by FACS analysis.

Using the FreeStyle™ 293 Expression System (Invitrogen), FreeStyle™ 293-F cells (Invitrogen) were transiently transfected with the 5 generated variants of human CD134 (see above). After 48-72 h, surface human CD134 expression on transfected cells was analyzed by FACS analysis. To this end, transfected cells were harvested and put at $1\text{-}2\times10^6$ cells/mL in ice-chilled PBS/BSA/NaN$_3$. Cells were incubated with or without 20.0 µg/mL chimeric human IgG4κ and/or IgG1K anti-human CD134 monoclonal antibodies clones 12H3 and 20E5 for 30 minutes at 4° C. After extensive washing in PBS/BSA/NaN$_3$, cells were subsequently incubated with 1:200 diluted PE-conjugated goat anti-human IgG (Fcγ specific) antibodies (Jackson ImmunoResearch) for 30 minutes at 4° C. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Figure 22:
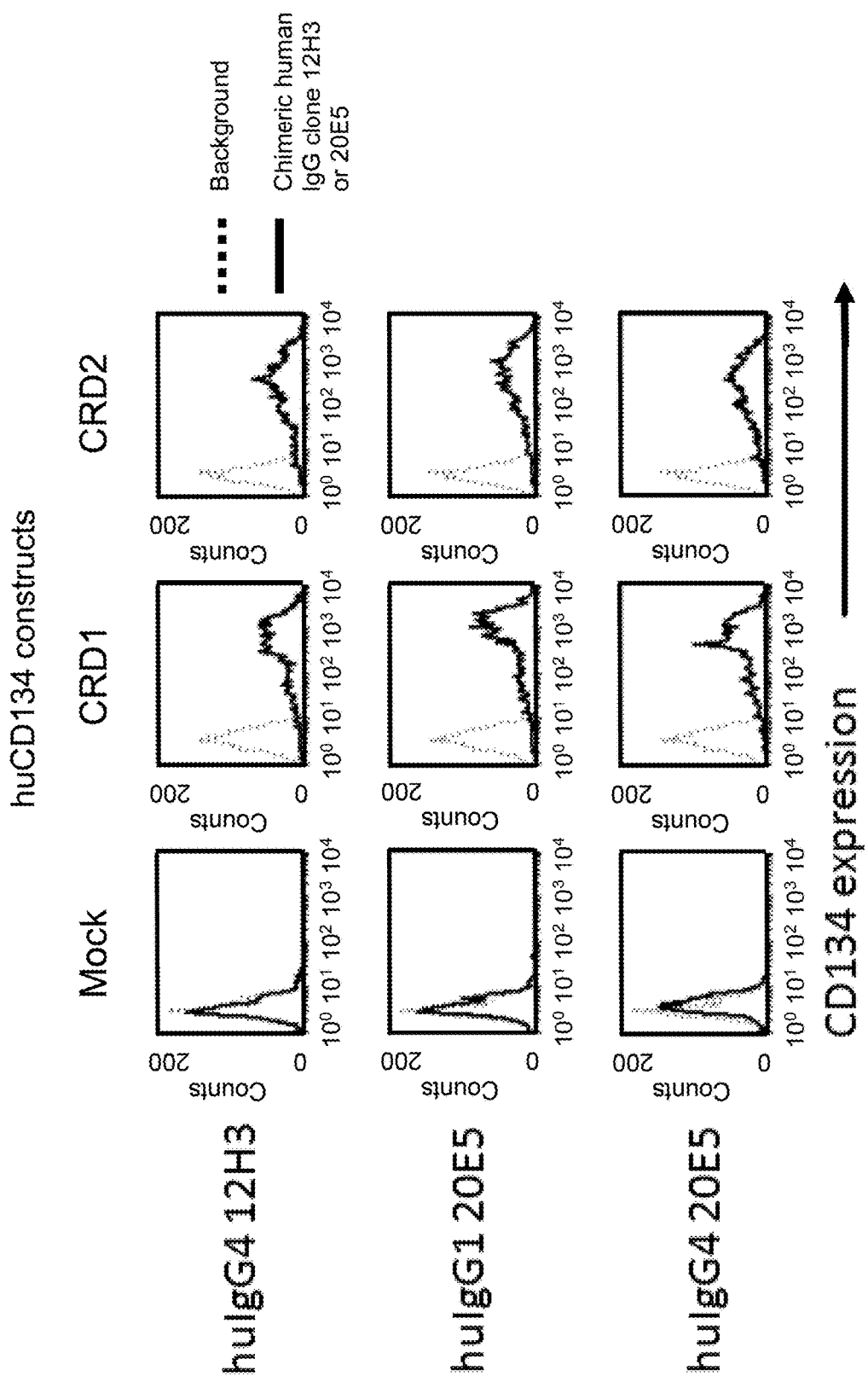
FIG. 22. Binding of chimeric human IgG4κ and/or IgG1κ anti-human CD134 antibodies clones 12H3 and 20E5 on 293-F cell line transiently transfected with full-length human CD134 construct (denoted 'CRD1') or with various truncated human CD134 constructs (denoted 'CRD2', 'CRD3', 'CRD4', and 'truncated (tc) CRD4').
Figure 22:
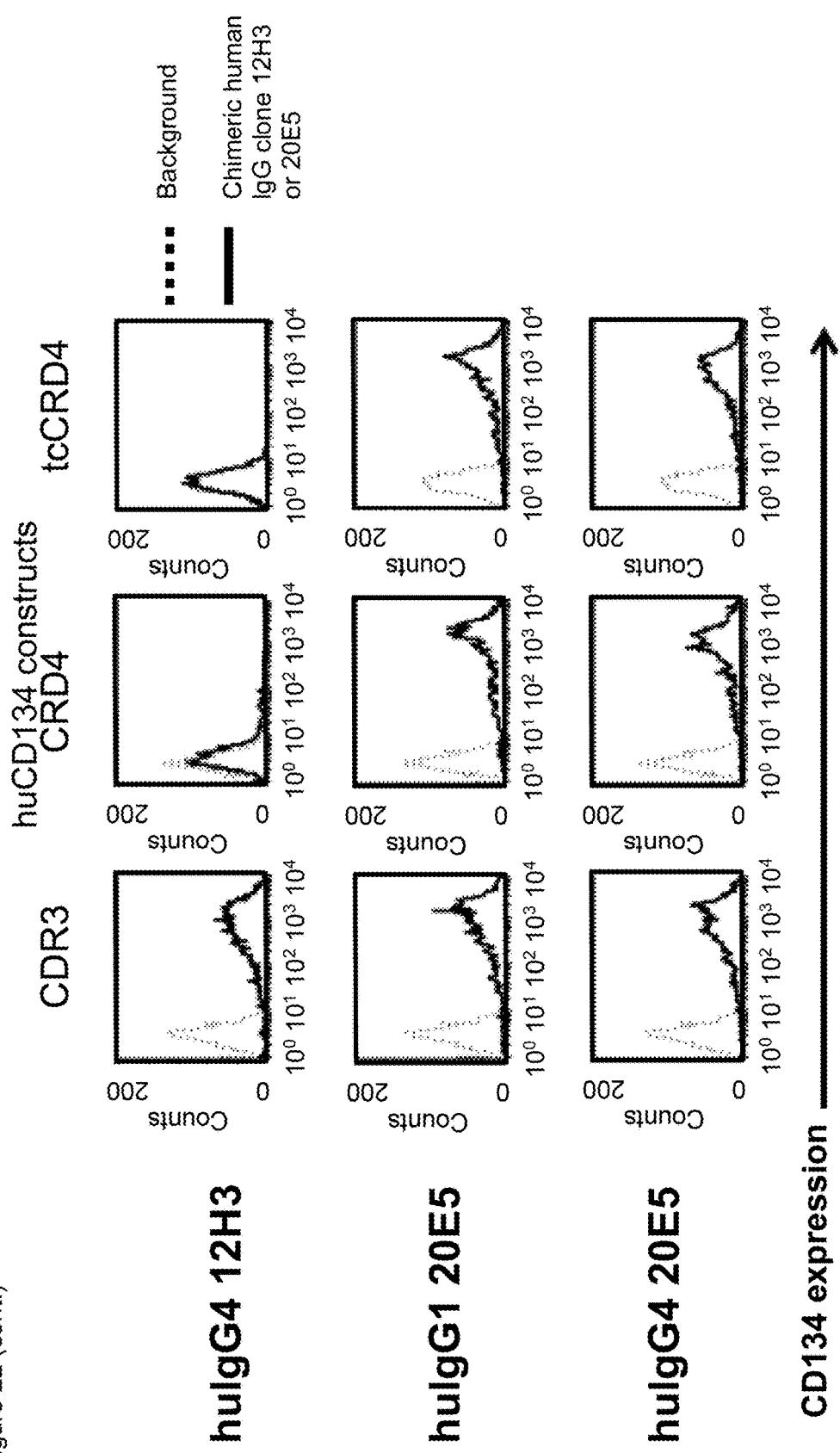

As shown in FIG. 22, both chimeric human IgG4κ and IgG1K anti-human CD134 monoclonal antibody clone 12H3, and chimeric human IgG4κ anti-human CD134 monoclonal antibody clone 20E5 demonstrated binding characteristics against various truncated human CD134 constructs on transfected cells, which were identical to binding characteristics of their corresponding parental mouse anti-human CD134 antibodies clones 12H3 and 20E5 counterparts (see Example 8 (b) above; for comparison, see FIG. 22 vs FIG. 21).

(b). Epitope Mapping of Chimeric Human IgG4κ Anti-Human CD134 Monoclonal Antibody Clone 12H3 Using Human CD134-Derived Peptide ELISA In order to further analyze the fine specificity of chimeric human IgG4κ anti-human CD134 monoclonal antibody clone 12H3, the location of the epitope recognized by chimeric human IgG4κ anti-human CD134 monoclonal antibody clone 12H3 was determined by epitope mapping. The ability of chimeric human IgG4κ anti-human CD134 monoclonal antibody clone 12H3 to bind with a human CD134-derived peptide, which corresponded to amino acid sequence of truncated CRD3 A1-module-CRD4 subdomain A1-module (according to definition of Latza et al. Eur J Immunol 1994; 24: 677-683), was determined by ELISA.

Ninety six-wells flat-bottom ELISA plates (Corning) were coated with 10 ng/well human CD134-derived peptide (synthesized by Pepscan Presto, Lelystad, The Netherlands), which corresponded to amino acid sequence of truncated CRD3 A1-module-CRD4 subdomain A1 module (see SEQ ID NO. 38) or with 10 ng/well human fibronectin-derived control peptide (synthesized by Pepscan Presto, Lelystad, The Netherlands), which corresponded to amino acid sequence of extra type III structural domain (see SEQ ID NO. 37) in PBS o/n at 4° C. After extensive washing in PBS/0.05% Tween 20, plates were blocked in PBS/0.05% Tween 20/1% BSA fraction V (Roche) for 1 hour at RT. Subsequently, plates were incubated with 0, 0.00005-50.0 (10-fold dilution steps in block buffer) g/mL chimeric human IgG4κ anti-human CD134 monoclonal antibody clone 12H3 or control human IgG4κ anti-human CD40 antibody (Biocult) for 1 hour at RT. After extensive washing in PBS/0.05% Tween 20, binding of antibodies was determined with 1:5000 diluted horseradish peroxidase-conjugated goat anti-human IgG Fcγ-specific antibodies (Jackson ImmunoResearch) for 1 hour at RT, followed by a ready-to-use solution of TMB substrate (Invitrogen) for colorimetric detection. After adding 1 M H$_2$SO$_4$, optical densities was measured at a wavelength of 450 nm (reference wavelength of 655 nm) using a microplate reader (BioRad).

Figure 23B:
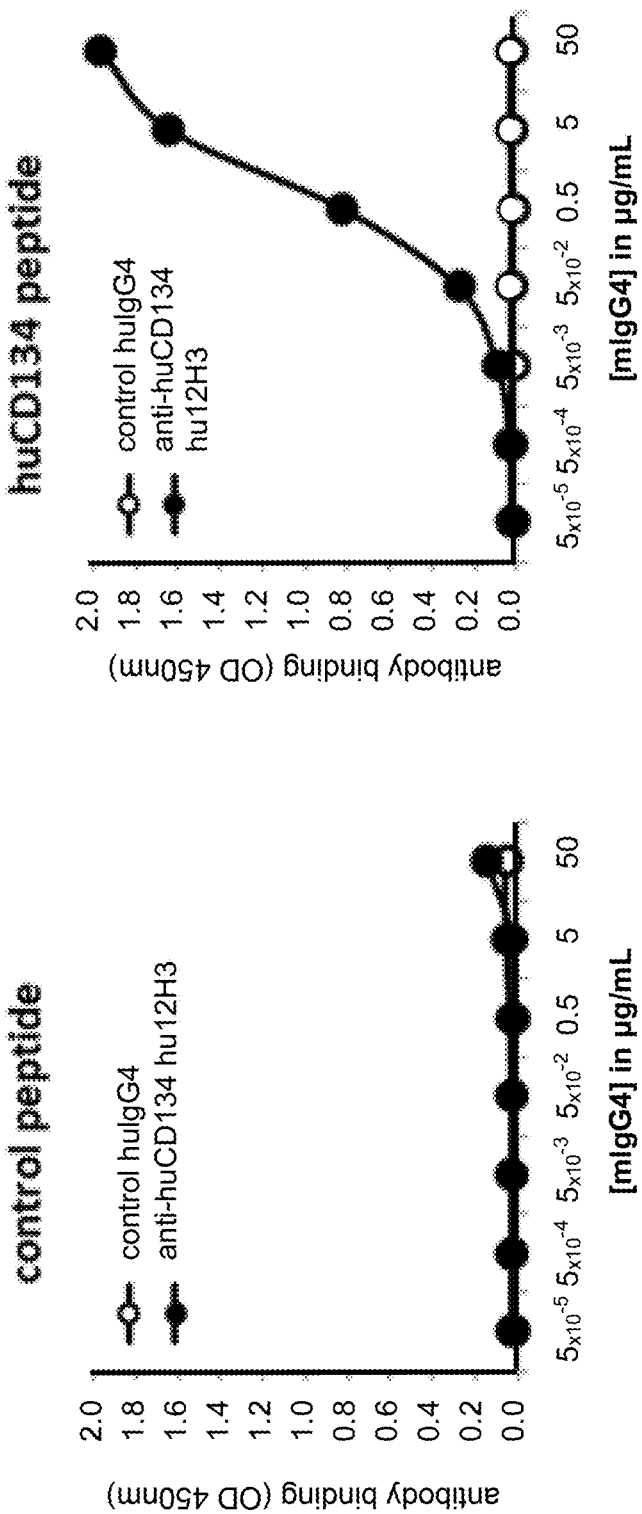

As shown in FIG. 23B (n=1), chimeric human IgG4κ anti-human CD134 monoclonal antibody clone 12H3 dose-dependently and specifically bound human CD134-derived peptide, whereas control human IgG4κ anti-human CD40 antibody demonstrated no binding to human CD134-derived peptide. Both chimeric human IgG4κ anti-human CD134 monoclonal antibody clone 12H3 and control human IgG4κ anti-human CD40 antibody demonstrated no binding to human fibronectin-derived control peptide.

These results demonstrated that chimeric human IgG4κ anti-human CD134 monoclonal antibody clone 12H3 specifically recognized an epitope on human CD134 (comparison of human CD134-derived peptide vs human fibronectin-derived control peptide). Furthermore, these results demonstrated that chimeric human IgG4κ anti-human CD134 monoclonal antibody clone 12H3 seemed to recognize a linear or non-linear/conformational epitope in truncated CRD3 A1-module-CRD4 subdomain A1-module (according to definition of Latza et al. Eur J Immunol 1994; 24: 677-683) with amino acid sequence 108-146 (i.e., 39-meric peptide RCRAGTQPLDSYKPGVDCAPCPPGHFSPGDN-QACKPWTN; see SEQ ID NO: 38) on extracellular human CD134.

Example 10. Generation of Humanized IgG4/Kappa Anti-Human CD134 Monoclonal Antibodies Clones 20E5 and 12H3

Based on determined murine V-regions (see Example 2 (b) above) of mouse anti-human CD134 antibodies clones 20E5 and 12H3, humanized antibody versions were generated.

Humanized variable light chain sequences and humanized variable heavy chain sequences of mouse anti-human CD134 antibodies clones 20E5 and 12H3 were obtained using PDL technology (performed by Panaroma Research Institute, Sunnyvale, Calif., USA). For humanized variable light chain and variable heavy chain amino acid sequences, see SEQ ID NOs: 62 (20E5-VL1), 63 (20E5-VL2), 64 (20E5-VH1), 65 (20E5-VH2), 66 (20E5-VH3), and SEQ ID NO. 67 (12H3-VL1), 68 (12H3-VL2), 69 (12H3-VH1), 70 (12H3-VH2), 71 (12H3-VH3).

After this design, *Cricetulus griseus*-optimized cDNA sequences (see SEQ ID NOs: 72, 73, 74 (coding for full length humanized heavy IgG4 chain clone 20E5 versions, i.e., VH1, VH2, VH3, respectively), SEQ ID NO. 75, 76 (coding for full length humanized light K chain clone 20E5 versions, i.e., 20E5_VL1, 20E5_VL2, respectively), SEQ ID NOs: 77, 78, 79 (coding for full length humanized heavy IgG4 chain clone 12H3 versions, i.e., VH1, VH2, VH3, resp.), and SEQ ID NO. 80, 81 (coding for full length humanized light K chain clone 12H3 versions, i.e., VL1, VL2, resp.)), were ordered at GENEART (Regensburg, Germany), which codes for a signal peptide followed by either the humanized variable heavy chain linked to human IgG4 constant region or followed by the humanized variable light chain linked to human kappa constant region: (1) for expression of humanized anti-human CD134 antibody clone 20E5 versions, a mouse immunoglobulin heavy chain signal peptide was used for both humanized heavy and light chains, and (2) for expression of humanized anti-human CD134 antibody clone 12H3 versions, a human immunoglobulin heavy chain signal peptide was used for humanized heavy chains and a human immunoglobulin kappa chain signal peptide for humanized light chains. Furthermore, all humanized antibodies were expressed as stabilized human IgG4 molecules according to Angal et al. (Mol. Immunol., Vol. 30, No. 1, pp. 105-108, 1993). Using suitable restriction enzymes, generated cDNAs were subcloned in pcDNA3.1-derived expression plasmids.

Humanized anti-human CD134 antibody clone 20E5 versions were expressed using the FreeStyle™ MAX CHO Expression System (Life Technologies). Humanized anti-human CD134 antibody clone 12H3 versions were expressed using the FreeStyle™ 293 Expression System (Life Technologies). Generated humanized antibodies were purified using affinity chromatography protein A columns (GE Healthcare). In this manner, six purified humanized versions of antibody clone 20E5 were generated, i.e., 20E5_VL1VH1, 20E5_VL1VH2, 2-E5_VL1VH3, 20E5_VL2VH1, 20E5_VL2VH2 and 20E5_VL2VH3, and six purified humanized versions of antibody clone 12H3 were generated, i.e., 12H3_VL1VH1, 12H3_VL1VH2, 12H3_VL1VH3, 12H3_VL2VH1, 12H3_VL2VH2 and 12H3_VL2VH3.

For humanized amino acid sequences, see SEQ ID NOs: 82, 83, 84 (coding for full length humanized heavy IgG4 chain clone 20E5 versions, i.e., VH1, VH2, VH3, resp.), SEQ ID NO. 85, 86 (coding for full length humanized light K chain clone 20E5 versions, i.e., VL1, VL2, resp.), SEQ ID NO. 87, 88, 89 (coding for full length humanized heavy IgG4 chain clone 12H3 versions, i.e., VH1, VH2, VH3, resp.), and SEQ ID NO. 90, 91 (coding for full length humanized light K chain clone 12H3 versions, i.e., VL1, VL2, resp.).

Example 11. Binding Characterization of Humanized IgG4/Kappa Anti-Human CD134 Monoclonal Antibodies Clones 20E5 an 12H3

(a). Binding of Humanized IgG4κ Anti-Human CD134 Monoclonal Antibody Clones 20E5 and 12H3 with Recombinant Human CD134:Human Fcγ Fusion Protein (ELISA)

Ninety six-wells flat-bottom ELISA plates (Corning) were coated with 50 ng/well recombinant human CD134:human Fcγ (IgG1) fusion protein (R&D Systems) in PBS o/n at 4° C. After extensive washing in PBS/0.05% Tween 20, plates were blocked in PBS/0.05% Tween 20/1% BSA fraction V (Roche) for 1 hour at RT. Subsequently, plates were incubated with 0, 0.0003-20.0 (3-fold dilution steps in block buffer) g/mL parental mouse anti-human CD134 antibody clone 120E5 or 12H3, chimeric human IgG4κ anti-human CD134 antibody clone 20E5 or 12H3, and six versions of humanized IgG4κ anti-human CD134 antibody clone 20E5 or 12H3 for 1 hour at RT. After extensive washing in PBS/0.05% Tween 20, binding of antibodies was determined with 1:5000 diluted horseradish peroxidase-conjugated goat anti-mouse (Fcγ specific) antibodies (Jackson ImmunoResearch) or with 1:4000 diluted horseradish peroxidase-conjugated goat anti-human K-specific antibodies (Southern Biotech) for 1 hour at RT, followed by a ready-to-use solution of TMB substrate (Invitrogen) for colorimetric detection. After adding 1 M $H_2SO_4$, optical densities were measured at a wavelength of 450 nm (reference wavelength of 655 nm) using a microplate reader (BioRad).

Figure 28A:
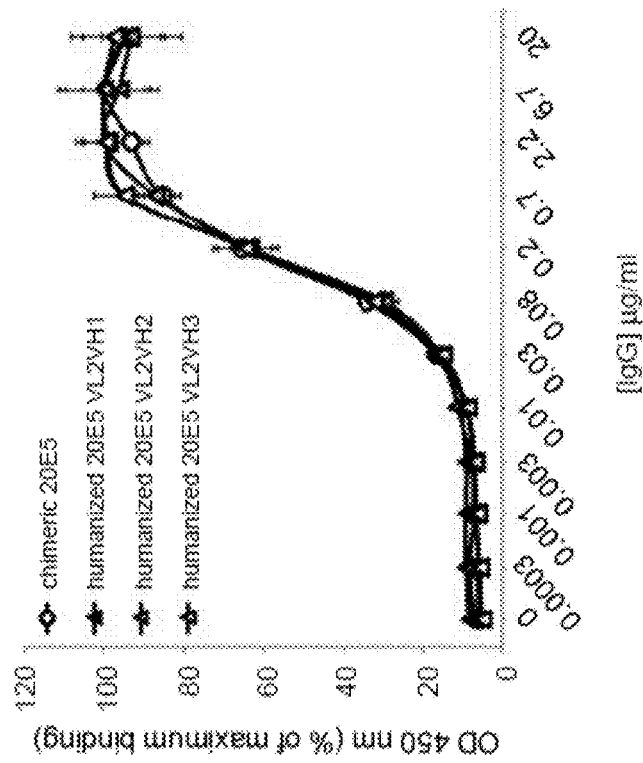
FIGS. 28A and 28B. Binding characteristics of humanized human IgG4κ anti-human CD134 antibody clone 20E5 versions VL1H1, VL1VH2, VL1VH3 (A) and VL2H1, VL2VH2, VL2VH3 (B) against plate-bound recombinant human CD134.
Figure 28B:
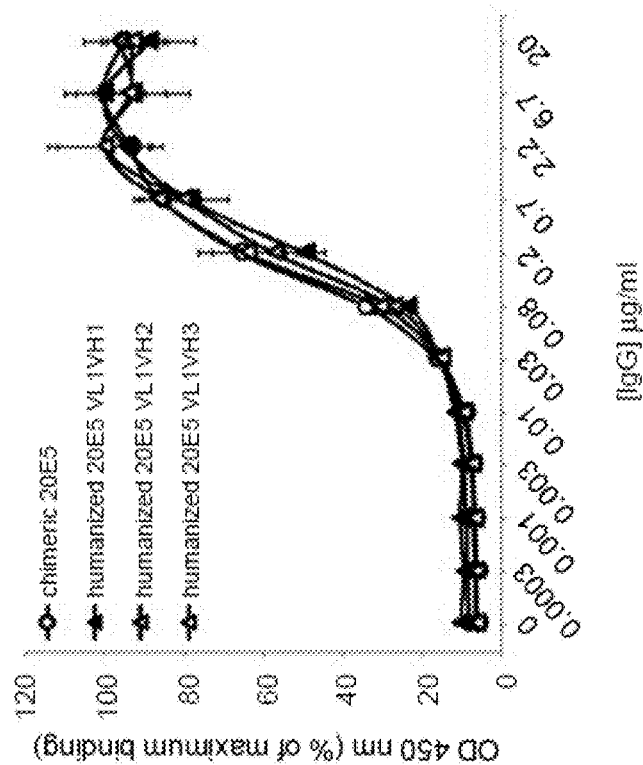

As shown in FIG. 28 (n=2), chimeric human IgG4κ anti-human CD134 antibody clone 20E5 and all six versions of humanized IgG4κ anti-human CD134 antibody clone 20E5 dose-dependently and specifically bound to recombinant human CD134. Chimeric human IgG4κ anti-human CD134 antibody clone 20E5 and humanized IgG4κ anti-human CD134 antibody clone 20E5 versions 20E5_VL1H3, 20E5_VL2H1, 20E5_VL2VH2 and 20E5_VL2VH3 showed identical titration curves, which indicated that their CD134 antigen binding affinity was identical (half-maximum binding $EC_{50} \approx 100$ ng/mL), whereas humanized IgG4κ anti-human CD134 antibody clone 20E5 version 20E5_VL1H1 and 20E5_VL1H2 seemed to show a slightly lower binding affinity ($EC_{50} \approx 150$ ng/mL). Due to usage of different immunoglobulin chain-specific secondary antibodies (i.e., mouse antibodies were detected with anti-Fcγ chain specific antibodies, while chimeric human and humanized antibodies were detected with anti-K chain specific antibodies), comparison between titration curve (data not shown) from parental mouse anti-human CD134 antibody clone 20E5 and titration curves from chimeric human and humanized IgG4κ anti-human CD134 antibody clone 20E5 versions could not be made.

Figure 29B:
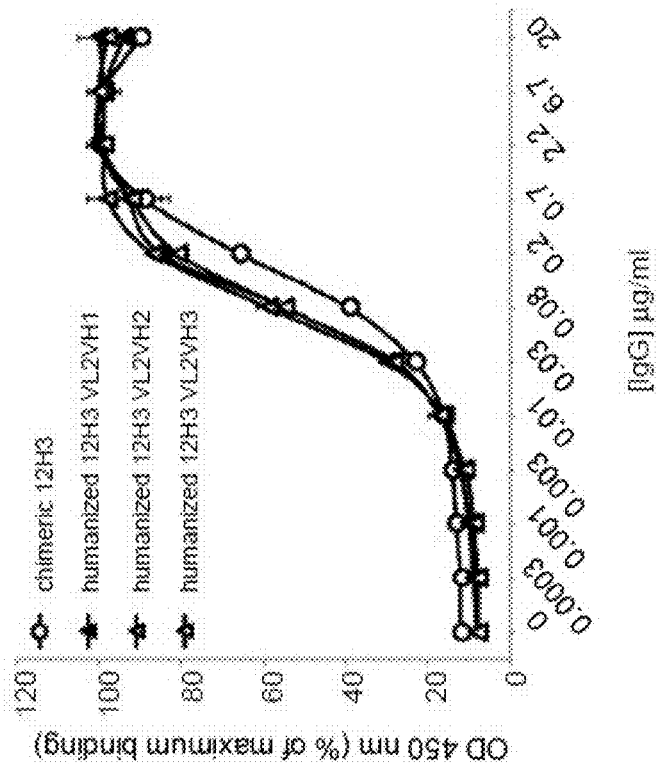
FIGS. 29A and 29B. Binding characteristics of humanized human IgG4κ anti-human CD134 antibody clone 12H3 versions VL1H1, VL1VH2, VL1VH3 (A) and VL2H1, VL2VH2, VL2VH3 (B) against plate-bound recombinant human CD134.
Figure 29A:
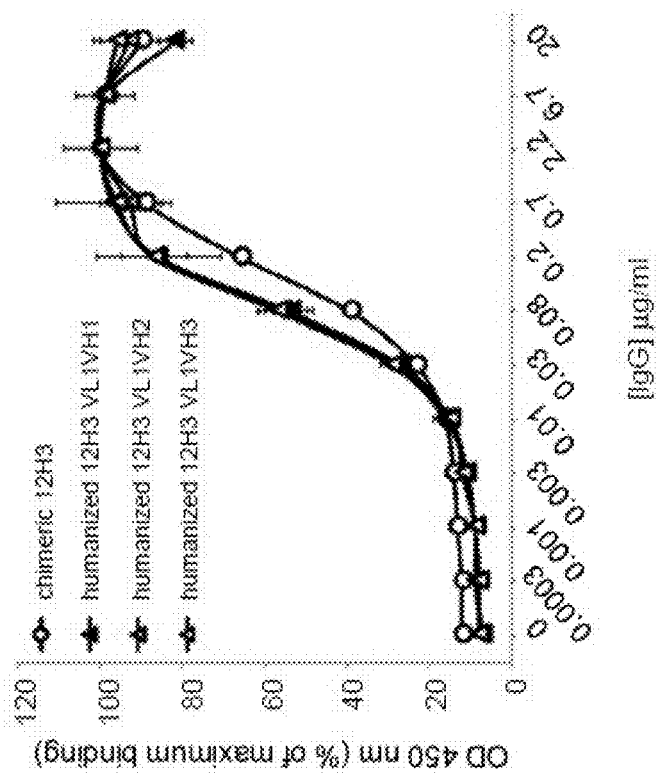

As shown in FIG. 29 (n=2), chimeric human IgG4κ anti-human CD134 antibody clone 12H3 and all six versions of humanized IgG4κ anti-human CD134 antibody clone 12H3 dose-dependently and specifically bound to recombinant human CD134. Chimeric human IgG4κ anti-human CD134 antibody clone 12H3 and humanized IgG4κ anti-human CD134 antibody clone 12H3—all six versions 12H3_VL1H1, 12H3_VL1H2, 12H3_VL1H3, 12H3_VL2H1, 12H3_VL2VH2 and 12H3_VL2VH3—showed non-identical titration curves, which indicated that all six humanized IgG4κ anti-human CD134 antibody clone 12H3 versions showed a slightly higher CD134 antigen binding affinity ($EC_{50} \approx 50$ ng/mL) than chimeric human IgG4κ anti-human CD134 antibody clone 12H3 ($EC_{50} \approx 100$ ng/mL). Due to usage of different immunoglobulin chain-specific secondary antibodies (i.e., mouse antibodies were detected with anti-Fcγ chain specific antibodies, while chimeric human and humanized antibodies were detected with anti-K chain specific antibodies), comparison between titration curve (data not shown) from parental mouse anti-human CD134 antibody clone 12H3 and titration curves from chimeric human and humanized IgG4κ anti-human CD134 antibody clone 12H3 versions could not be made.

(b). Competition of Humanized IgG4κ Anti-Human CD134 Monoclonal Antibody Clone 12H3 with Biotinylated Parental Mouse Anti-Human CD134 Monoclonal Antibody Clone 12H3 for Binding with Recombinant Human CD134:Human Fcγ Fusion Protein (ELISA).

Figure 30:
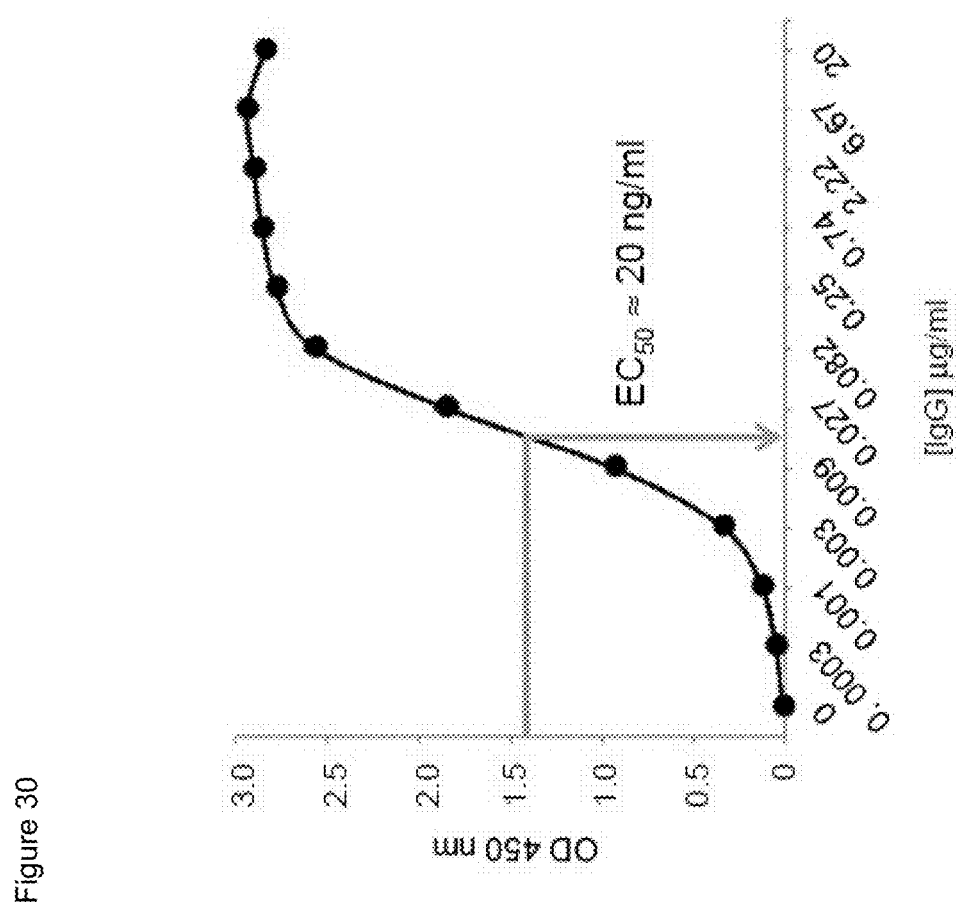
FIG. 30. Binding characteristic of biotinylated parental mouse anti-human CD134 antibody clone 12H3 against plate-bound recombinant human CD134.

Prior to performing the competition ELISA measurements, the $EC_{50}$ of biotinylated (using N-hydroxysuccinimido-biotin from Pierce) parental mouse anti-human CD134 monoclonal antibody clone 12H3 was determined (see below for method), and was identified to be about 20 ng/mL (see FIG. 30, n=3). Displacement of the biotinylated parental mouse anti-human CD134 monoclonal antibody clone 12H3 at its the identified $EC_{50}$ concentration by unlabeled parental mouse anti-human CD134 antibody clone 12H3, chimeric human IgG4κ anti-human CD134 antibody clone 12H3, and six versions of humanized IgG4κ anti-human CD134 antibody clone 12H3 was subsequently investigated.

Ninety six-wells flat-bottom ELISA plates (Corning) were coated with 50 ng/well recombinant human CD134:human Fcγ (IgG1) fusion protein (R&D Systems) in PBS o/n at 4° C. After extensive washing in PBS/0.05% Tween 20, plates were blocked in PBS/0.05% Tween 20/1% BSA fraction V (Roche) for 1 hour at RT. Subsequently, plates were incubated with 0, 0.001-60.0 (3-fold dilution steps in block buffer) g/mL unlabeled parental mouse anti-human CD134 antibody clone 12H3, chimeric human IgG4κ anti-human CD134 antibody clone 12H3, or six versions of humanized IgG4κ anti-human CD134 antibody clone 12H3 in combination with 20 ng/mL ($EC_{50}$) biotinylated parental mouse anti-human CD134 monoclonal antibody clone 12H3 for 1 hour at RT. After extensive washing in PBS/0.05% Tween 20, binding of biotinylated parental mouse anti-human CD134 monoclonal antibody clone 12H3 was determined with 1:5000 diluted horseradish peroxidase-conjugated streptavidin (Jackson ImmunoResearch) for 1 hour at RT, followed by a ready-to-use solution of TMB substrate (Invitrogen) for colorimetric detection. After adding 1 M $H_2SO_4$, optical densities were measured at a wavelength of 450 nm (reference wavelength of 655 nm) using a microplate reader (BioRad).

Figure 31B:
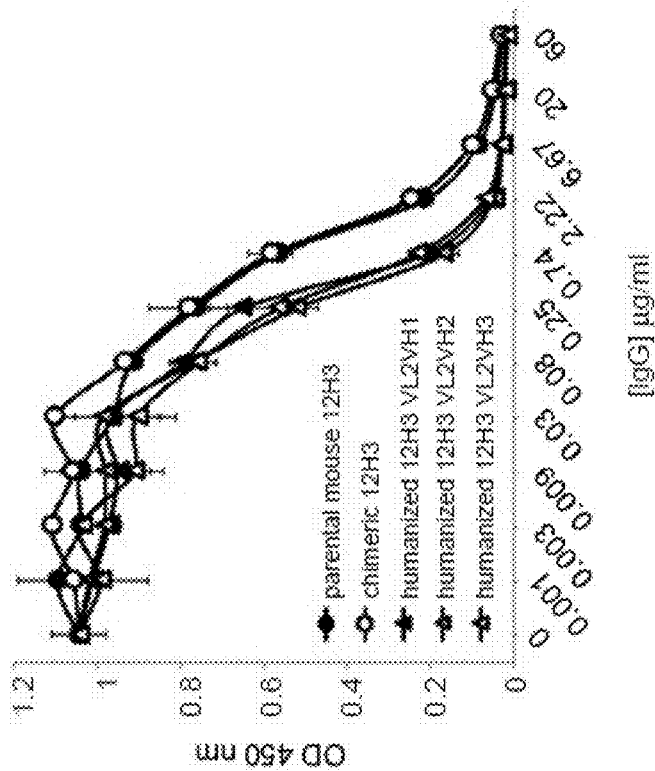
FIGS. 31A and 31B. Competition characteristics of humanized human IgG4κ anti-human CD134 antibody clone 12H3 versions VL1H1, VL1VH2, VL1VH3 (A) and VL2H1, VL2VH2, VL2VH3 (B) with biotinylated parental mouse anti-human CD134 antibody clone 12H3 (at an $EC_{50}$ of 20 ng/mL) for binding to plate-bound recombinant human CD134.
Figure 31A:
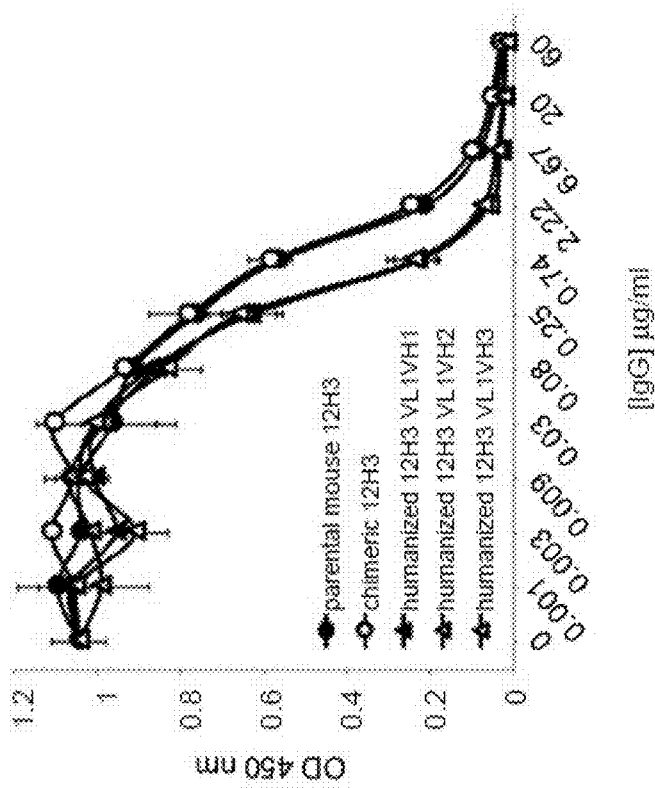

As shown in FIG. 31 (n=2), unlabeled parental mouse anti-human CD134 antibody clone 12H3 and unlabeled chimeric human IgG4κ anti-human CD134 antibody clone 12H3 demonstrated identical displacement of biotinylated parental mouse anti-human CD134 monoclonal antibody clone 12H3, which indicated that parental mouse anti-human CD134 antibody clone 12H3 and chimeric human IgG4κ anti-human CD134 antibody clone 12H3 exhibited an identical CD134 antigen binding affinity (half-maximum displacement or inhibition ($IC_{50}$) of biotinylated parental mouse anti-human CD134 monoclonal antibody clone 12H3 at ≈750 ng/mL). All six unlabeled humanized IgG4κ anti-human CD134 antibody clone 12H3 versions—12H3_VL1H1, 12H3_VL1H2, 12H3_VL1H3, 12H3_VL2H1, 12H3_VL2VH2 and 12H3_VL2VH3—demonstrated similar displacement of biotinylated parental mouse anti-human CD134 monoclonal antibody clone 12H3, which indicated that all six unlabeled humanized IgG4κ anti-human CD134 antibody clone 12H3 versions exhibited a similar CD134 antigen binding affinity ($IC_{50}$≈250-300 ng/mL).

These results demonstrated that all six humanized IgG4κ anti-human CD134 antibody clone 12H3 versions showed a higher CD134 antigen binding affinity than parental mouse anti-human CD134 antibody clone 12H3 and chimeric human IgG4κ anti-human CD134 antibody clone 12H3.

(c). Binding of Humanized IgG4κ Anti-Human CD134 Monoclonal Antibody Clones 20E5 and 12H3 with Full-Length Human CD134 Construct Expressed on 293-F Cell Line (FACS)

In order to analyze the binding of humanized IgG4κ anti-human CD134 monoclonal antibody clones 20E5 and 12H3 in detail, the binding capacity of humanized IgG4κ anti-human CD134 monoclonal antibody clones 20E5 and 12H3 with surface human full-length CD134 on (stable transfectants) 293-F cell lines was determined by flow cytometry, and, furthermore, compared with the binding characteristics of their corresponding parental mouse anti-human CD134 antibody counterparts.

Figure 32A:
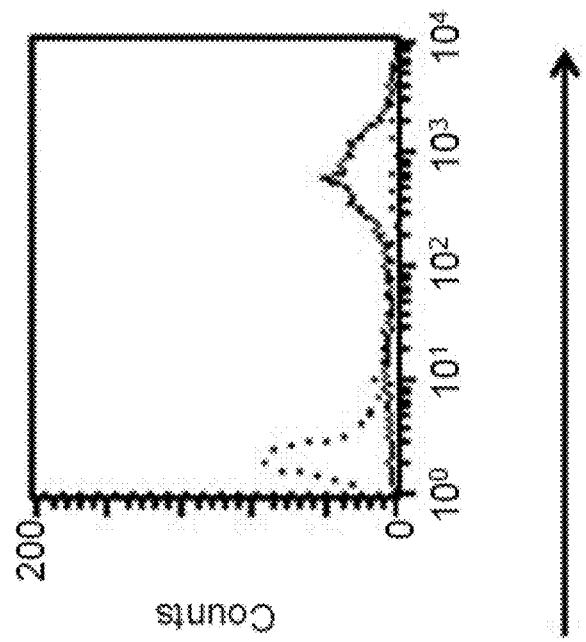
FIGS. 32A and 32B. Expression levels of human full-length CD134 on stably transfected 293-F cell line clone no. 5 (A) and on clone no. 23 (B).
Figure 32B:
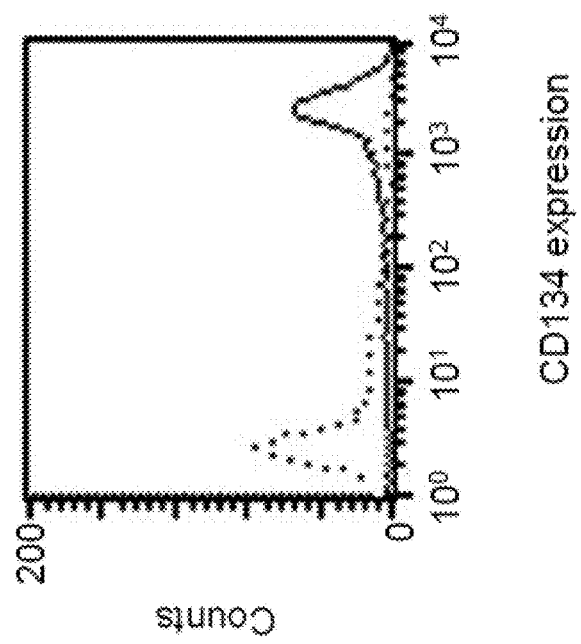

Full-length human CD134 (SEQ ID NO. 1) was re-cloned in a pcDNA3.1-derived expression plasmid (see Example 11 (d) below). This full-length human CD134 plasmid was transfected in FreeStyle™ 293-F cells (Life Technologies) using the FreeStyle™ 293 Expression System (Life Technologies). Stable human full-length CD134-transfected cells (clone no. 5 with high surface CD134 expression level and clone no. 23 with intermediate surface CD134 expression level; see FIG. 32) were selected using 125 μg/mL G418 (Gibco), and were harvested and put at $1-2 \times 10^6$ cells/mL in ice-chilled PBS/BSA/NaN$_3$ supplemented with 50 μg/mL purified human IgG (Sigma; blocking Fcγ receptors). Cells were incubated with 0, 0.005-50 μg/mL (10-fold dilution steps in PBS/BSA/NaN$_3$; all clone 20E5 versions) or 0.002-20 μg/mL (10-fold dilution steps in PBS/BSA/NaN$_3$; all clone 12H3 versions) parental mouse anti-human CD134 antibody clone 20E5 or 12H3, chimeric human IgG4κ anti-human CD134 antibody clone 20E5 or 12H3, and six versions of humanized IgG4κ anti-human CD134 antibody clone 20E5 or 12H3 for 30 minutes at 4° C. In parallel, mouse IgG1κ isotype control (BD Biosciences; 50.0 or 20.0 μg/mL) and chimeric human IgG4κ isotype control (clone ch5D12 from PanGenetics; 50.0 or 20.0 μg/mL) were used as negative controls. After extensive washing in PBS/BSA/NaN$_3$, cells were subsequently incubated with 1:200 diluted PE-conjugated goat anti-mouse IgG (Fcγ specific) antibodies (Jackson ImmunoResearch) or with 1:200 diluted PE-conjugated goat anti-human IgG (Fcγ specific) antibodies (Jackson ImmunoResearch) for 30 minutes at 4° C. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

Figure 33A:
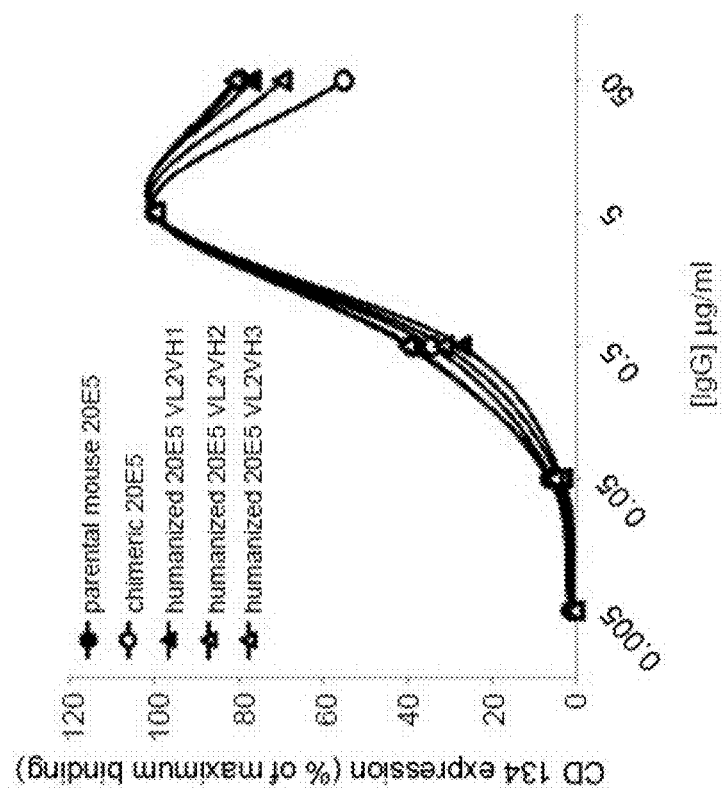
FIGS. 33A and 33B. Binding characteristics of humanized human IgG4κ anti-human CD134 antibody clone 20E5 versions VL1H1, VL1VH2, VL1VH3 (A) and VL2H1, VL2VH2, VL2VH3 (B) against surface human CD134 on stably transfected 293-F cell line clone no. 5.
Figure 33B:
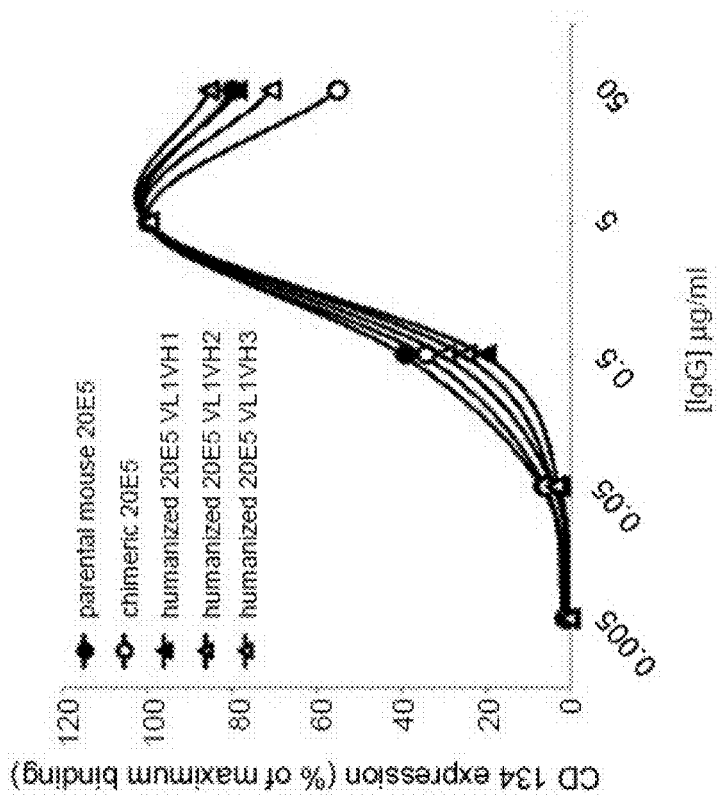

As shown in FIG. 33 (human full-length CD134-transfected cells clone no. 5 with high surface CD134 expression level; n=1), parental mouse anti-human CD134 antibody clone 20E5, chimeric human IgG4κ anti-human CD134 antibody clone 20E5 and all six versions of humanized IgG4κ anti-human CD134 antibody clone 20E5 dose-dependently and specifically bound to cell surface expressed human CD134. Parental mouse anti-human CD134 antibody clone 20E5, chimeric human IgG4κ anti-human CD134 antibody clone 20E5 and humanized IgG4κ anti-human CD134 antibody clone 20E5 versions 20E5_VL1H3, 20E5_VL2H1, 20E5_VL2VH2 and 20E5_VL2VH3 showed similar titration curves, which indicated that their CD134 antigen binding affinity is very similar, whereas humanized IgG4κ anti-human CD134 antibody clone 20E5 version VL1H1 and VL1H2 seemed to show a slightly lower binding affinity.

Figure 34B:
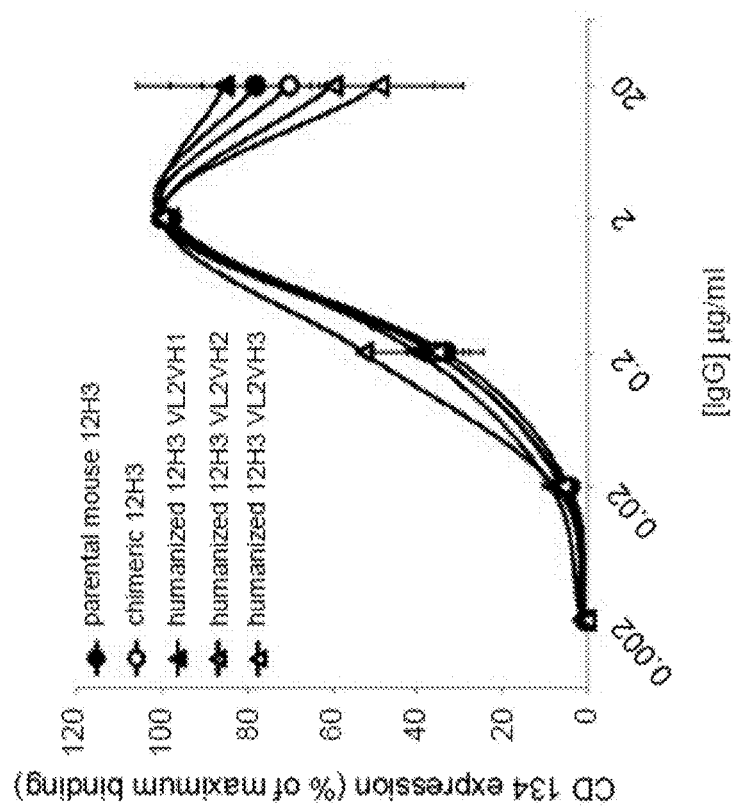
FIGS. 34A and 34B. Binding characteristics of humanized human IgG4κ anti-human CD134 antibody clone 12H3 versions VL1H1, VL1VH2, VL1VH3 (A) and VL2H1, VL2VH2, VL2VH3 (B) against surface human CD134 on stably transfected 293-F cell line clone no. 5.
Figure 34A:
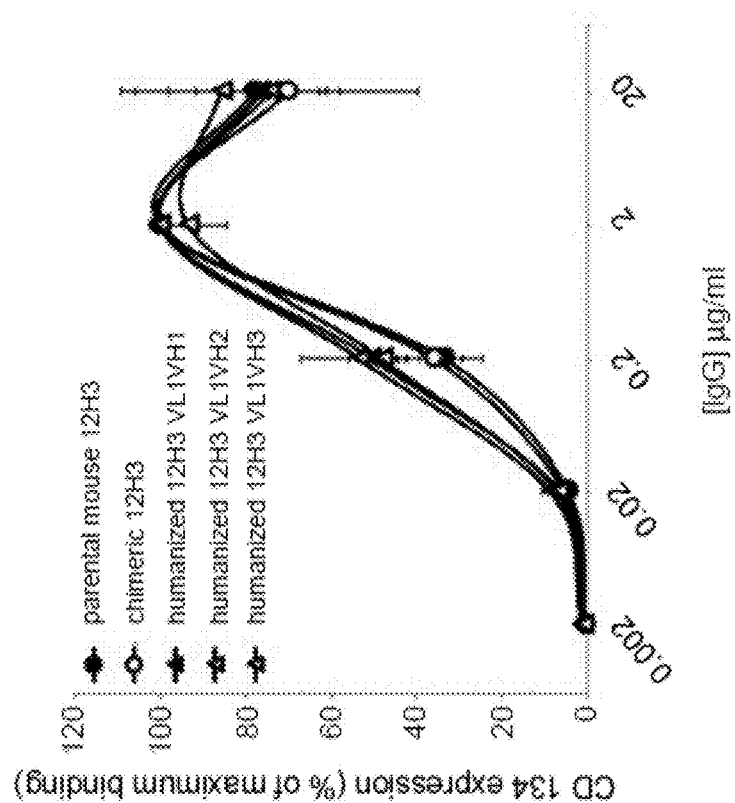

As shown in FIG. 34 (human full-length CD134-transfected cells clone no. 5 with high surface CD134 expression level; n=2), parental mouse anti-human CD134 antibody clone 12H3, chimeric human IgG4κ anti-human CD134 antibody clone 12H3 and all six versions of humanized IgG4κ anti-human CD134 antibody clone 12H3 dose-dependently and specifically bound to cell surface expressed human CD134. Parental mouse anti-human CD134 antibody clone 12H3, chimeric human IgG4κ anti-human CD134 antibody clone 12H3 and humanized IgG4κ anti-human CD134 antibody clone 12H3 versions 12H3_VL2H1 and 12H3_VL2VH3, showed identical titration curves, which indicated that their CD134 antigen binding affinity is identical, whereas humanized IgG4κ anti-human CD134 antibody clone 12H3 version 12H3_VL1H1, 12H3_VL1H2, 12H3_VL1H3 and 12H3_VL2H2 seemed to show a slightly higher binding affinity.

Figure 35A:
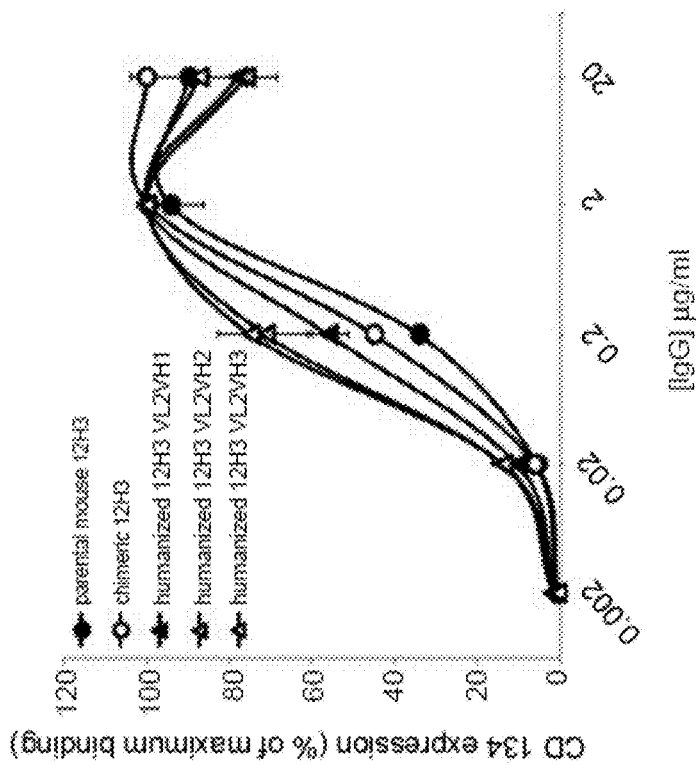
FIGS. 35A and 35B. Binding characteristics of humanized human IgG4κ anti-human CD134 antibody clone 12H3 versions VL1H1, VL1VH2, VL1VH3 (A) and VL2H1, VL2VH2, VL2VH3 (B) against surface human CD134 on stably transfected 293-F cell line clone no. 23.
Figure 35B:
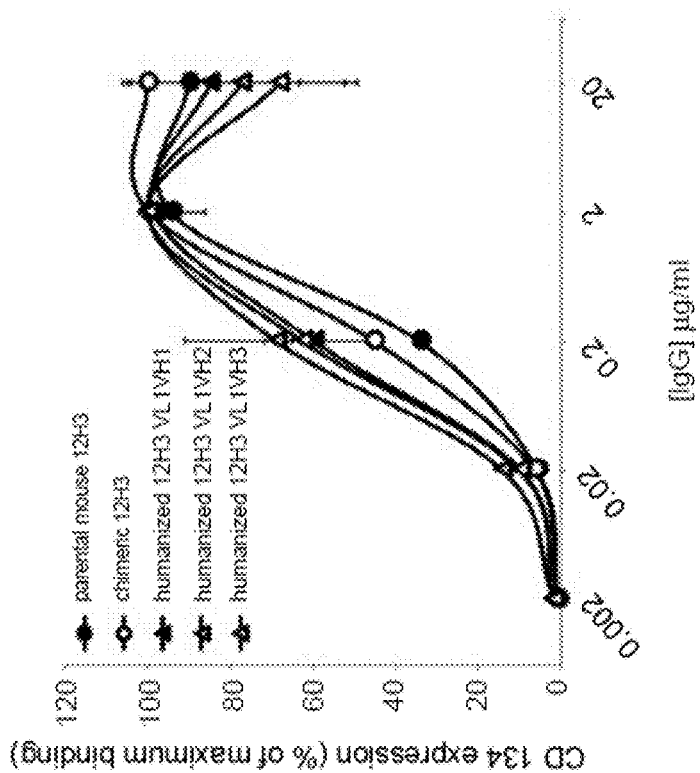
Figure 36A:
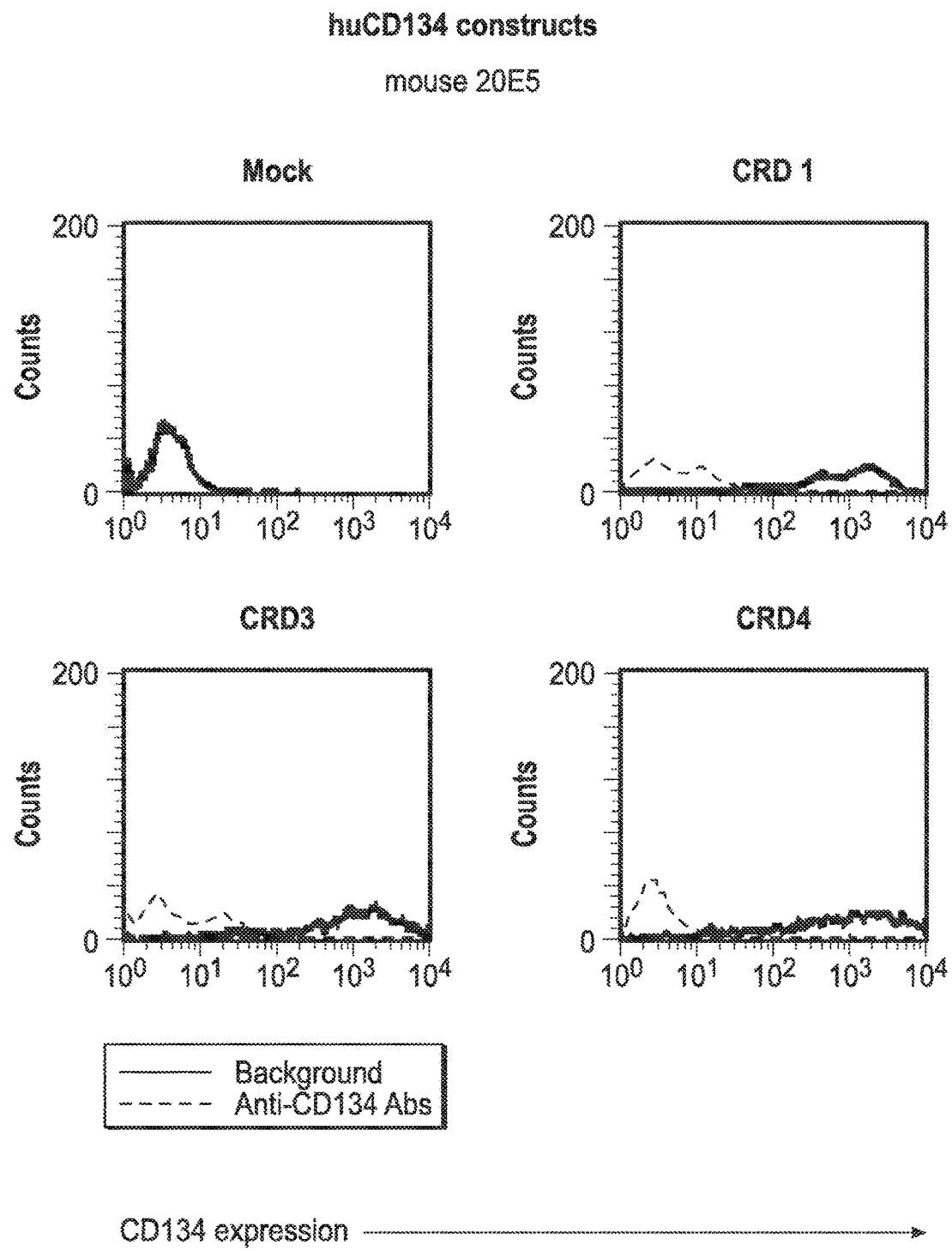
FIGS. 36A-I. Binding of humanized human IgG4κ anti-human CD134 antibody clone 12H3 versions VL1H1, VL1VH2, VL1VH3, VL2H1, VL2VH2, VL2VH3 on 293-F cell line transiently transfected with full-length human CD134 construct (denoted 'CRD1') or with various truncated human CD134 constructs (denoted 'CRD3' and 'CRD4').
Figure 36B:
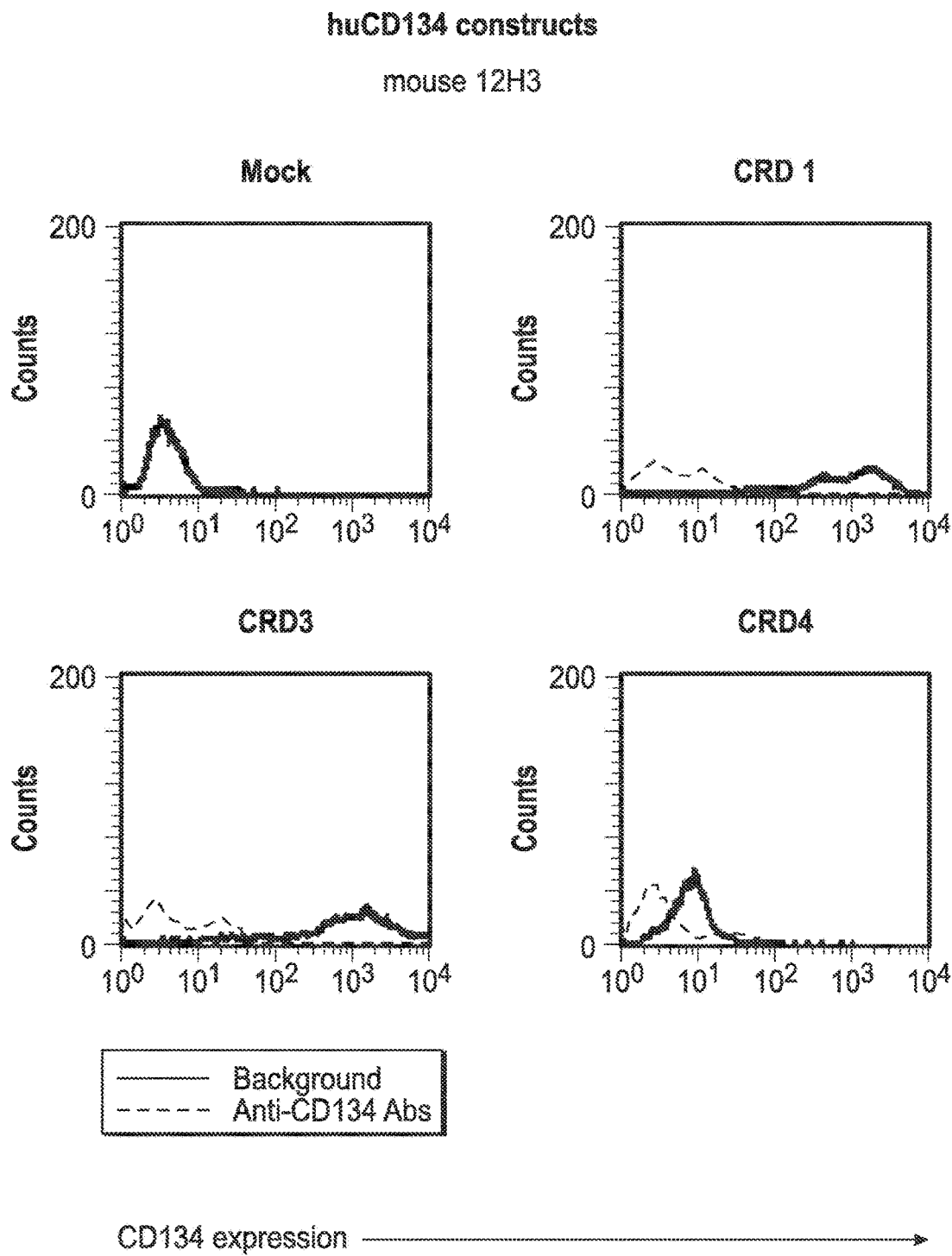
Figure 36C:
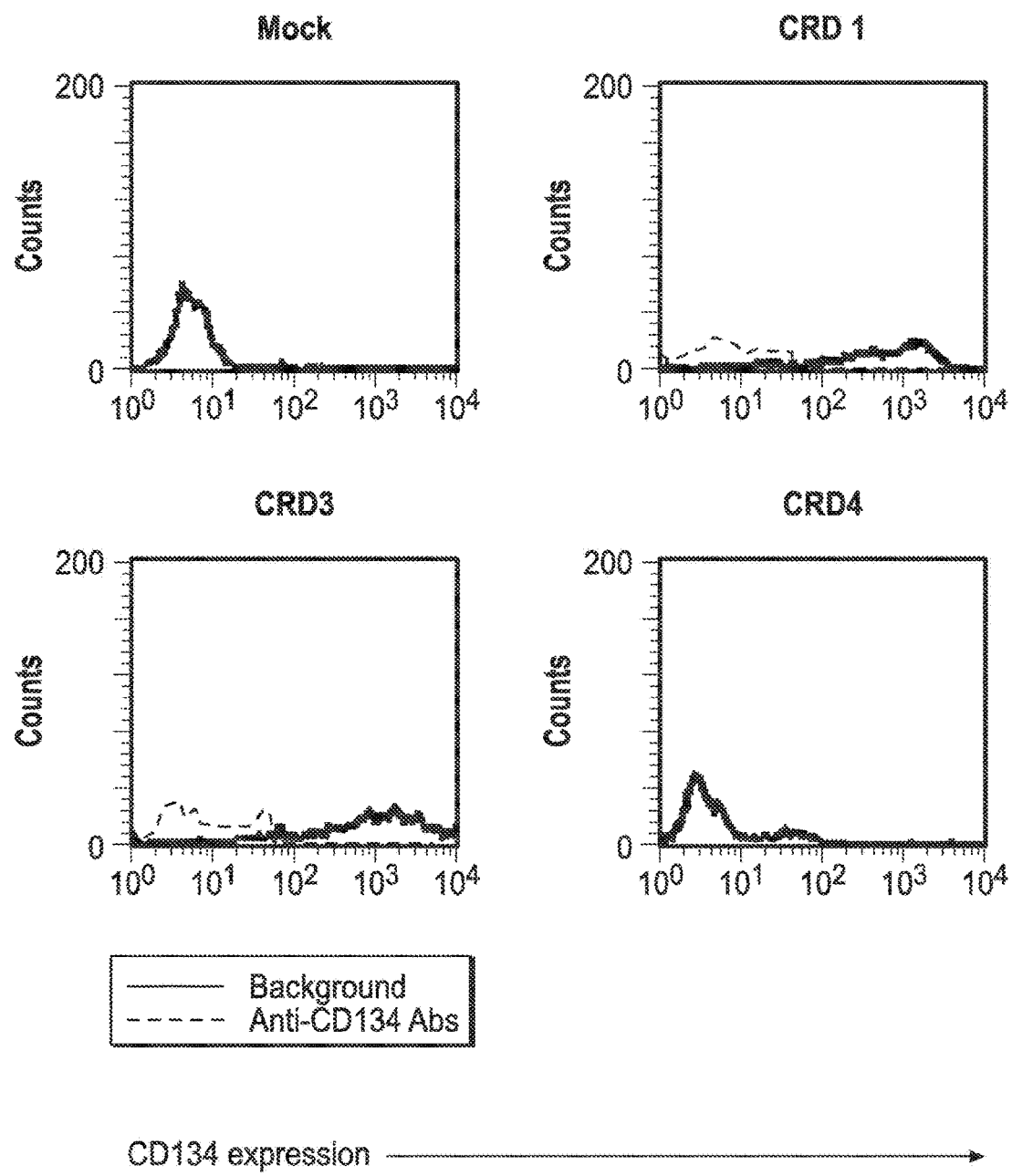
Figure 36D:
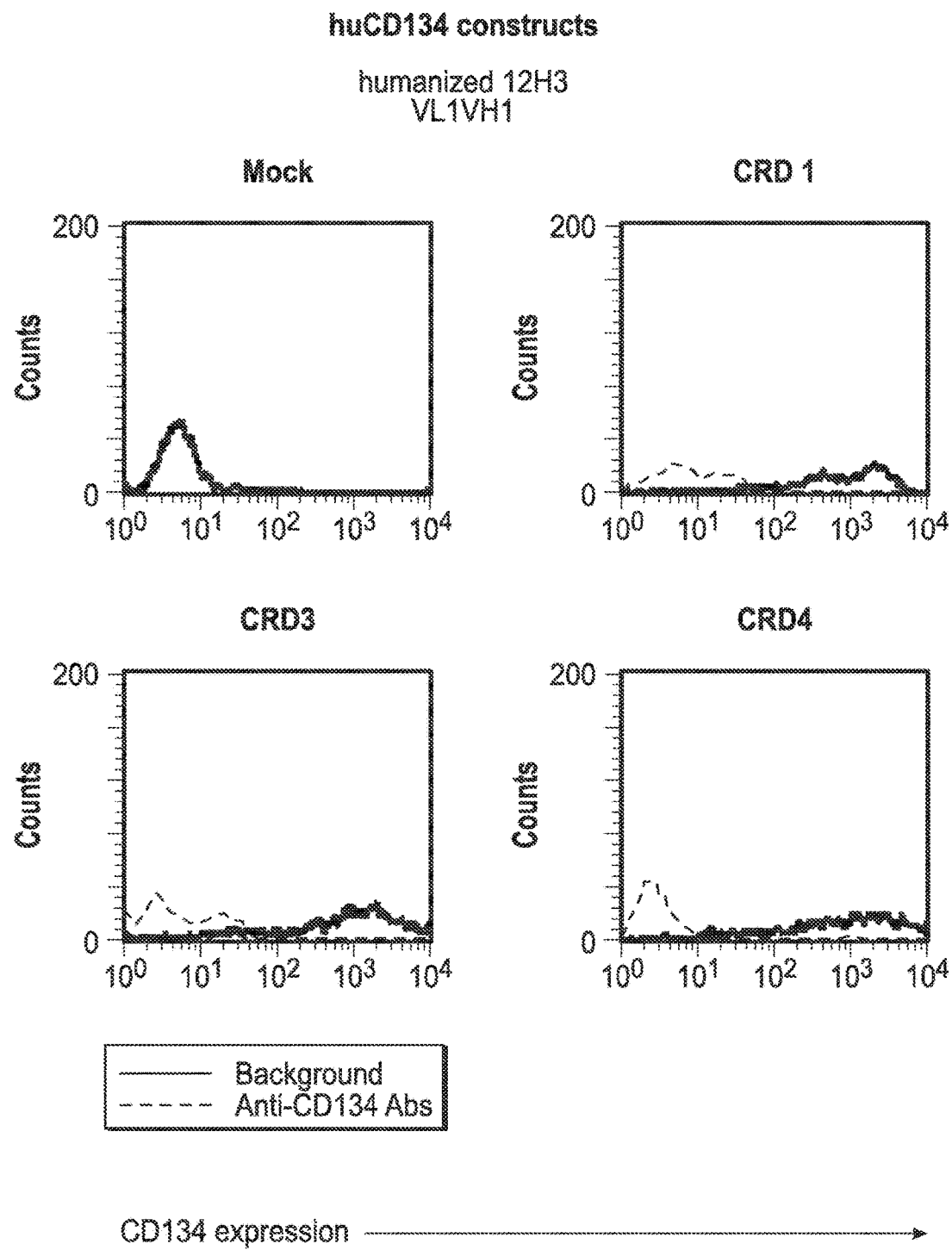
Figure 36E:
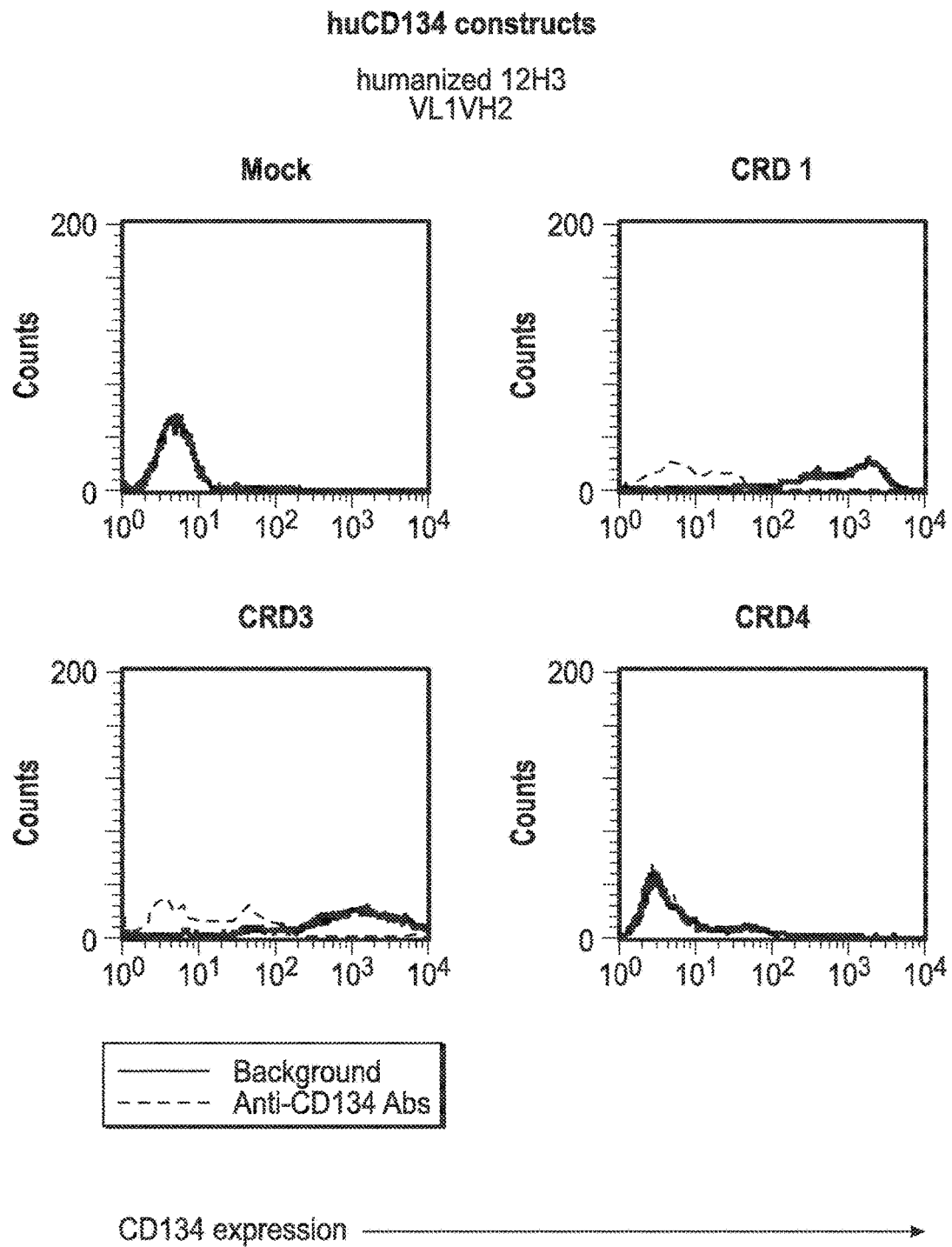
Figure 36F:
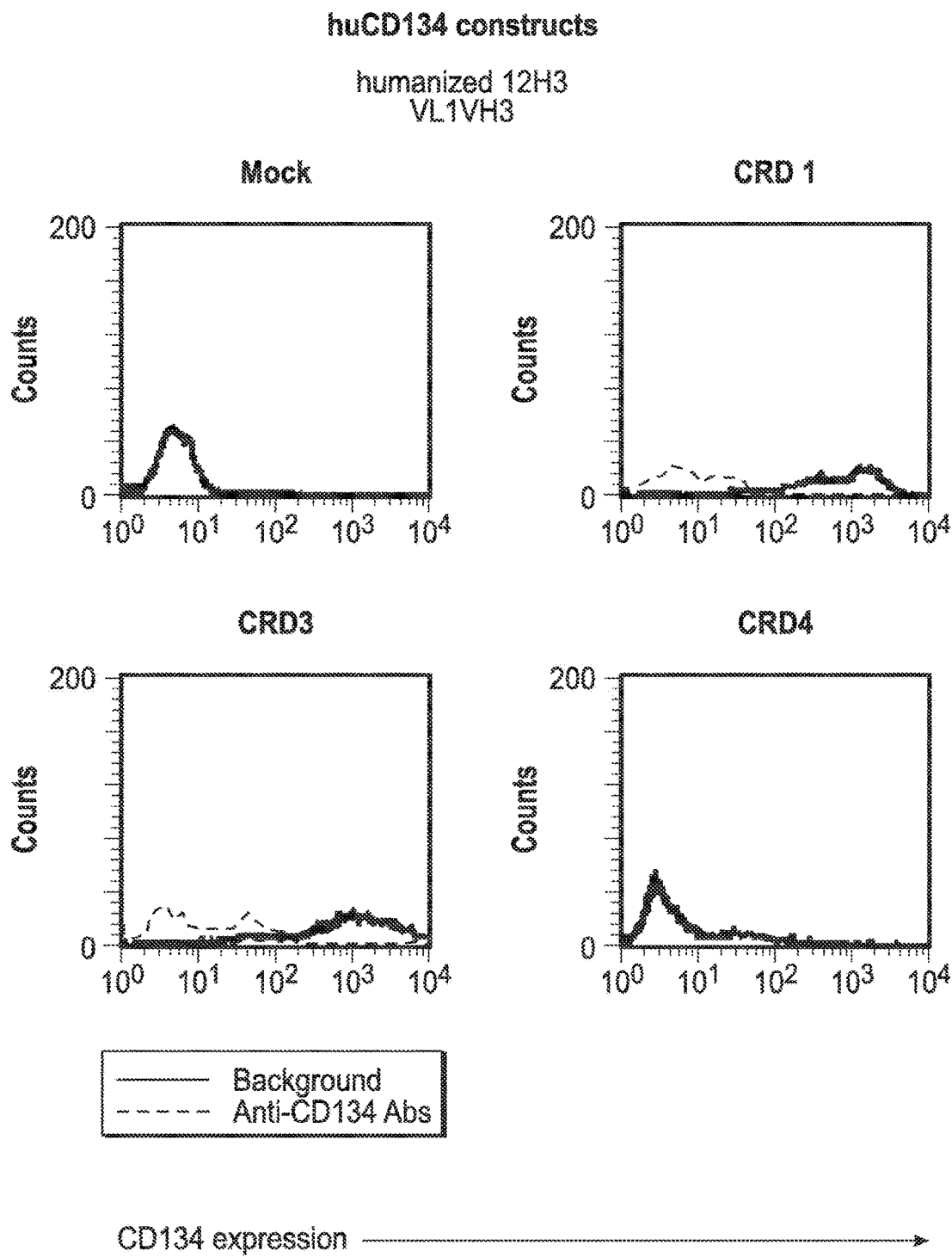
Figure 36G:
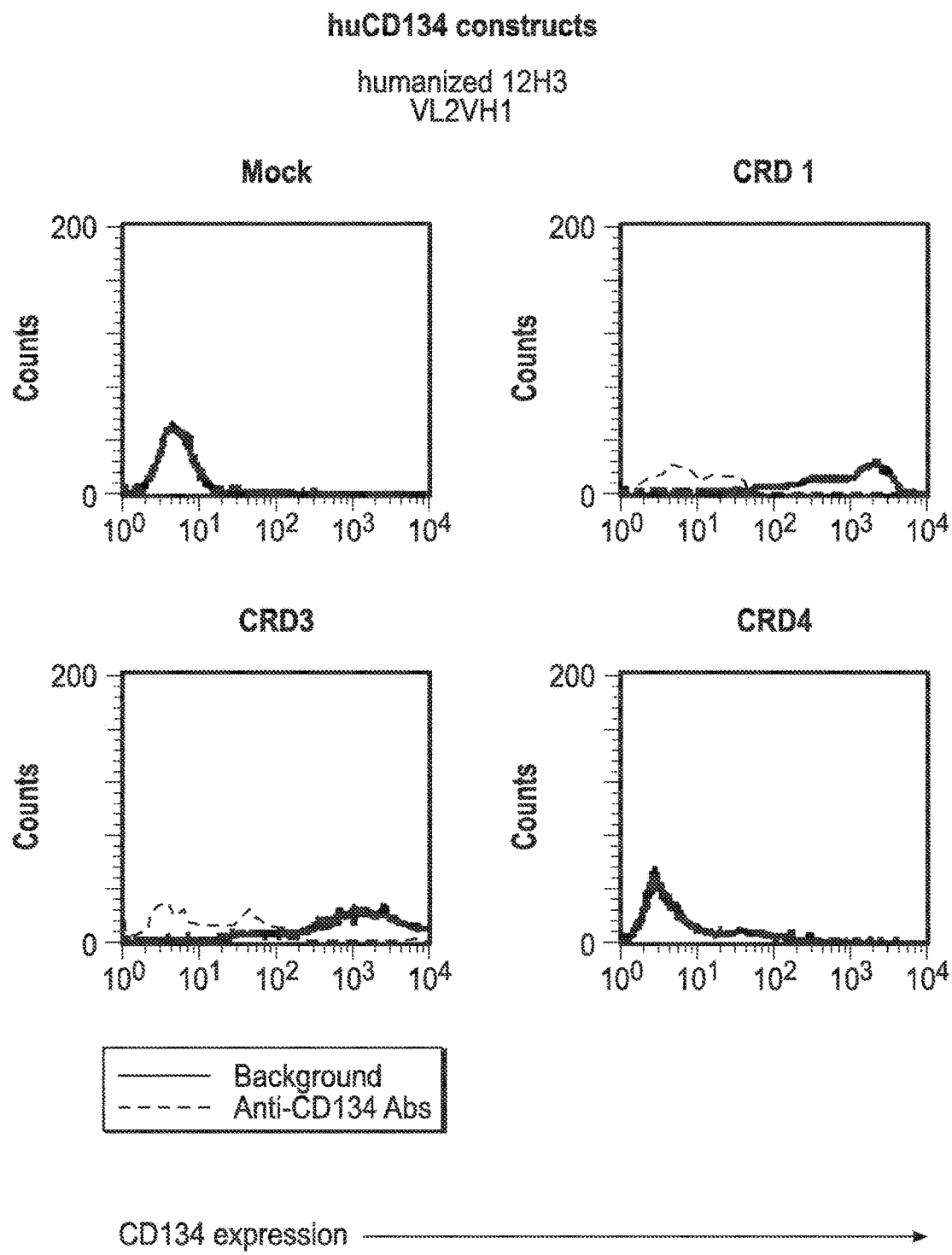
Figure 36H:
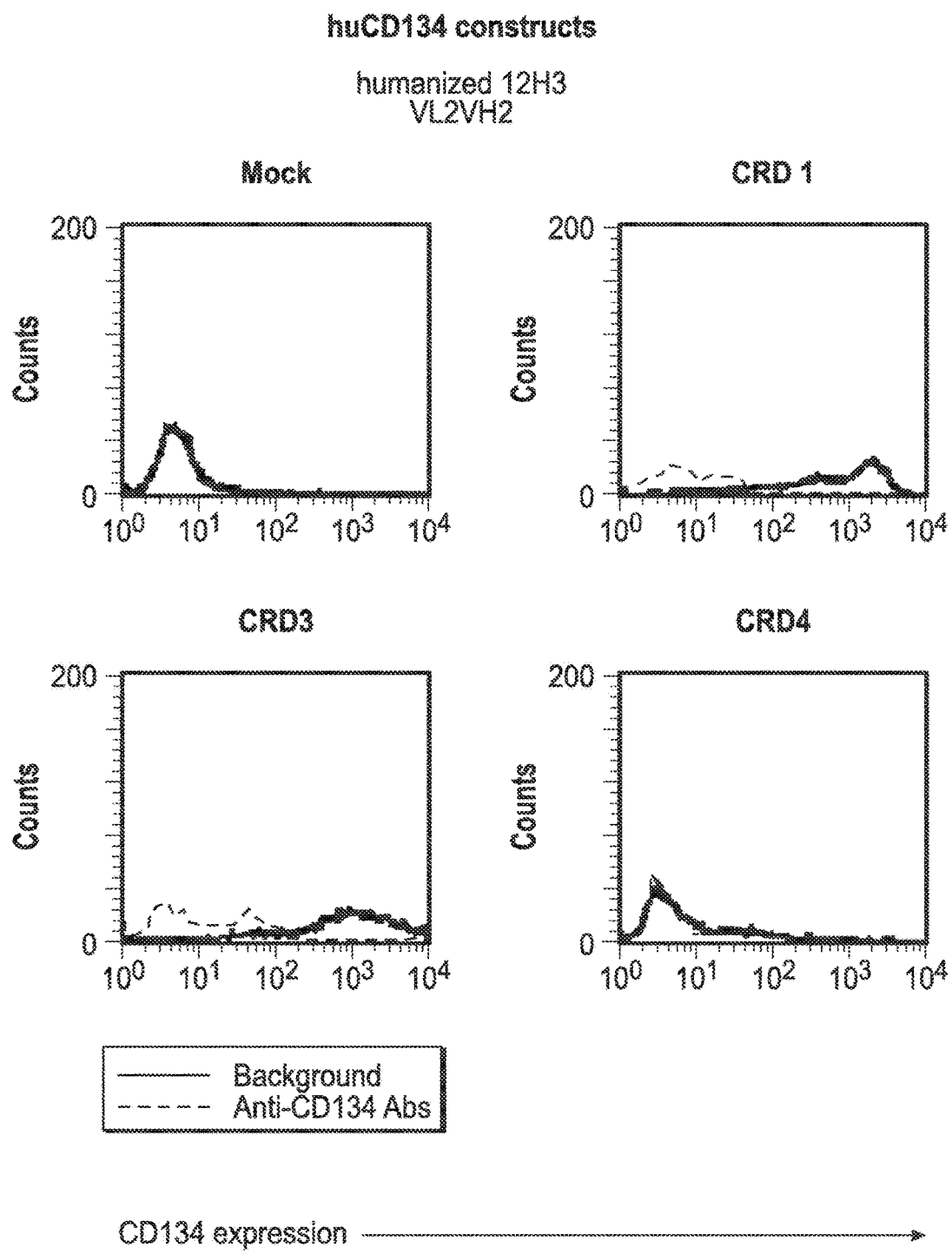
Figure 36I:
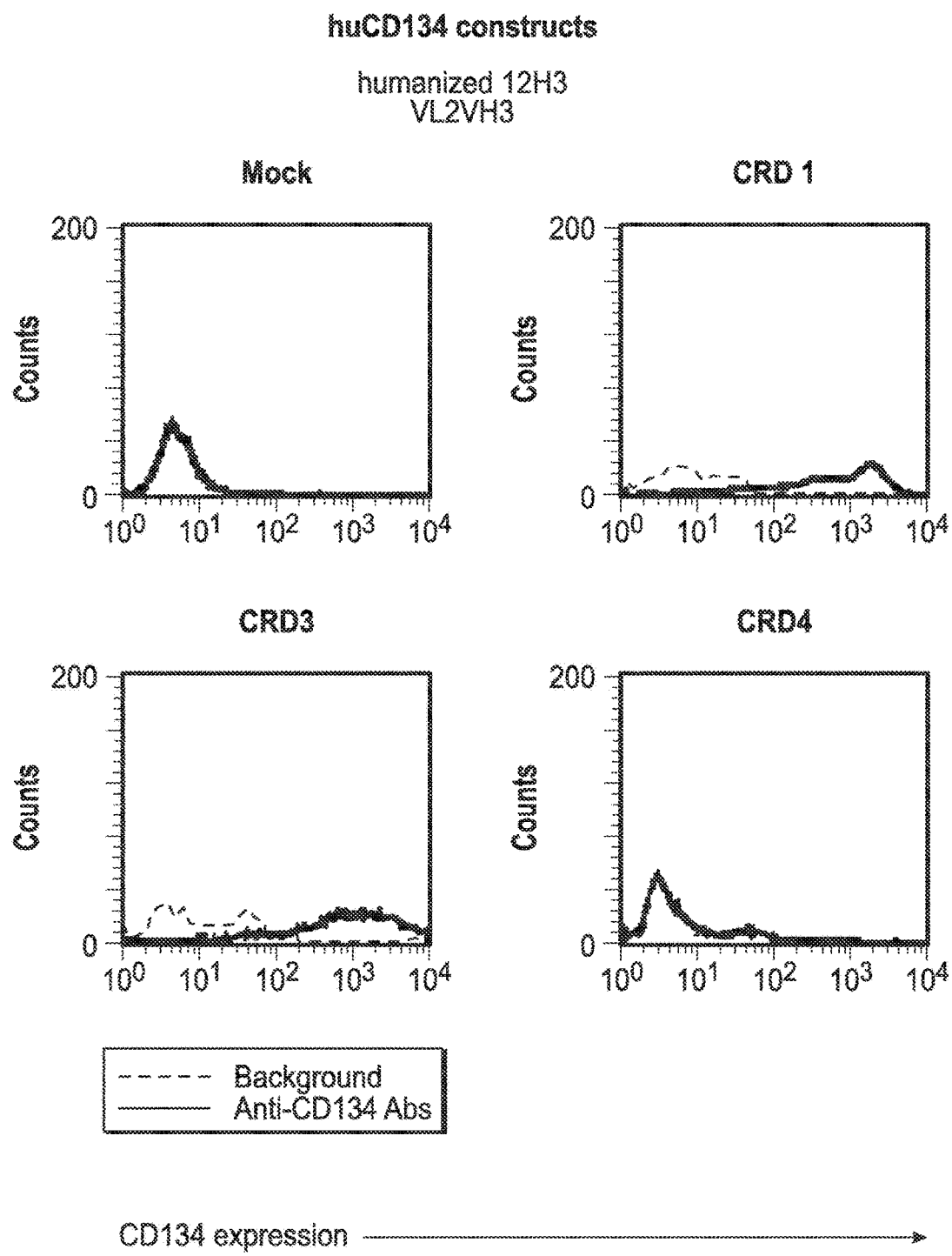

As shown in FIG. 35 (human full-length CD134-transfected cells clone no. 23 with intermediate surface CD134 expression level; n=2), parental mouse anti-human CD134 antibody clone 12H3, chimeric human IgG4κ anti-human CD134 antibody clone 12H3 and all six versions of humanized IgG4κ anti-human CD134 antibody clone 12H3 dose-dependently and specifically bound to cell surface expressed human CD134. Parental mouse anti-human CD134 antibody clone 12H3 and chimeric human IgG4κ anti-human CD134 antibody clone 12H3 showed similar titration curves, which indicated that their CD134 antigen binding affinity is similar ($EC_{50}$>200 ng/mL), whereas all six humanized IgG4κ anti-human CD134 antibody clone 12H3 versions—12H3_VL1H1, 12H3_VL1H2, 12H3_VL1H3, 12H3_VL2H1, 12H3_VL2VH2 and 12H3_VL2VH3—seemed to show a higher binding affinity ($EC_{50}$<200 ng/mL).

Collectively, these flow cytometric results demonstrated that humanized IgG4κ anti-human CD134 antibody clone 20E5 versions 20E5_VL1H3, 20E5_VL2H1, 20E5_VL2VH2, 20E5_VL2VH3, parental mouse anti-human CD134 antibody clone 20E5 and chimeric human IgG4κ anti-human CD134 antibody clone 20E5 showed a similar CD134 antigen binding affinity, whereas humanized IgG4κ anti-human CD134 antibody clone 20E5 version 20E5_VL1H1 and 20E5_VL1H2 seemed to show a slightly lower CD134 antigen binding affinity. In addition, these results demonstrated that all six humanized IgG4κ anti-human CD134 antibody clone 12H3 versions showed a higher CD134 antigen binding affinity than parental mouse anti-human CD134 antibody clone 12H3 and chimeric human IgG4κ anti-human CD134 antibody clone 12H3.

(d). Binding of Humanized IgG4κ Anti-Human CD134 Monoclonal Antibody Clones 12H3 and 20E5 with Full-Length Human CD134 Construct and Various Truncated Human CD134 Constructs Expressed on 293-F Cell Line (FACS Domain Mapping).

In order to analyze the fine specificity of humanized IgG4κ anti-human CD134 monoclonal antibody clones 12H3 and 20E5, the epitope location recognized by humanized IgG4κ anti-human CD134 monoclonal antibody clones 12H3 and 20E5 was determined by domain mapping. The ability of humanized IgG4κ anti-human CD134 monoclonal antibody clones 12H3 and 20E5 to bind to truncated human CD134 constructs, expressed on the surface of (HEK-derived) 297-F cells, was determined by flow cytometric analysis.

Based on literature (Swiss-Prot: P43489.1; Latza et al. Eur J Immunol 1994; 24: 677-683; Bodmer et al. Trends Biochem Sci 2002; 27: 19-26; Compaan et al. Structure 2006; 14: 1321-1330; US Patent Publ. No. 2011/0028688), cysteine-rich domains (CRD) and a hinge-like structure in the extracellular region of human CD134 were identified. CRDs are coded CRD1, CRD2, (truncated) CRD3, (truncated) CRD4 (see FIG. 20). CRDs contain topologically distinct types of modules, called an A-module and a B-module (see also FIG. 20). A-modules are C-shaped structures, and B-modules are S-shaped structures. A typical CRD is usually composed of A1-B2-modules or A2-B1-modules (or, less frequently, a different pair of modules, like A1-B1) with 6 conserved cysteine residues, wherein the numeral denotes the number of disulphide bridges within each module (see also FIG. 20). As shown in FIG. 20, 3 different human CD134 constructs were generated and expressed: (1) full-length human CD134 construct, which starts with N-terminal CRD1 (i.e., CRD1 A1-B2-module covers amino acids 29-65), and therefore denoted as 'CRD1', and comprised amino acids 1-277 (see SEQ ID NO: 1), (2) 'CRD3' construct, which starts with N-terminal CRD3 (i.e., CRD3 A1-B1-module covers amino acids 108-146 (according to Compaan et al. Structure 2006; 14: 1321-1330) or truncated CRD3 A1-module covers amino acids 108-126 (according to Latza et al. Eur J Immunol 1994; 24: 677-683)), and comprised amino acids 108-277 linked to signal peptide amino acids 1-28 (see SEQ ID NO: 31), (3) 'CRD4' construct, which consists of N-terminal CRD4 or CRD3 subdomain B1-module/truncated CRD4 A1-module (i.e., CRD4 A1-B1-module covers amino acids 127-167 (Latza et al. Eur J Immunol 1994; 24: 677-683) or a combination (not shown in FIG. 20) of CRD3 subdomain B1-module with truncated CRD4 A1-module covers amino acids 127-146 with amino acids 147-167, respectively (Compaan et al. Structure 2006; 14: 1321-1330)), and comprised amino acids 127-277 linked to signal peptide amino acids 1-28 (see SEQ ID NO: 32). By assembly PCR using Accuprime™ Pfx DNA Polymerase (Invitrogen), these 3 human CD134 constructs were generated using primers shown in Table 2.

TABLE 2

| Primer No.* | Sequence | SEQ ID No. | Direction | Gene |
| --- | --- | --- | --- | --- |
| 362 | CTCGGATCCGCCACCATGTGCGTG | 51 | sense | CD134 leader |
| 363 | AGAATTCTTATTAGATCTTGGCCA | 55 | antisense | CD134 end |
| 366 | ACTGTCACTGGAAGGTGCAGGGCT | 54 | sense | CRD3 |
| 367 | AGCCCTGCACCTTCCAGTGACAGT | 56 | antisense | CRD3 |
| 368 | ACTGTCACTGGACCCTGCCCCCCT | 57 | sense | CRD4 |
| 369 | AGGGGGGCAGGGTCCAGTGACAGT | 58 | antisense | CRD4 |

*Primer No. according to Bioceros internal coding system

Briefly, cDNA encoding amino acids 1-28 of signal peptide and cDNA encoding amino acids 66-277 of human CD134 were amplified using respectively primer pair 362/367 and 366/363 in a PCR reaction with full-length human CD134 as a template. Subsequently, 'CRD3' construct was generated by using these two PCR products in an assembly PCR using primer pair 362/363. The cDNA encoding 'CRD3' construct was subcloned into a pcDNA3.1-derived expression plasmid using suitable restriction sites. Similarly, 'CRD4' construct (amino acids 1-28 of signal peptide linked to amino acid 127-277) was generated and subcloned in pcDNA3.1-derived expression plasmids using the corresponding primers shown in abovementioned table. Furthermore, full-length human CD134 (SEQ ID NO: 1) was also re-cloned in a pcDNA3.1-derived expression plasmid.

Using the FreeStyle™ 293 Expression System (Life Technologies), FreeStyle™ 293-F cells (Life Technologies) were transiently transfected with the 3 generated variants of human CD134. After 48 h, surface human CD134 expression on transfected cells was analyzed by FACS analysis. To this end, transfected cells were harvested and put at $1-2\times10^6$ cells/mL in ice-chilled PBS/BSA/$NaN_3$ supplemented with 50 µg/mL purified human IgG (Sigma; blocking Fcγ receptors). Cells were incubated with 20.0 µg/mL parental mouse anti-human CD134 monoclonal antibodies clones 12H3 and 20E5 with 20.0 µg/mL chimeric human IgG4κ anti-human CD134 antibody clones 12H3 and 20E5, with 20.0 µg/mL of six versions of humanized IgG4κ anti-human CD134 antibody clone 12H3 and with 20.0 µg/mL humanized IgG4κ anti-human CD134 antibody clone 20E5 version 20E5_VL1VH1 for 30 minutes at 4° C. In parallel, 20.0 µg/mL mouse IgG1κ isotype control (BD Biosciences) and 20.0 µg/mL chimeric human IgG4κ isotype control (clone ch5D12 from PanGenetics) were used as negative controls. After extensive washing in PBS/BSA/NaN$_3$, cells were subsequently incubated with 1:200 diluted PE-conjugated goat anti-mouse IgG (Fcγ specific) antibodies (Jackson ImmunoResearch) or with 1:200 diluted PE-conjugated goat anti-human IgG (Fcγ specific) antibodies (Jackson ImmunoResearch) for 30 minutes at 4° C. for 30 minutes at 4° C. After extensive washing in PBS/BSA/NaN$_3$, cells were subsequently incubated with 1:200 diluted PE-conjugated goat anti-mouse IgG (Fcγ specific) antibodies (Jackson ImmunoResearch) for 30 minutes at 4° C. After extensive washing in PBS/BSA/NaN$_3$, cells were fixed in 2% formaldehyde in PBS/BSA/NaN$_3$ for 30 minutes at 4° C. Binding of antibodies was measured using flow cytometry (FACSCalibur; BD Biosciences).

As shown in FIG. 36, parental mouse anti-human CD134 antibodies clone 12H3, chimeric human IgG4κ anti-human CD134 antibody clone 12H3, and all six humanized IgG4κ anti-human CD134 antibody clone 12H3 recognized full-length (denoted as 'CRD1' construct) human CD134 and truncated human CD134 variant that lacked CRD1-CRD2 (denoted as 'CRD3' construct) on transfected 293-F cells, whereas parental mouse anti-human CD134 antibodies clone 12H3, chimeric human IgG4κ anti-human CD134 antibody clone 12H3, and all six humanized IgG4κ anti-human CD134 antibody clone 12H3 showed no binding on mock-transfected 293-F cells. In contrast, binding of parental mouse anti-human CD134 antibody clone 12H3, chimeric human IgG4κ anti-human CD134 antibody clone 12H3, and all six versions of humanized IgG4κ anti-human CD134 antibody clone 12H3 against truncated human CD134 variant that lacked CRD1-CRD2-truncated CRD3 A1-module (denoted as 'CRD4' construct) was very weak or negative, whereas parental mouse anti-human CD134 antibody clone 20E5 showed strong binding against this truncated human CD134 variant that lacked CRD1-CRD2-truncated CRD3 A1-module (denoted as 'CRD4' construct) on transfected 293-F cells, which confirmed that these latter 293-F cells expressed this surface truncated CD134 version.

Figure 37:
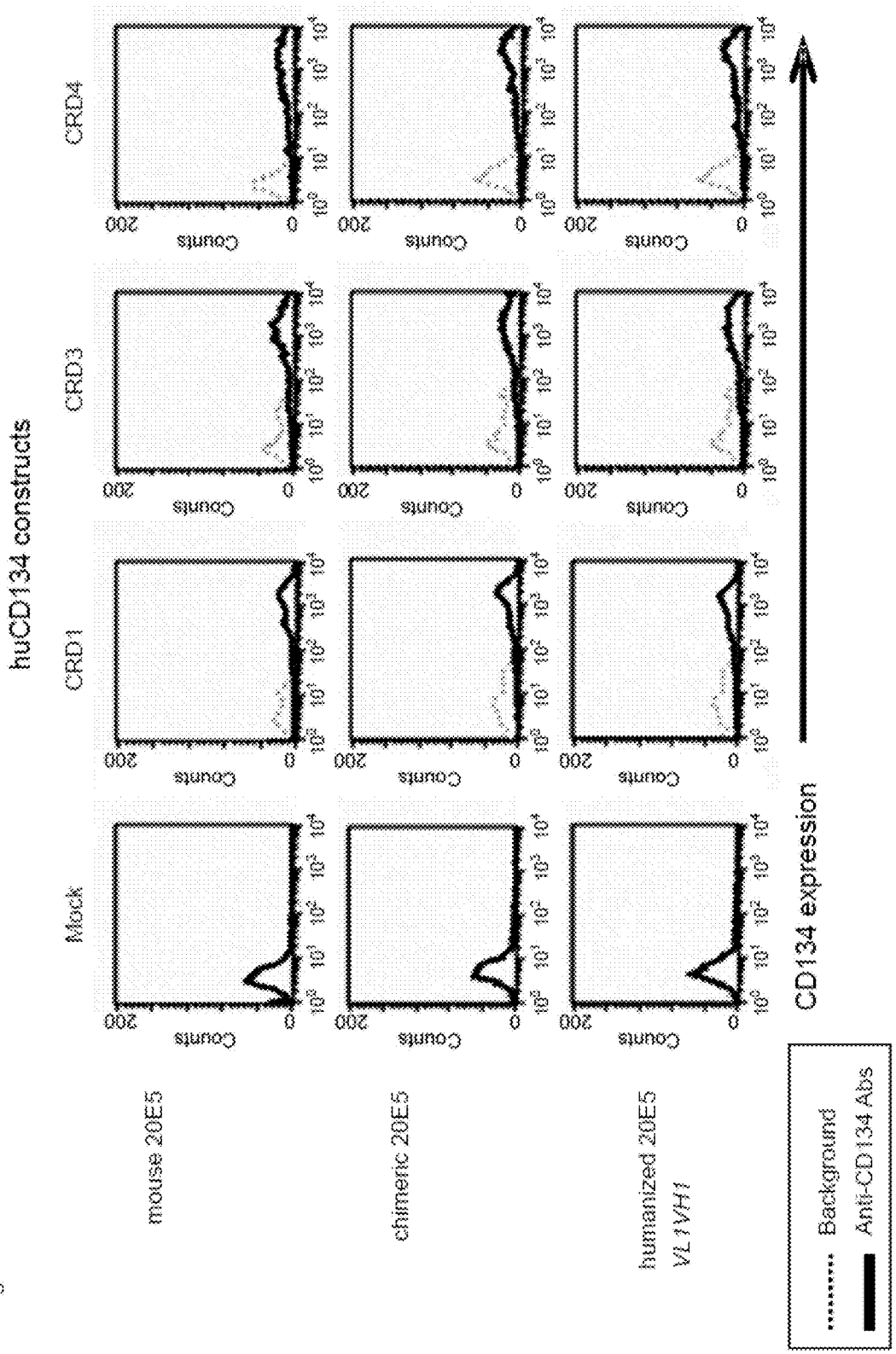
FIG. 37. Binding of humanized human IgG4κ anti-human CD134 antibody clone 20E5 version VL1H1 on 293-F cell line transiently transfected with full-length human CD134 construct (denoted 'CRD1') or with various truncated human CD134 constructs (denoted 'CRD3' and 'CRD4').

As shown in FIG. 37, parental mouse anti-human CD134 antibodies clone 20E5, chimeric human IgG4κ anti-human CD134 antibody clone 20E5, and humanized IgG4κ anti-human CD134 antibody clone 20E5 version 20E5_VL1VH1 recognized full-length (denoted as 'CRD1' construct) human CD134, truncated human CD134 variant that lacked CRD1-CRD2 (denoted as 'CRD3' construct), and truncated human CD134 variant that lacked CRD1-CRD2-truncated CRD3 A1-module (denoted as 'CRD4' construct) on transfected 293-F cells, whereas parental mouse anti-human CD134 antibodies clone 20E5, chimeric human IgG4κ anti-human CD134 antibody clone 20E5, and humanized IgG4κ anti-human CD134 antibody clone 20E5 version 20E5_VL1VH1 showed no binding on mock-transfected 293-F cells.

These results demonstrated that parental mouse anti-human CD134 antibodies clones 12H3 and 20E5, chimeric human IgG4κ anti-human CD134 antibody clones 12H3 and 20E5, all six humanized IgG4κ anti-human CD134 antibody clone 12H3, and humanized IgG4κ anti-human CD134 antibody clone 20E5_VL1VH1 specifically recognized human CD134 (comparison of full-length human CD134 transfection vs mock transfection). Furthermore, these results demonstrated that anti-human CD134 antibodies clones 12H3 and 20E5 seemed to recognize dissimilar human CD134 epitopes, which is evidenced by respective lack of binding (using clone 12H3) vs strong binding (using clone 20E5) with truncated human CD134 variant that lacked CRD1-CRD2-truncated CRD3 A1-module (denoted as 'CRD4' construct). These results demonstrated that mouse anti-human CD134 antibody clone 12H3, chimeric human IgG4κ anti-human CD134 antibody clone 12H3, and all six humanized IgG4κ anti-human CD134 antibody clone 12H3 did not seem to recognize a human CD134 epitope in CRD1 and CRD2. Mouse anti-human CD134 antibody clone 20E5, chimeric human IgG4κ anti-human CD134 antibody clone 20E5, and humanized IgG4κ anti-human CD134 antibody clone 20E5 VL1VH1 did not seem to recognize a human CD134 epitope in CRD1, CRD2, and truncated CRD3 A1-module (according to definition of Latza et al. Eur J Immunol 1994; 24: 677-683). These results demonstrated that mouse anti-human CD134 antibody clone 12H3, chimeric human IgG4κ anti-human CD134 antibody clone 12H3, and all six humanized IgG4κ anti-human CD134 antibody clone 12H3 seemed to recognize a linear or non-linear/conformational epitope in truncated CRD3 A1-module (according to definition of Latza et al. Eur J Immunol 1994; 24: 677-683) with amino acid sequence 108-126 (i.e., 19-meric peptide RCRAGTQPLDSYKPGVDCA; see SEQ ID NO: 34) on extracellular human CD134, or amino acid sequence 108-126 (i.e., 19-meric peptide RCRAGTQPLDSYKPGVDCA; see SEQ ID NO: 34) formed a part for binding to a non-linear/conformational epitope in truncated CRD3 A1-module/CRD4 A1-B1-module (according to definition of Latza et al. Eur J Immunol 1994; 24: 677-683), and possibly in the hinge-like structure, with amino acid sequence 108-214 (see SEQ ID NO: 35) on extracellular human CD134. These results demonstrated that mouse anti-human CD134 antibody clone 20E5, chimeric human IgG4κ anti-human CD134 antibody clone 20E5, and humanized IgG4κ anti-human CD134 antibody clone 20E5_VL1VH1 seemed to recognize a linear or non-linear/conformational epitope in CRD4 A1-B1-module (according to definition of Latza et al. Eur J Immunol 1994; 24: 677-683), and possibly in the hinge-like structure, with amino acid sequence 127-214 (SEQ ID NO: 92) on extracellular human CD134.

(e). Competition of Humanized IgG4κ Anti-Human CD134 Monoclonal Antibody Clone 12H3 with Biotinylated Parental Mouse Anti-Human CD134 Monoclonal Antibody Clone 12H3 for Binding with Surface Human CD134 on Stably Transfected 293-F Cell Line Clone No. 5 (FACS)

Figure 38:
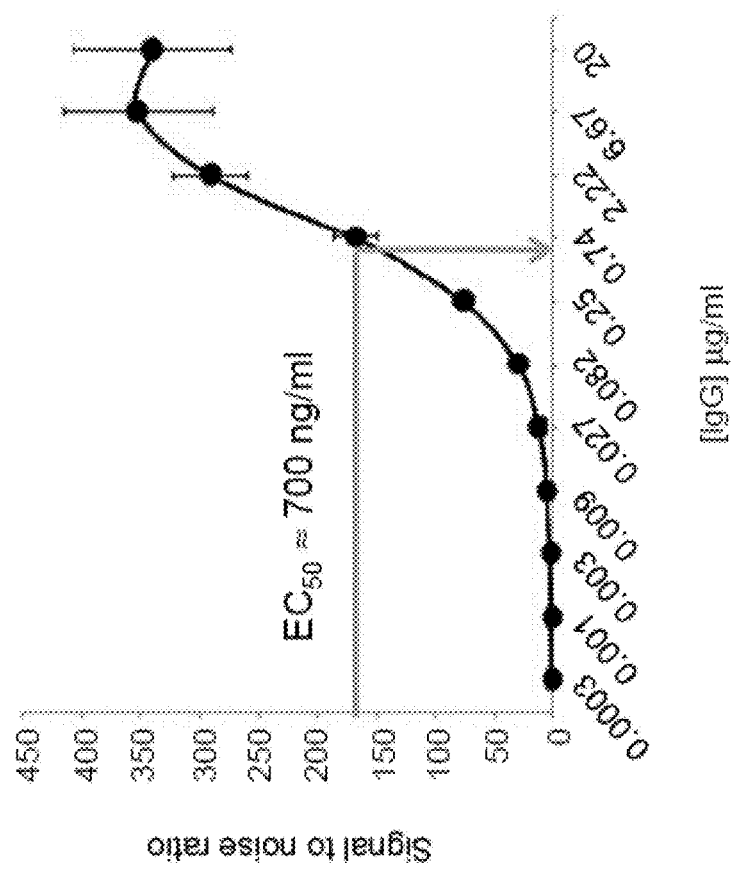
FIG. 38. Binding characteristic of biotinylated parental mouse anti-human CD134 antibody clone 12H3 against surface human CD134 on stably transfected 293-F cell line clone no. 5.

Prior to performing the competition flow cytometric measurements, the EC$_{50}$ of biotinylated (using N-hydroxysuccinimido-biotin from Pierce) parental mouse anti-human CD134 monoclonal antibody clone 12H3 was determined (see below for method), and was identified to be about 700 ng/mL (see FIG. 38, n=2). Displacement of the biotinylated parental mouse anti-human CD134 monoclonal antibody clone 12H3 at the identified EC$_{50}$ concentration by unlabeled parental mouse anti-human CD134 antibody clone 12H3, chimeric human IgG4κ anti-human CD134 antibody clone 12H3, and six versions of humanized IgG4κ anti-human CD134 antibody clone 12H3 was subsequently investigated.

Full-length human CD134 (SEQ ID NO 1) was re-cloned in a pcDNA3.1-derived expression plasmid (see Example 11 (c) above). This full-length human CD134 plasmid was transfected in FreeStyle™ 293-F cells (Life Technologies) using the FreeStyle™ 293 Expression System (Life Technologies). Stable human full-length CD134-transfected cells (clone no. 5 with high surface CD134 expression level see FIG. 32) were selected using 125 µg/mL G418 (Gibco), and were harvested and put at 1-2×10⁶ cells/mL in ice-chilled PBS/BSA/NaN$_3$ supplemented with 50 µg/mL purified human IgG (Sigma; blocking Fcγ receptors). Cells were incubated with 0.003-50.0 (5-fold dilution steps in PBS/BSA/NaN$_3$) unlabeled parental mouse anti-human CD134 antibody clone 12H3, chimeric human IgG4κ anti-human CD134 antibody clone 12H3, and six versions of humanized IgG4κ anti-human CD134 antibody clone 12H3 in combination with 700 ng/mL (EC$_{50}$) biotinylated parental mouse anti-human CD134 monoclonal antibody clone 12H3 for 30 minutes at 4° C. After extensive washing in PBS/BSA/NaN$_3$, binding of biotinylated parental mouse anti-human CD134 monoclonal antibody clone 12H3 was determined with 1:200 diluted PE-conjugated streptavidin (Jackson ImmunoResearch) for 30 minutes at 4° C. After extensive washing in PBS/BSA/NaN$_3$, cells were fixed in 2% formaldehyde in PBS/BSA/NaN$_3$ for 30 minutes at 4° C. Binding of biotinylated parental mouse anti-human CD134 monoclonal antibody clone 12H3 was measured using flow cytometry (FACSCalibur; BD Biosciences).

Figure 39A:
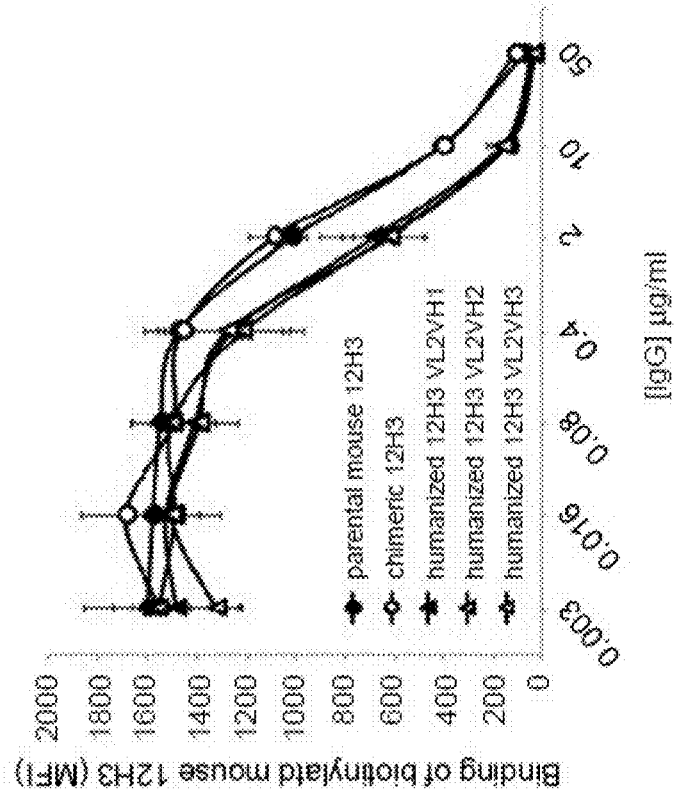
FIGS. 39A and 39B. Competition characteristics of humanized human IgG4κ anti-human CD134 antibody clone 12H3 versions VL1H1, VL1VH2, VL1VH3 (A) and VL2H1, VL2VH2, VL2VH3 (B) with biotinylated parental mouse anti-human CD134 antibody clone 12H3 (at an EC50 of 700 ng/mL) for binding to surface human CD134 on stably transfected 293-F cell line clone no. 5.
Figure 39B:
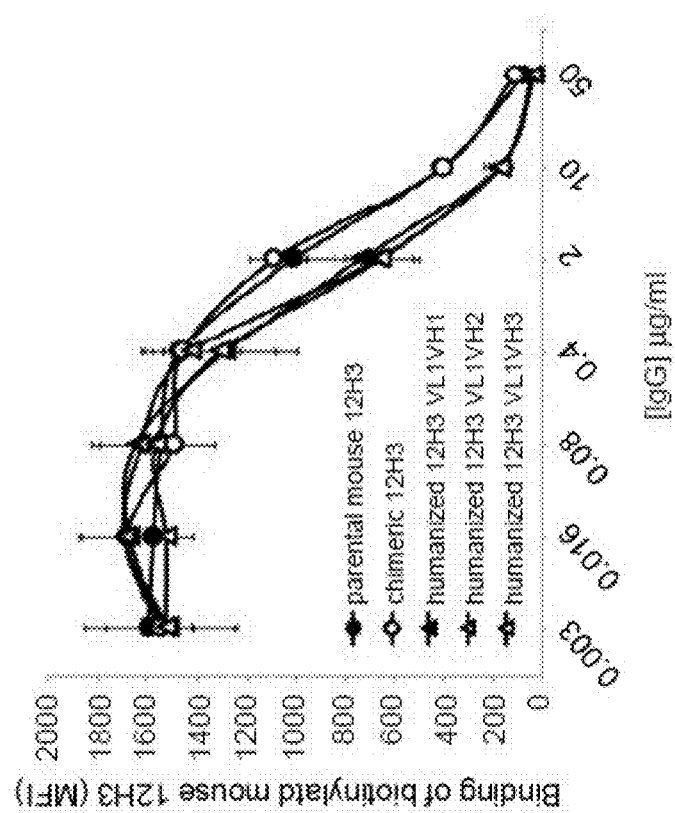

As shown in FIG. 39 (n=2), unlabeled parental mouse anti-human CD134 antibody clone 12H3 and unlabeled chimeric human IgG4κ anti-human CD134 antibody clone 12H3 demonstrated identical displacement of biotinylated parental mouse anti-human CD134 monoclonal antibody clone 12H3, which indicated that parental mouse anti-human CD134 antibody clone 12H3 and chimeric human IgG4κ anti-human CD134 antibody clone 12H3 exhibited an identical CD134 antigen binding affinity (half-maximum displacement or inhibition (IC$_{50}$) of biotinylated parental mouse anti-human CD134 monoclonal antibody clone 12H3 at ≈3.5 µg/mL). All six unlabeled humanized IgG4κ anti-human CD134 antibody clone 12H3 versions—12H3_VL1H1, 12H3_VL1H2, 12H3_VL1H3, 12H3_VL2H1, 12H3_VL2VH2 and 12H3_VL2VH3—demonstrated identical displacement of biotinylated parental mouse anti-human CD134 monoclonal antibody clone 12H3, which indicated that all six unlabeled humanized IgG4κ anti-human CD134 antibody clone 12H3 versions exhibited an identical CD134 antigen binding affinity (IC$_{50}$≈1.5 µg/mL).

These results demonstrated that all six humanized IgG4κ anti-human CD134 antibody clone 12H3 versions showed a higher CD134 antigen binding affinity than parental mouse anti-human CD134 antibody clone 12H3 and chimeric human IgG4κ anti-human CD134 antibody clone 12H3.

Example 12. Anti-CD134 Antibodies Suppress FOX3P Expression in Treg Cells

Treg Isolation and Expansion:
Leukopacks were purchased from Biological Specialties (Colamar, Pa.) and red blood cells lysed with ACK buffer (Stemcell technologies, Vancouver, BC, Canada) on ice. Cells were washed and resuspended in AutoMACS running buffer. Tregs were isolated with the CD4+ CD25+ CD127dim/− Treg kit on both an AutoMACS Pro and/or LD columns with a QuadroMACS, all from Miltenyi Biotech (San Diego, Calif.) following manufacturer's instructions. Tregs were counted and 1×10⁶ Tregs/well were expanded in 24-well plates in TexMACS medium with Treg expansion beads (MACSiBead particles pre-loaded with CD3 and CD28 antibodies; Miltenyi Biotech) following manufacturer's instructions. The cells were cultured at a ratio of 4 beads/cell in the presence of ~500 IU/mL of IL-2 and Rapamycin (100 nM). 5 days after the isolation, the cells were transferred to a 6 well/plate and 40 µl of beads/well and media with IL-2 (500 IU/ml) and Rapamycin (100 nM) were added. Medium containing IL-2 was added as needed and cells were transferred to 10 mm round dish plates and expanded further. After 30 days, beads were removed with a MACSiMAG before downstream applications.

Treg Activation:
Expanded Tregs were labeled with Celltrace Violet as per manufacturer's instructions (Life Technologies, Grand Island, N.Y.). 1.5×10⁵ expanded Tregs and 3×10⁵ Treg Expansion beads (MACSiBead particles pre-loaded with CD3 and CD28 antibodies; Miltenyi Biotech) were plated in round-bottom 96-well plates and incubated at 37° C. in X-VIVO 15 medium supplemented with 5% serum, 1% Pen-Strep and ~500 IU/mL of IL-2 with or without 12H3 (0.5 and 5 µg/ml) and/or human OX40L (1 µg/ml, R&D Systems) and anti-His mAb (1 µg/ml, R&D Systems). After 3 days, cells were restimulated with Leukocyte Activation Cocktail, with BD GolgiPlug (2 µl/ml, BD Biosciences, San Jose, Calif.) for 5 hours, washed and stained with LIVE/DEAD® Fixable Near-IR Dead Cell Stain Kit (Life Technologies) following manufacturer's instructions. Cells were washed once and intracellular staining was performed following fixation/permeabilization with Foxp3/Transcription Factor Staining Buffer Set (eBioscience, San Diego, Calif.) according to the manufacturer's protocol. The following antibodies were used CD3 V500 (clone SP34-2, BD Biosciences); FOXP3 PE (clone 206D, Biolegend); CD4 PerCP (clone OKT4, Biolegend); and OX40 (clone ACT35, eBioscience). Cells were incubated for 30 minutes at 4° C. and washed. Cells were run in a BD Canto flow cytometer (BD Biosciences) and analyzed using FlowJo (Ashland, Oreg.), gating on live singlets CD3+CD4+. Geometric Mean fluorescent intensity derived from anti-FOXP3 PE (R-Phycoerythrin) (geoMFI) was recorded.

Figure 40:
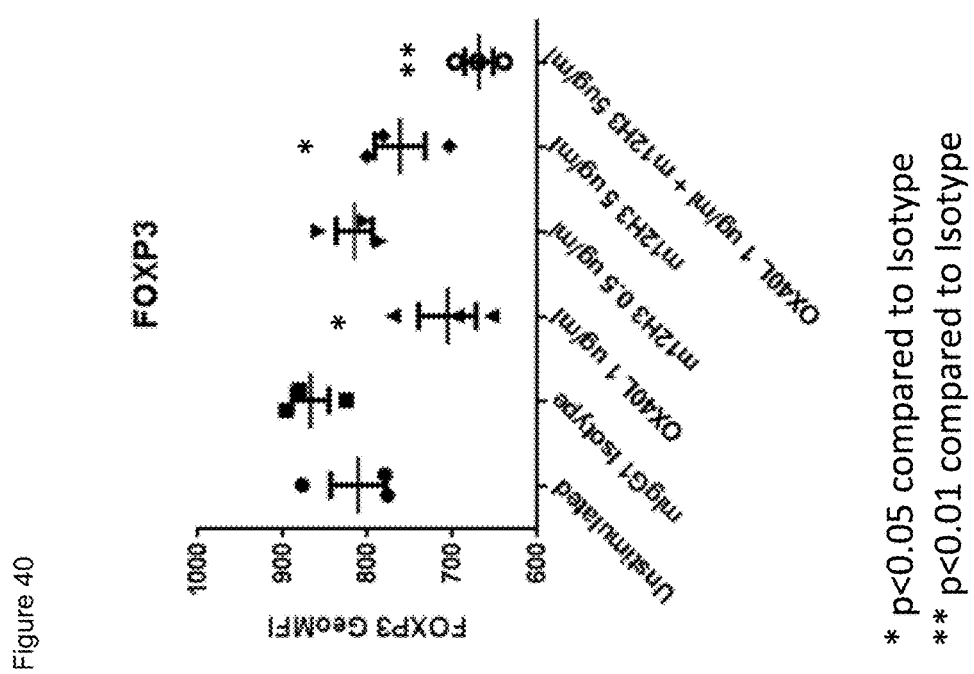
FIG. 40. Downregulation of FOXP3 expression in expanded Tregs (CD4+CD25+CD127 dim/−) by soluble OX40L and soluble mouse anti-human CD134 12H3 IgG1 antibody at indicated concentrations. Y axis shows FOXP3 geometric mean fluorescence intensity (GeoMFI) detected using anti-FOX3P antibody coupled to PE. m12H3=mouse 12H3 IgG1. The data represent a triplicate sample from one donor.

FIG. 40 shows that both the mouse anti-human CD134 antibody 12H3 (IgG1) and human OX40L decreased FOXP3 expression in expanded Tregs (CD4+CD25− CD127 dim/−). When 12H3 and OX40L were used in combination, the effect on FOXP3 expression suppression was additive. The results suggest that that the mouse anti-human antibody 12H13 affects Treg function directly, and not only through its role on effector T cells. The data represents a triplicate sample from one donor.

Example 13. Plate Bound Humanized Anti-CD134 Antibodies Ameliorate Treg Suppression of Teff Cells Effect of humanized anti-CD134 antibodies 12H3 VL1VH1 or 12H3 VL1VH2 (both IgG4/κ) on Treg suppression of Teff function was evaluated.

Tregs were isolated, expanded and activated as described in Example 12. Where indicated, round bottom 96-well-plates were coated with 12H3 VL1VH1 or 12H3 VL1VH2 antibodies or isotype controls (10 µg/ml) diluted in PBS. Plates were incubated for 2 hours at 37° C., then rinsed and used in the suppression assay. CD4+ effector T cells (Teff) isolated from the same donor as the Tregs were purified from frozen PBMCs using an AutoMACS Pro and CD4+ isolation kit from Miltenyi Biotech according to manufacturer's specifications. The Teff cells were then labeled with Celltrace™ Violet dye as per manufacturer's instructions (Life Technologies, Grand Island, N.Y.). Teff cells were resuspended in X-VIVO 15 medium supplemented with 5% serum, 1% Pen-Strep. 1×10⁵ cells were added to each well. Tregs were added at Treg:Teff ratio of 0:1 (Teffs alone), 1:2, 1:4 and 1:8. Treg Suppression Inspector beads (Miltenyi Biotech) were washed and added to the wells at a ratio of 1 bead per cell (Teff or Treg). Final volume in each well was adjusted to 200 µl. Plates were incubated at 37° C. for 4 days. Cells were restimulated with Leukocyte Activation Cocktail, with BD GolgiPlug (2 µl/ml, BD Biosciences, San Jose, Calif.) for 5 hours, washed and stained with LIVE/DEAD® Fixable Near-IR Dead Cell Stain Kit (Life Technologies) following manufacturer's instructions. Cells were washed and surface stain was performed with APC-coupled anti-OX40 (allophycocyanin) (clone ACT35, eBioscience) followed by intracellular staining. Fixation/permeabilization with Foxp3/Transcription Factor Staining Buffer Set (eBioscience, San Diego, Calif.) according to the manufacturer's protocol. The following antibodies were used: CD3 V500 (clone SP34-2, BD Biosciences); CD4 FITC (clone RPA-T4, BioLegend). Cells were incubated for 30 minutes at 4° C. and washed. Cells were run in a BD Canto flow cytometer (BD Biosciences) and analyzed using FlowJo (Ashland, Oreg.), gating on live singlets CD3+ CD4+ Celltrace+.

Figure 41:
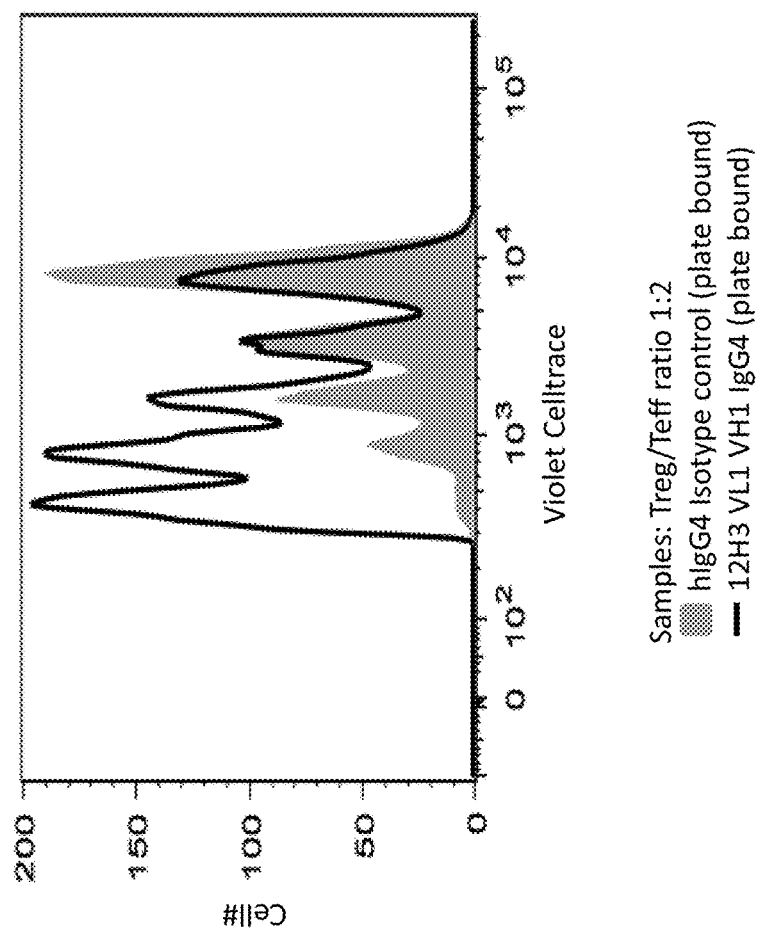
FIG. 41. Histogram of FACS analyses showing dampened inhibitory effect of Tregs on Teff proliferation by plate bound humanized anti-human CD134 12H3 VL1VH1 antibody when compared to the isotype control. Teff cells were detected with Celltrace™ Violet dye. Treg:Teffector ratio was 1:2.

Plate-bound humanized 12H3 antibodies dampened the inhibition by Tregs on Teff proliferation. FIG. 41 shows the histogram of FACS analyses comparing the proliferation of Teff cells stimulated with Treg suppression inspector beads (Miltenyi, San Diego, Calif.) and treated with plate bound 12H3 VL1VH1 or isotype control IgG4 in the presence of Tregs at Treg/Teff ratio 1:2. Compared to isotype control (hIgG4), 12H3 VL1VH1 dampened the inhibitory effect of Tregs on Teff proliferation, as indicated by the increase in cell numbers in the successive peaks (lowere fluorescent intensity) representing subsequent cell divisions detected with Celltrace™ Violet dye. Celltrace™ Violet dye binds to activated amine groups inside the cells.

Figure 42A:
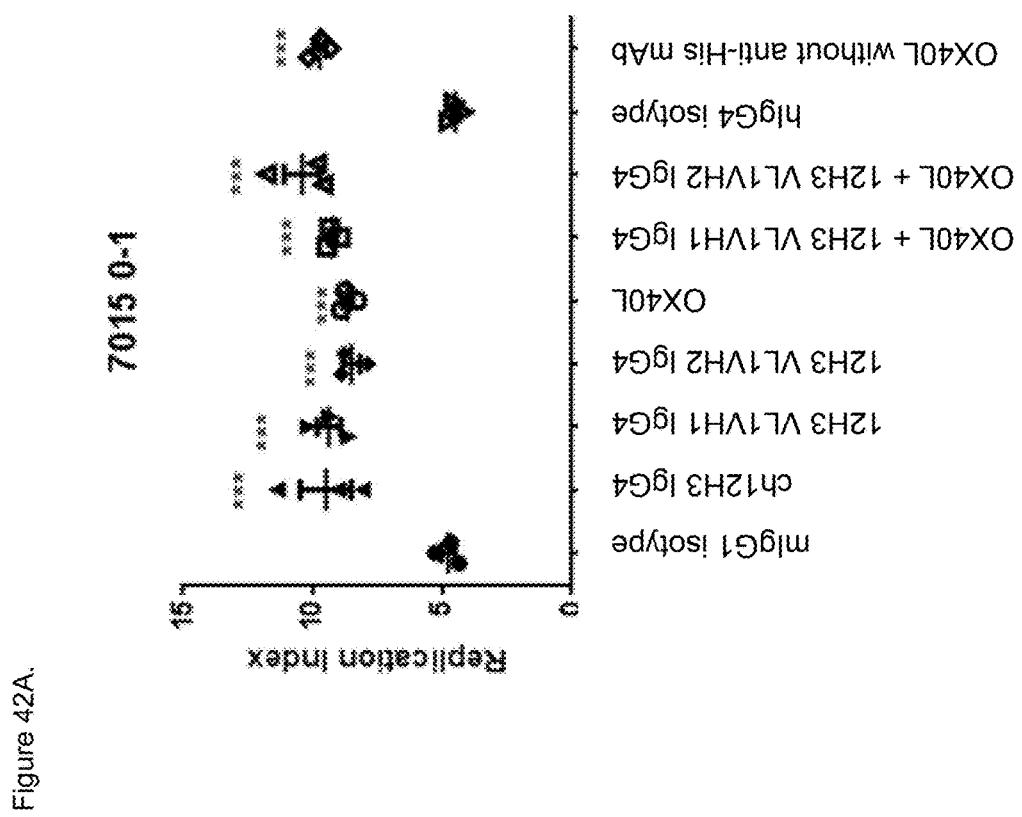
FIGS. 42A and 42B. Effect of indicated plate bound anti-human CD134 antibodies on proliferation of Teff cells at Treg:Teff ratio 0:1 (no Tregs) (FIG. 42A) or 1:4 (FIG. 42B) isolated from donor 7015, plotted as a function of replication index. M=mouse; ch=chimeric; h=human. *p<0.05; p<0.01;*p<0.001 compared to mIgG1 isotype control. Human OX40L was used with (OX40L) or without (OX40L no His) anti-His antibody.
Figure 42B:
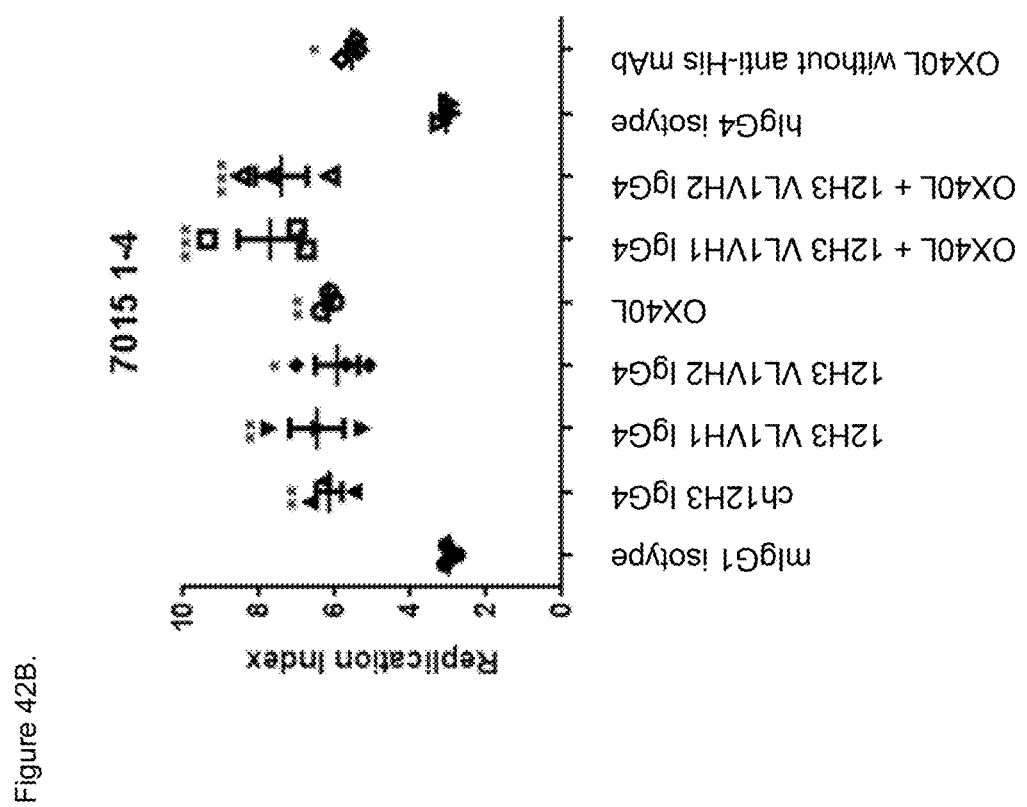

FIG. 42 shows the effect of chimeric 12H3 (human IgG4/κ), humanized 12H3 VL1VH1 or 12H3 VL1VH2 (both IgG4/κ) alone or in combination with OX40L (5 µg/mL)/anti-His mAb (5 µg/mL) on the replication of Teff cells at Treg:Teff ratio of 0:1 (FIG. 42A) or 1:4 (FIG. 42B) on cells isolated from one donor. In the absence of Tregs (FIG. 42A), CD2/CD3/CD28 stimulator beads alone induced proliferation in human CD134 expressing Teffs (i.e. isotype control). The chimeric and humanized anti-CD134 antibodies as well as OX40L stimulated the proliferation of CD4+ T cells when compared to the isotype control. Proliferation was slightly increased with a combination of 2H3 VL1VH2 (SF2) with OX40L. In the presence of Tregs (FIG. 42B), CD2/CD3/CD28 stimulator beads alone induced less CD4 T cells proliferation when compared to proliferation of CD4 T cells without Treg suppression (replication index about 3 vs about 5). Treg suppression was dampened in the presence of chimeric 12H3, humanized 12H3 VL1VH1 and 12H3 VL1VH2 as well as OX40L. Presence of the combination of 12H3 VL1VH1 or 12H3 VL1VH2 and OX40L demonstrated a slightly synergistic effect. In the Figure, Teff cell proliferation is expressed as a replication index, which is a measure of fold-expansion of the Teff cells that have divided at least once in response to a stimulus (e.g., number of cells in millions at the end of the culture that have undergone at least one division).

Table 3 summarizes the effect of 12H3 VH1VH2 IgG4/κ on effect on Teff proliferation in the presence of Tregs at Treg/Teff ratio 0:1, 1:2 and 1:4 for 12H3 VL1VH2 (IgG4κ) in cells obtained from 5 donors. Degree of proliferation was expressed as Replicaton Index. In the absence of Tregs, 12H3 VL1VH2 stimulated Teff cell proliferation in all donor-derived cells when compared to the isotype control (with Teff activated using CD2/CD3/CD28 beads). In the presence of Tregs either at 1:2 or 1:4 Treg/Teff ratio, presence of 12H3 VL1VH2 dampened the Treg suppression in all donor-derived cells.

The results indicate that 12H3 VL1VH1 and 12H3 VL1VH2 have an effect on CD4 effector T cells inducing their proliferation, and that the antibodies renders Teffs somewhat resistant to Tregs or that Tregs themselves are less suppressive in the presence of the antibodies.

TABLE 3

| | Treg/Teff ratio | | | | | |
|---|---|---|---|---|---|---|
| | 0:1 | | 1:2 | | 1:4 | |
| Donor | Isotype control | 12H3 VL1VH2 | Isotype control | 12H3 VL1VH2 | Isotype control | 12H3 VL1VH2 |
| 1 | 10.40 | 13.90 | 3.02 | 5.33 | 3.77 | 5.23 |
| 2 | 10.50 | 12.10 | 4.60 | 5.82 | 5.01 | 5.21 |
| 3 | 5.23 | 10.24 | 4.76 | 6.00 | 4.54 | 5.23 |
| 4 | 5.60 | 10.67 | 4.56 | 6.05 | 5.02 | 5.51 |
| 5 | 4.81 | 8.66 | 3.61 | 4.71 | 3.69 | 4.81 |

Example 14. Optimization of Humanized Antibodies

Optimization of Humanized 20E5 Antibodies.

HCDR2 of humanized heavy chain variable regions (VH) 20E5_VH1, 20E5_VH2 and 20E5_VH3 contain an isomerization motif at VH residue positions 56-57 (DG, D56G57). To test the effect of substitutions at position 56, the aspartate (D) residue is mutated to glycine (G), alanine (A), serine (S) or glutamate (E).

HCDR3 of humanized heavy chain variable regions 20E5_VH1, 20E5_VH2 and 20E5_VH3 contain a methionine (M) at position 106 (M106). The methionine is likely buried to a large extent, however, to reduce oxidation risk, the methionine at position 106 is mutated to leucine (L) or isoleucine (I).

Position 11 in the humanized heavy chain variable regions 20E5_VH1, 20E5_VH2 and 20E5_VH3 contain a valine (V). Substitutions at this position may have a structural impact on the antibody and hence its function (Klein et al mAbs 5:22-33, 2013). To test the effect of substitutions at position 11, the valine (V) residue is mutated to leucine (L).

The mutations are incorporated to each heavy chain variable region 20E5_VH1, 20E5_VH2 and 20E5_VH3 using standard methods. The mutant HCDR2 sequences are shown in Table 4 and the mutant HCDR3 sequences are shown in Table 5. Optimized humanized 20E5 variable regions containing single substitutions are shown in Table 6. Alignment of the parental and optimized VH regions is shown in FIG. 43A and FIG. 43B. The names of the optimized VH regions indicate the parental VH and the substitution made. Additional optimized variable regions can be generated by making substitutions simultaneously at positions 11, 56 and/or 106 using standard methods.

The resulting VH regions are paired with the light chain variable regions 20E5_VL1 or 20E5 VL2 and the resulting antibodies are expressed as IgG4/using standard methods. The antibodies are tested for their binding to CD134 using ELISA according to protocol described in Example 11A. The antibodies are further tested for their ability to induce proliferation of Teff cells and dampen the inhibitory effect of Tregs on Teff proliferation using the protocols described in Example 13. The antibodies having comparable properties than the parental humanized 20E5 antibodies are selected for further studies.

TABLE 4

| SEQ ID NO: | HCDR2 Sequence | Substitution |
|---|---|---|
| 135 | YINPYNGGTKYNEKFKG | D56G |
| 136 | YINPYNAGTKYNEKFKG | D56A |
| 137 | YINPYNSGTKYNEKFKG | D56S |
| 138 | YINPYNEGTKYNEKFKG | D56E |

TABLE 5

| SEQ ID NO: | HCDR3 sequence | Substitution |
|---|---|---|
| 139 | YYGSSLSLDY | M106L |
| 140 | YYGSSLSIDY | M106I |

TABLE 6

| SEQ ID NO: | Name of optimized VH name |
|---|---|
| 101 | 20E5_VH1_D56G |
| 102 | 20E5_VH2_D56G |
| 103 | 20E5_VH3_D56G |
| 104 | 20E5_VH1D56A |
| 105 | 20E5_VH2_D56A |
| 106 | 20E5_VH3_D56A |
| 107 | 20E5_VH1D56S |
| 108 | 20E5_VH2_D56S |
| 109 | 20E5_VH3_D56S |
| 110 | 20E5_VH1D56E |
| 111 | 20E5_VH2_D56E |
| 112 | 20E5_VH3_D56E |
| 113 | 20E5_VH1M106L |
| 114 | 20E5_VH2_M106L |
| 115 | 20E5_VH3_M106L |
| 116 | 20E5_VH1M106I |
| 117 | 20E5_VH2_M106I |
| 118 | 20E5_VH3_M106I |
| 149 | 20E5_VH1_V11L |
| 150 | 20E5_VH2_V11L |
| 151 | 20E5_VH3_V11L |

Optimization of Humanized 12H3 Antibodies.

HCDR2 of humanized heavy chain variable regions (VH) 12H3_VH1, 12H3_VH2 and 12H3_VH3 contain a deamidation motif (NNG) at residues 54-56 ($N_{54}N_{55}G_{56}$). To minimize deamidation risk, asparagine at position 55 (N55) is mutated to glutamine (Q), alanine (A) or glutamate (E).

HCDR3 of humanized heavy chain variable regions 12H3_VH1, 12H3_VH2 and 12H3_VH3 contain a methionine (M) at position 99 (M99). The methionine is likely buried to a large extent, however, to reduce oxidation risk, the methionine at position 99 is mutated to leucine (L) or isoleucine (I).

Position 11 in the humanized heavy chain variable regions 12H3_VH1, 12H3_VH2 and 12H3_VH3 contain a valine (V). Substitutions at this position may have a structural impact on the antibody and hence its function (Klein et al mAbs 5:22-33, 2013). To test the effect of substitutions at position 11, the valine (V) residue is mutated to leucine (L).

The mutations are incorporated to each heavy chain variable region 12H3_VH1, 12H3_VH2 and 12H3_VH3 using standard methods. The mutant HCDR2 sequences are shown in Table 7 and the mutant HCDR3 sequences are shown in Table 8. Optimized humanized 12H3 variable regions containing single substitutions are shown in Table 9. Alignment of the parental and optimized VH regions are shown in FIG. 44. The names of the optimized VH regions indicate the parental VH and the substitution made. Additional optimized variable regions can be generated by making substitutions simultaneously at positions 11, 55 and/or 99 using standard methods.

The resulting VH regions are paired with the light chain variable regions 12H3_VL1 or 12H3 VL2 and the resulting antibodies are expressed as IgG4/κ using standard methods. The antibodies are tested for their binding to CD134 using ELISA according to protocol described in Example 11A. The antibodies are further tested for their ability to induce proliferation of Teff cells and dampen the inhibitory effect of Tregs on Teff proliferation using the protocols described in Example 13. The antibodies having comparable properties than the parental humanized 12H3 antibodies are selected for further studies

TABLE 7

| SEQ ID NO: | HCDR2 Sequence | Substitution |
|---|---|---|
| 141 | GIYPNQGGSTYNQNFKD | N55Q |
| 142 | GIYPNAGGSTYNQNFKD | N55A |
| 143 | GIYPNEGGSTYNQNFKD | N55E |

TABLE 8

| SEQ ID NO: | HCDR3 sequence | Substitution |
|---|---|---|
| 144 | LGYHGPHLDFDV | M99L |
| 145 | IGYHGPHLDFDV | M99I |

TABLE 9

| SEQ ID NO: | Name of optimized VH name |
|---|---|
| 119 | 12H3_VH1_N55Q |
| 120 | 12H3_VH2_N55Q |
| 121 | 12H3_VH3_N55Q |
| 122 | 12H3_VH1_N55A |
| 123 | 12H3_VH2_N55A |
| 124 | 12H3_VH3_N55A |
| 125 | 12H3_VH1_N55E |
| 126 | 12H3_VH2_N55E |
| 127 | 12H3_VH3_N55E |
| 128 | 12H3_VH1_M99L |
| 129 | 12H3_VH2_M99L |
| 130 | 12H3_VH3_M99L |
| 131 | 12H3_VH1_M99I |
| 132 | 12H3_VH2_M99I |
| 133 | 12H3_VH3_M99I |
| 146 | 12H3_VH1_V11L |
| 147 | 12H3_VH2_V11L |
| 148 | 12H3_VH3_V11L |

What is claimed:

1. A method of enhancing an immune response in a subject in need thereof comprising administering to the subject an antibody that binds human CD134 for a time sufficient to enhance the immune response, wherein the antibody comprises a light chain variable region (VL) comprising the amino acid sequence of SEQ ID NO: 98 or the amino acid sequence of SEQ ID NO: 98 having 1, 2 or 3 amino acid substitutions and a heavy chain variable region (VH) comprising the amino acid sequence of SEQ ID NO:134 or the amino acid sequence of SEQ ID NO:134 having 1, 2 or 3 amino acid substitutions.

2. A method of treating cancer in a subject in need thereof comprising administering to the subject an antibody that binds human CD134 for a time sufficient to treat the cancer, wherein the antibody comprises a light chain variable region (VL) comprising the amino acid sequence of SEQ ID NO: 98 or the amino acid sequence of SEQ ID NO: 98 having 1, 2 or 3 amino acid substitutions and a heavy chain variable region (VH) comprising the amino acid sequence of SEQ ID NO:134, or the amino acid sequence of SEQ ID NO:134 having 1, 2 or 3 amino acid substitutions.

3. The method of claim 2, wherein the cancer is prostate cancer, colon cancer, lung cancer, hematological malignancy, melanoma or bladder cancer.

4. The method of claim 1, wherein the VH comprises the amino acid sequence of SEQ ID NO: 97 or the amino acid sequence of SEQ ID NO: 97 having 1, 2 or 3 amino acid substitutions in the VH of SEQ ID NO: 97.

5. The method of claim 2, wherein the VH comprises the amino acid sequence of SEQ ID NO: 97 or the amino acid sequence of SEQ ID NO: 97 having 1, 2 or 3 amino acid substitutions in the VH of SEQ ID NO: 97.

6. The method of claim 1, wherein the HCDR3 comprises the amino acid sequence of SEQ ID NOs: 8, 139 or 140, wherein the HCDR2 comprises the amino acid sequence of SEQ ID NOs: 7, 135, 136, 137 or 138, and wherein the HCDR1 comprises the amino acid sequence of SEQ ID NO: 6.

7. The method of claim 1, wherein:
a. the VL comprises the amino acid sequence of SEQ ID NOs: 62 or 63; and the VH comprises the amino acid sequence of SEQ ID NOs: 64, 65, 66, 101, 102, 103, 104, 105, 106, 107, 108, 109, 110, 111, 112, 113, 114, 115, 116, 117, 118, 149, 150 or 151, optionally having 1, 2 or 3 amino acid substitutions at the VH linear amino acid residue positions 11, 56 or 106; or
b. the VL and the VH comprise the amino acid sequences of
i. SEQ ID NOs: 62 and 64, respectively;
ii. SEQ ID NOs: 62 and 65, respectively;
iii. SEQ ID NOs: 62 and 66, respectively;
iv. SEQ ID NOs: 63 and 64, respectively;
v. SEQ ID NOs: 63 and 65, respectively; or
vi. SEQ ID Nos: 63 and 66, respectively.

8. The method of claim 2, wherein:
a. the VL comprises the amino acid sequence of SEQ ID NOs: 62 or 63; and the VH comprises the amino acid sequence of SEQ ID NOs: 64, 65, 66, 101, 102, 103, 104, 105, 106, 107, 108, 109, 110, 111, 112, 113, 114, 115, 116, 117, 118, 149, 150 or 151, optionally having 1, 2 or 3 amino acid substitutions at the VH linear amino acid residue positions 11, 56 or 106; or
b. the VL and the VH comprise the amino acid sequences of
i. SEQ ID NOs: 62 and 64, respectively;
ii. SEQ ID NOs: 62 and 65, respectively;
iii. SEQ ID NOs: 62 and 66, respectively;
iv. SEQ ID NOs: 63 and 64, respectively;
v. SEQ ID NOs: 63 and 65, respectively; or
vi. SEQ ID Nos: 63 and 66, respectively.

9. The method of claim 1, wherein the VL comprises the amino acid sequence of SEQ ID NO: 63 and the VH comprises the amino acid sequence of SEQ ID NO: 66.

10. The method of claim 2, wherein the VL comprises the amino acid sequence of SEQ ID NO: 63 and the VH comprises the amino acid sequence of SEQ ID NO: 66.

11. The method of claim 1, wherein the 1, 2 or 3 amino acid substitutions at the VH linear amino acid residue positions are V11L, D56G, D56A, D56S, D56E, M106L or M106I.

12. The method of claim 1, wherein the antibody is humanized or deimmunized.

13. The method of claim 1, wherein the antibody is an agonist of CD134.

14. The method of claim 1, wherein the antibody is of IgG1, IgG2, IgG3 or IgG4 isotype.

15. The method of claim 1, wherein the antibody comprises a substitution in an Fc region.

16. The method of claim 15, wherein the substitution modulates binding of the antibody to an Fc gamma receptor (FcγR) or to a neonatal Fc receptor (FcRn).

17. The method of claim 16, wherein the substitution comprises a S267E/L328F substitution, an E233D/G237D/H268D/P271G/A330R substitution, a V234A/G237A/

P238S/H268A/V309L/A330S/P331S substitution, or a M252Y/S254T/T256E substitution, wherein residue numbering is according to the EU Index.

* * * * *